US011191811B2

(12) United States Patent
Karsenty et al.

(10) Patent No.: US 11,191,811 B2
(45) Date of Patent: Dec. 7, 2021

(54) OSTEOCALCIN AS A TREATMENT FOR FRAILTY ASSOCIATED WITH AGING

(71) Applicant: THE TRUSTEES OF COLUMBIA UNIVERSITY IN THE CITY OF NEW YORK, New York, NY (US)

(72) Inventors: Gerard Karsenty, New York, NY (US); Paula Mera, New York, NY (US); Emilio Arteaga-Solis, Brooklyn, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 299 days.

(21) Appl. No.: 15/528,085

(22) PCT Filed: Nov. 19, 2015

(86) PCT No.: PCT/US2015/061590
§ 371 (c)(1),
(2) Date: May 18, 2017

(87) PCT Pub. No.: WO2016/081728
PCT Pub. Date: May 26, 2016

(65) Prior Publication Data
US 2017/0319660 A1  Nov. 9, 2017

Related U.S. Application Data

(60) Provisional application No. 62/081,861, filed on Nov. 19, 2014.

(51) Int. Cl.
A61K 38/22 (2006.01)
A61K 38/39 (2006.01)
C07K 14/78 (2006.01)
A61K 9/00 (2006.01)

(52) U.S. Cl.
CPC ............ *A61K 38/22* (2013.01); *A61K 9/0019* (2013.01); *A61K 38/39* (2013.01); *C07K 14/78* (2013.01)

(58) Field of Classification Search
None
See application file for complete search history.

(56) References Cited

U.S. PATENT DOCUMENTS

| | | |
|---|---|---|
| 4,059,589 A | 11/1977 | Scherberich et al. |
| 4,250,088 A | 2/1981 | Yang |
| 4,405,712 A | 9/1983 | Vande Woude et al. |
| 4,426,330 A | 1/1984 | Sears |
| 4,448,764 A | 5/1984 | Smith et al. |
| 4,469,863 A | 9/1984 | Ts'o et al. |
| 4,522,811 A | 6/1985 | Eppstein et al. |
| 4,534,894 A | 8/1985 | Cerami et al. |
| 4,534,899 A | 8/1985 | Sears |
| 4,631,211 A | 12/1986 | Houghten et al. |
| 4,650,764 A | 3/1987 | Temin et al. |
| 4,801,742 A | 1/1989 | Quirk et al. |
| 4,946,778 A | 8/1990 | Ladner et al. |
| 5,013,556 A | 5/1991 | Woodle et al. |
| 5,034,506 A | 7/1991 | Summerton et al. |
| 5,108,921 A | 4/1992 | Low et al. |
| 5,213,804 A | 5/1993 | Martin et al. |
| 5,216,141 A | 6/1993 | Benner |
| 5,227,170 A | 7/1993 | Sullivan |
| 5,235,033 A | 8/1993 | Summerton et al. |
| 5,264,221 A | 11/1993 | Tagawa et al. |
| 5,354,844 A | 10/1994 | Beug et al. |
| 5,356,633 A | 10/1994 | Woodle et al. |
| 5,386,023 A | 1/1995 | Sanghvi et al. |
| 5,395,619 A | 3/1995 | Zalipsky et al. |
| 5,416,016 A | 5/1995 | Low et al. |
| 5,417,978 A | 5/1995 | Tari et al. |
| 5,459,127 A | 10/1995 | Felgner et al. |
| 5,462,854 A | 10/1995 | Coassin et al. |
| 5,469,854 A | 11/1995 | Unger et al. |
| 5,512,295 A | 4/1996 | Kornberg et al. |
| 5,521,291 A | 5/1996 | Curiel et al. |
| 5,527,528 A | 6/1996 | Allen et al. |
| 5,534,259 A | 7/1996 | Zalipsky et al. |
| 5,543,152 A | 8/1996 | Webb et al. |
| 5,543,158 A | 8/1996 | Gref et al. |

(Continued)

FOREIGN PATENT DOCUMENTS

| | | |
|---|---|---|
| EP | 0464533 B1 | 7/1998 |
| JP | 2010-503681 A | 2/2010 |

(Continued)

OTHER PUBLICATIONS

Kim et al. (2010, J. Korean Med. Sci. 25:985-991).*
Abreu et al. (2012, IBMS BoneKEy 9, Article No. 239, doi:10.1038/bonekey.2012.239).*
Fernández-Real et al. (2009, J. Clin. Endocrinol. Metab. 94:237-245).*
Levinger et al. (Mar. 21, 2014, Bone 64:8-12).*
Srikanthan et al. (2010, PLoS ONE 5(5):e10805 doi:10.1371/journal.pone.0010805).*
Maggio et al. (2013, Curr. Opin. Clin. Nutr. Metab. Care 16:3-13).*
Burns et al. (2010, Arch. Neurol. 67(4): 428-433).*
Yu, 2015, Int. J. Nursing Sci. 199-203.*

(Continued)

*Primary Examiner* — Elizabeth C. Kemmerer
(74) *Attorney, Agent, or Firm* — Hunton Andrews Kurth LLP

(57) ABSTRACT

Methods and compositions for treating frailty in mammals, preferably humans, are provided. The methods generally involve modulation of the OST-PTP signaling pathway or the PTP-1B signaling pathway involving gamma-carboxylase and osteocalcin, e.g., by administration of undercarboxylated/uncarboxylated osteocalcin. The methods comprise alleviating at least one of: muscle wasting or a lung disorder while also alleviating at least one of: a metabolic disorder, a male reproductive disorder, or a cognitive disorder.

24 Claims, 52 Drawing Sheets

Specification includes a Sequence Listing.

(56) References Cited

U.S. PATENT DOCUMENTS

| | | | |
|---|---|---|---|
| 5,547,932 A | 8/1996 | Curiel et al. | |
| 5,556,948 A | 9/1996 | Tagawa et al. | |
| 5,580,575 A | 12/1996 | Unger et al. | |
| 5,583,020 A | 12/1996 | Sullivan | |
| 5,591,721 A | 1/1997 | Agrawal et al. | |
| 5,595,756 A | 1/1997 | Bally et al. | |
| 5,602,240 A | 2/1997 | Mesmaeker et al. | |
| 5,637,684 A | 6/1997 | Cook et al. | |
| 5,644,048 A | 7/1997 | Yau | |
| 5,681,707 A | 10/1997 | Hosoda et al. | |
| 5,733,761 A | 3/1998 | Treco et al. | |
| 5,830,682 A | 11/1998 | Moore | |
| 6,270,985 B1 | 8/2001 | Gottschalk et al. | |
| 6,303,326 B1 | 10/2001 | Felton et al. | |
| 6,350,902 B2 | 2/2002 | Hill et al. | |
| 6,452,035 B2 | 9/2002 | Dupont et al. | |
| 6,511,958 B1 | 1/2003 | Atkinson et al. | |
| 6,514,514 B1 | 2/2003 | Atkinson et al. | |
| 6,560,471 B1 | 5/2003 | Heller et al. | |
| 6,828,151 B2 | 12/2004 | Borchers et al. | |
| 6,899,871 B2 | 5/2005 | Kasahara et al. | |
| 8,883,739 B2 * | 11/2014 | Karsenty | A61K 38/39 514/21.3 |
| 9,746,463 B2 * | 8/2017 | Karsenty | A61P 3/00 |
| 10,052,364 B2 * | 8/2018 | Karsenty | A61K 38/22 |
| 2003/0158302 A1 | 8/2003 | Chaput et al. | |
| 2003/0199615 A1 | 10/2003 | Chaput et al. | |
| 2004/0023390 A1 | 2/2004 | Davidson et al. | |
| 2004/0082018 A1 | 4/2004 | Ekema et al. | |
| 2004/0157864 A1 | 8/2004 | Wu et al. | |
| 2006/0052327 A1 | 3/2006 | Liu et al. | |
| 2006/0063699 A1 | 3/2006 | Larsen | |
| 2006/0257492 A1 | 11/2006 | Wen et al. | |
| 2006/0292670 A1 | 12/2006 | Ting et al. | |
| 2007/0059731 A1 | 3/2007 | Kerppola | |
| 2007/0099831 A1 | 5/2007 | Morley | |
| 2010/0048409 A1 | 2/2010 | Karsenty et al. | |
| 2010/0190697 A1 * | 7/2010 | Karsenty | A61P 3/06 514/1.1 |
| 2013/0028902 A1 * | 1/2013 | Karsenty | A61K 38/39 424/139.1 |
| 2013/0034572 A1 | 2/2013 | Stanimirovic et al. | |
| 2013/0034590 A1 | 2/2013 | Uchegbu et al. | |

FOREIGN PATENT DOCUMENTS

| | | |
|---|---|---|
| JP | 2010503681 A | 2/2010 |
| WO | 8701130 | 2/1987 |
| WO | 9412650 | 6/1994 |
| WO | 9531560 | 11/1995 |
| WO | 9629411 | 9/1996 |
| WO | 9915650 | 4/1999 |
| WO | 0049162 A1 | 8/2000 |
| WO | 2008033518 A2 | 3/2008 |
| WO | 2011090971 A2 | 7/2011 |
| WO | 2011090971 A3 | 7/2011 |
| WO | WO 2014/152497 | 9/2014 |

OTHER PUBLICATIONS

Notice of Reasons for Rejection dated Dec. 10, 2019 issued in Japanese Patent application No. 2017-527206.

Extended European Search Report dated Oct. 24, 2018 for European National phase application No. 15861955.1.

Oury, Franck et al., "Maternal and Offspring Pools of Osteocalcin Influence Brain Development and Function," Cell, vol. 155, No. 1, pp. 228-241, Sep. 26, 2013.

Oury, Franck et al., "Osteocalcin Regulates Murine and human Fertility through a Pancreas-bone-testis Axis," Journal of Clinical Investigation, vol. 123, No. 6, pp. 2421-2433, Jun. 3, 2013.

Woods, Adam J. et al., "Cognitive Frailty: Frontiers and Challenges," Journal of Nutrition, Health and Aging, vol. 17, No. 9, pp. 741-743, Oct. 21, 2013.

Mera, Paula et al., "Osteocalcin Regulates Muscle Function and Mass," Journal of Bone and Mineral Research, vol. 29, No. Supple 1, p. S50, Feb. 2014.

Isaacson, Janalee et al., "Physiology of Mechanotransduction: How do Muscle and Bone "Talk" to One Another?," Clinical Review in Bone Metabolism, vol. 12, No. 2, pp. 77-85, Dec. 25, 2013.

Ferron, Mathieu et al., "Osteocalcin Differentially Regulates, beta. cell and Adipocyte Gene Expression and Affects the Development of Metabolic Diseases in Wild-Type Mice," Proceedings National Academy of Sciences PNAS, National Academy of Sciences, vol. 105, No. 13, p. 5266-5270, Apr. 1, 2008.

Ducy, Patricia et al., "Increased bone Formation in Osteocalcin-Deficient Mice," Nature, vol. 382, No. 6590, pp. 448-452, Aug. 1, 1996.

Croasdell, G., "American Society for Bone and Mineral Research—2015 Annual Meeting, Seattle, Washington, USA," Drugs of the Future, vol. 40, No. 11, pp. 777-779, Oct. 9-12, 2015.

Luca De, Toni et al., "Uncaboxylated Osteocalcin Stimulates 25-Hydroxy Vitamin D. Production in Leydig Cell Line Though a GPRC6a-Dpendent Pathway," Endocrinology, vol. 155, No. 11, pp. 4266-4274, Nov. 1, 2014.

Engblom, Camilla et al., "Osteoblasts Remotely Supply Lung Tumors with Cancer-Promoting SiglecF high Neurophils," Science, vol. 358, No. 6367, pp. eaa15081, Dec. 1, 2017.

Fewtrell, M.S. et al., "Undercarboxylated Osteocalcin and Bone Mass in 8-12 year old Children with Cystic Fibrosis," Journal of Cystic Fibrosis, vol. 7, No. 4, pp. 307-312, Jul. 1, 2008.

Krogsgaard-Larsen, POVL et al., "A Textbook of Drug Design and Development," Chapter 5, pp. 113-191, 1991.

Bundgaard, Hans "Means to Enhance Penetration," Advanced Drug Delivery Reviews, vol. 8, pp. 1-38, 1992.

Huse, William D. et al., "Generation of a Large Combinatorial Library of the Immunoglobulin Repertoire in Phage Lamba," Research Article, vol. 246, pp. 1275-1281, Dec. 8, 1989.

Agrawal, Sudhir et al., "Antisense Therapeutics," Curr. Opin, Chemical Biol., vol. 2, pp. 519-528, 1998.

Agrawal, Sudhir et al., "Pharmacokinetics of Oligonucleotides," CIBA Found, vol. 209, pp. 60-78, 1997.

Zhao, Qiuyan et al., "Cellular Distribution of Phosphorothioate Oligonucleotide Following Intravenous Administration in Mice," Antisense & Nucleic Acid Drug Development, vol. 8, pp. 451-458, 1998.

Elbashir, Sayda M. et al., "Duplexes of 21-Nucleotide RNs Mediate RNA Interference in Cultured Mammalian Cells," Nature, vol. 411. pp. 494-498, May 24, 2001.

Baulcombe, David C. "RNA as a Target and an Initiator of Post-Transcriptional Gene Silencing in Trangenic Plants," Plant Molecular Biology, vol. 32, pp. 79-88, 1996.

Timmons, Lisa et el., "Specific Interference by ingested dsRNA," Nature, vol. 395, p. 854, Oct. 29, 1998.

Wianny, Florence et al., "Specific Interference with Gene Function by Double-Stranded RNA in Early Mouse Development," Nat. Cell Biology, vol. 2, pp. 70-75, Feb. 2000.

Svoboda, Petr et al., "Selective Reduction of Dormant Maternal MRNAs in Mouse Oocytes by RNA Interference," Developement, vol. 127, pp. 4147-4156, 2000.

Pardridge, William M. "Drug Targeting to the Brain," Pharmaceutical Research, vol. 24, No. 9, pp. 1733-1744, Sep. 2007.

Beduneau, Arnaud et al., "Brain Targeting using Novel Lipid Nanovectors," Journal of Controlled Release, vol. 126, pp. 44-49, 2008.

Kreuter, Jorg et al., "Direct Evident that Polysorbate-80-Coated Poly(Butylcyanoacrylate) Nanoparticles Deliver Drugs to the CNS via Specific Mechanism requiring Prior Binding of Drug to the Nanoparticles," Pharm. Res., vol. 20, pp. 409-416, 2003.

Lu, Wei et al., "Cationic Albumin-Conjugated Pegylated Nanoparticles Allow Gene Delivery into Brain Tumors via Intravenous Administration," Cancer Res., vol. 66, pp. 11878-11887, Dec. 15, 2006.

Muzyczka, N. "Use of Adeno-Associated Virus as a General Transduction Vector for Mammalian Cells," Curr. Top. Microbiol. immunol., vol. 158, pp. 97-129, 1992.

(56) References Cited

OTHER PUBLICATIONS

Laface, Drake et al., "Gene Transfer into Hematopoietic Progenitor Cells Mediated by an Adeno-Associated Virus Vector," Virology, vol. 162, pp. 483-486, 1988.
Zhou et al., "Adeno-Associated Virus 2-Mediated Gene Transfer in Murine Hematopoietic Progenitor Cells," Experimental Hematology, vol. 21, pp. 928-933, 1993.
Flotte, Terence R. et al., "Stable in vivo Expression of the Cystic Fibrosis Transmembrane Conductance Regulator with an Adeno-Associated Virus Vector," Proc. Natl. Acad. Sci. USA, vol. 90, pp. 10613-11617, Nov. 1993.
Goodman, Stacey et al., "Recombiant Adeno-Associated Virus-Mediated Gene Transfer into Hematopoietic Progenitor Cells," Blood, vol. 84, No. 5, pp. 1492-1500, Sep. 1, 1994.
Kaplitt, Michael G. et al., "Long-term Gene Expression and Phenotypic Correction using Adeno-Associated Virus Vectors in the Mammalian Brain," Nature Genetics, vol. 8, pp. 148-154, Oct. 1994.
Lebkowski, Jane S. et al., "Adeno-Associated Virus: A Vector System for Efficient Introduction and integration of DNA into a Variety of Mammalian Cell Types," Molecular and Cellular Biology, vol. 8, No. 10, pp. 3988-3996, Oct. 1988.
Samulski, Richard Jude et al., "Helper-Free Stocks of Recombinant Adeno-Associated Viruses: Normal Integration Does not Require Viral Gene Expression," Journal of Virology, vol. 63, No. 9, pp. 2833-3828, Sep. 1989.
Shelling & Smith, "Gene Therapy," vol. 1, pp. 165-169, 1994.
Yoder et al., Blood, Suppl. 1, vol. 82, p. 347A, 1993.
Zhou, Shang Zhen et al., "Adeno-Associated Virus 2-Mediated High Efficiency Gene Transfer into Immature and Mature Subsets of Hematopoietic Progenitor Cells in Human Humbilical Cord Blood," J. Exp. Med, vol. 179, pp. 1867-1875, Jun. 1994.
Hermonat, Paul L. et al., "Use of Adeno-Associated Virus as a Mammalian DNA Cloning Vector: Transduction of Neomycin Resistance into Mammalian Tissue Culture Cells," Proc. Natl. Acad. Sci. USA, vol. 81, pp. 6466-6470, Oct. 1984.
Tratschin, Jon-Duri et al., "A Human Parvovirus, Adeno-Associated Virus, as a Eucaryotic Vector: Transient Expression and Encapsidation of the Procaryotic Gene for Chloramphenicol Acetyltransferase," Molecular and Cellular Biology, vol. 4, No. 10, pp. 2072-2081, Oct. 1984.
McLaughlin, Susan K. et al., "Adeno-Associated Virus General Transduction Vectors: Analysis of Proviral Structures," Journal of Virology, vol. 62, No. 6, pp. 1963-1973, Jun. 1988.
Flotte, Terence R. et al., "Gene Expression from Adeno-associated Virus Vectors in Airway Epithelial Cells," American Journal of Respiratory Cell and Molecular Biology, vol. 7, No. 3, pp. 349-356, Sep. 1992.
Luo, F. et al., "Adeno-Associated Virus 2-Mediated Transfer and Functional Expression of a Gene Encoding the Human Granulocyte-Macrophage Colony-Stimulating Factor," Blood, vol. 82, Sippl. 1, p. 303A, 1994.
Ohi, Seigo et al., "Construction and Replication of an Adeno-associated Virus Expression Vector that Contains Human 8-globin cDNA," Gene, vol. 89, pp. 279-282, 1990.
Walsh, Christopher E. et al., "Regulated high Level Expression of a Human y-globin Gene introduced into Erythroid Cells by an Adeno-associated Virus Vector," Proc. Natl. Acad. Sci. USA, vol. 89, pp. 7257-7261, Aug. 1992.
Wei, Jing-Fang et al., "Expression of the Human Glucocerebrosidase and Arylsulfatase A genes in Murine and Patient Primary Fibroblasts Transduced by an Adeno-associated virus vector," Gene Therapy, vol. 1. pp. 261-268, 1994.
Russell, David W. et al., "Foamy Virus Vectors," Journal of Virology, vol. 70, No. 1, pp. 217-222, Jan. 1996.
Wu, Min et al., "Packaging Cell Lines for Simian Foamy Virus Type 1 Vectors," Journal of Virology, vol. 73, No. 5, pp. 4498-4501, May 1999.
Naldini, Luigi et al., "In vivo Gene Delivery and Stable Transduction of Nondividing Cells by a Lentiviral Vector," Science, vol. 272, pp. 263-267, Apr. 12, 1996.
Poeschla, Eric et al., "Development of HIV Vectors for Anti-HIV Gene Therapy," Proc. Natl. Acad. Sci. USA, vol. 93, p. 11385-11399, Oct. 1996.
Srinivasakumar, Narasimhachar et al., "The Effect of Viral Regulatory Protein expression on Gene Delivery by Human Immunodeficiency Virus Type 1 Vectors Produced in Stable Packaging Cell Lines," Journal of Virology, vol. 71, No. 8, pp. 5841-5848, Aug. 1997.
Zufferey, Romain et al., "Multiply Attenuated Lentiviral Vector Achieves Efficient Gene Delivery in Vivo," Nature Biotechnology, vol. 15, pp. 871-875, Sep. 1997.
Kim, V. Narry et al., "Minimal Requirement for a Lentivirus Vector Based on Human Immunodeficiency Virus Type 1," Journal of Virology, vol. 72, No. 1, pp. 811-816, Jan. 1998.
Johnston, Julie C. et al., "Minimum Requirements for Efficient Transduction of Dividing an Nondividing Cells by Feline immunodeficiency Virus Vectors," Journal of Virology, vol. 73, No. 6, pp. 4991-5000, Jun. 1999.
Johnston, James et al., "Productive infection of Human Peripheral Blood Mononuclear Cells by Feline Immunodeficiency Virus: Implications for Vector Development," Journal of Virology, vol. 73, No. 3, pp. 2491-2498, Mar. 1999.
Poeschla, Eric M. et al., "Efficient Transduction of Nondividing human Cells by Feline Immunodeficiency virus Lentiviral Vectors," Nature Medicine, vol. 4, No. 3, pp. 354-357, Mar. 1998.
Friedmann, Theodore, "Progress Toward Human Gene Therapy," Science, vol. 244, pp. 1275-1281, Jun. 16, 1989.
Mulligan, Richard C. "The Basic Science of Gene Therapy," science, vol. 260, pp. 926-932, May 14, 1993.
Crystal, Ronald G. "Transfer of Genes to Humans: Early Lessons and Obstacles to Success," Science, vol. 270, pp. 404-410, Oct. 20, 1995.
Morgan, Richard A. "Human Gene Therapy," Biopharm, vol. 6, No. 1, pp. 32-35, 1993.
"The Development of Human Gene Therapy," Cold Spring Harbor Laboratory Press, pp. 1-735, 1999.
Lee, Allison Jane et al., "Measurement of Osteocalcin," Ann Clin Biochem, vol. 37, pp. 432-446, 2000.
Kim et al. "Integrative Physiology: Defined Novel Metabolic Roles of Osteocalcin," J. Korean Med. Sci, vol. 25, pp. 985-999 (Jun. 17, 2010).
Sambrook et al. "Corticosteroid Osteoperosis," British Journal of Rheumatology, vol. 34, pp. 8-12 (Jan. 1, 1995).
International Search Report for International Application No. PCT/US2015/061590 dated Feb. 3, 2016.
International Written Opinion for International Application No. PCT/US2015/061590 dated Feb. 3, 2016.
Beaucage, Serge L. et al., "Tetrahedron Report No. 329," Tetrahedron, vol. 49, No. 10, pp. 1925-1936, 1993.
Letsinger, Robert L. et al., "Phosphoramidate Analogs of Oligonucleotides," J. Org. Chem., vol. 35, No. 11, pp. 3800-3803, 1970.
Sprinzl, Mathias et al., "Enzymatic Incorporation of ATP and CTP Analogues into the 3' End of tRNA," Eur. J. Biochem, vol. 81, pp. 579-589, 1977.
Letsinger, R.L. et al., "Effects of Pendant Groups at Phosphorus on binding Properties of d-ApA Analogues," Nucleic Acids Research, vol. 14, No. 8, pp. 3487-3499, 1986.
Sawai, Hiroaki et al., "Synthesis and Properties of Oligoadenylic Acids Containing 2'-5' Phosphoramide Linkage," Chemistry Letters, pp. 805-808, 1984.
Letsinger, Robert L. et al., "Cationic Oligonucleotides,"J. Am. Chem. Soc., vol. 110, pp. 4470-4471, 1998.
Pauwels, R. et al., "Biological Activity of New 2-5A Analogues," Chemica Scripta, vol. 26, pp. 141-145, 1986.
Mag, Matthias et al., "Synthesis and Selective Cleavage of an Oligodeoxynucleotide Containing a bridged Internucleotide 5'-phosphorothioate Linkage," Nucleic Acids Research, vol. 19, No. 7, pp. 1437-1441, 1991.

(56) References Cited

OTHER PUBLICATIONS

Wolfgang, K. et al., "Synthesis of Oligodeoxynucleoside Phosphorodithiates via Thioamidites," J. Am. Chem. Soc., vol. 111, pp. 2321-2322, 1989.
Egholm, Michael et al., "Peptide Acids (PNA). Oligonucleotide Analogues with an Achiral Peptide Bakbone," J. Am. Chem. Soc., vol. 114, pp. 1895-1897, 1992.
Meier, Chris et al., "Peptide Nucleic Acids (PNAs)—Unusual Properties of Nonionic Oligonucleotide Analogues," Angew. Chem. Int. Ed. Engl., vol. 31, No. 9, pp. 1008-1010, 1992.
Egholm, Michael et al., "PNA Hybridizes to Complementary Oligonucleotides Obeying the Watson-Crick Hydrogen-bonding Rules," Nature, vol. 365, pp. 566-568, Oct. 7, 1993.
Carlsson, Christina et al., "Screening for Genetic Mutations," Nature, vol. 380, p. 207, Mar. 21, 1996.
Dempcy, Robert O. et al., "Synthesis of a Thyrnidyl Pentamer of Deoxyribonucleic Guanidine and Binding Studies with DNA Homopolynucleotides," Proc. Natl. Acad. Sci. USA, vol. 92, pp. 6097-6101, Jun. 1995.
Von Kiedrowski, Gunter et al., "Parabolic Growth of a Self-Replicating hexadeoxynucleotide Bearing a 3'-5'-Phosphoamidate Linage," Angew. Chem. Int. Ed. Engl., vol. 30, No. 4, pp. 423-426, 1991.
Jung, Paul M. et al., "Hybridization of Alternating Cationic/Anionic Oligonucleotides to RNA Segments" Nucleosides & Nucleotides, vol. 13, Nos. 6 & 7, pp. 1597-1605, 1994.
De Mesmaeker, Alain et al., "Novel Backbone Replacements for Oligonucleotides," Chapter 2, ASC Symposium Series 5810, pp. 1-16, 1994.
Maddry, Joseph A. et al., "Sysnthesis of Nonionic Oligonucleotide Analogues" Chapter 3, ASC Symposium Series 5810, pp. 1-12, 1994.
De Mesmaeker, Alain et al., "Comparison of Rigid and Flexible Backbones in Antisense Oligonucleotides," Bioorganic & Medicinal Chemistry Letters, vol. 4, No. 3, pp. 395-398, 1994.
Gao, Xiaolian et al., "Unusual Confirmation of a 3'-thioformacetal Linkage in a DNA Duplex," Journal of Biomolecular NMR, vol. 4. pp. 17-34, 1994.
"Sequence Analysis Primer," M. Stockton Press, New York, Eds. pp. 1-150, 1991.
Herdewijn, Piet et al., "Hexopyranosyl-Like Oligonucleotides," Chapter 6, ASC Symposium Series 580, pp. 1-20, 1994.
Bolli, M. et al., ". . . -Bicyclo-DNA: Synthesis, Characterization, and Pairing Properties of . . . " Chapter 7, ASC Symposium Series 580, pp. 1-18, 1994.
Ferron, Mathieu et al., "Intermittent Injections of Osteocalcin Improve Glucose Metabolism and Prevent Type 1 Diabetes in Mice," Bone, vol. 50. pp. 568-575, 2012.
Mayorga, Arthur J. et al., "Antidepressant-Like Behavioral Effects in 5-Hydroxytryptamine and 5-Hydroxytryptamine Receptor Mutant Mice," The Journal of Pharmacology and Experimental Therapeutics, vol. 298, No. 3, pp. 1101-1107, 2001.
Steru, Lucien et al., "The Tail Suspension Test: A New Method for Screening Antidepressant in Mice," Psychopharmacology, vol. 85, pp. 367-370, 1985.
David, Denis J. et al.. "Neurogenesis-Dependent and -Independent Effects of Fluoxetine in an Animal Model of Anxiety/Depression," Neuron, vol. 62, pp. 479-493, May 28, 2009.
Morris, R.G.M. et al., "Place Navigation Impaired in Rats with Hippocampal Lesions," Nature, vol. 297, pp. 681-683, Jun. 24, 1982.
D'Hooge, Rudi et al., "Neurocognitive and Psychotiform Behavioral Alterations and Enhanced Hippocampal Long-Term Potentiation in Transgenic Mice Displaying Neuropathological Features of Human . . . " The Journal of Neuroscience, vol. 25, No. 28, pp. 6539-6549, Jul. 13, 2005.
Crawley, Jacqueline N. "Expiratory Behavior Models of Anxiety in mice," Neuroscience & Biobehavioral Reviews, vol. 9, pp. 37-44, 1985.
Lira, Alena et al., "Altered Depression-Related Behaviors and Functional Changes in the Dorsal Raphe Nucleus of Serotonin Transporter-Deficient Mice," Biological Psychiatry, vol. 54, pp. 960-971, 2003.
Holmes, A. et al., "Behavioral Profile of Wild Mice in the Elevated Plus-Maze Test for Anxiety," Physiology & Behavior, vol. 71, pp. 509-516, 2000.
Sahay, Amar et al., "Increasing Adult Hippocampal Neurogenesis is Sufficient to Improve Pattern Separation," Nature, vol. 472, pp. 466-470, Apr. 28, 2011.
Dryan, John F. et al., "The Tail suspension test as a model for assessing Antidepressant Activity Review of Pharmacological and Genetic Studies in Mice," Neuroscience and Biobehavioral Reviews, vol. 29, pp. 571-625, 2005.
Denny, Christine A. et al., "4- to 6-Week-Old Adult-Born Hippocampal Neurons Influence Novelty-evoked Exploration and Contextual Fear Conditioning," Hippocampus, vol. 22, pp. 1188-1201, 2012.
Oury, Franck et al., "Maternal and Offspring Pools of Osteocalcin Influence Brain Development and Functions," Cell, vol. 155, pp. 228-241, Sep. 26, 2013.
Oury, Franck et al., "Endocrine Regulation of Male Fertility by the Skeleton," Cell, vol. 144, pp. 796-809, Mar. 4, 2011.
Lee, Na Kyung et al., "Endocrine Regulation of Energy Metabolism by the Skeleton," Cell, vol. 130, pp. 456-469, Aug. 10, 2007.
Sebastian, David et al., "CPT I Overexpression Protects L6E9 Muscle Cells from fatty Acid-Induced Insulin Resistance," Am. J, Physiol Endoscrinol Metab, vol. 292, pp. E677-E686, 2007.
Qiu, Yunping et al., "A Distince Metabolic Signature of human Colorectal Cancer with Prognostic Potential," Clin Cancer Res, vol. 20, No. 8, pp. 2136-2146, 2014.
Serasinghe, Madhavika N. et al., "Mitochondrial Division in Requisite to RAS-Induced Transformatoin and Targeted by Oncogenic MAPK Pathway Inhibitors," Molecular Cell, vol. 57, pp. 521-536, 2015.
Wang-Sattler, Rui et al., "Novel Biomarkers for Pre-Diabetes Identified by Metabolomics," Molecular Systems Biology, vol. 8, pp. 1-11, 2012.
Aranibar, Nelly et al., "Identification of 1- and 3-Methylhistidine as Biomarkers of Skeletal muscle Toxicity by Nuclear Magnetic resonance-based Metabolic Profiling," Analytical Biochemistry, vol. 410, pp. 84-91, 2011.
Gharaibeh, Burhan et al., "Isolation of a Slowly Adhering Cells Fraction Containing Stem Cells from Murine Skeletal Muscle by the Preplate Technique," Nature Protocols, vol. 3, No. 9, pp. 1501-1509, 2008.
Hauschka, Peter V. et al., "Osteocalcin and Matrix Gla Protein: Vitamin K-Dependent Proteins in Bone," Physiological Reviews, vol. 69, No. 3, pp. 990-1047, Jul. 1989.
Price, Paul A. "GLA-Containing Proteins of Bone," Connective Tissue Research, vol. 21, pp. 51-60, 1989.
Ducy, Patricia et al., "The Osteoblast: A Sophisticated Fibroblast under Central Surveillance," Science, vol. 289, pp. 1501-1504, Sep. 1, 2000.
Harada, Shun-Ichi et al., "Control of Osteoblast Function and Regulation of Bone Mass," Nature, vol. 423, pp. 349-355, May 15, 2003.
Poser, James W. et al., "Isolation and Sequence of the Vitamin K-dependent Protein from Human Bone," The Journal of Biological Chemistry, vol. 255, No. 18, pp. 8685-8691, Sep. 25, 1980.
Poser, James W. et al., "A Method for Decarboxylation of . . . ," The Journal of Biological Chemistry, vol. 254, No. 2, pp. 431-436, Jan. 25. 1979.
Ducy, Patricia et al., "Increased Bone Formation in Osteocalcin-Deficient Mice," Nature, vol. 382, pp. 448-451, Aug. 1, 1996.
Garnero, Patrick et al., "Charaterization of Immunoreactive Forms of Human Osteocalcin Generated In Vivo and In Vitro," Journal of Bone and Mineral Research, vol. 9, No. 2, pp. 255-264, 1994.
Taylor, Arch K. et al., "Multiple Osteocalcin Fragments in Human Urine and Serum as Detected by a Midmolecule Osteocalcin Radioimmunoassay," Journal of Clinical Endocrinology & Metabolism, vol. 70, No. 2, pp. 467-472, Feb. 1990.

(56) References Cited

OTHER PUBLICATIONS

Ferron, Mathieu et al., "Insulin Signaling in Osteoblasts integrates Bone Remodeling and Energy Metabolism," Cell, vol. 142, pp. 296-308, July 23, 2010.
Oury, Franck et al., "Endocrine Regulation of Make Fertility by the Skeleton," Cell, vol. 144, pp. 796-809, March 4, 2011.
Bruning, Jens C. et al., "A Muscle-Specific Insulin Receptor Knockout Exhibits Features of the Metabolic Syndrome of NIDDM without Altering Glucose Tolerance," Molecular Cell, vol. 2, pp. 559-569, Nov. 1996.
Da Cruz, Sandrine et al., "Elevated PGC-1 Activity Sustains Mitochondrial Biogenesis and Muscle Function without Extending Survival in a Mouse Model of Inherited ALS," Cell Metabolism, vol. 15, pp. 778-786, May 2, 2012.
Handschin, Christoph et al., "The Role of Exercise and PGC1 in Inflammation and Chronic Disease," Nature, vol. 454, pp. 463-469. Jul. 24, 2008.
Ruas, Jorge L. et at., "A PGC-1 Isoform induced by Resistance Training Regulates Skeletal Muscle Hypertrophy," Cell, vol. 151, pp. 1319-1331, Dec. 7, 2012.
Wojtaszewski, Jorgen F.P. et al., "Exercise Modulates Postreceptor Insulin Signaling end Glucose Transport in Muscle-Specific Insulin Receptor Knockout Mice," Journal of Clinical Investigations, vol. 104, pp. 1257-1264, 1999.
Lopez-Llasaca, Marco et al., "Linkage of G Protein-Coupled Receptors to the MAPK Signaling Pathway Through PI 3-Kinase," Science, vol. 275, pp. 394-397, Jan. 17, 1997.
Gibala, Martin J. et al., "Tricarboxylic Acid Cycle Intermediate Pool Size and Estimated Cycle Flux in Human Muscle During Exercise," Am. J. Physiol., vol. 275, pp. E235-242, 1998.
Sahlin, K. et al., "Tricarboxylic Acid Cycle Intermediates in Human Muscle During Prolonged Exercise," Am. J. Physiol, vol. 259, pp. C834-841, 1990.
Hawley, John A. et al., "Integrative Biology of Exercise," Cell, vol. 159, pp. 738-749, Nov. 6, 2014.
Koves, Timothy R. et al., "Peroxisome Proliferator-Activated Receptor-y Co-Activator 1-mediated Metabolic Remodeling of Skeletal Myocytes Mimics Exercise Training and Reverses Lipid-induced Mitochondrial inefficiency," The Journal of Biological Chemistry, vol. 280, No. 39. pp. 33588-33598, Sep. 30, 2005.
O'Neill, Hayley M. et al., "AMPK Phophorylation of ACC2 is Required for Skeletal Muscle Fatty Acid Oxidation and Insulin Sensitivity in Mice," Diabetologia, vol. 57, pp. 1693-1702, 2014.
Watt, Matthew J. et al., "Triacyiglcerol Lipases and Metabolic Control: Implications of Health and Disease," Am. J. Physiol Endocrinol Metab., vol. 299, pp. E162-E168, Jan. 12, 2010.
Stahl, Andreas et al., "Fatty Acid Transport Proteins: A Current View of a Growing Family," Trends in Endocrinology & Metabolism, vol. 12, No. 6, pp. 266-273, Aug. 2001.
Pedersen, Bente K. et al., "Muscles, Exercise and Obesity: Skeletal Muscle as a Secretory Organ," nat Rev. Endocrinol., vol. 8, pp. 457-465, 2012.
Li, Yan et al., "IL-6 Receptor Expression and IL-6 Effects Change during Osteoblast Differentiation," Cytokine, vol. 43, pp. 165-173, 2008.
Tamura, Tatsuya et al., "Soluble Interleukin-6 Receptor Triggers Osteoclast Formation by Interleukin 6," Proc. Natl, Acad. Sci. UDS, vol. 90, p. 11924-11928, Dec. 1993.
Karsenty, Gerard et al., "Reaching a Genetic and Molecular Understanding of Skeletal Development," Developmental Cell, vol. 2, pp. 389-406, Apr. 2002.
Palmqvist, Py et al., "IL-6, Leukemia Inhibitory Factor, and Oncostatin M Stimulate Bone Resorption and Regulate the Expression of Receptor Activator of NF-kB Ligand, Osteoprotegerin, and Receptor Activator of NF-kB in Mouse Calvariae," The Journal of Immunology, vol. 169, pp. 3353-3362, 2002.

Adelman, John P. et al., "In vitro Deletional Mutagenesis for Bacterial Production of the 20,000-Dalton Form Human Pituitary Growth Hormone," DNA, vol. 2, No. 3, pp. 183-193, 1983.
Cho, Charles Y. et al., "An Unnatural Biopolymer," Science, vol. 261, pp. 1303-1305, Sep. 3, 1993.
Simon, Reyna J. et al., "Peptoids: A Modular Approach to Drug Discovery," Proc. Natl. Acad. Sci. USA, vol. 89, pp. 9367-9371, Oct. 1992.
Schumacher, Ton N.M. et al., "Identification of D-Peptide Ligands Through Mirror-Image Phage Display," Science, vol. 271, pp. 1854-1857, Mar. 29, 1996.
Brody, Edward N. et al., "The Use of Aptamers in Large Arrays for Molecular Diagnostics," Molecular Diagnosis, vol. 4, No. 4, pp. 381-388, 1999.
Houghten, Richard A. "General Method for the Rapid Solid-Phase Synthesis of Large Numbers of Peptides: Specificity of Antigen-Antibody Interaction at the Level of Individual Amino Acids," Proc. Natl. Acad. Sci. USA, vol. 82, pp. 5131-5135, Aug. 1985.
Bowie, James U. et al., "Deciphering the Message in Protein Sequences: Tolerance to Amino Acid Substitutions," Science, vol. 247, pp. 1306-1310, 1990.
Lesk, Arthur M. "Computational Molecular Biology, Sources and Methods for Sequence Analysis," Oxford University Press, New York, pp. 1-264, 1988.
Smith, Douglas W. et al., "Biocomputing, Informatics and Genome Projects," Academic Press, New York, pp. 1-344, 1993.
Grittin, Annette M. et al., "Methods in Molecular Biology, Computer Analysis of Sequence Data Part l," Humana Press, New Jersey, pp. 1-381, 1994.
Heijne, Gunnar Von, "Sequence Analysis in Molecular Biology, Treasure Trove or Trivial Pursuit," Academic Press, pp. 1-196, 1987.
Karlin, Samuel et al., "Applications and Statistics for multiple high-Scoring Segments in Molecular Sequences," Proc. Natl. Acad. Sci. USA, vol. 90, pp. 5873-5877, Jun. 1993.
Needleman, Saul B. et al., "A General Method Applicable to the Search for Similarities in the Amino Acid Sequence of Two Proteins," J. Mol. Biol., vol. 48, pp. 443-453, 1970.
Supplementary European Search Report for EP 0232262 dated Jun. 18, 1989.
Bennett, Donald et al., "Kinetic Characterization of the interaction of Biotinylated Human Interleukin 5 with an Fc Chimera of its Receptor Subunit and Development of an ELISA Screening Assay using Real-Time interaction Biosensor Analysis," Journal of Molecular Recognition, vol. 8, pp. 52-58, 1995.
Johanson, Kyung et al., Binding Interactions of Human Interleukin 5 with Its Receptor Subunit, The Journal of Biological Chemistry, vol. 270, No. 16, pp. 9459-9471, Apr. 21, 1995.
Bentley, Michael D. et al., "Reductive Amination Using Poly(ethylene glycol) Acetaldehyde Hydrate Generated in Situ: Applications to Chitosan and Lysozyme," Journal of Pharmaceutical Sciences, vol. 87, No. 11, pp. 1446-1449, Nov. 1998.
Creighton, Thomas E. "Proteins, Structures and Molecular Properties," 2nd Edition, W.H. Freeman and Company, pp. 1-522, 1993.
Johnson, Conner B. "Posttranslational Covalent Modifications of Proteins," Academic Press, New York, pp. 1-19, 1983.
Seifter, Sam et al., "Analysis for Protein Modifications and Nonprotein Cofactors," Methods in Enzymology, vol. 182, pp. 626-646, 1990.
Rattan, Suresh I. S. et al., "Protein Synthesis, Posttranstational Modifications, and Aging," vol. 663, pp. 48-62, 1992.
Communication pursuant to Article 94(3) EPC dated Apr. 2, 2020 for European Application No. 15861955.1.
Notice of Reasons for Rejection dated Nov. 10, 2020 issued in Japanese Patent Application No. 2017-527206.
Pre-Appeal Report dated Jun. 4, 2021 for Japanese Patent Application No. 2017-527206.

* cited by examiner

Osteocalcin SC Infusion Increases Glucose Tolerance in WT Mice

| GTT | t0 | t15 | t30 | t60 | t120 |
|---|---|---|---|---|---|
| PBS | 103 | 362 | 358 | 258 | 198 |
|  | 114 | 345 | 309 | 221 | 164 |
|  | 115 | 371 | 331 | 281 | 203 |
|  | 115 | 384 | 343 | 272 | 192 |
| Mean | 111.8 | 365.5 | 335.3 | 258.0 | 189.3 |
| SD | 5.9 | 16.4 | 20.7 | 26.4 | 17.4 |

| OC 0.3ng/hr | 94 | 311 | 287 | 198 | 151 |
|---|---|---|---|---|---|
|  | 93 | 273 | 261 | 213 | 186 |
|  | 94 | 298 | 290 | 192 | 142 |
|  | 98 | 321 | 304 | 241 | 188 |
|  | 98 | 331 | 310 | 250 | 182 |
|  | 93 | 314 | 288 | 212 | 155 |
| Mean | 95.0 | 308.0 | 290.0 | 217.7 | 167.3 |
| SD | 2.4 | 20.3 | 17.0 | 23.2 | 20.3 |
| P | 0.000 | 0.002 | 0.005 | 0.034 | 0.116 |

| OC 3ng/hr | 104 | 338 | 298 | 253 | 192 |
|---|---|---|---|---|---|
|  | 104 | 285 | 261 | 213 | 158 |
|  | 98 | 291 | 270 | 182 | 151 |
|  | 106 | 342 | 302 | 233 | 173 |
|  | 84 | 277 | 258 | 203 | 148 |
|  | 95 | 318 | 283 | 231 | 163 |
| Mean | 98.5 | 308.5 | 278.7 | 219.2 | 164.2 |
| SD | 8.2 | 28.0 | 18.7 | 25.1 | 16.3 |
|  | 0.025 | 0.007 | 0.002 | 0.047 | 0.049 |

FIG. 2 ={"Blood Glucose (mg/dl)"}

Osteocalcin SC Infusion Increases Insulin Sensitivity in WT Mice

| ITT(%) | | t0 | t15 | t30 | t60 | t90 | t120 |
|---|---|---|---|---|---|---|---|
| PBS | | 110.59 | 97.775 | 89.009 | 72.825 | 84.289 | 103.17 |
| | | 96.426 | 93.729 | 75.523 | 63.385 | 72.151 | 86.312 |
| | | 99.798 | 95.752 | 91.032 | 72.151 | 79.568 | 90.357 |
| | | 92.38 | 90.357 | 80.917 | 68.105 | 76.871 | 86.312 |
| | | 95.078 | 86.312 | 71.477 | 60.013 | 74.848 | 93.055 |
| | | 105.87 | 99.798 | 85.637 | 76.871 | 80.917 | 96.426 |
| | Mean | 100.0 | 94.0 | 82.3 | 68.9 | 78.1 | 92.6 |
| | SD | 7.0 | 5.0 | 7.7 | 6.3 | 4.4 | 6.5 |
| OC 0.3ng/hr | | 111.19 | 101.08 | 72.924 | 60.65 | 75.09 | 84.477 |
| | | 95.307 | 90.253 | 65.704 | 51.986 | 62.816 | 77.978 |
| | | 95.307 | 87.365 | 69.314 | 56.318 | 67.148 | 70.758 |
| | | 106.14 | 98.195 | 77.256 | 64.26 | 67.87 | 85.921 |
| | | 89.531 | 85.199 | 67.87 | 58.484 | 62.094 | 67.87 |
| | | 102.53 | 90.975 | 74.368 | 54.152 | 70.036 | 80.866 |
| | Mean | 100.0 | 92.2 | 71.2 | 57.6 | 67.5 | 78.0 |
| | SD | 8.0 | 6.2 | 4.3 | 4.5 | 4.8 | 7.3 |
| | P | 0.996 | 0.536 | 0.012 | 0.017 | 0.000 | 0.010 |
| OC 3ng/hr | | 98.825 | 95.37 | 79.475 | 60.124 | 67.726 | 77.402 |
| | | 107.81 | 83.621 | 74.637 | 59.433 | 63.58 | 89.15 |
| | | 86.386 | 78.093 | 67.726 | 53.214 | 64.271 | 73.255 |
| | | 106.43 | 94.679 | 79.475 | 62.889 | 73.255 | 83.621 |
| | | 90.532 | 77.402 | 61.507 | 46.994 | 58.742 | 74.637 |
| | | 109.88 | 89.841 | 76.71 | 65.653 | 82.239 | 85.695 |
| | Mean | 100.0 | 86.5 | 73.3 | 58.1 | 68.3 | 80.6 |
| | SD | 9.8 | 8.0 | 7.2 | 6.8 | 8.4 | 6.4 |
| | | 0.993 | 0.060 | 0.042 | 0.005 | 0.024 | 0.040 |

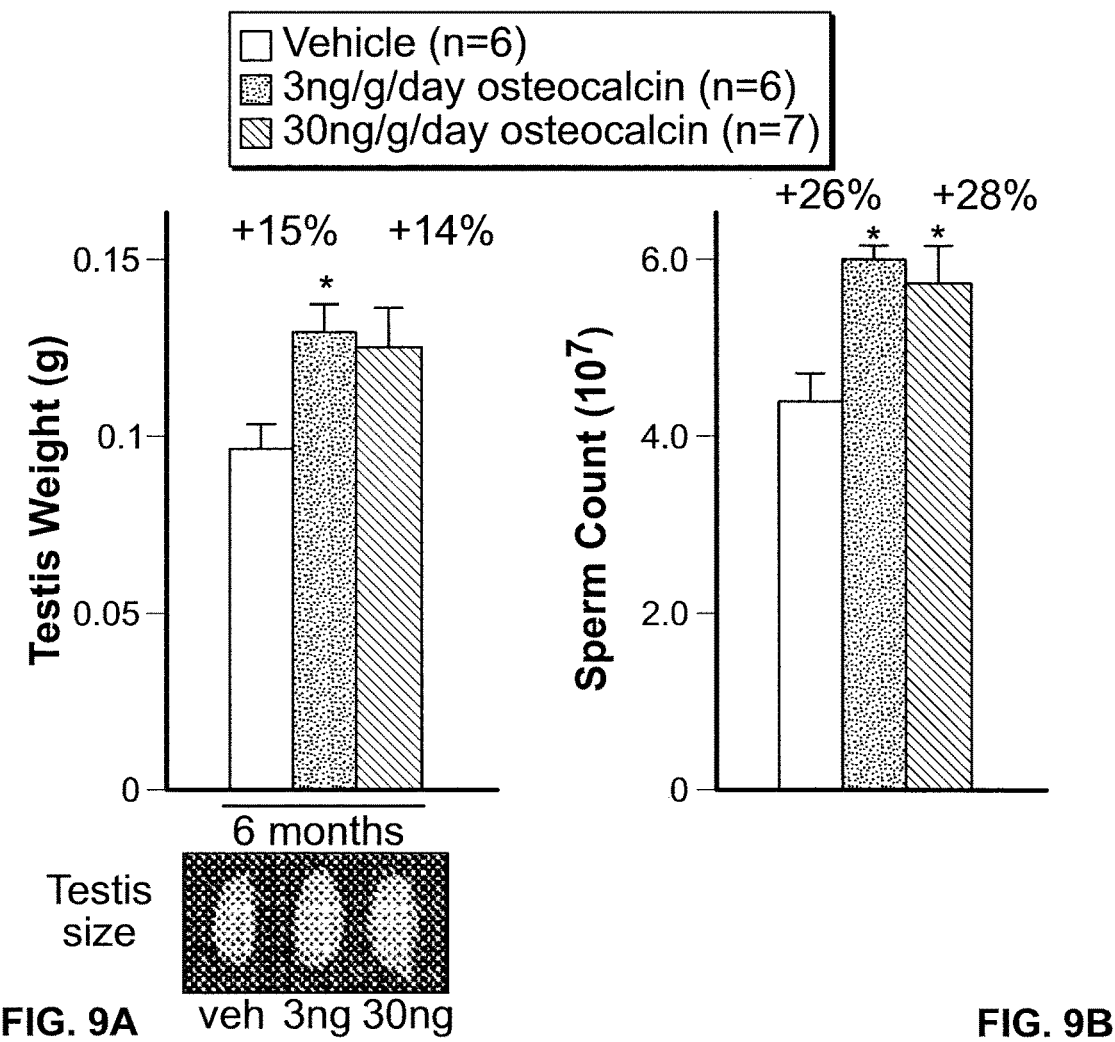
FIG. 9A
FIG. 9B
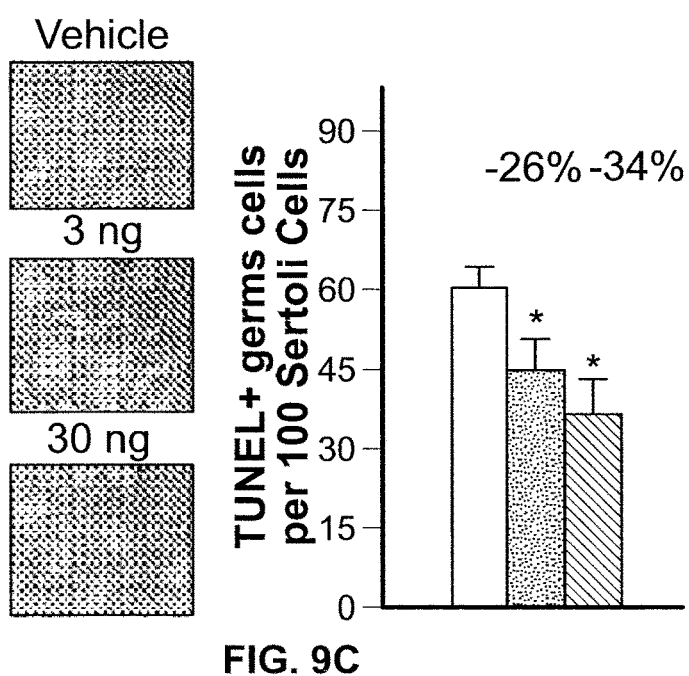
FIG. 9C
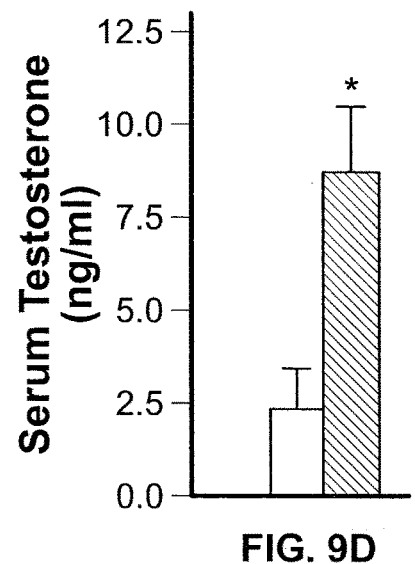
FIG. 9D

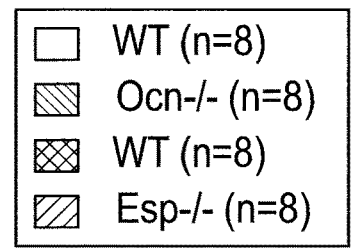
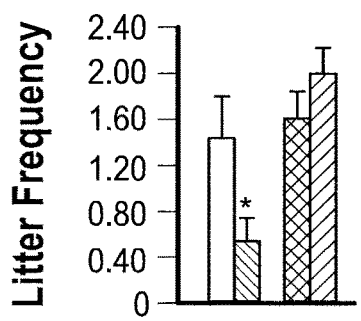
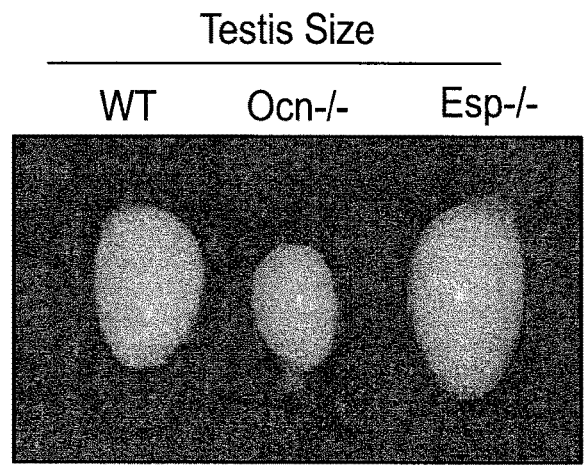
FIG. 10G
FIG. 10H
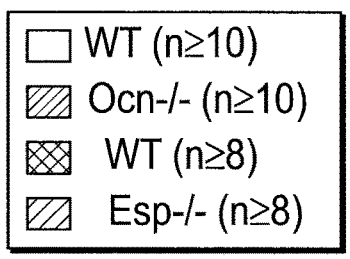
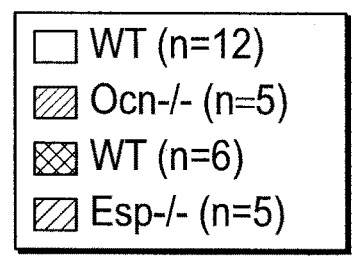
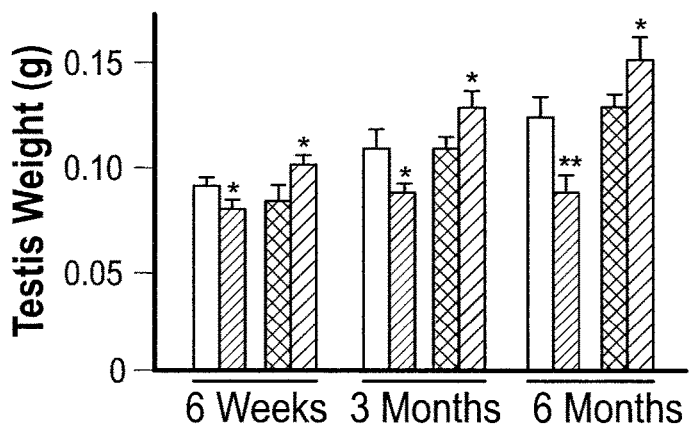
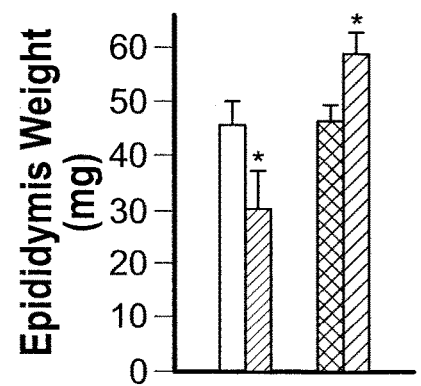
FIG. 10I
FIG. 10J

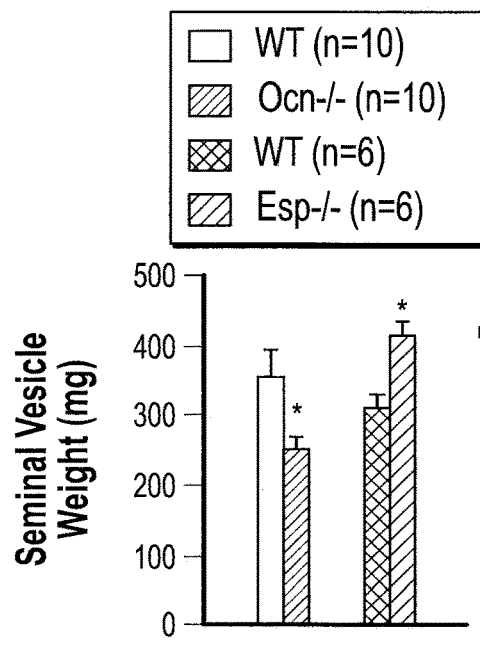
FIG. 10K
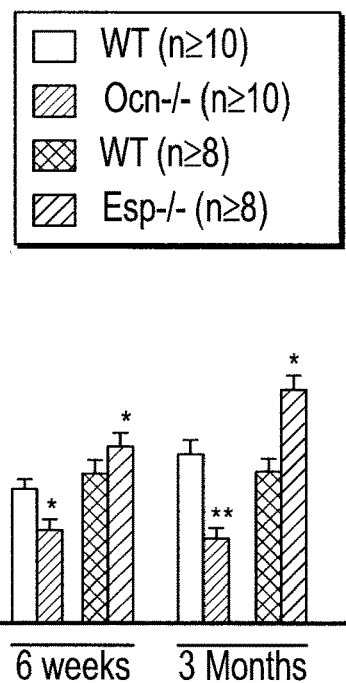
FIG. 10L
| | Testosterone (ng/mL) | Estradiol (pg/ML) | Progesterone (ng/mL) |
|---|---|---|---|
| WT (Breeders) (n=10) | 13.60 ± 0.72 | 12.24 ± 0.82 | 13.14 ± 1.27 |
| Ocn-/- (Breeders) (n=9) | 2.70 ± 0.53* | 28.09 ± 2.89* | 12.28 ± 1.59 |
| WT (Non-Breeders) (n=10) | 2.07 ± 0.60 | 28.9 ± 3.27 | |
| Ocn-/- (Non-Breeders) (n=7) | 0.49 ± 0.12* | 61.60 ± 6.57* | |
| WT (Breeders) (n=10) | 13.34 ± 1.12 | 21.24 ± 2.27 | 8.78 ± 1.25 |
| Esp-/- (Breeders) (n=9) | 23.50 ± 1.77* | 18.54 ± 1.81 | 10.32 ± 0.70 |
| WT (Non-Breeders) (n=6) | 2.03 ± 1.35* | 16.02 ± 1.64 | |
| Esp-/- (Non-Breeders) (n=5) | 13.46 ± 1.19* | 19.80 ± 1.82 | |
FIG. 10M

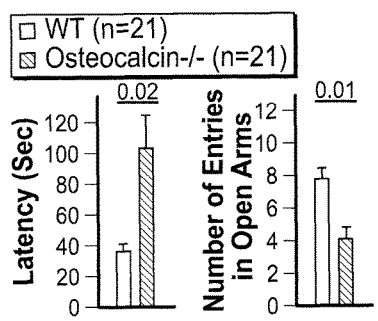 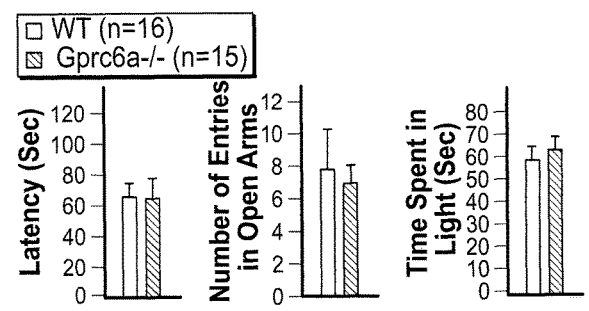
FIG. 11A  FIG. 11B
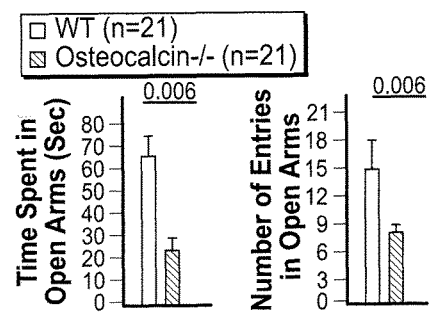 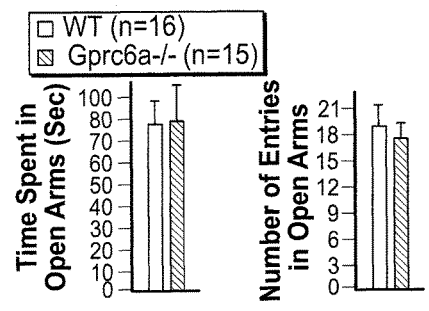
FIG. 11C  FIG. 11D

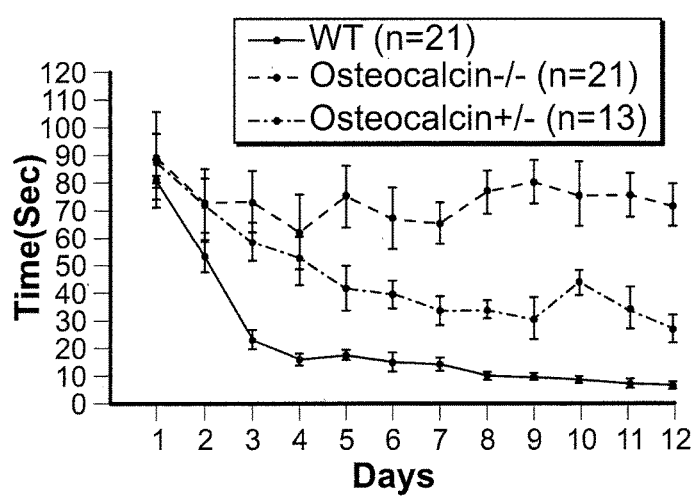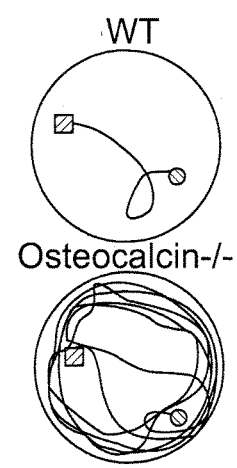
FIG. 11K
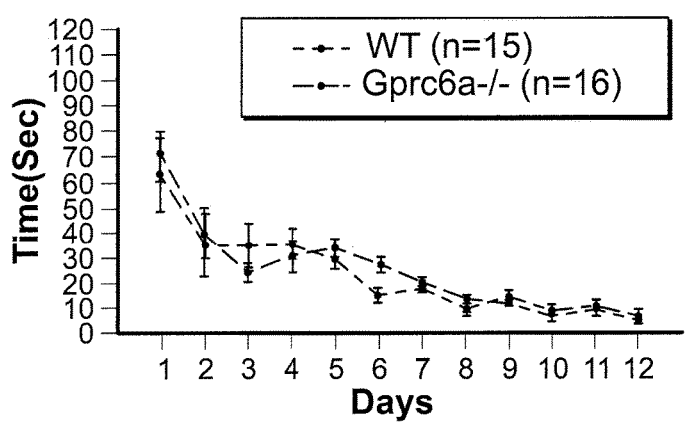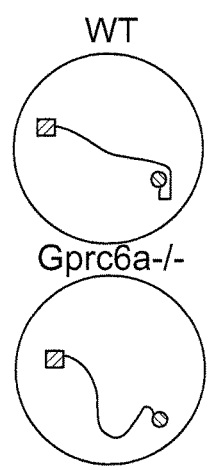
FIG. 11L

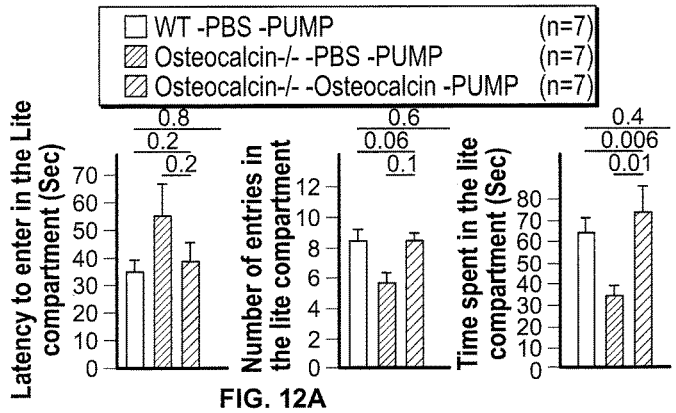
FIG. 12A
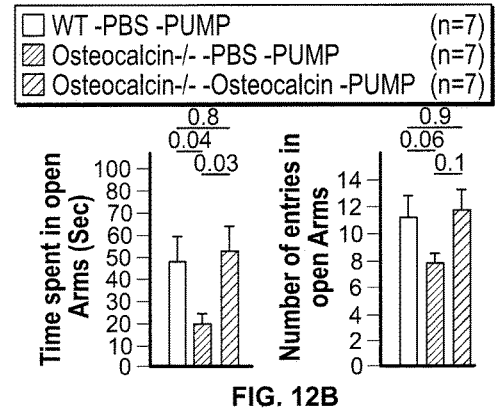
FIG. 12B
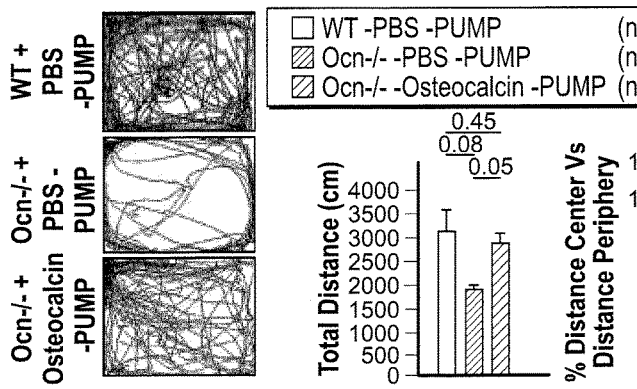
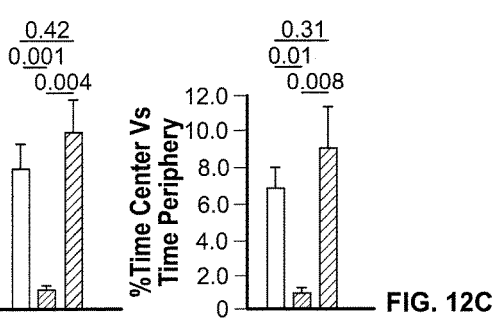
FIG. 12C

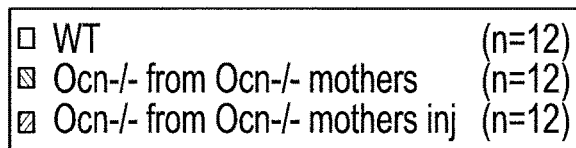
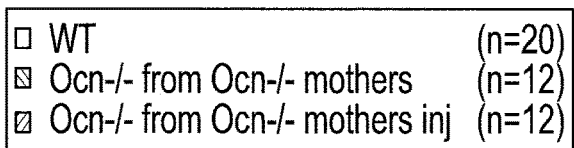
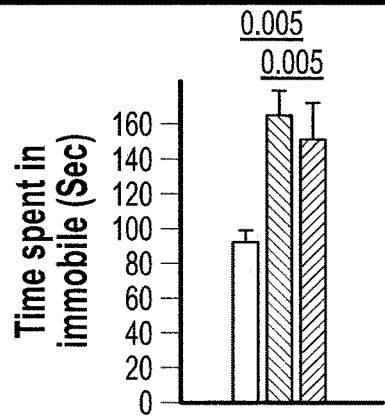
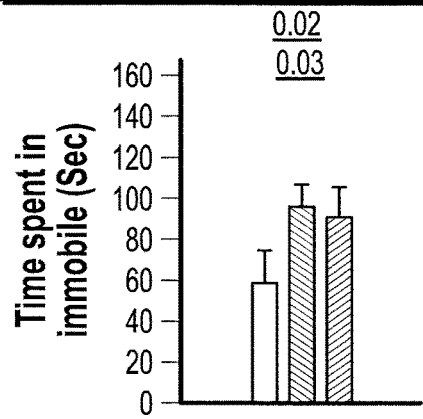
FIG. 13D  FIG. 13E
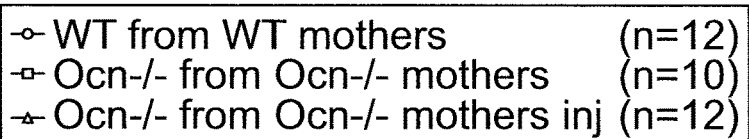
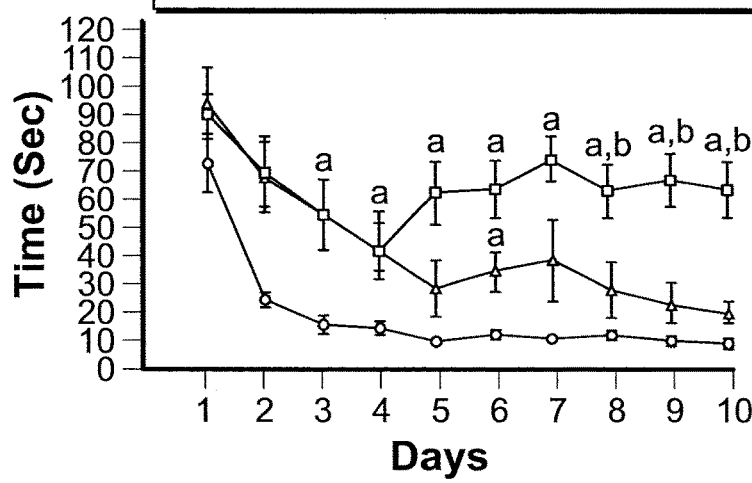
FIG. 13F
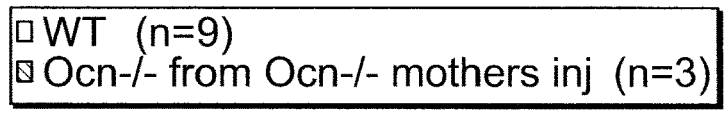
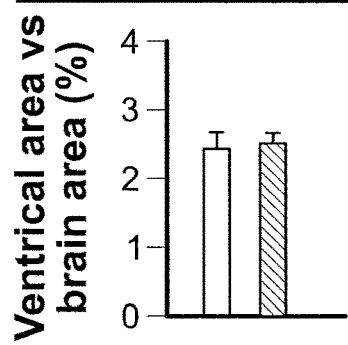
FIG. 13G

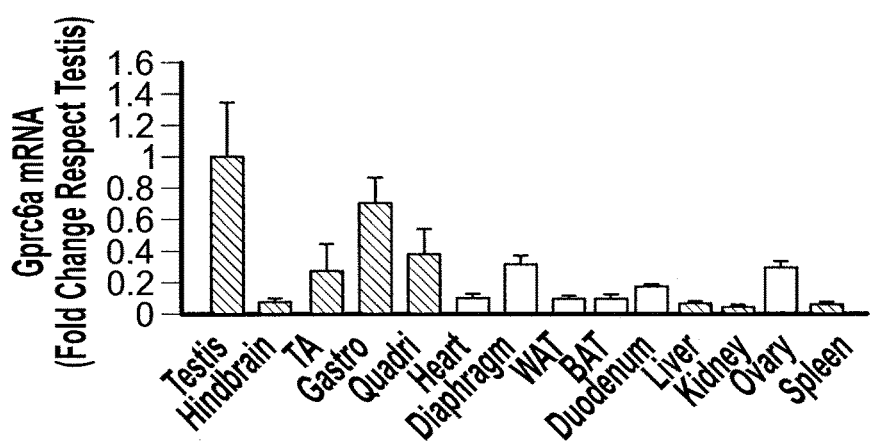 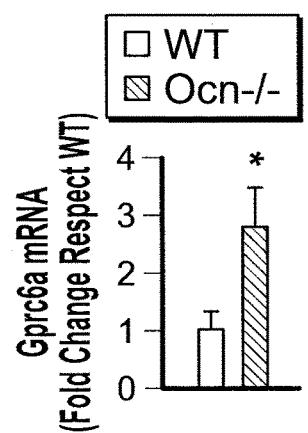
FIG. 17A  FIG. 17B
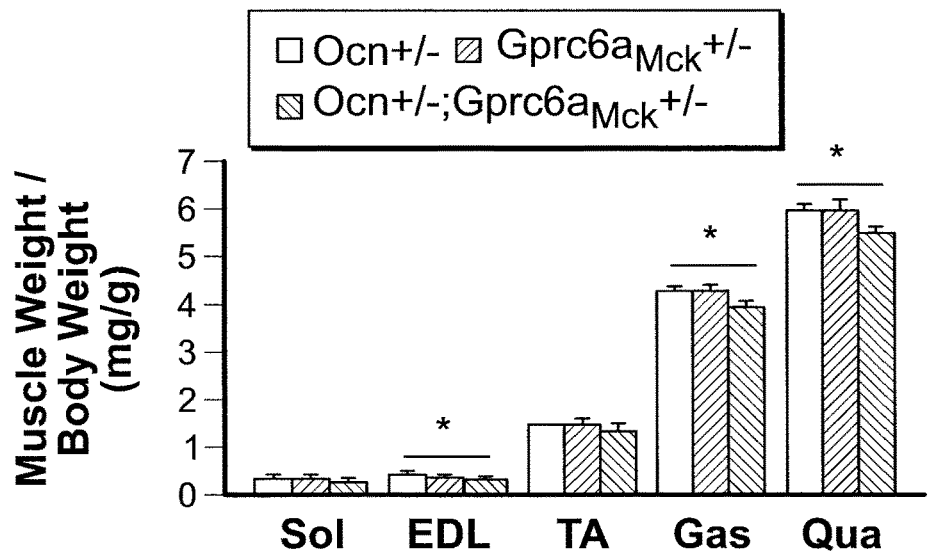
FIG. 18A
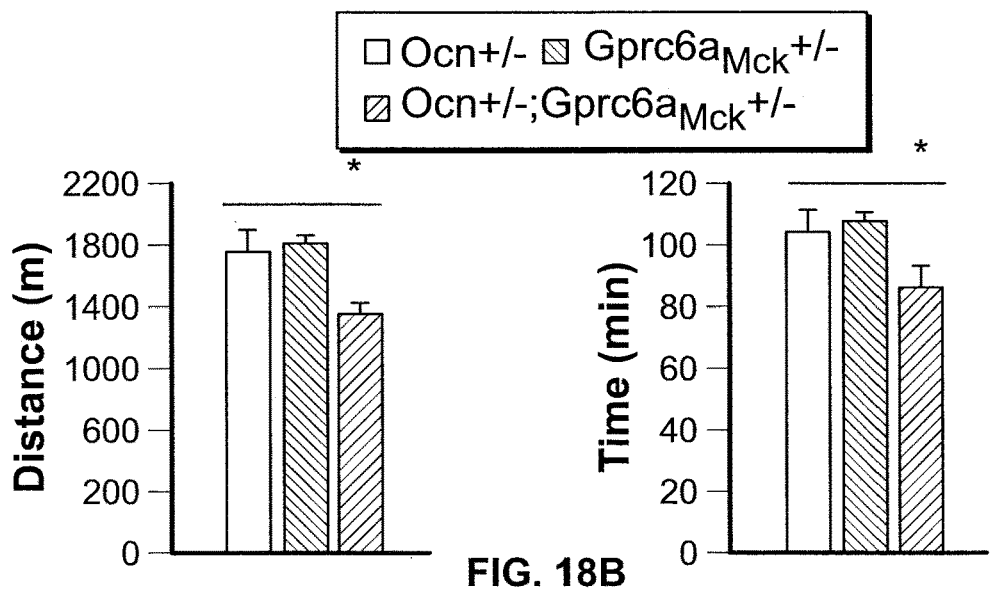
FIG. 18B

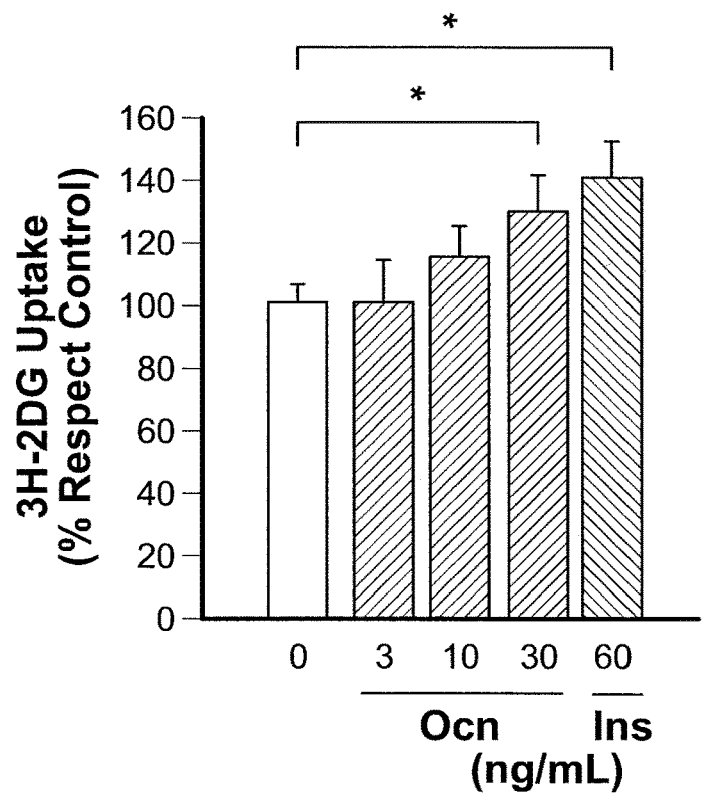
FIG. 19A
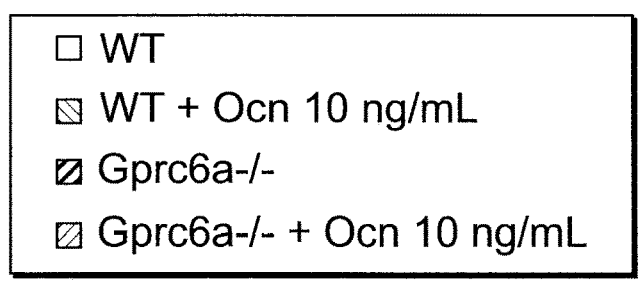
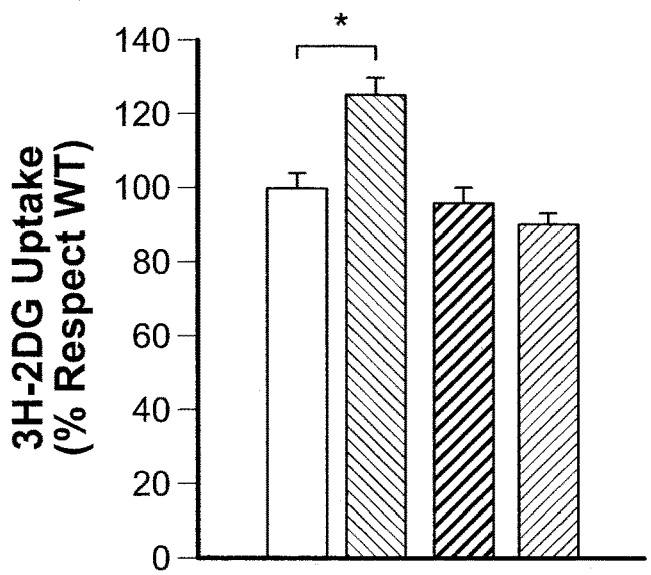
FIG. 19B

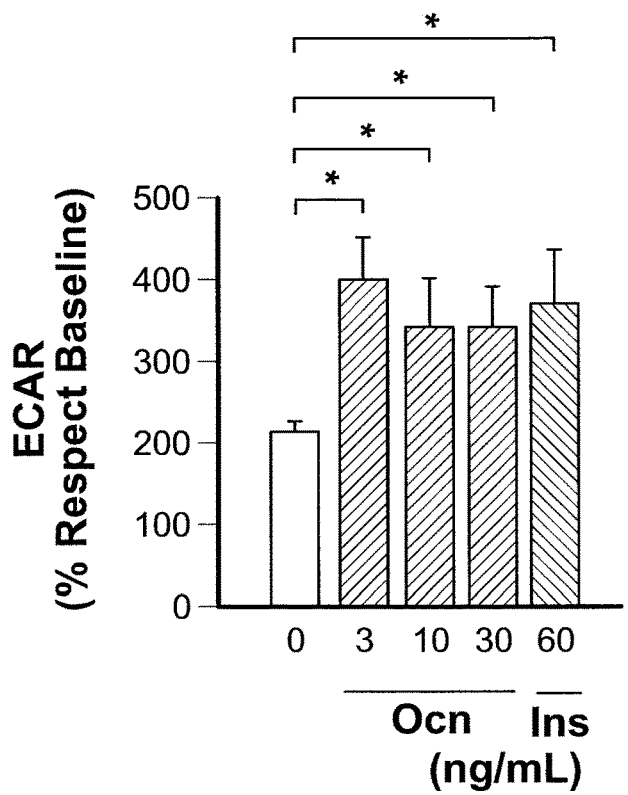
FIG. 20A
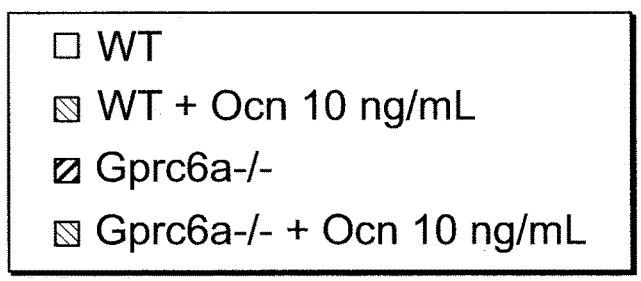
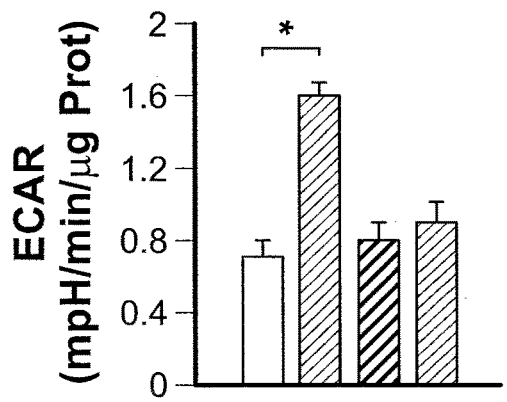
FIG. 20B
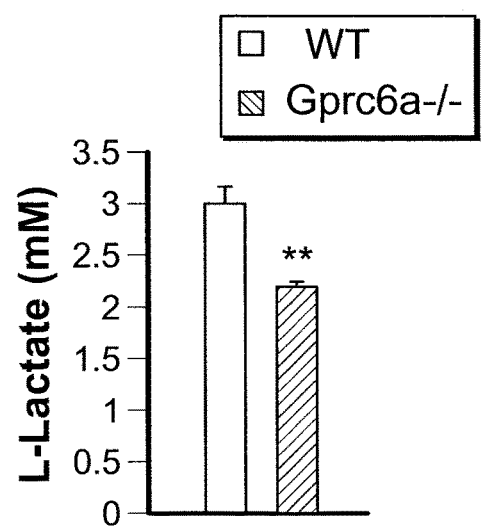
FIG. 20C

Osteocalcin promotes S6K phosphorylation and protien synthesis
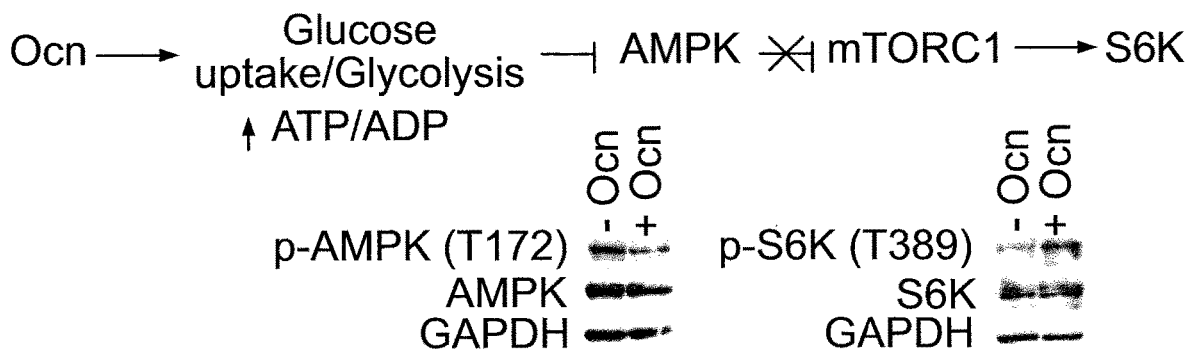
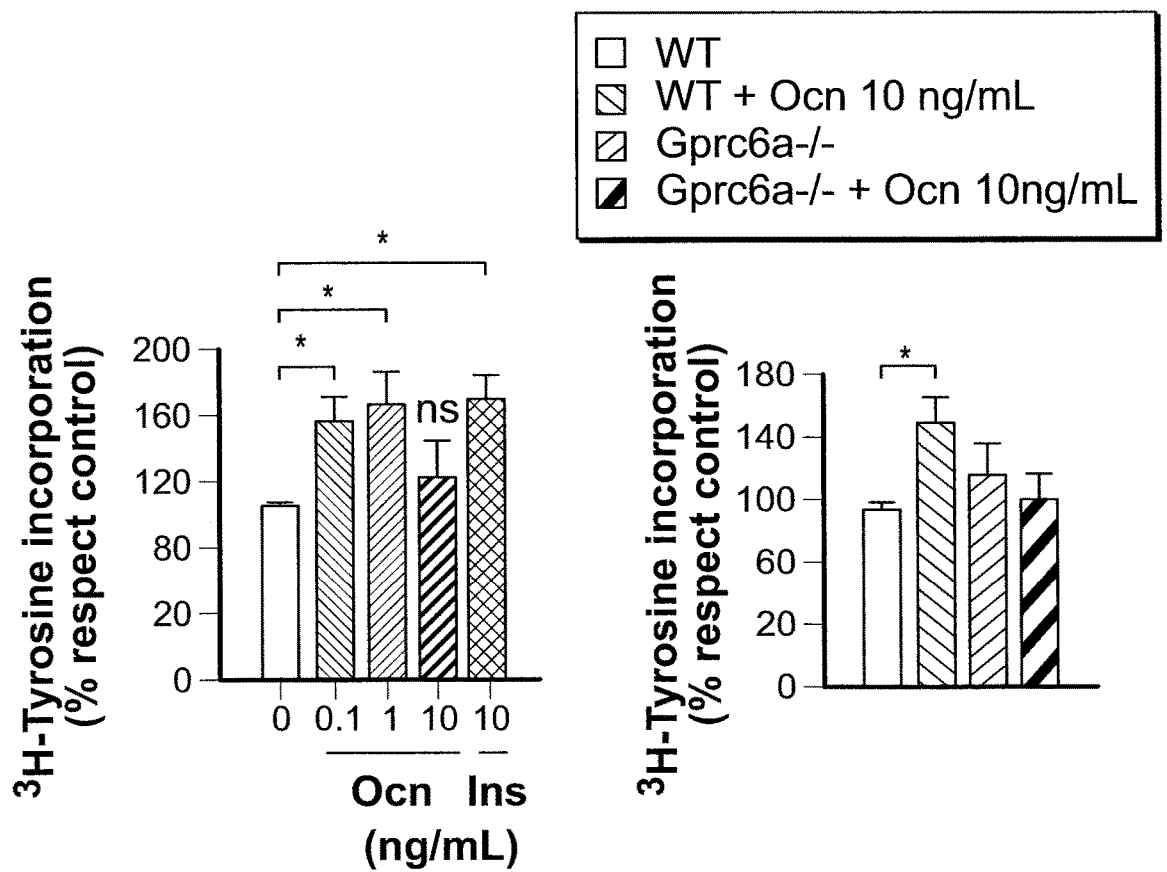
FIG. 23

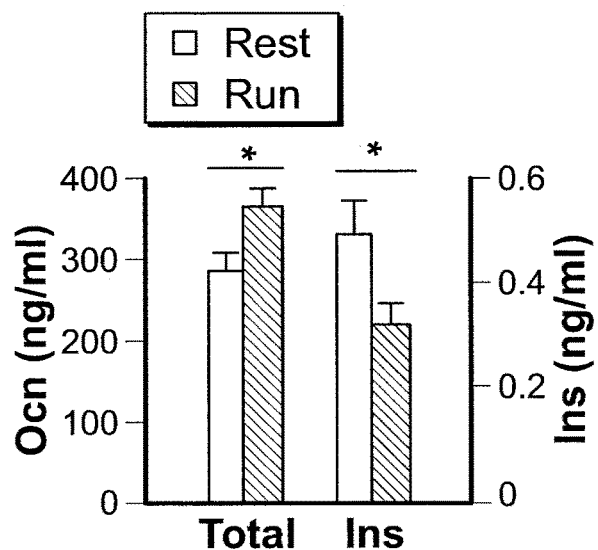
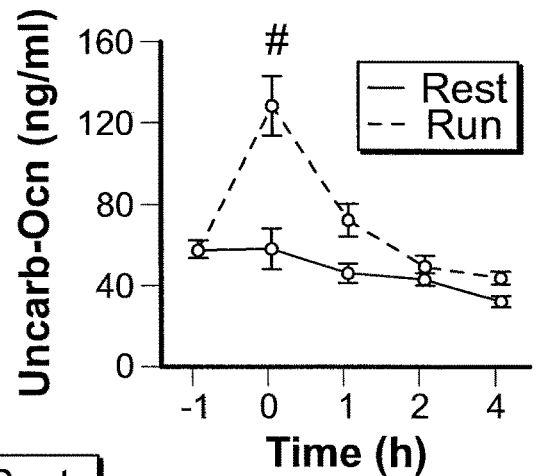
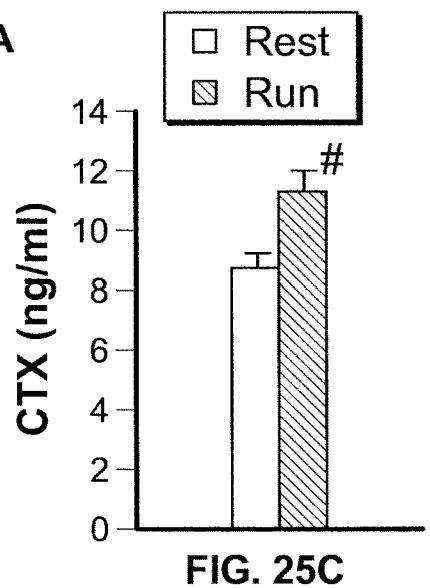
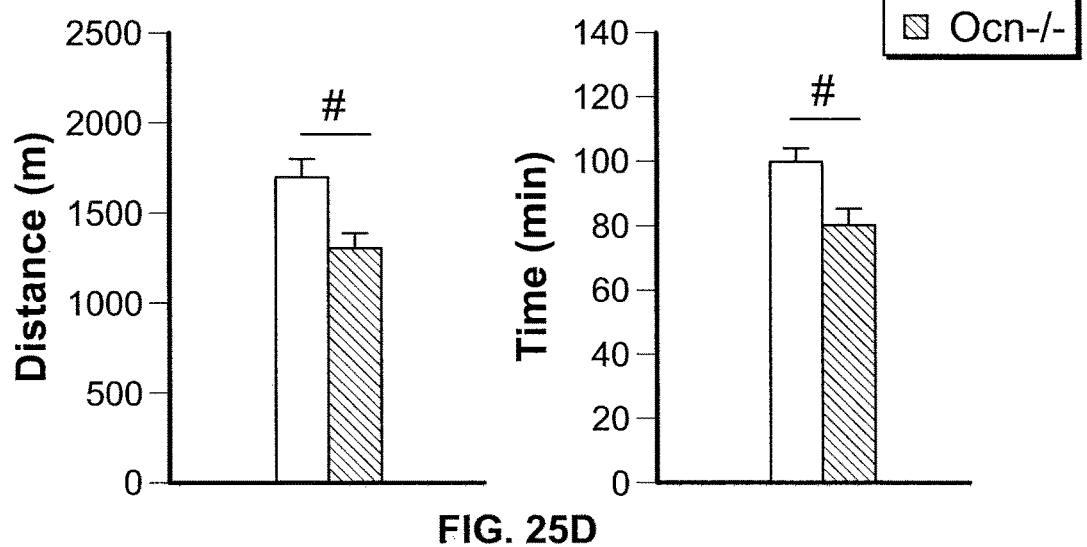
FIG. 25A
FIG. 25B
FIG. 25C
FIG. 25D

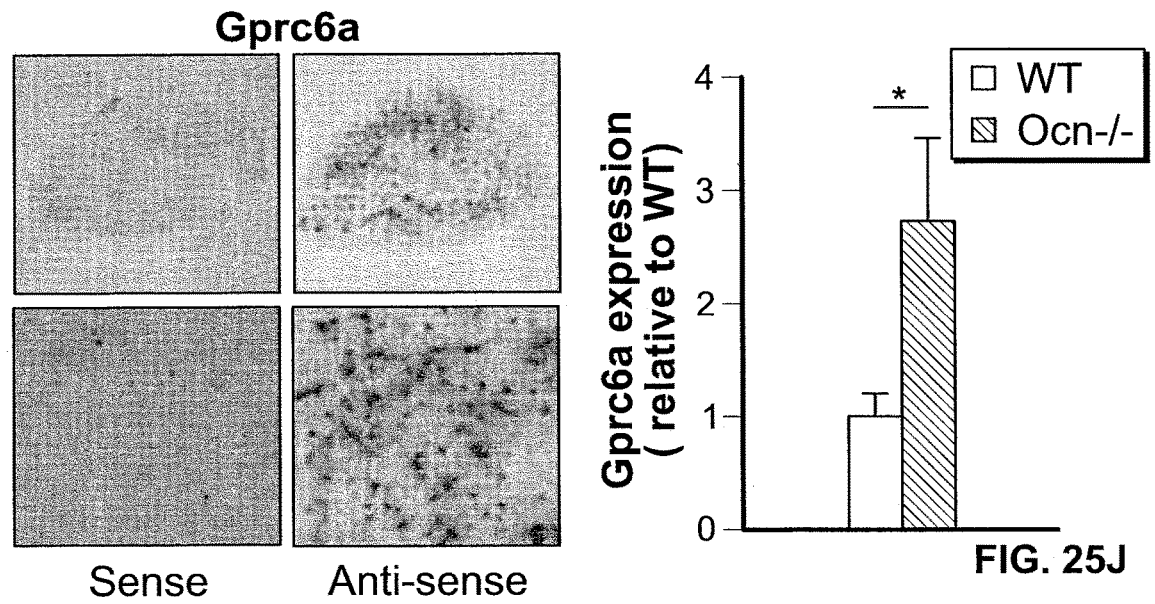
FIG. 25I
FIG. 25J
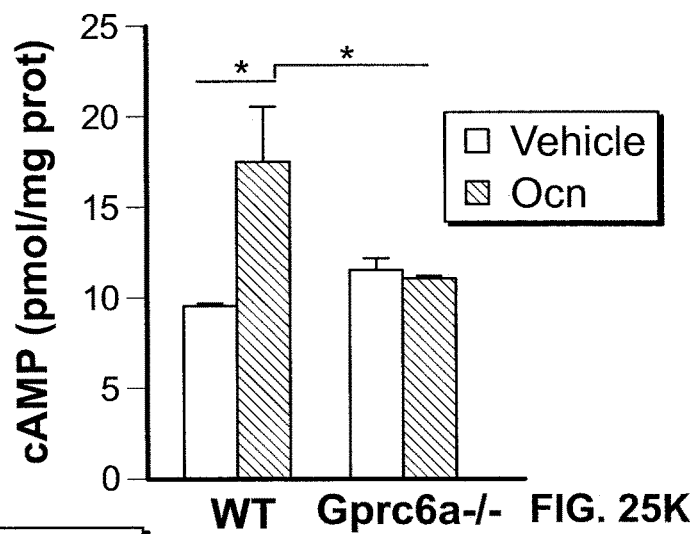
FIG. 25K
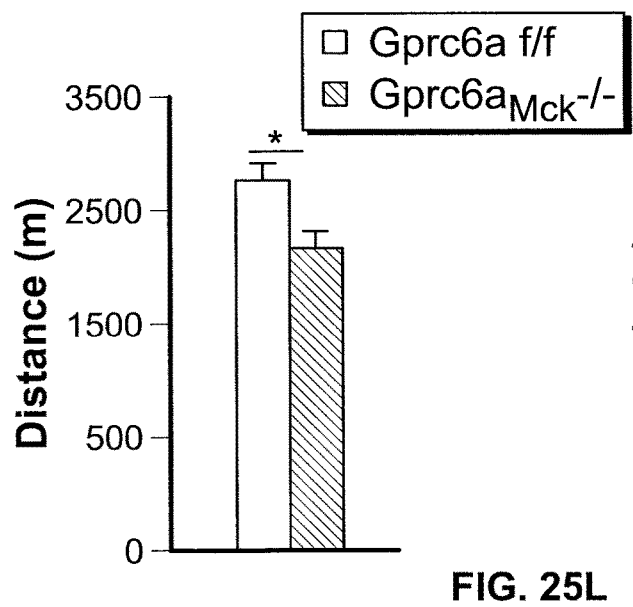
FIG. 25L

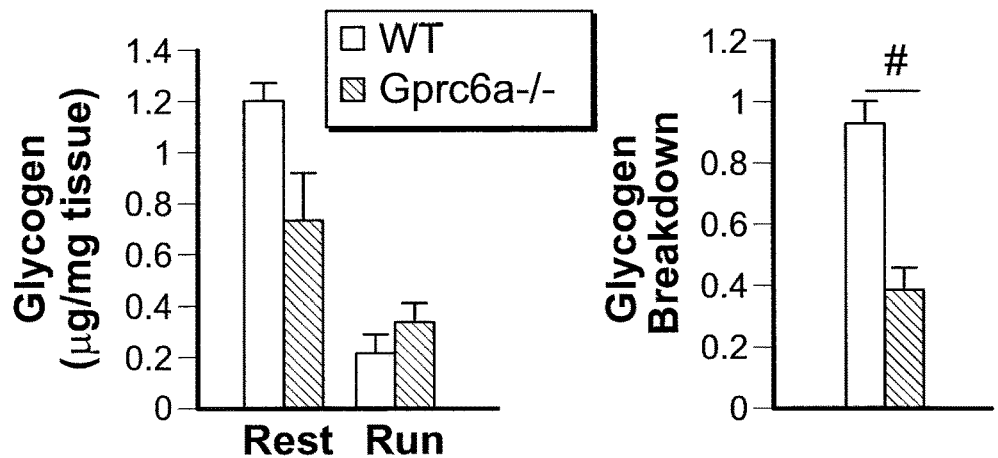
FIG. 26K
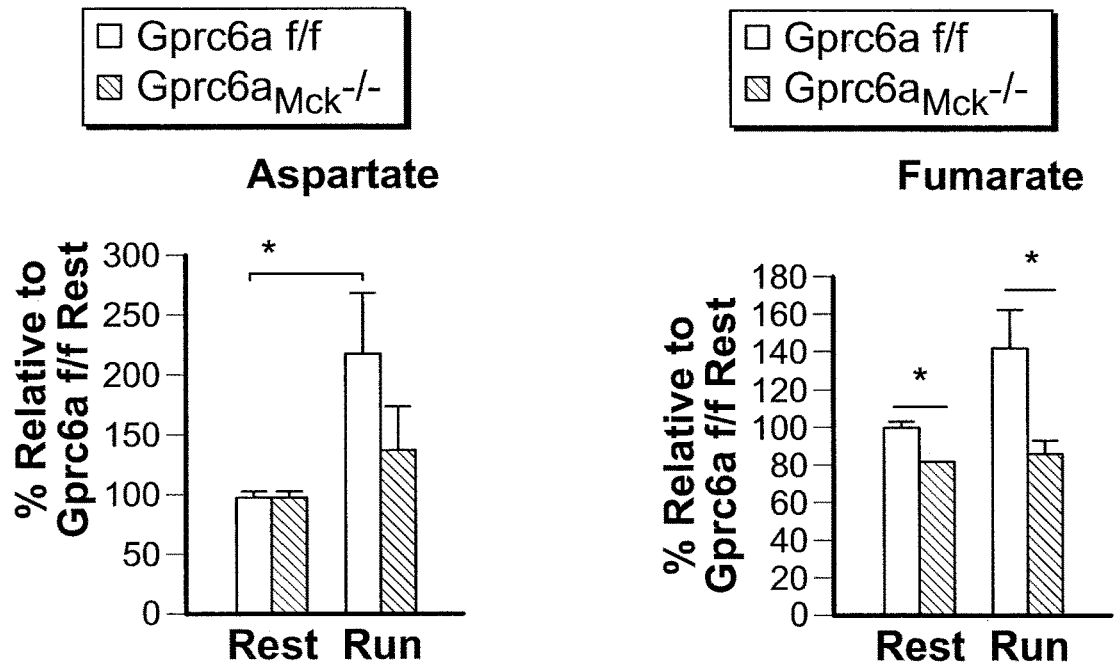
FIG. 27A
FIG. 27B
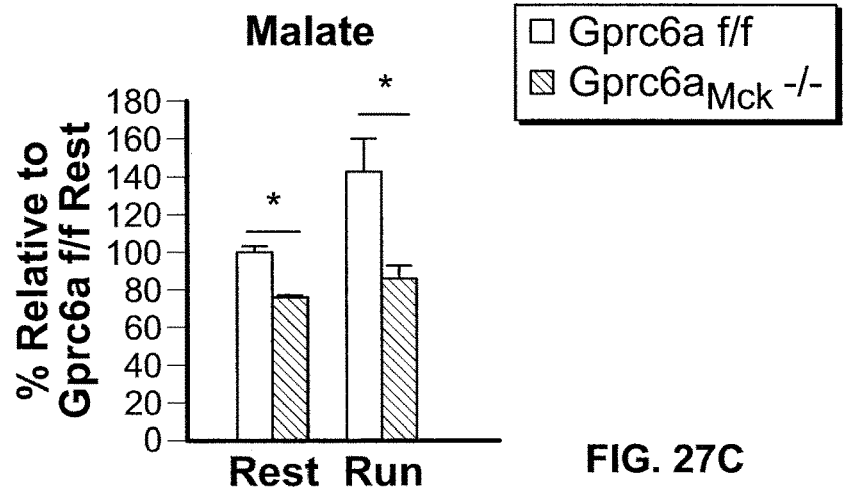
FIG. 27C

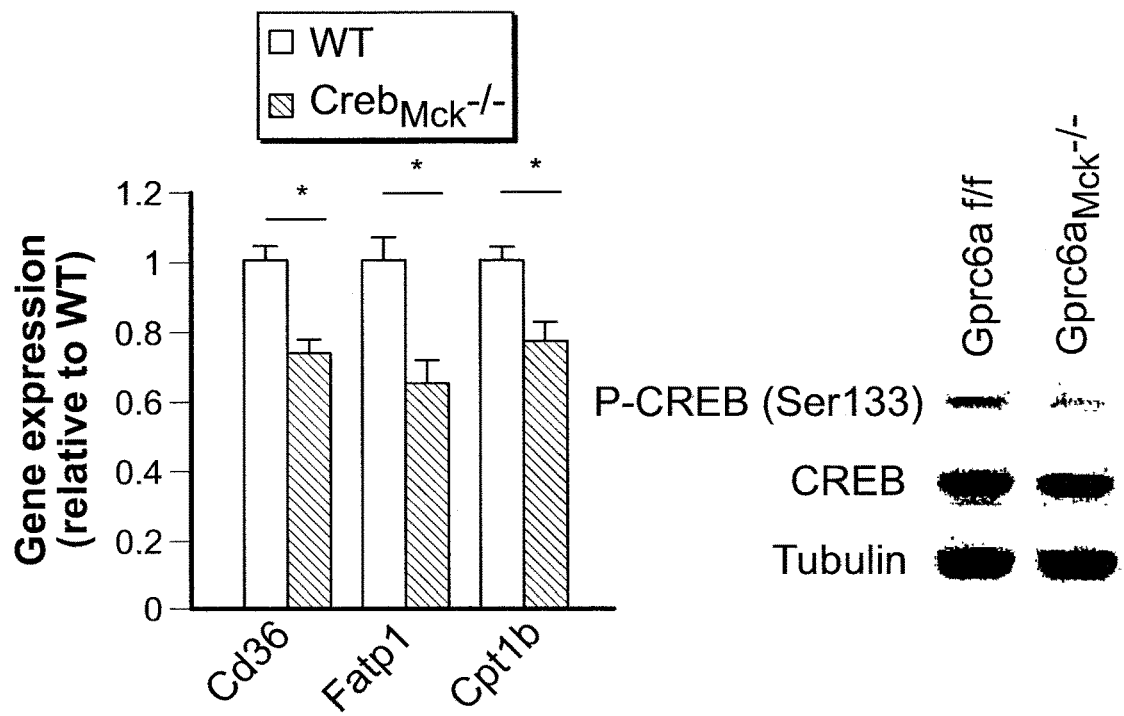
FIG. 28J  FIG. 28K
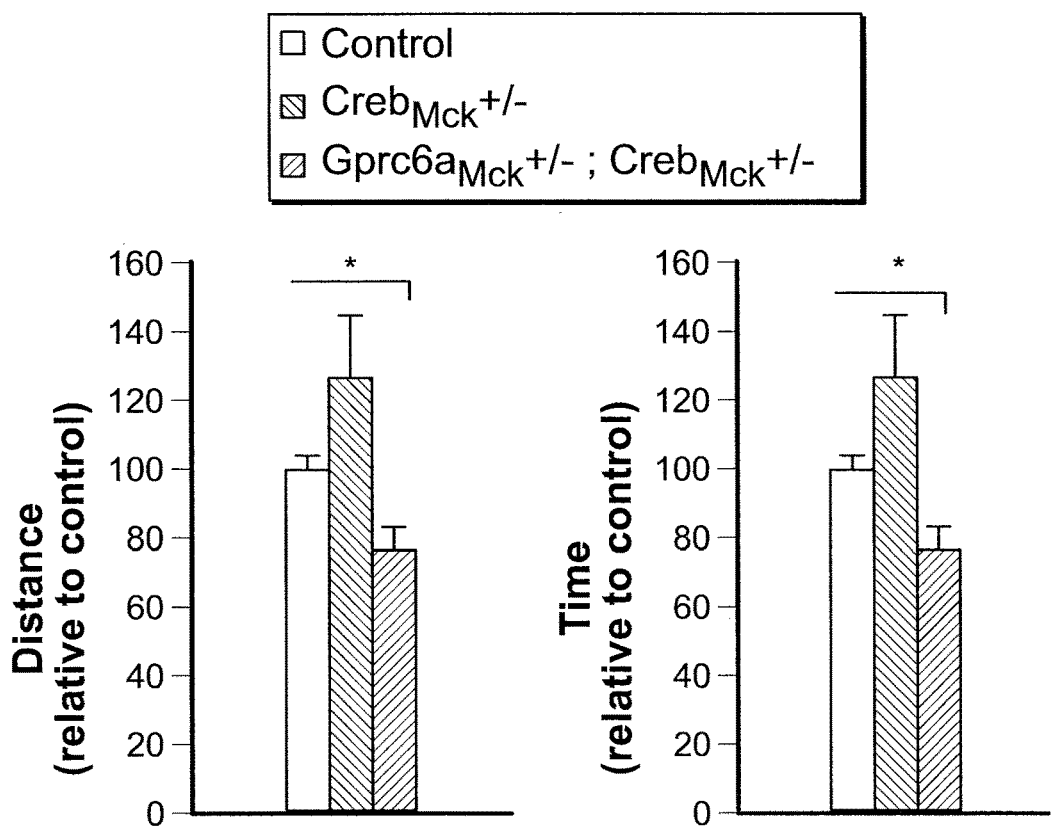
FIG. 28L

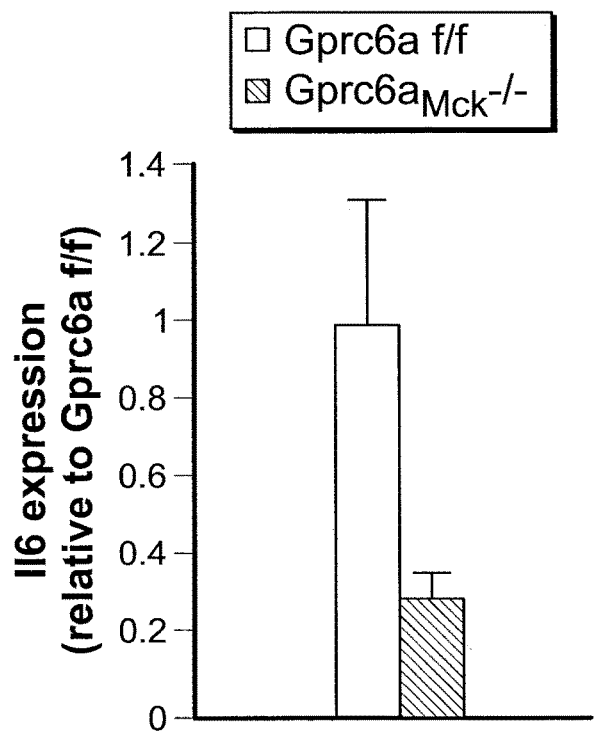
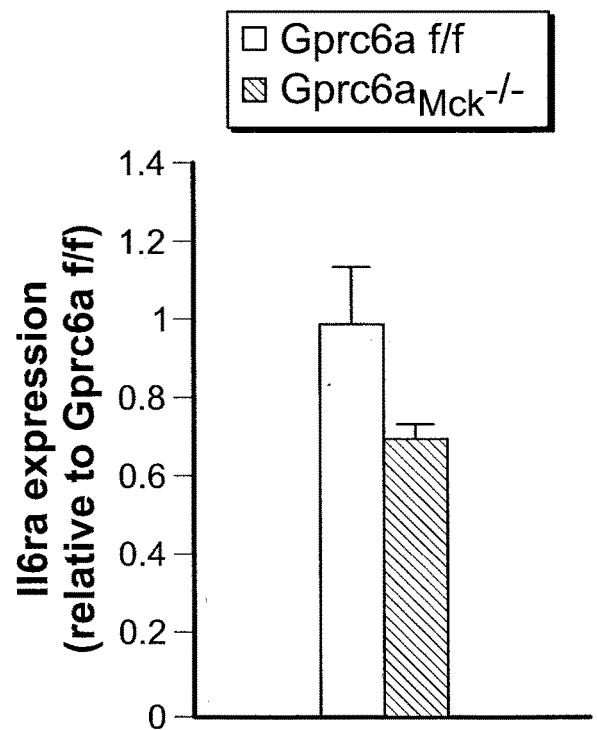
FIG. 29A  FIG. 29B
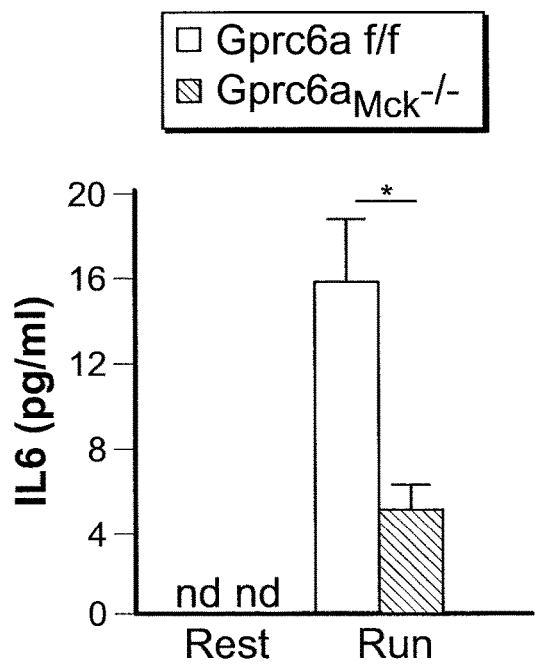
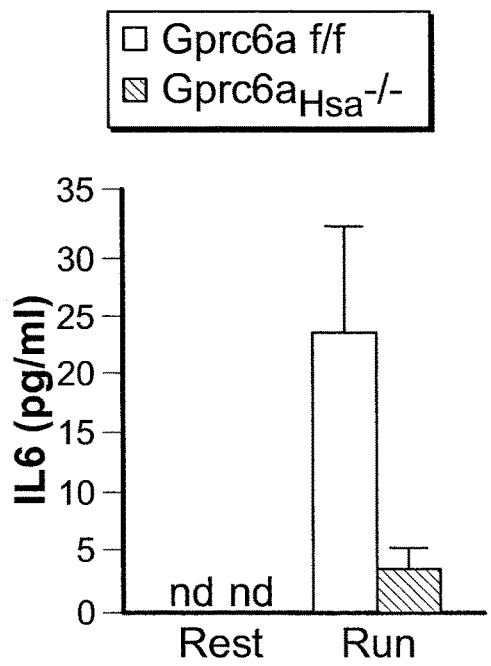
FIG. 29C  FIG. 29D

OSTEOCALCIN AS A TREATMENT FOR FRAILTY ASSOCIATED WITH AGING

CROSS REFERENCE TO RELATED APPLICATIONS

This application is the U.S. national phase under 35 U.S.C. § 371 of International Patent Application No. PCT/US2015/061590, filed Nov. 19, 2015, and relates to and claims the benefit and priority from U.S. Provisional Patent Application Ser. No. 62/081,861, filed Nov. 19, 2014, the disclosures of which are incorporated herein by reference in their entireties.

STATEMENT OF GOVERNMENT INTEREST

This invention was made with Government support under grant R01 AR045548 awarded by the National Institutes of Health. The government has certain rights in the invention.

FIELD OF THE INVENTION

The present invention is directed to methods for treating disorders associated with aging in mammals. Such disorders include metabolic disorders, male reproductive disorders, cognitive disorders, muscle wasting, and lung disorders.

BACKGROUND OF THE INVENTION

Osteocalcin, one of the very few osteoblast-specific proteins, has several features of a hormone. For instance, it is synthesized as a pre-pro-molecule and is secreted in the general circulation (Hauschka et al., 1989, Physiol. Review 69:990-1047; Price, 1989, Connect. Tissue Res. 21:51-57 (discussion 57-60)). Because of their exquisite cell-specific expression, the osteocalcin genes have been intensively studied to identify osteoblast-specific transcription factors and to define the molecular bases of bone physiology (Ducy et al., 2000, Science 289:1501-1504; Harada & Rodan, 2003, Nature 423:349-355).

Osteocalcin is the most abundant non-collagenous protein found associated with the mineralized bone matrix and it is currently being used as a biological marker for clinical assessment of bone turnover. Osteocalcin is a small (46-50 amino acid residues) bone specific protein that contains 3 gamma-carboxylated glutamic acid residues in its primary structure. The name osteocalcin (osteo, Greek for bone; calc, Latin for lime salts; in, protein) derives from the protein's ability to bind $Ca^{2+}$ and its abundance in bone. Osteocalcin undergoes a peculiar post-translational modification whereby glutamic acid residues are carboxylated to form gamma-carboxyglutamic acid (Gla) residues; hence osteocalcin's other name, bone Gla protein (Hauschka et al., 1989, Physiol. Review 69:990-1047).

Mature human osteocalcin contains 49 amino acids with a predicted molecular mass of 5,800 kDa (Poser et al., 1980, J. Biol. Chem. 255:8685-8691). Osteocalcin is synthesized primarily by osteoblasts and ondontoblasts and comprises 15 to 20% of the non-collagenous protein of bone. Poser et al., 1980, J. Biol. Chem. 255:8685-8691 showed that mature osteocalcin contains three carboxyglutamic acid residues which are formed by post-translational vitamin K-dependent modification of glutamic acid residues. The carboxylated Gla residues are at positions 17, 21 and 24 of mature human osteocalcin. Some human osteocalcin has been shown to contain only 2 Gla residues (Poser & Price, 1979, J. Biol. Chem. 254:431-436).

Osteocalcin has several features of a hormone. Ducy et al., 1996, Nature 382:448-452 demonstrated that mineralized bone from aging osteocalcin-deficient mice was two times thicker than that of wild-type. It was shown that the absence of osteocalcin led to an increase in bone formation without impairing bone resorption and did not affect mineralization. Multiple immunoreactive forms of human osteocalcin have been discovered in circulation (Garnero et al., 1994, J. Bone Miner. Res. 9:255-264) and also in urine (Taylor et al., 1990, J. Clin. Endocrin. Metab. 70:467-472). Fragments of human osteocalcin can be produced either during osteoclastic degradation of bone matrix or as the result of the catabolic breakdown of the circulating protein after synthesis by osteoblasts.

SUMMARY OF THE INVENTION

The present invention provides methods of treating frailty associated with aging. As used herein, "frailty" refers to a complex of disorders that frequently arise when a human ages. Frailty is characterized by at least two or more of the following disorders or conditions associated with aging: (a) muscle wasting; (b) lung disorders involving bronchoconstriction such as asthma, bronchitis, or chronic obstructive pulmonary disease; (c) metabolic disorders such as metabolic syndrome, glucose intolerance, type 1 diabetes, type 2 diabetes, atherosclerosis, or obesity; (d) male reproductive disorders such as male infertility, low sperm count, impaired sperm motility, impaired sperm viability, low testosterone levels, reduced libido, erectile dysfunction, underdevelopment of testes, or excess apoptosis in testes; (e) cognitive disorders such as cognitive loss due to neurodegeneration associated with aging (which may include anxiety, depression, memory loss, or learning difficulties).

In some embodiments, frailty includes: (a) muscle wasting or (b) a lung disorder involving bronchoconstriction such as asthma, bronchitis, or chronic obstructive pulmonary disease. In such embodiments, the frailty also includes one or more of: (c) a metabolic disorder such as metabolic syndrome, glucose intolerance, type 1 diabetes, type 2 diabetes, atherosclerosis, or obesity; (d) a male reproductive disorder such as male infertility, low sperm count, impaired sperm motility, impaired sperm viability, low testosterone levels, reduced libido, erectile dysfunction, underdevelopment of testes, or excess apoptosis in testes; or (e) a cognitive disorder such as cognitive loss due to neurodegeneration associated with aging (which may include anxiety, depression, memory loss, or learning difficulties).

In some embodiments, frailty includes: (a) muscle wasting and (b) a lung disorder involving bronchoconstriction such as asthma, bronchitis, or chronic obstructive pulmonary disease as well as, optionally, one or more of: (c) a metabolic disorder such as metabolic syndrome, glucose intolerance, type 1 diabetes, type 2 diabetes, atherosclerosis, or obesity; (d) a male reproductive disorder such as male infertility, low sperm count, impaired sperm motility, impaired sperm viability, low testosterone levels, reduced libido, erectile dysfunction, underdevelopment of testes, or excess apoptosis in testes; or (e) a cognitive disorder such as cognitive loss due to neurodegeneration associated with aging (which may include anxiety, depression, memory loss, or learning difficulties).

Described herein are methods of treating frailty comprising administering to a patient suffering from frailty a pharmaceutical composition comprising a therapeutically effective amount of undercarboxylated/uncarboxylated osteocalcin and a pharmaceutically acceptable carrier or excipient. In some embodiments, the methods comprise alleviating at least one of (a) or (b) above, i.e., at least one of muscle wasting or a lung disorder, while at the same time alleviating at least one of (c)-(e) above, i.e., metabolic disorders, male reproductive disorders, or cognitive disorders.

In some embodiments of the methods of treating frailty disclosed herein, the methods comprise alleviating at least (a) muscle wasting and at least one of (c)-(e) metabolic disorders, male reproductive disorders, or cognitive disorders. In some embodiments of the methods of treating frailty disclosed herein, the methods comprise alleviating at least (b) a lung disorder and at least one of (c)-(e) metabolic disorders, male reproductive disorders, or cognitive disorders.

In some embodiments, the methods comprise alleviating at least (a) muscle wasting and (c) a metabolic disorder. In some embodiments, the methods comprise alleviating at least (a) muscle wasting and (d) a male reproductive disorder. In some embodiments, the methods comprise alleviating at least (a) muscle wasting and (e) a cognitive disorder.

In some embodiments, the methods comprise alleviating at least (b) a lung disorder and (c) a metabolic disorder. In some embodiments, the methods comprise alleviating at least (b) a lung disorder and (d) a male reproductive disorder. In some embodiments, the methods comprise alleviating at least (b) a lung disorder and (e) a cognitive disorder.

In some embodiments, the methods comprise alleviating (a) muscle wasting and (b) a lung disorder. In some embodiments, the methods comprise alleviating (a) muscle wasting and (b) a lung disorder as well as at least one of (c)-(e) metabolic disorders, male reproductive disorders, or cognitive disorders. In some embodiments, the methods comprise alleviating (a) muscle wasting and (b) a lung disorder as well as (c) a metabolic disorder. In some embodiments, the methods comprise alleviating (a) muscle wasting and (b) a lung disorder as well as (d) a male reproductive disorder. In some embodiments, the methods comprise alleviating (a) muscle wasting and (b) a lung disorder as well as (e) a cognitive disorder.

In some embodiments, the methods comprise alleviating (a) muscle wasting, (b) a lung disorder, (c) a metabolic disorder, (d) a male reproductive disorder, and (e) a cognitive disorder.

In some embodiments, a human patient suffering from "frailty" is a patient who is at least 55 years of age. In some embodiments, the patient is at least 60, 65, 70, 75, or 80 years old. In certain embodiments, the patient is a human who is between 55 and 80 years old, between 60 and 75 years old, or between 65 and 70 years old. In certain embodiments, the patient is a human who is between 55 and 60 years old, between 65 and 70 years old, between 70 and 75 years old, between 75 and 80 years old, between 80 and 85 years old, or between 85 and 90 years old.

In certain versions of the methods, the various disorders in the embodiments listed above are alleviated by administering to the patient a pharmaceutical composition comprising a form of osteocalcin, e.g., undercarboxylated/uncarboxylated osteocalcin. In some embodiments, the osteocalcin is human osteocalcin. In some embodiments, the osteocalcin is completely uncarboxylated human osteocalcin.

The present invention also provides methods of treating frailty in a patient comprising administering to a patient suffering from frailty a pharmaceutical composition comprising an agent that modulates the OST-PTP signaling pathway or the PTP-1B signaling pathway, wherein the agent reduces OST-PTP phosphorylase expression or activity or reduces PTP-1B phosphorylase expression or activity, reduces gamma-carboxylase expression or activity, or increases the level of undercarboxylated/uncarboxylated osteocalcin. In certain embodiments, the agent is undercarboxylated/uncarboxylated osteocalcin. In certain embodiments, the agent is human undercarboxylated/uncarboxylated osteocalcin.

In certain embodiments, the agent inhibits the expression or activity of OST-PTP, inhibits the expression or activity of PTP-1B, inhibits the expression or activity of gamma-carboxylase, inhibits phosphorylation of gamma-carboxylase, inhibits carboxylation of osteocalcin, or decarboxylates osteocalcin. In certain embodiments, the agent is selected from the group consisting of a small molecule, an antibody, or a nucleic acid.

In certain embodiments where the agent is undercarboxylated/uncarboxylated osteocalcin, at least one of the glutamic acids in the undercarboxylated/uncarboxylated osteocalcin at the positions corresponding to positions 17, 21 and 24 of mature human osteocalcin is not carboxylated. In certain embodiments, all three of the glutamic acids in the undercarboxylated/uncarboxylated osteocalcin at the positions corresponding to positions 17, 21 and 24 of mature human osteocalcin are not carboxylated.

In certain embodiments, the undercarboxylated/uncarboxylated osteocalcin is a preparation of undercarboxylated/uncarboxylated osteocalcin in which more than about 20% of the total Glu residues at the positions corresponding to positions 17, 21 and 24 of mature human osteocalcin in the preparation are not carboxylated. In certain embodiments, the undercarboxylated/uncarboxylated osteocalcin shares at least 80% amino acid sequence identity with mature human osteocalcin when the undercarboxylated/uncarboxylated osteocalcin and mature human osteocalcin are aligned for maximum sequence homology. In certain embodiments, the undercarboxylated/uncarboxylated osteocalcin shares about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98% amino acid sequence identity with mature human osteocalcin when the undercarboxylated/uncarboxylated osteocalcin and mature human osteocalcin are aligned for maximum sequence homology. In certain embodiments, the undercarboxylated/uncarboxylated osteocalcin differs at 1, 2, 3, 4, 5, 6, 7, 8, 9, or 10 amino acid residues from mature human osteocalcin.

In certain embodiments, at least one of the glutamic acids in the undercarboxylated/uncarboxylated osteocalcin at the positions corresponding to positions 17, 21 and 24 of mature human osteocalcin is not carboxylated. In certain embodiments, all three of the glutamic acids in the undercarboxylated/uncarboxylated osteocalcin at the positions corresponding to positions 17, 21 and 24 of mature human osteocalcin are not carboxylated.

In certain embodiments, the undercarboxylated/uncarboxylated osteocalcin is a polypeptide selected from the group consisting of:
  (a) a fragment comprising mature human osteocalcin missing the last 10 amino acids from the C-terminal end;
  (b) a fragment comprising mature human osteocalcin missing the first 10 amino acids from the N-terminal end;
  (c) a fragment comprising amino acids 62-90 of SEQ ID NO:2;

(d) a fragment comprising amino acids 1-36 of mature human osteocalcin;
(e) a fragment comprising amino acids 13-26 of mature human osteocalcin;
(f) a fragment comprising amino acids 13-46 of mature human osteocalcin; and
(g) variants of the above.

In certain embodiments, the pharmaceutical composition comprises a small molecule selected from the group consisting of warfarin, vitamin K inhibitors, and biologically active fragments or variants thereof. In a particular embodiment, the small molecule is warfarin. In another particular embodiment, the agent is a small molecule that increases the activity or expression of osteocalcin.

In certain embodiments, the pharmaceutical composition comprises an antibody or antibody fragment that binds to and inhibits the activity of OST-PTP, PTP-1B, or gamma-carboxylase. Preferably, the antibody or antibody fragment is a monoclonal antibody. In certain embodiments, the antibody or antibody fragment binds to the extracellular domain of OST-PTP or PTP-1B. In particular embodiments, the OST-PTP is human OST-PTP or the PTP-1B is human PTP-1B. In certain embodiments, the OST-PTP is the mouse OST-PTP of SEQ ID NO:11 or an OST-PTP having an amino acid sequence that is substantially homologous or identical to SEQ ID NO:11. In certain embodiments, the OST-PTP is an OST-PTP having an amino acid sequence that is at least 70% homologous or identical to SEQ ID NO:11. In certain embodiments, the PTP-1B is human PTP-1B of SEQ ID NO:17 or a PTP-1B having an amino acid sequence that is substantially homologous or identical to SEQ ID NO: 17. In certain embodiments, the PTP-1B is a PTP-1B having an amino acid sequence that is at least 70%, at least 80%, at least 90%, at least 95%, or at least 98% homologous or identical to SEQ ID NO:17.

In certain embodiments, the pharmaceutical composition comprises a nucleic acid that inhibits the expression or activity of OST-PTP, PTP-1B, or gamma-carboxylase. In certain embodiments, the nucleic acid is an antisense oligonucleotide or a small interfering RNA (siRNA). In certain embodiments, the nucleic acid is an isolated nucleic acid that is selected from the group consisting of an antisense DNA, antisense RNA, and siRNA, which nucleic acid is sufficiently complementary to SEQ ID NO:10 or a sequence that is substantially homologous or identical to SEQ ID NO:10 to permit specific hybridization to SEQ ID NO:10 or a sequence that is substantially homologous or identical to SEQ ID NO:10, and wherein the hybridization prevents or reduces expression of OST-PTP in osteoblasts. In certain embodiments, the nucleic acid is an isolated nucleic acid that is selected from the group consisting of an antisense DNA, antisense RNA, and siRNA, which nucleic acid is sufficiently complementary to SEQ ID NO:16 or a sequence that is substantially homologous or identical to SEQ ID NO:16 to permit specific hybridization to SEQ ID NO:16 or a sequence that is substantially homologous or identical to SEQ ID NO:16, and wherein the hybridization prevents or reduces expression of PTP-1B in osteoblasts.

In certain embodiments, the pharmaceutical composition comprises about 0.5 mg to about 5 g, about 1 mg to about 1 g, about 5 mg to about 750 mg, about 10 mg to about 500 mg, about 20 mg to about 250 mg, or about 25 mg to about 200 mg, of the agent. In certain embodiments, the pharmaceutical composition comprises an agent that is formulated into a controlled release preparation. In certain embodiments, the pharmaceutical composition comprises an agent that is chemically modified to prolong its half life in the human body.

In certain embodiments, the pharmaceutical composition for treating frailty comprises an undercarboxylated/uncarboxylated osteocalcin polypeptide comprising an amino acid sequence (SEQ ID NO: 13)
YLYQWLGAPVPYPDPLX$_1$PRRX$_2$VCX$_3$LNPDCDELADHIGFQEAYRRFY
GPV wherein
X$_1$, X$_2$ and X$_3$ are each independently selected from an amino acid or amino acid analog, with the proviso that if X$_1$, X$_2$ and X$_3$ are each glutamic acid, then X$_1$ is not carboxylated, or less than 50 percent of X$_2$ is carboxylated, and/or less than 50 percent of X$_3$ is carboxylated,
or said osteocalcin polypeptide comprises an amino acid sequence that is different from SEQ. ID. NO:13 at 1 to 7 positions other than X$_1$, X$_2$ and X$_3$; and/or
wherein said amino acid sequence can include one or more amide backbone substitutions.

In certain embodiments, the osteocalcin polypeptide of SEQ. ID. NO:13 is a fusion protein. In certain embodiments, the arginine at position 43 of SEQ. ID. NO:13 is replaced with an amino acid or amino acid analog that reduces susceptibility of the osteocalcin polypeptide to proteolytic degradation. In certain embodiments, the arginine at position 44 of SEQ. ID. NO:13 is replaced with β-dimethyl-arginine. In certain embodiments, the osteocalcin polypeptide is a retroenantiomer of uncarboxylated human osteocalcin (1-49).

The present invention also provides a method of treating frailty in mammals by modulating the OST-PTP signaling pathway or the PTP-1B signaling pathway, the method comprising administering an agent that reduces OST-PTP phosphorylase activity or reduces PTP-1B phosphorylase activity, reduces gamma-carboxylase activity, or increases undercarboxylated/uncarboxylated osteocalcin, wherein the agent is administered in an amount that treats frailty.

The present invention provides the use of an agent that reduces OST-PTP phosphorylase activity, reduces PTP-1B phosphorylase activity, reduces gamma-carboxylase activity, and/or increases undercarboxylated/uncarboxylated osteocalcin as a medicament for treating frailty.

The present invention provides the use of an undercarboxylated/uncarboxylated osteocalcin polypeptide, or mimetic thereof, for the manufacture of a medicament for treatment of frailty in humans.

The present invention also provides the use of an agent that reduces OST-PTP phosphorylase activity, reduces PTP-1B phosphorylase activity, reduces gamma-carboxylase activity, and/or increases undercarboxylated/uncarboxylated osteocalcin for the manufacture of a medicament for treatment of frailty in humans.

In certain embodiments of the uses described herein, the agent inhibits phosphorylation of gamma-carboxylase. In certain embodiments, the agent increases the level of undercarboxylated/uncarboxylated osteocalcin. In certain embodiments, the agent increases the ratio of undercarboxylated/uncarboxylated osteocalcin compared to carboxylated osteocalcin. In certain embodiments, the agent inhibits carboxylation of osteocalcin. In certain embodiments, the agent decarboxylates osteocalcin.

In certain embodiments of the uses described herein, the agent is undercarboxylated/uncarboxylated osteocalcin. Thus, the present invention provides undercarboxylated/uncarboxylated osteocalcin for use in the treatment of frailty in humans.

Also disclosed herein are methods of treating or preventing muscle wasting comprising administering to a patient suffering from muscle wasting a pharmaceutical composition comprising a therapeutically effective amount of undercarboxylated/uncarboxylated osteocalcin and a pharmaceutically acceptable carrier or excipient. In such embodiments, the patient may or may not suffer from frailty.

In some embodiments, the patient suffering from and in need of treatment for muscle wasting is a human who is not suffering from frailty and is at least 55 years of age. In some embodiments, the patient is at least 60, 65, 70, 75, or 80 years old. In certain embodiments, the patient is a human who is between 55 and 80 years old, between 60 and 75 years old, or between 65 and 70 years old. In certain embodiments, the patient is a human who is between 55 and 60 years old, between 65 and 70 years old, between 70 and 75 years old, between 75 and 80 years old, between 80 and 85 years old, or between 85 and 90 years old.

Also disclosed herein are methods of treating or preventing a lung disorder comprising administering to a patient suffering from a lung disorder a pharmaceutical composition comprising a therapeutically effective amount of undercarboxylated/uncarboxylated osteocalcin and a pharmaceutically acceptable carrier or excipient. In some embodiments, the lung disorder is asthma, bronchitis, or chronic obstructive pulmonary disease. In such embodiments, the patient may or may not suffer from frailty.

In some embodiments, the patient suffering from and in need of treatment for a lung disorder is a human who is not suffering from frailty and is at least 55 years of age. In some embodiments, the patient is at least 60, 65, 70, 75, or 80 years old. In certain embodiments, the patient is a human who is between 55 and 80 years old, between 60 and 75 years old, or between 65 and 70 years old. In certain embodiments, the patient is a human who is between 55 and 60 years old, between 65 and 70 years old, between 70 and 75 years old, between 75 and 80 years old, between 80 and 85 years old, or between 85 and 90 years old.

The present invention also provides methods of treating or preventing muscle wasting in a patient comprising administering to a patient suffering from muscle wasting a pharmaceutical composition comprising an agent that modulates the OST-PTP signaling pathway or the PTP-1B signaling pathway, wherein the agent reduces OST-PTP phosphorylase expression or activity or reduces PTP-1B phosphorylase expression or activity, reduces gamma-carboxylase expression or activity, or increases the level of undercarboxylated/uncarboxylated osteocalcin. In certain embodiments, the agent is undercarboxylated/uncarboxylated osteocalcin. In certain embodiments, the agent is human undercarboxylated/uncarboxylated osteocalcin. In such embodiments, the patient may or may not suffer from frailty.

The present invention also provides methods of treating or preventing a lung disorder in a patient comprising administering to a patient suffering from a lung disorder a pharmaceutical composition comprising an agent that modulates the OST-PTP signaling pathway or the PTP-1B signaling pathway, wherein the agent reduces OST-PTP phosphorylase expression or activity or reduces PTP-1B phosphorylase expression or activity, reduces gamma-carboxylase expression or activity, or increases the level of undercarboxylated/uncarboxylated osteocalcin. In certain embodiments, the agent is undercarboxylated/uncarboxylated osteocalcin. In certain embodiments, the agent is human undercarboxylated/uncarboxylated osteocalcin. In some embodiments, the lung disorder is asthma, bronchitis, or chronic obstructive pulmonary disease. In such embodiments, the patient may or may not suffer from frailty.

BRIEF DESCRIPTION OF THE FIGURES

FIG. 9. Analysis of testis weight and size (lower panel) (A), sperm count (B), apoptosis (C), and testosterone serum levels (D) in WT mice injected once daily with vehicle (veh) or a dose of osteocalcin (0, 3 or 30 ng/g) from 2 to 4 months of age.

FIG. 17. Gprc6a is expressed in skeletal muscle. (A) Gprc6a mRNA in various tissues from wild-type mice. (B) Comparison of Gprc6a mRNA from wild-type and Osteocalcin$^{-/-}$ mice.

FIG. 18. Decreased muscle mass and functions in young Osteocalcin$^{+/-}$; Gprc6a$_{Mck}$$^{+/-}$ mice. (A) Ratio of muscle weight to body weight for various muscles in 3-month old Osteocalcin$^{-/-}$, Gprc6a$_{Mck}$$^{+/-}$, and Osteocalcin$^{+/-}$; Gprc6a$_{Mck}$$^{+/-}$ mice for various muscle types. (B) Comparison of distances run and time spent running by 3-month old Osteocalcin$^{-/-}$, Gprc6a$_{Mck}$$^{+/-}$, and Osteocalcin$^{+/-}$; Gprc6a$_{Mck}$$^{+/-}$ mice. Gprc6a$_{Mck}$$^{+/-}$ mice have one copy of Gprc6a disrupted.

FIG. 19. Osteocalcin favors glucose uptake. (A) Effect of increasing amounts of uncarboxylated osteocalcin on $^3$H-2-deoxyglucose uptake in wild-type mice. The effect of insulin is also shown for comparison. (B) Effect of uncarboxylated osteocalcin on 3H-2-deoxyglucose uptake in wild-type and Gprc6a$^{-/-}$ mice.

FIG. 20. Osteocalcin favors glycolysis. (a) Effect of increasing amounts of uncarboxylated osteocalcin on change in extracellular acidification rate (ECAR) in wild-type mice. The effect of insulin is also shown for comparison. (B) Effect of uncarboxylated osteocalcin on ECAR of wild-type and Gprc6a$^{-/-}$ mice. (C) L-lactate production in wild-type and Gprc6a$^{-/-}$ mice.

FIG. 23. Osteocalcin promotes S6K phosphorylation and protein synthesis.

Figure 1:
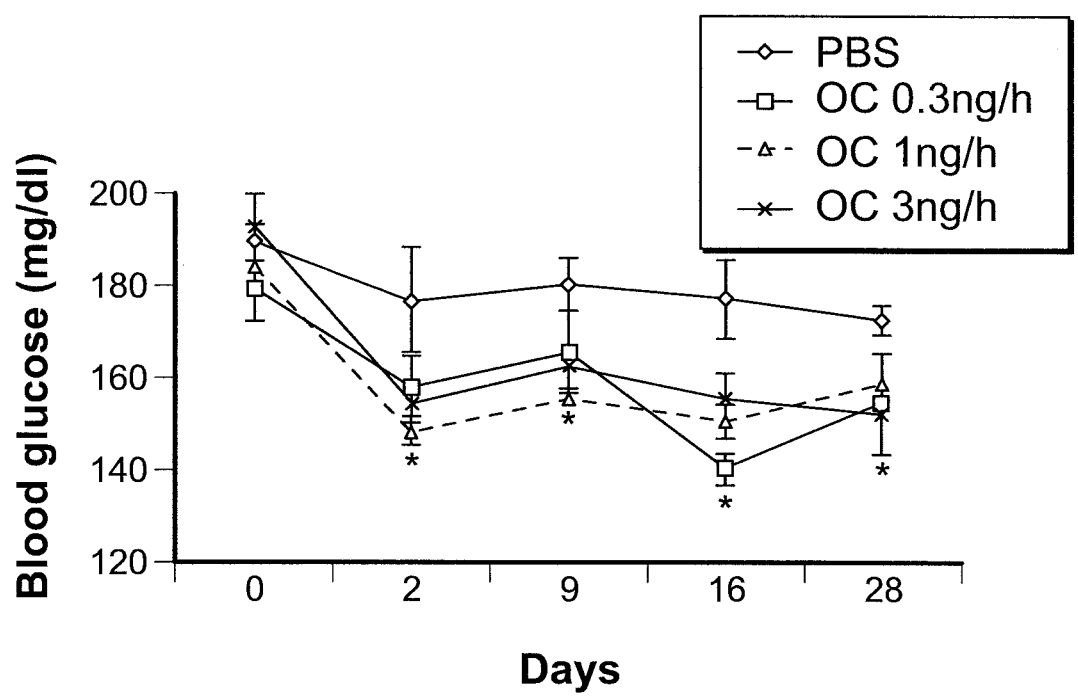
FIG. 1. Osteocalcin subcutaneous infusion decreases glycemia in wild-type mice. Indicated doses of recombinant osteocalcin or PBS were infused subcutaneously for 28 days in wild-type mice. Blood glucose was measured at indicated days.

FIG. 26. Osteocalcin signaling in myofibers promotes glucose uptake. (A) $VO_2$, (B) $VO_2$ max and (C) RER in female Gprc6af/f and Gprc6a$_{Mck}$–/– mice during a gradual speed increase test. (D-E) Uptake of $^3$H-2-deoxyglucose ($^3$H-2-DG) in WT and Gprc6a–/– myotubes treated with vehicle or Ocn (dose indicated in panel D, 10 ng/ml in panel E). (F) Uptake of $^3$H-2-DG in glycolytic (Gly—white quadriceps) and oxidative (Ox—red quadriceps) muscles after a single bout of exercise in Gprc6af/f and Gprc6a$_{Mck}$$^{-/-}$ mice (n=4 per group). (G) Blood glucose levels in Gprc6af/f and Gprc6a$_{Mck}$–/– mice after running on a treadmill until exhaustion (n=4 per group). (H) Blood glucose levels in Gprc6af/f and Gprc6a$_{Hsa}$–/– mice after running on a treadmill until exhaustion (n=4 per group). (I) Western blot analyses of Akt phosphorylation (Ser473) in WT myotubes treated with Ocn (10 ng/ml) and in muscles of WT mice injected with Ocn (500 ng/g) after a single bout of exercise. (J) Western blot analyses of Akt phosphorylation (Ser473) in Gprc6af/f and Gprc6a$_{Mck}$–/– muscles after a single bout of exercise. (K) Glycogen content and glycogen breakdown in Gprc6af/f and Gprc6a$_{Mck}$–/– muscles at rest and after exercise.

FIG. 27. Osteocalcin signaling in myofibers promotes glucose utilization. (A-C) Aspartate and TCA cycle metabolites accumulation in muscles of Gprc6af/f and Gprc6a$_{Mck}$–/– mice at rest and after a single bout of exercise (n=6 per group). (D) $^{13}$C-labeled TCA metabolites and lactate in muscles of Gprc6af/f and Gprc6a$_{Mck}$–/– mice and (E) Gprc6af/f and Gprc6a$_{Hsa}$–/– mice after a single bout of exercise (n=3 per group). (F) Oxygen consumption rate (OCR) in myofibers cultured in KHR buffer containing 25 mM glucose.

FIG. 28. Osteocalcin signaling in myofibers favors uptake and oxidation of fatty acids. (A-B) Acylcarnitine levels in muscles and plasma of Gprc6af/f and Gprc6a$_{Mck}$–/– mice, at rest and after a single bout of exercise (n=4-6 per group). (C) OCR in myofibers cultured in KHR buffer containing 3 mM oleic acid. (D) ATP accumulations in muscles of Gprc6af/f and Gprc6a$_{Mck}$–/– mice after a single bout of exercise (n=6 per group). (E) Western blot analysis of HSL phosphorylation (Ser563) in muscles of Gprc6af/f and Gprc6a$_{Mck}$–/– mice after a single bout of exercise. (F-G) Cd36, Fatp1 and Cpt1b expression in WT and Gprc6a–/– myotubes or WT myotubes treated with Ocn (10 ng/ml). (H) Fatp1 expression in muscles of Gprc6af/f; Gprc6a$_{Mck}$–/– and Ocn+/–; Gprc6a$_{Mck}$+/– mice, at rest and after a single bout of exercise (n=4-6 per group). (I) Western blot analysis of FATP1 in muscle of Gprc6af/f and Gprc6a$_{Mck}$–/– mice after exercise. (J) Cd36, Fatp1 and Cpt1b expression in muscles of Creb f/f and Creb$_{Mck}$–/– mice after a single bout of exercise. (K) Western blot analysis of CREB phosphorylation (Ser133) in muscles of Gprc6af/f and Gprc6a$_{Mck}$–/– mice after a single bout of exercise. (L) Performance during endurance exercise of 3 month-old Gprc6a$_{Mck}$+/–; Creb$_{Mck}$+/–, Creb$_{Mck}$+/– and control mice (n=8-13 per group).

FIG. 29. (A-B) Il6 and Il6rα expression in Gprc6af/f and Gprc6a$_{Mck}$–/– muscles after a single bout of exercise. (C) Circulating IL-6 levels Gprc6af/f and Gprc6a$_{Mck}$–/– mice after a single bout of exercise. (D) Circulating IL-6 levels Gprc6af/f and Gprc6a$_{Hsa}$–/– mice after a single bout of exercise. (E) Total and uncarboxylated osteocalcin levels in wild-type and IL-6–/– mice. (F) Ocn, Rankl, and Opg expression following treatment with IL6 and IL6Rα. (G-H) Change in CTX expression after exercise in IL-6–/– and Gprc6a$_{Mck}$–/– mice.

FIG. 30. (A-B) Circulating levels of total and uncarb-Ocn in 2 to 9 month-old female and male mice (n=5-7 per group). (C) Circulating levels of PINP, a bone formation marker in mice of various ages (n=5-7 per group). (D) Osteocalcin (Ocn) expression in femur in mice of various ages (n=4 per age). (E) Circulating uncarb-Ocn levels in 3, 6 and 12 month-old female and male mice at rest and after a single bout of exercise (n=5-7 per group). (F) Circulating total Ocn levels in 2 to 33 year-old female and male rhesus macaque monkeys (n=5-7 per group). (G) Circulating total Ocn levels in 11 to 78 year-old women and men (n=6 per group).

FIG. 31. Osteocalcin treatment increases muscle function in young and old WT mice. (A-B) Performance during endurance exercise of 3 month-old WT, Gprc6af/f and Gprc6a$_{Mck}$–/– female mice treated with Ocn (n=6-10 per group). (C) Performance during endurance exercise of 12 and 15 month-old WT female mice treated with Ocn (n=6-10 per group). (D) Western blot analysis of Akt phosphorylation (Ser473) in muscles of WT mice injected with Ocn (500 ng/g) after a single bout of exercise. (E) Western blot analysis of AMPK phosphorylation (Thr179) in muscles of WT mice injected with Ocn (500 ng/g) after a single bout of exercise. (F) Western blot analysis of HSL phosphorylation (Ser563) in muscles of WT mice injected with Ocn (500 ng/g) after a single bout of exercise. (G) Uptake of $^3$H-2-DG in glycolytic (Gly—white quadriceps) and oxidative (Ox—red quadriceps) muscles after a single bout of exercise in 15 month-old WT mice receiving Ocn before running (n=5 per group). (H) Performance during endurance exercise of 10 month-old WT mice receiving Ocn for 28 days (n=7 per group). (I) Expression of Cd36, Fatp1 and Cpt1b in gastrocnemius of 10 month-old WT mice receiving Ocn for 28 days (n=7 per group). (J) Western blot analysis of Akt phosphorylation (Ser473) in muscles of WT mice receiving Ocn for 28 days (n=7 per group). (K) Schematic representation of how osteocalcin signaling in myofibers and IL-6 cooperate to increase exercise capacity.

DETAILED DESCRIPTION OF THE INVENTION

Disclosed herein are methods of treating frailty. Treating frailty means actively intervening after onset of frailty to slow down, ameliorate symptoms of, minimize the extent of, or reverse the frailty in a patient who is known to have, or is suspected of having, frailty. Alleviating muscle wasting, a lung disorder, a metabolic disorder, a male reproductive disorder, or a cognitive disorder means actively intervening after onset of the muscle wasting, lung disorder, metabolic disorder, male reproductive disorder, or cognitive disorder to slow down, ameliorate symptoms of, minimize the extent of, or reverse the muscle wasting, lung disorder, metabolic disorder, male reproductive disorder, or cognitive disorder in a patient who is known to have, or is suspected of having, muscle wasting, lung disorder, metabolic disorder, male reproductive disorder, or cognitive disorder.

Frailty is characterized by at least two or more of the following disorders or conditions associated with aging: (a) muscle wasting; (b) lung disorders; (c) metabolic disorders; (d) male reproductive disorders; and (e) cognitive disorders.

"Muscle wasting," sometimes referred to as sarcopenia, is a progressive loss of muscle mass and functions. It is a nearly universal hallmark of aging and often occurs after bone mass decreases. It cellular and molecular underpinnings are unknown.

"Lung disorders" include diseases and conditions in which bronchoconstriction plays a role, e.g., asthma, bronchitis, or chronic obstructive pulmonary disease.

"Metabolic disorders" include metabolic syndrome, glucose intolerance, type 1 diabetes, type 2 diabetes, atherosclerosis, and obesity.

"Male reproductive disorders" include male infertility, low sperm count, impaired sperm motility, impaired sperm viability, low testosterone levels, reduced libido, erectile dysfunction, underdevelopment of testes, and excess apoptosis in testes.

"Cognitive disorders" include conditions characterized by temporary or permanent loss, either total or partial, of the ability to learn, memorize, solve problems, process information, reason correctly, or recall information, where the loss arises as a result of the normal aging process. In some embodiments, the cognitive disorder is the result of such age-related factors as a specific neurodegenerative disease (e.g., Alzheimer's disease, Parkinson's disease, Huntington's disease, or amyotrophic lateral sclerosis) or vascular conditions (e.g., stroke, ischemia) in the brain. When the cognitive disorder is memory loss, the loss may occur in short term or long term memory. Cognitive disorders also include various forms of dementia.

In some embodiments of the methods of treating frailty disclosed herein, the methods comprise alleviating at least one of (a) muscle wasting or (b) a lung disorder, while at the same time alleviating at least one of (c) a metabolic disorder, (d) a male reproductive disorder, or (e) a cognitive disorder.

In some embodiments of the methods of treating frailty disclosed herein, the methods comprise alleviating at least (a) muscle wasting and at least one of (c)-(e) metabolic disorders, male reproductive disorders, or cognitive disorders. In some embodiments of the methods of alleviating frailty disclosed herein, the methods comprise alleviating at least (b) a lung disorder and at least one of (c)-(e) metabolic disorders, male reproductive disorders, or cognitive disorders.

In some embodiments, the methods comprise alleviating at least (a) muscle wasting and (c) a metabolic disorder. In some embodiments, the methods comprise alleviating at least (a) muscle wasting and (d) a male reproductive disorder. In some embodiments, the methods comprise alleviating at least (a) muscle wasting and (e) a cognitive disorder.

In some embodiments, the methods comprise alleviating at least (b) a lung disorder and (c) a metabolic disorder. In some embodiments, the methods comprise alleviating at least (b) a lung disorder and (d) a male reproductive disorder. In some embodiments, the methods comprise alleviating at least (b) a lung disorder and (e) a cognitive disorder.

In some embodiments, the methods comprise alleviating (a) muscle wasting and (b) a lung disorder. In some embodiments, the methods comprise alleviating (a) muscle wasting and (b) a lung disorder as well as at least one of (c)-(e) metabolic disorders, male reproductive disorders, or cognitive disorders. In some embodiments, the methods comprise alleviating (a) muscle wasting and (b) a lung disorder as well as (c) a metabolic disorder. In some embodiments, the methods comprise alleviating (a) muscle wasting and (b) a lung disorder as well as (d) a male reproductive disorder. In some embodiments, the methods comprise alleviating (a) muscle wasting and (b) a lung disorder as well as (e) a cognitive disorder.

In some embodiments, the methods comprise alleviating (a) muscle wasting, (b) a lung disorder, (c) a metabolic disorder, (d) a male reproductive disorder, and (e) a cognitive disorder.

A "patient" is a mammal, preferably a human, but can also be a companion animal such as dogs or cats, or farm animals such as horses, cattle, pigs, or sheep. In certain embodiments, the patient is a human who is at least 55, 60, 65, 70, 75, or 80 years old. In certain embodiments, the patient is a human who is between 55 and 80 years old, between 60 and 75 years old, or between 65 and 70 years old. In certain embodiments, the patient is a human who is between 55 and 60 years old, between 65 and 70 years old, between 70 and 75 years old, between 75 and 80 years old, between 80 and 85 years old, or between 85 and 90 years old.

A patient in need of treatment for frailty includes a patient known to have, or suspected of having, or is at risk of developing, frailty. Such a patient in need of treatment could be, e.g., a mammal known to have low undercarboxylated/uncarboxylated osteocalcin levels. Patients in need of treatment by the methods of the present invention include patients who are known to be in need of therapy to increase serum undercarboxylated/uncarboxylated levels in order to treat frailty.

A patient in need of treatment of frailty by the methods of the present invention does not include a patient being administered the therapeutic agents described herein only for a purpose other than to treat frailty. Thus, e.g., a patient in need of treatment of frailty by the methods of the present invention does not include a patient being treated with osteocalcin only for the purpose of alleviating a bone mass disease, or a metabolic disorder such as metabolic syndrome, glucose intolerance, type 1 diabetes, type 2 diabetes, atherosclerosis, or obesity. Nor does it include a patient being treated with osteocalcin only for the purpose of causing an increase in glucose tolerance, an increase in insulin production, an increase insulin sensitivity, an increase in pancreatic beta-cell proliferation, an increase in adiponectin serum level, a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, or a decrease in the thickness of arterial plaque.

A patient in need of treatment of frailty by the methods of the present invention also does not include a patient being treated with osteocalcin only for the purpose of alleviating a male reproductive disorder or a cognitive disorder.

A patient in need of treatment of frailty by the methods of the present invention also does not include a patient being treated with osteocalcin that is not undercarboxylated/uncarboxylated osteocalcin, e.g., fully carboxylated osteocalcin.

Data herein show that osteocalcin signaling in myofibers favors adaptation to exercise because it increases uptake and utilization of glucose into the tricarboxylic acid cycle and promotes fatty acids utilization. Osteocalcin signaling in myofibers is also the main determinant of the exercise-induced upregulation of Interleukin-6, a myokine that favors the generation of bioactive osteocalcin and of nutrients made available for myofibers. Furthermore, circulating osteocalcin levels decline steeply before mid-life and do not increase during exercise in older mice. This explains why exogenous osteocalcin increases exercise capacity in young mice and confers to 15 month-old mice exercise capacity of 3 month-old mice. Thus there is an osteocalcin-interleukin-6 axis that is necessary to enhance muscle function during exercise and can be harnessed to reverse age-induced decline in exercise capacity.

Data herein show that, by signaling in myofibers, osteocalcin favors adaptation to exercise because it promotes glucose uptake and utilization in the tricarboxylic acid (TCA) cycle as well as utilization of FAs. Osteocalcin signaling in myofibers is also responsible for most of the increase during exercise of the circulating levels of interleukin-6 (IL-6) a myokine that favors glucose and FA production, and signals in osteoblasts to favor the production of bioactive osteocalcin. In contrast, circulating osteocalcin levels decrease sharply before mid-life in all species tested, and do not increase during exercise in older mice to the same extent than in young mice. In agreement with the functions of osteocalcin and with the evolution of its circulating levels over time, exogenous osteocalcin increases the exercise capacity of young mice and confers to 12 to 15 month-old mice the exercise capacity of 3 month-old mice. These results reveal the existence of a crosstalk between osteocalcin signaling in myofibers and IL-6 that, along with the ability of IL-6 to generate glucose and FAs, promotes adaptation to exercise and can be harnessed to increase the exercise capacity of young mice and normalize that of older ones.

Osteocalcin Signaling in Myofibers Favors Adaptation to Exercise

Measuring the circulating levels of undercarboxylated and biologically active osteocalcin in various physiological situations revealed that a long-term, aerobic-based exercise (40 minutes run on a treadmill at 30 cm/s, thereafter referred to as exercise) increased osteocalcin levels two-fold in 3 month-old wild-type (WT) mice because of an increase in bone resorption, the arm of bone remodeling responsible for osteocalcin decarboxylation (Ferron et al., 2010, Cell 142: 296-308). A molecular explanation for this increase in bone resorption during exercise is presented below as part of muscle signaling to bone. Circulating osteocalcin levels also increased in young women after a bout of exercise. In view of these observations whether osteocalcin regulates adaptation to exercise was tested. Given the influence of testosterone on physical activity and the low circulating testosterone levels in male Osteocalcin (Ocn)-/- mice (Oury et al., 2011, Cell 144:796-809), this question was addressed in female mice.

Figure 25E:
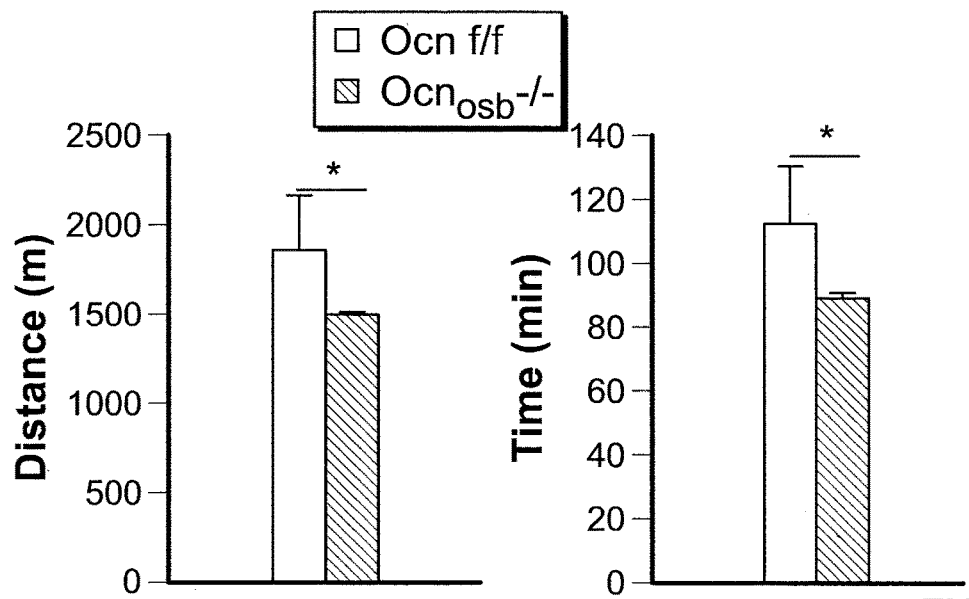
FIG. 25. Osteocalcin signaling in myofibers is necessary for muscle function during exercise. (A) Serum total osteocalcin (Ocn) and insulin (Ins) levels measured in mice at rest or after a single bout of exercise (40 min, 30 cm/s running on a treadmill) (n=7 per group). (B) Serum uncarboxylated (uncarb)-Ocn levels measured in mice at rest and 0, 1, 2 and 4 hours after a single bout of exercise (40 min, 30 cm/s running on a treadmill) (n=7 per group). (C) Serum CTX levels in mice at rest and after a single bout of exercise (n=7 per group). (D) Performance during endurance exercise of 3 month-old female Ocn-deficient and WT littermates (n=8-10 per group). (E) Performance during endurance exercise of 3 month-old Ocn f/f and Ocn$_{Osb}$–/– littermates (n=3-5 per group). (F) Performance during endurance exercise of 3 month-old female Gprc6a-deficient and WT littermates (n=8-10 per group). (G) Gprc6a expression in various tissues. (H) Gprc6a expression in EDL and soleus muscles (n=3). (I) In situ hybridization analysis of Gprc6a expression in soleus muscle. (J) Gprc6a expression in WT and Ocn–/– muscles (n=6 per group). (K) cAMP accumulation in WT and Gprc6a–/– myotubes treated with vehicle or Ocn (10 ng/ml). (L) Performance during endurance exercise of 3 month-old female Gprc6af/f and Gprc6a$_{Mck}$–/– mice (n=8-10 per group). (M) Performance during endurance exercise of 3 month-old female Gprc6af/f and Gprc6a$_{Hsa}$–/– mice (n=8-10 per group). (N) Performance during endurance exercise of 3 month-old female Ocn+/–; Gprc6a$_{Mck}$+/– mice and control littermates (n=8-10 per group).
Figure 25F:
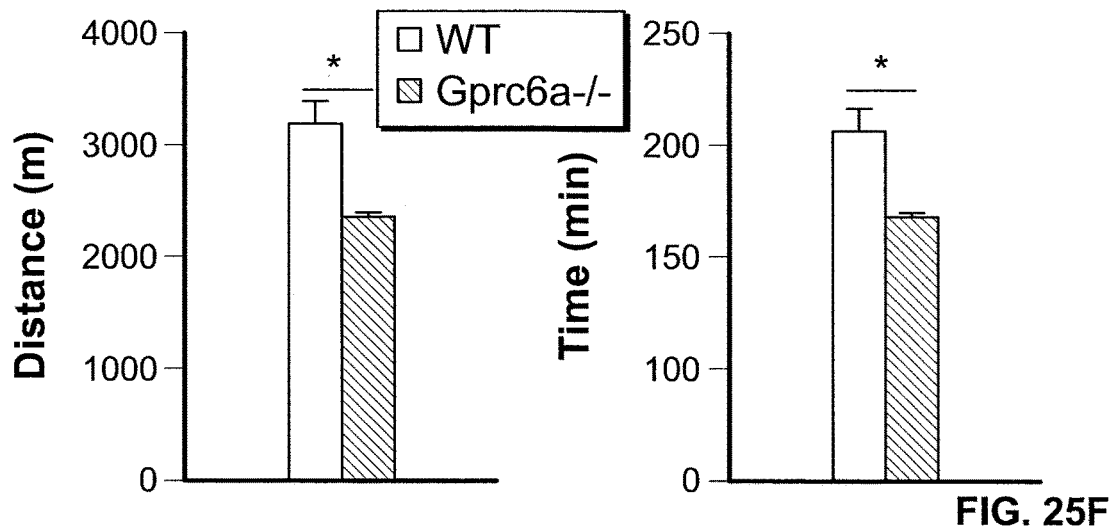

When forced to run on a treadmill at a constant speed until exhaustion, 3, 6 and 9 month-old Ocn-/- mice run 30% less time and distance than WT littermates (FIG. 25D). This was caused by the absence of signaling from bone to muscle, since the same decline in exercise capacity was also observed in mice lacking osteocalcin only in osteoblasts and post-natally (FIG. 25E). This decline in exercise capacity was not observed in 2 month-old Ocn-/- mice indicating that this phenotype is not of developmental origin. Three month-old mice lacking osteocalcin receptor, a GPCR termed Gprc6a (Oury et al., 2011, Cell 144:796-809), experienced the same decrease in exercise capacity as Ocn-/- mice (FIG. 25F).

Figure 25G:
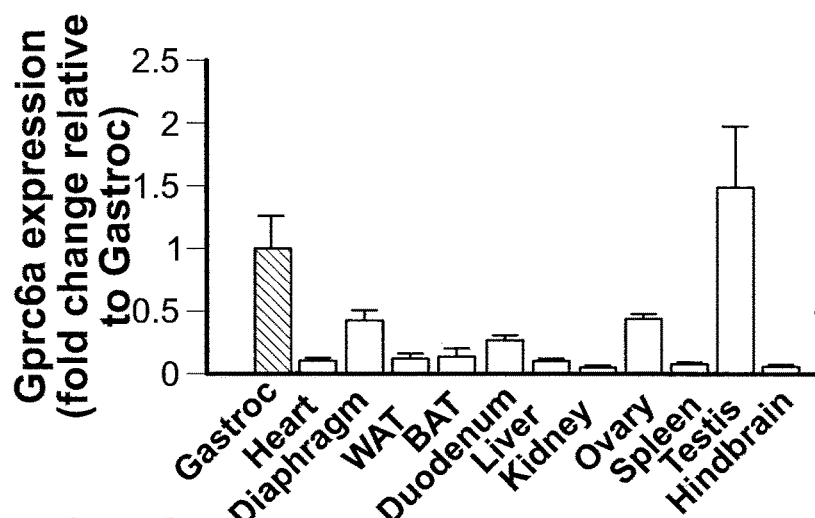
Figure 25H:
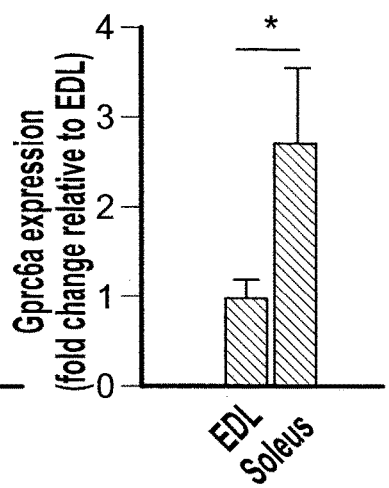

Ocn-/- and Gprc6a-/- mice display metabolic and/or behavioral abnormalities that make the interpretation of any phenotype linked to exercise difficult. To exclude these confounding factors and determine if osteocalcin promotes adaptation to exercise by signaling in skeletal muscle, Gprc6a expression and function in this tissue were studied. A qPCR survey showed that Gprc6a was more highly expressed in skeletal muscles than in most tissues and more so in oxidative muscles (soleus), which are needed for prolonged effort, than in glycolytic muscles (EDL), while in situ hybridization analysis demonstrated that Gprc6a is expressed in myofibers (FIG. 25G-I). Gprc6a expression was three-fold higher in Ocn-/- than in WT muscle and osteocalcin did not increase cAMP production in Gprc6a-/- myotubes as it did in WT ones (FIG. 25J-K). These data suggested that Gprc6a might mediate osteocalcin signal in myofibers. To test this hypothesis, mice harboring a floxed allele of Gprc6a were crossed with Mck-Cre or Hsa-Cre deleter mice (Bruning et al., 1998, Molecular Cell 2:559-569). Gprc6a expression was decreased over 50% in skeletal muscles of $Gprc6a_{Mck}$-/- and $Gprc6a_{Hsa}$-/- mice and glucose tolerance and insulin sensitivity were normal in these mutant mice.

Figure 25M:
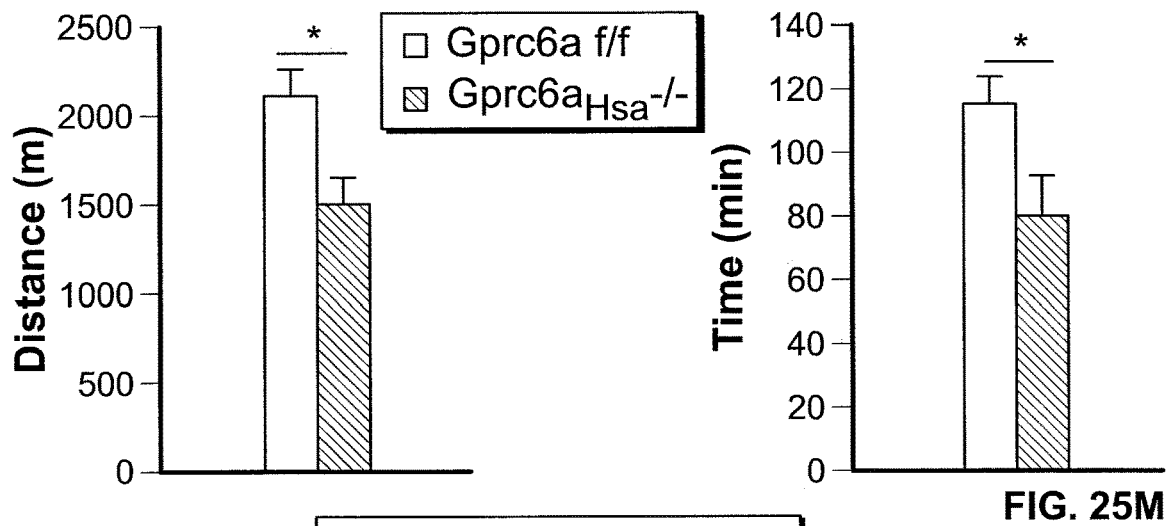
Figure 25N:
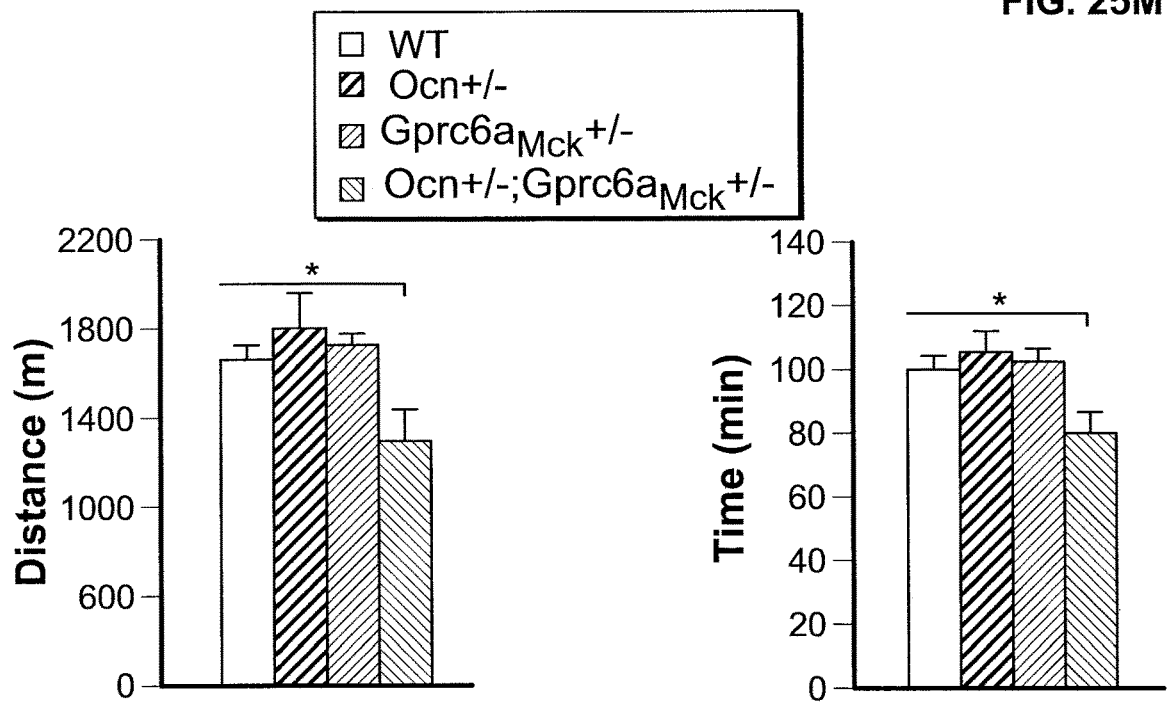

Starting at 3 months of age, $Gprc6a_{Mck}$-/- and $Gprc6a_{Hsa}$-/- mice experienced a decrease in exercise capacity of equal severity as the one noted in Ocn-/- mice (FIG. 25L-M). This was not due to a disruption of the intrinsic properties of muscle, since the excitation-contraction coupling and resistance to fatigue were similar in muscles isolated from $Gprc6a_{Mck}$-/- and control mice. The same decrease in exercise capacity was seen in compound mutant mice lacking one allele of Osteocalcin and one allele of Gprc6a in myofibers (Ocn+/-; $Gprc6a_{Mck}$+/-), thus demonstrating that osteocalcin favors adaptation to exercise by signaling through Gprc6a in myofibers (FIG. 25N). On the other hand, multiple evidences suggested that osteocalcin does not favor adaptation to exercise by signaling in the heart: Gprc6a expression is 20-fold lower in the heart than in skeletal muscle; heart function is normal in $Gprc6a_{Mck}$-/- and Ocn-/- mice; more directly, deleting Gprc6a only in cardiomyocytes does not affect exercise capacity of mice (FIG. 25G).

Figure 26A:
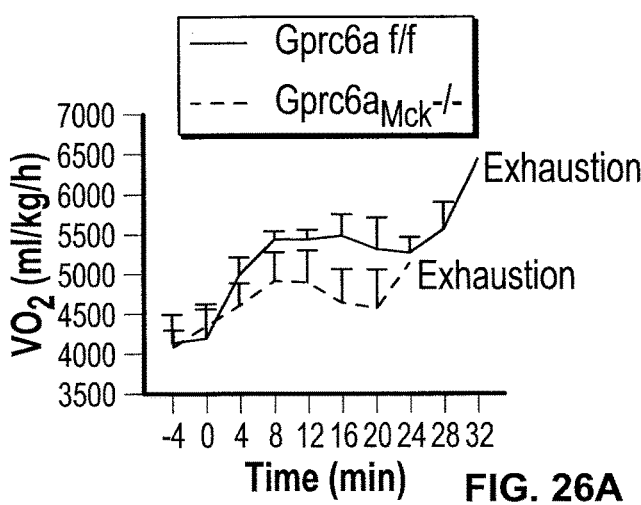
Figure 26B:
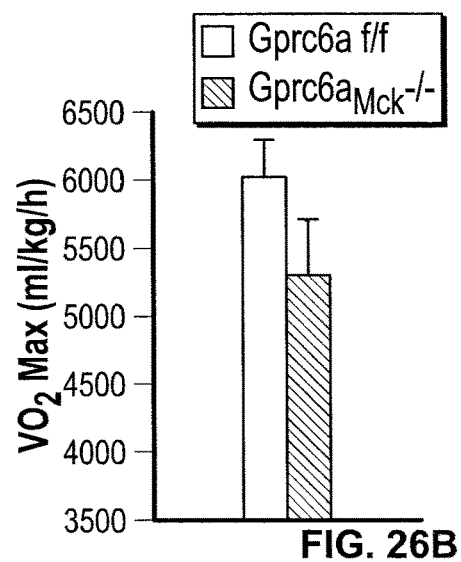
Figure 26C:
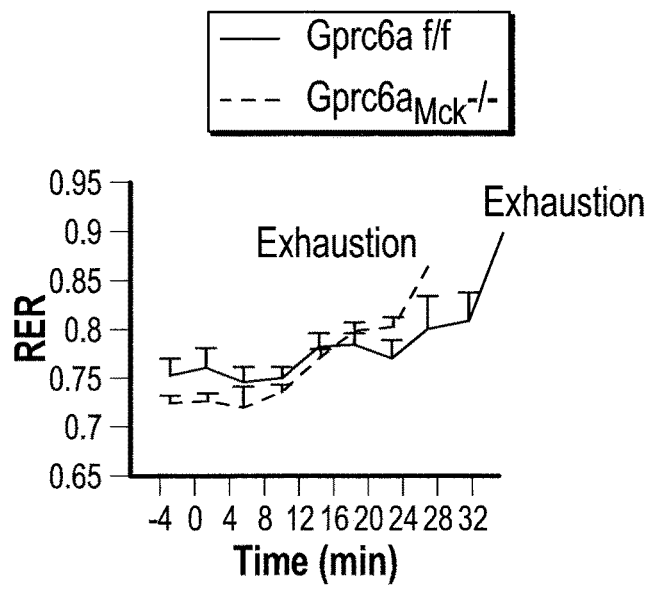

Osteocalcin Signaling in Myofibers Promotes Glucose Uptake and Utilization During Exercise To determine how osteocalcin signaling in myofibers favors adaptation to exercise, nutrient utilization via indirect calorimetry in $Gprc6a_{Mck}$-/- and control mice running on a treadmill at an increasing speed until exhaustion was measured. In the conditions of this assay, the maximal oxygen consumption was decreased around 20% in all $Gprc6a_{Mck}$-/- mice analyzed whereas their respiratory exchange ratio was similar to the one of control mice (FIG. 26A-C). These results suggesting that osteocalcin signaling in myofibers promotes aerobic capacity during exercise led us to test if osteocalcin signaling in myofibers affects mitochondrial number/respiration and/or the uptake and utilization of nutrients.

The number of mitochondria in muscles was the same in 3 month-old Ocn-/- mice that already have a poor exercise capacity, and WT littermates. Expression of the transcriptional determinant of mitochondrial biogenesis and muscle adaptation to exercise Pgc1α (Da Cruz et al., 2012, Cell Metabol. 15:778-786; Handschin and Spiegelman, 2008, Nature 454:463-469; Ruas et al., 2012, Cell 151:1319-1331), and of its target genes was similar in muscles of Ocn-/-, $Gprc6a_{Mck}$-/- and control mice after exercise. The activities of the mitochondrial proteins COX and SDH were the same in Gprc6a$_{Mck}$-/- and control muscles, and there was no difference in mitochondria respiration between WT and Gprc6a-/- myofibers cultured in the presence of glucose, pyruvate, and amino acids. Given their negative nature, these results need to be interpreted cautiously. They indicate however, that the ability of osteocalcin signaling in myofibers to favor adaptation to exercise is not secondary to a measurable effect on mitochondrial number or respiration. This led to an investigation of whether osteocalcin signaling in myofibers influences nutrient uptake and utilization during exercise.

Figure 26D:
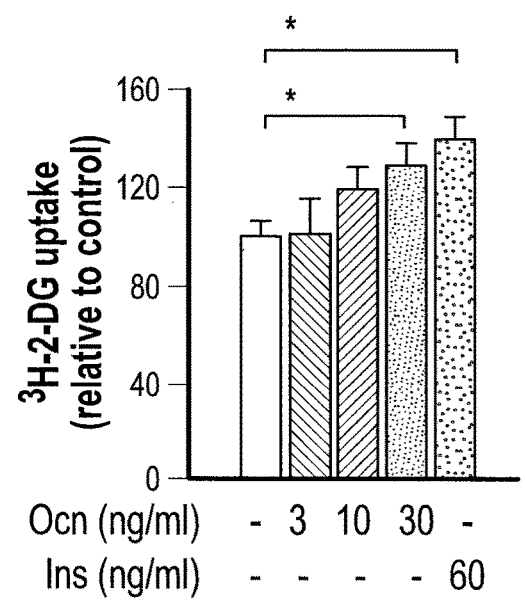
Figure 26E:
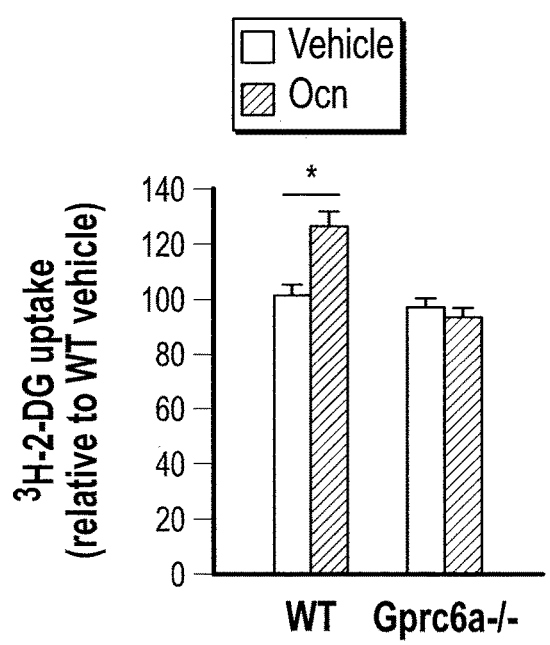
Figure 26F:
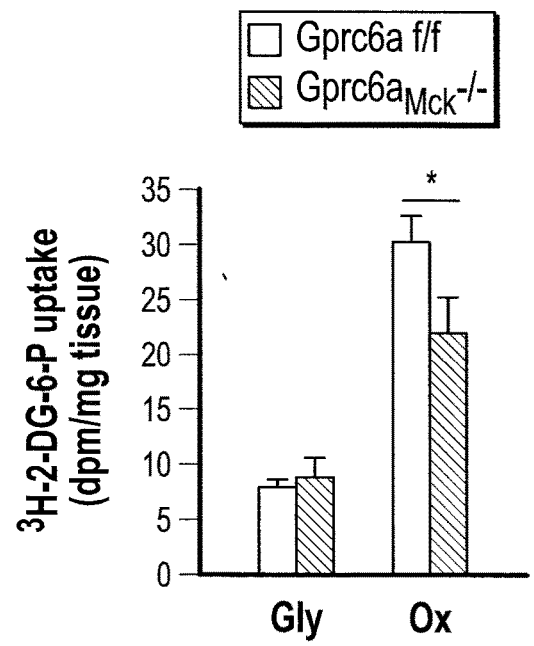
Figure 26G:
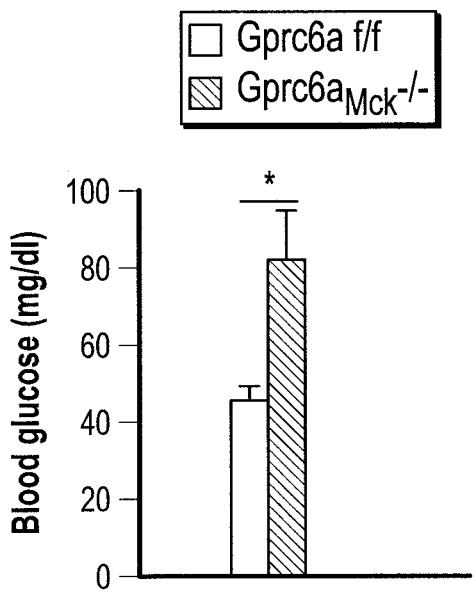
Figure 26H:
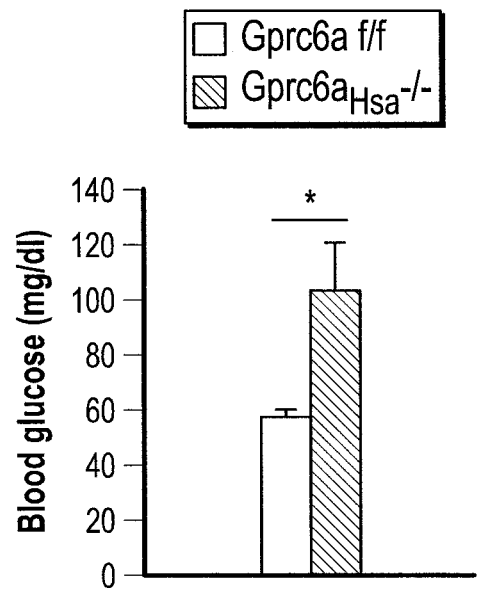

The main nutrient used by muscle to generate energy at the onset of exercise is glucose and osteocalcin increased the uptake of $^3$H-2-deoxyglucose ($^3$H-2DG) in WT but not in Gprc6a-/- myotubes (FIG. 26D-E). To exclude the involvement of other secreted molecules, this experiment was performed in serum-free conditions. In agreement with these results in vivo, the uptake of $^3$H-2DG was significantly decreased in oxidative muscles that are the more heavily solicited, but not in glycolytic muscles in Gprc6a$_{Mck}$-/- mice after exercise (FIG. 26F). This decrease in glucose uptake in muscles of Gprc6a$_{Mck}$-/- mice provides an explanation for why blood glucose levels were two-fold higher in Gprc6a$_{Mck}$-/- and Gprc6a$_{Hsa}$-/- than in control mice after exercise (FIG. 26G-H). Of note, such an increase in blood glucose levels after exercise was not observed in mice lacking insulin signaling in muscle (Wojtaszewski et al., 1999, J. Clin. Invest. 104:1257-1264); this suggests that osteocalcin and insulin exerts distinct functions in myofibers.

Figure 26I:
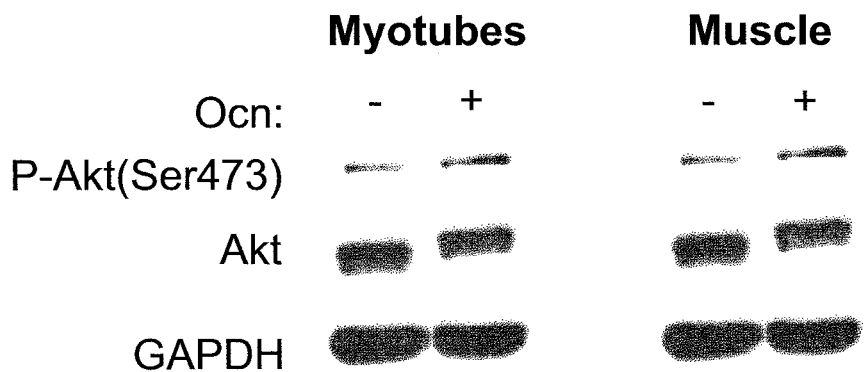
Figure 26J:

Osteocalcin did not affect the expression in muscles of the glucose transporters Glut1 and Glut4 at rest or after exercise. Rather, it promoted the translocation of GLUT4 to the plasma membrane of C2C12 myoblasts that express both Gprc6a and Glut4. A similar increase in the accumulation of GLUT4 was observed after exercise in WT but not in Gprc6a$_{Mck}$-/- mice (FIG. 26I). Signaling through GPCRs can favor PI3K activation, leading to Akt phosphorylation, an event that favors the translocation of GLUT4 to the plasma membrane (Lopez-Ilasaca et al., 1997, Science 275: 394-397). In agreement with this notion, Akt phosphorylation in muscles of Gprc6a$_{Mck}$-/- mice was decreased compared to muscles of control mice after exercise. Osteocalcin induced phosphorylation of Akt in cultured myotubes or muscles of WT mice and a PI3K inhibitor abrogated the ability of osteocalcin to induce GLUT4 translocation in myoblasts (FIG. 26I-J).

Figure 27D:
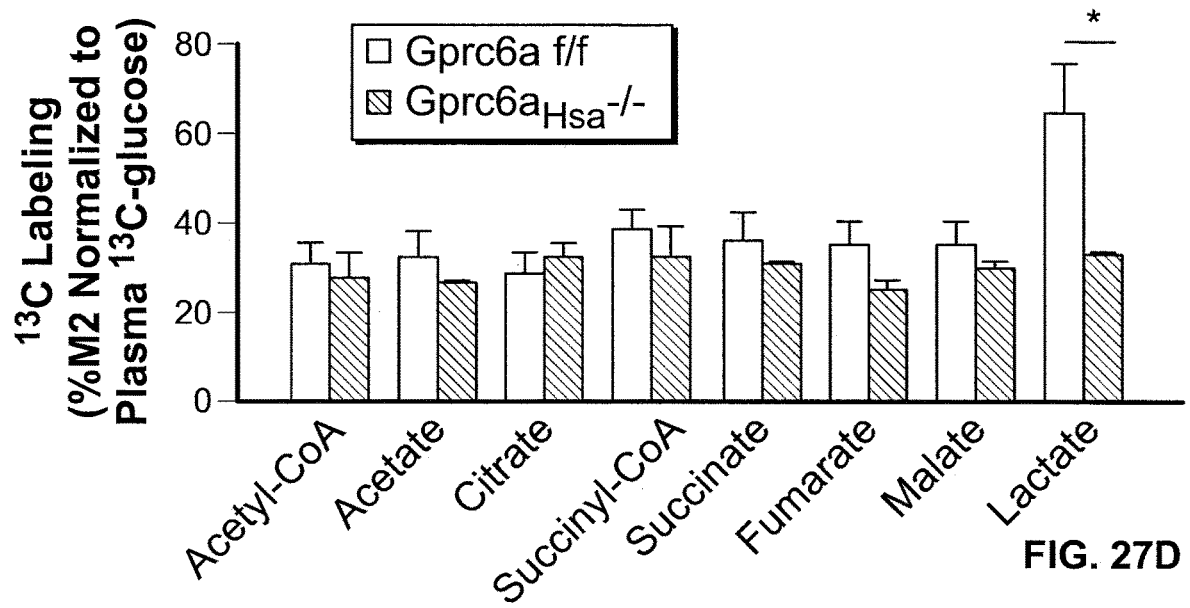
Figure 27E:
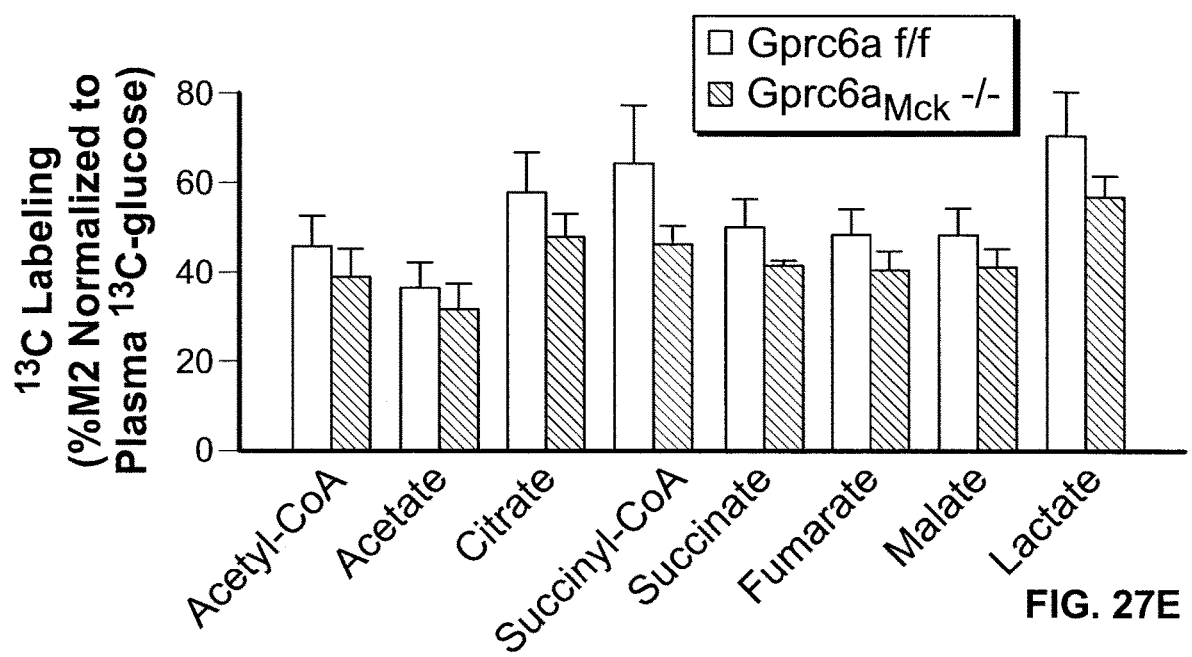
Figure 27F:
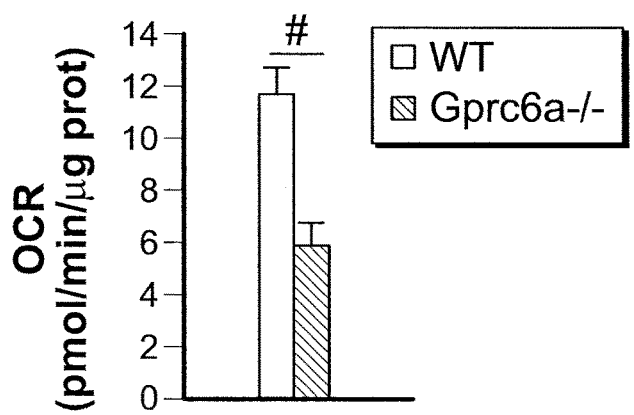

Glucose in myofibers is stored in the form of glycogen that is broken down into glucose during exercise. Exercise-induced glycogen breakdown, defined by the difference between muscle glycogen levels at rest and after exercise, was significantly decreased in muscle of Gprc6a$_{Mck}$-/- compared to those of control mice (FIG. 26K). This decline in the ability to generate glucose from glycogen is likely to contribute to the decreased exercise capacity observed in Gprc6a$_{Mck}$-/- mice. During exercise, glucose is degraded in myofibers to generate acetyl-CoA that enters the tricarboxylic acid (TCA) cycle to be fully oxidized (oxidative phosphorylation). A metabolomics analysis performed in muscle before and after exercise showed that the accumulation of aspartate, a reliable indicator of the cellular levels of oxaloacetate that is needed to increase the activity of the TCA cycle, and of fumarate and malate, the two TCA cycle intermediates that increase the most during exercise (Gibala et al., 1998, Am. J. Physiol. 275:E235-242; Sahlin et al., 1990, Am. J. Physiol. 259:C834-841), did not rise to the same extent in muscles of Gprc6a$_{Mck}$-/- than in those of control mice after exercise (FIG. 27A-C). In agreement with these observations, the accumulation of $^{13}$C-labeled TCA intermediates and lactate was decreased in muscle Gprc6a$_{Mck}$-/- and Gprc6a$_{Hsa}$-/- mice injected with $^{13}$C-glucose just prior to exercise (FIG. 27D-E). These results, indicating that the utilization of glucose in the TCA cycle is decreased during exercise in muscle of mice lacking osteocalcin signaling in myofibers, explain why the oxygen consumption rate (OCR) is markedly lower in Gprc6a-/- than WT myofibers when the only available substrate for these myofibers is glucose (FIG. 27F).

Osteocalcin Signaling in Myofibers Favors FA Utilization During Exercise

During an endurance exercise, there is a progressive increase of lipolysis and fatty acid (FA) uptake and oxidation in skeletal muscle (Hawley et al., 2014; Koves et al., 2005). Thus whether osteocalcin signaling in myofibers also affects uptake and/or utilization of FAs during exercise was tested by measuring muscle and plasma levels of acylcarnitines, a reliable indicator of FA metabolism (Overmyer et al., 2015).

Figure 28A:
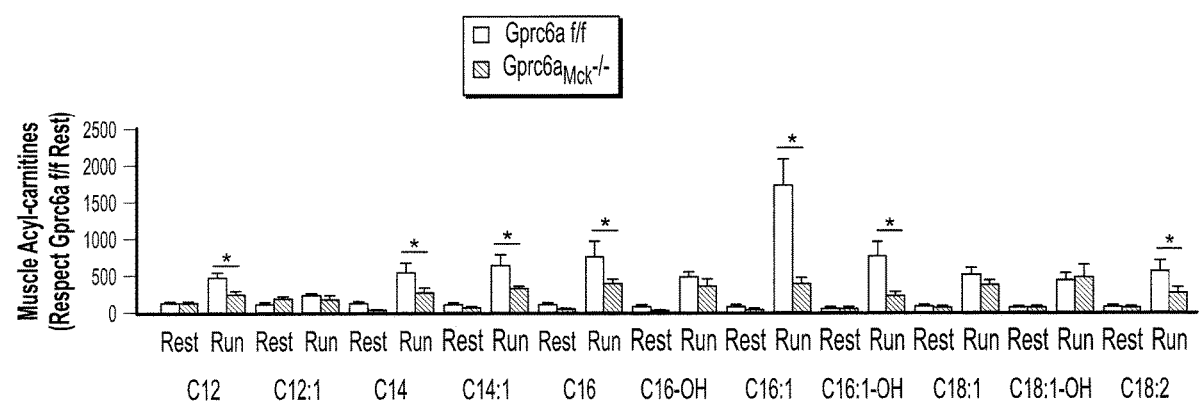
Figure 28B:
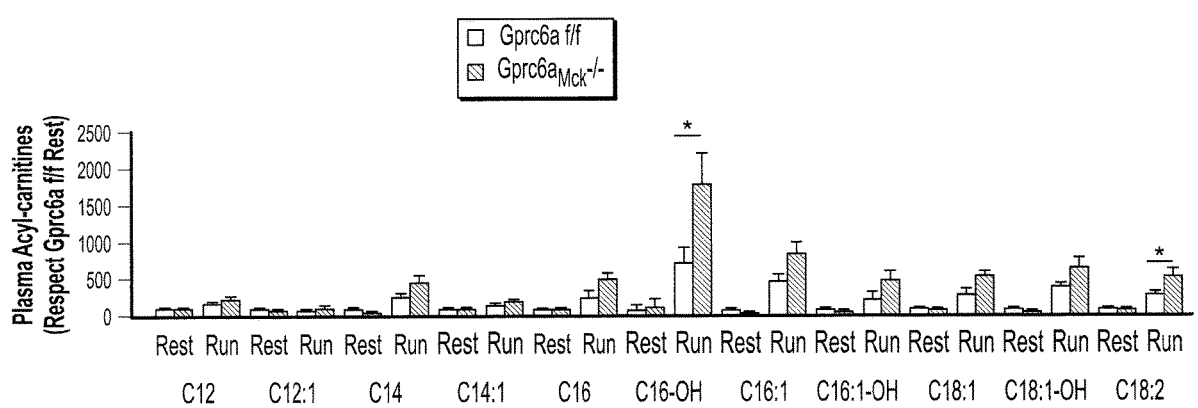
Figure 28C:
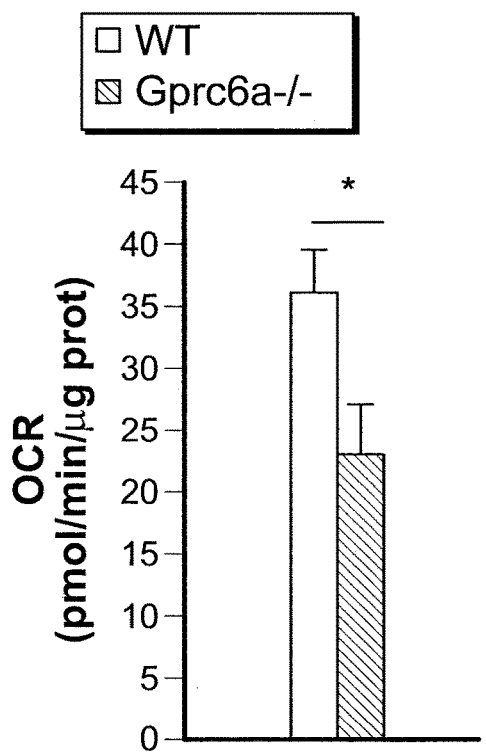

It was found that the accumulation of long and medium-chain acylcarnitines observed in muscles of control mice after exercise did not occur to the same extent in muscles of Gprc6a$_{Mck}$-/- mice (FIG. 28A). There was instead a significant rise in acylcarnitine accumulation in the plasma in Gprc6a$_{Mck}$-/- mice (FIG. 28B). Moreover, the levels of free L-carnitine that significantly declined in muscles of controls mice after exercise did not do so in Gprc6a$_{Mck}$-/- mice. These results suggest that osteocalcin signaling in myofibers is needed for efficient FA utilization during exercise. These results provide an explanation for why osteocalcin could not increase $^{14}$C-oleate oxidation in Gprc6a-/- myotubes as it did in WT ones and for why the OCR was significantly lower in Gprc6a-/- than WT myofibers when oleate was the only substrate available to these myofibers (FIG. 28C).

Figure 28D:
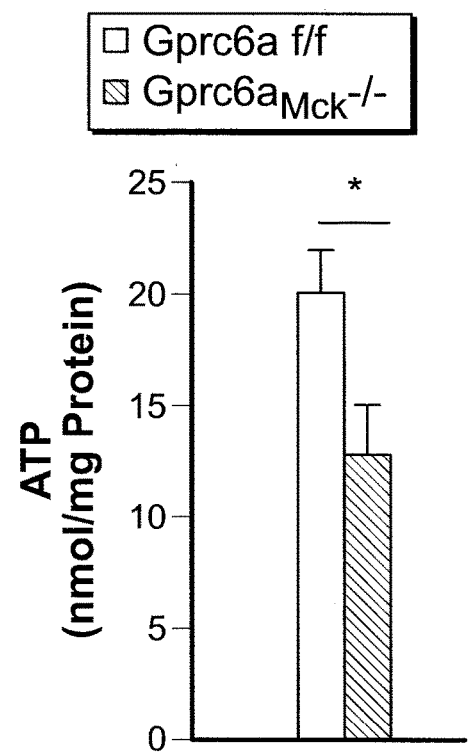

In sum, the metabolic analyses performed in Gprc6a$_{Mck}$-/- mice before and after exercise showed that osteocalcin signaling in myofibers favors uptake and utilization of glucose and FAs. Thus, osteocalcin should be necessary to generate the ATP required for optimum muscle performance during exercise. In agreement with this hypothesis, ATP levels were significantly lower in muscles of Gprc6a$_{Mck}$-/- mice than in those of controls after exercise (FIG. 28D).

Figure 28E:
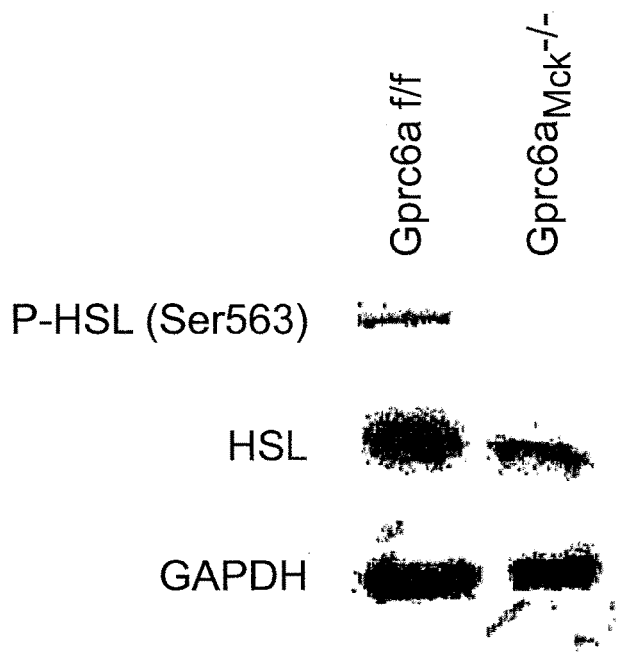

The regulation of FA uptake and utilization by osteocalcin occurs in part through post-transcriptional mechanisms. The cellular energy sensor AMPK favors FA utilization during exercise by increasing the activity of CPT1B following its phosphorylation at Thr172 (O'Neill et al., 2014, Diabetologia 57:1693-1702); this phosphorylation however, was markedly weaker in muscles of Gprc6a$_{Mck}$-/- than in those of control mice after exercise. The enzyme hormone sensitive lipase (HSL) favors hydrolysis of intramyocellular triglycerides into free fatty acids in muscle once it is phosphorylated at Ser563 (Watt and Spriet, 2010, Am. J. Physiol. Endocrinol. Metab. 299:E162-168). While osteocalcin enhanced HSL phosphorylation at ser563 in muscle of WT mice, this phosphorylation event was weaker in muscles of Gprc6a$_{Mck}$-/- than in those of control mice after exercise (FIG. 28E).

Figure 28F:
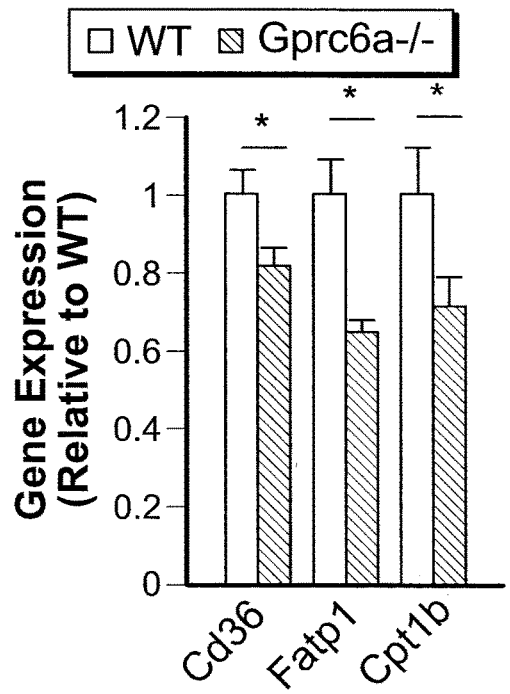
Figure 28G:
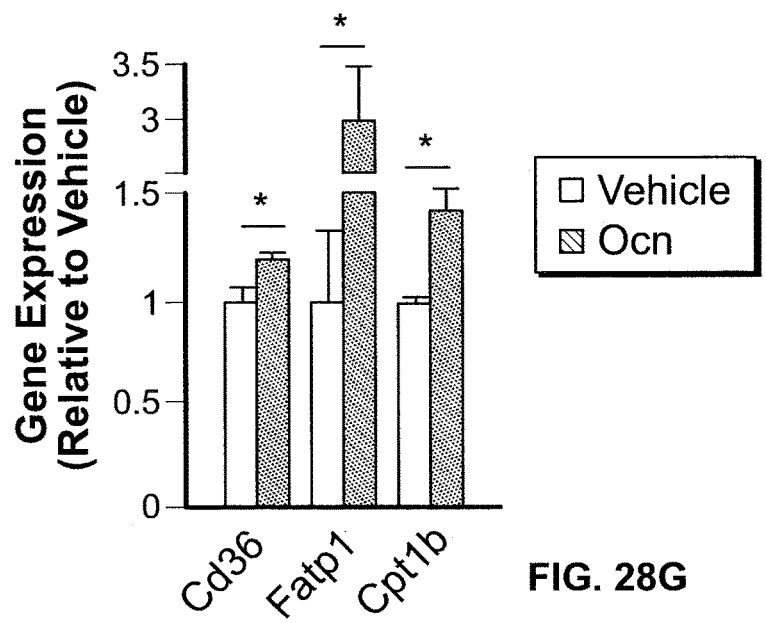
Figure 28H:
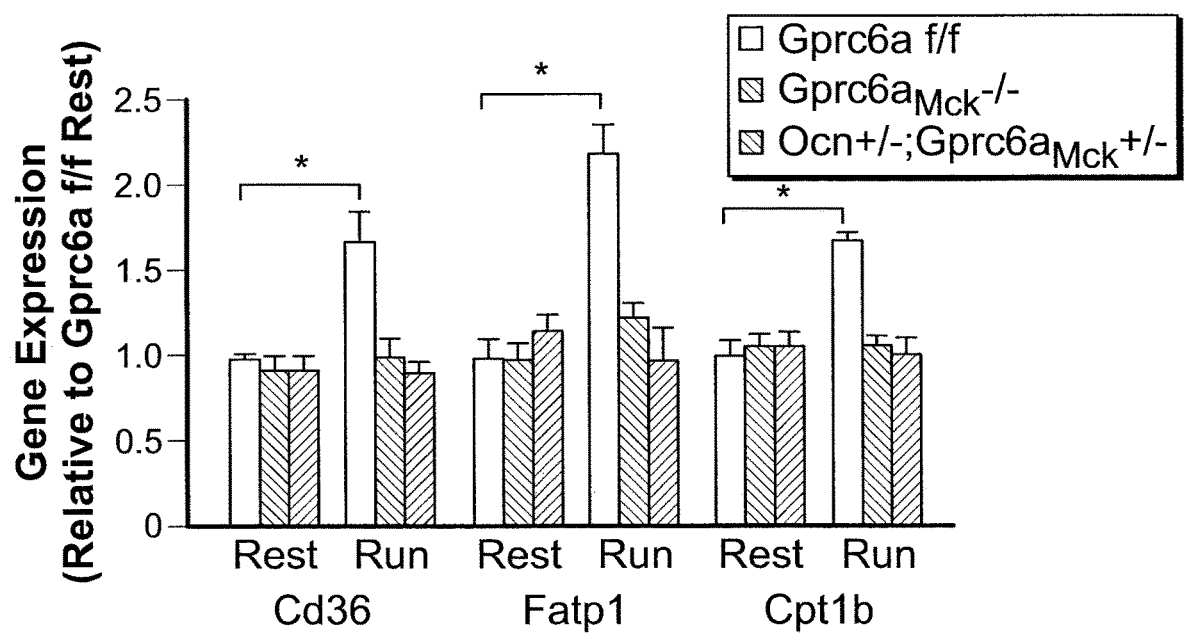
Figure 28I:
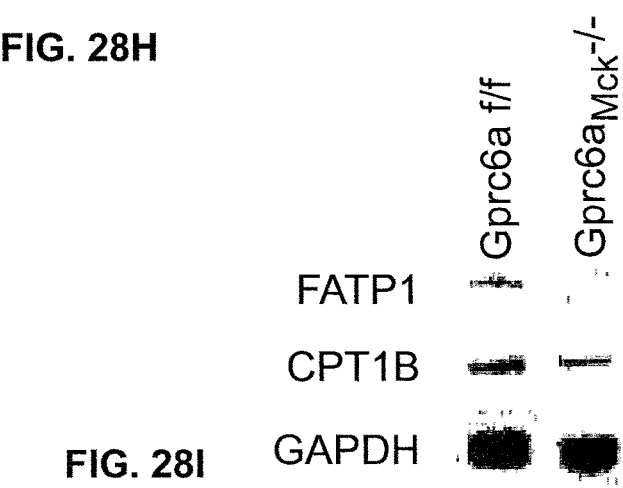

Osteocalcin also used transcriptional mechanisms to favor FA uptake and utilization in muscle. The expression of Cd36 and Fatp1 that facilitate the uptake of long-chain FAs into cells, and of Cpt1b that promotes their transport across the mitochondrial membrane (Stahl et al., 2001, Trends Endocrinol. Metab. 12:266-273), was decreased in Gprc6a-/- myotubes and osteocalcin increased expression of Fatp1 and Cpt1b and to a lesser extent of Cd36 in WT myotubes (FIG. 28F-G). This explains why Cd36, Fatp1 and Cpt1b expression did not increase in muscles of Gprc6a$_{Mck}$-/- or Ocn+/-; Gprc6a$_{Mck}$+/- mice to the same extent as in those of control mice after exercise (FIG. 28H); the same was true for FATP1 and CPT1B accumulation in Gprc6a$_{Mck}$-/- muscles. The lower expression of Fatp1 in Creb-/- than control myotubes, the decreased phosphorylation of CREB in muscle of Gprc6a$_{Mck}$-/- mice compared to those of control mice after exercise and the fact that the exercise capacity of Gprc6a$_{Mck}$+/-; Creb$_{Mck}$+/- mice is similar to the one of Ocn-/- and Gprc6a$_{Mck}$-/- mice all suggest that CREB may be a transcriptional mediator of the osteocalcin regulation of FAs uptake and utilization in myofibers. (FIG. 28J-L).

A Crosstalk Between Osteocalcin and Interleukin-6 Determines Adaptation to Exercise The involvement of transcriptional events in the osteocalcin regulation of FA utilization in muscle during exercise led to a transcriptomic analysis in muscles of control and Gprc6a$_{Mck}$-/- mice in search of genes regulated by osteocalcin and that would modulate its regulation of muscle function during exercise. This analysis revealed that the gene whose expression was the most decreased in Gprc6a$_{Mck}$-/- muscle after exercise was the one encoding interleukin-6 (IL-6), a myokine whose circulating levels raise during exercise and that exerts multiple effects on energy metabolism (Pedersen and Febbraio, 2012, Nat. Rev. Endocrinol. 8:457-465). The same was true, albeit to a lower extent, for the soluble IL-6 receptor. Consistent with this observation, Il6 and Il6rα expression in myofibers, and IL-6 content in muscle were markedly lower in Gprc6a$_{Mck}$-/- and Gprc6a$_{Hsa}$-/- than in muscles of control mice after exercise and osteocalcin increased the expression of Il6 in WT but not Gprc6a-/- myotubes (FIG. 29B-C). Moreover, the rise in circulating IL-6 levels normally induced by exercise in mice was decreased 68% and 82% in Gprc6a$_{Mck}$-/- and Gprc6a$_{Hsa}$-/- mice respectively (FIG. 29C-D). This latter result identifies osteocalcin as a major regulator of Il6 expression in muscle and indicates that the majority of the increase in IL-6 circulating levels observed after exercise is due to an increase in muscle derived IL-6.

The massive decrease in the rise of circulating IL-6 levels in Gprc6a$_{Mck}$-/- mice may explain in part the increase in fat mass noted in these mutant mice. Of note. no other myokines known to influence exercise were affected by the absence of osteocalcin signaling in myofibers.

Figure 29E:
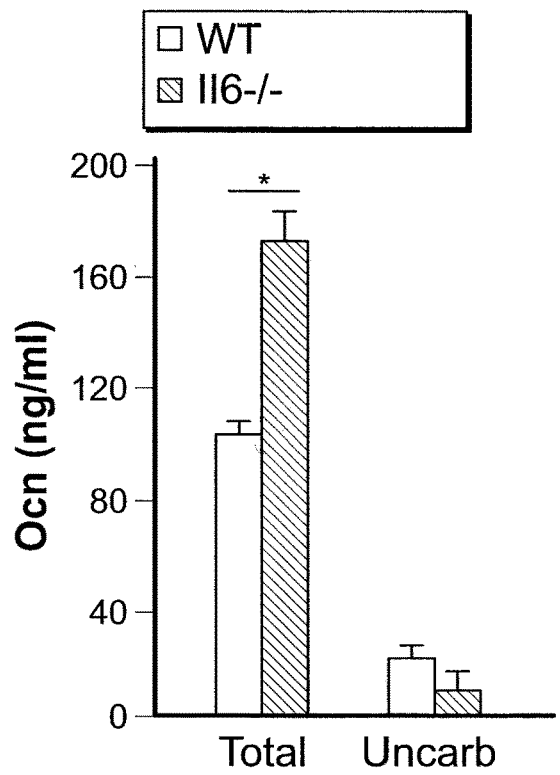
Figure 29F:
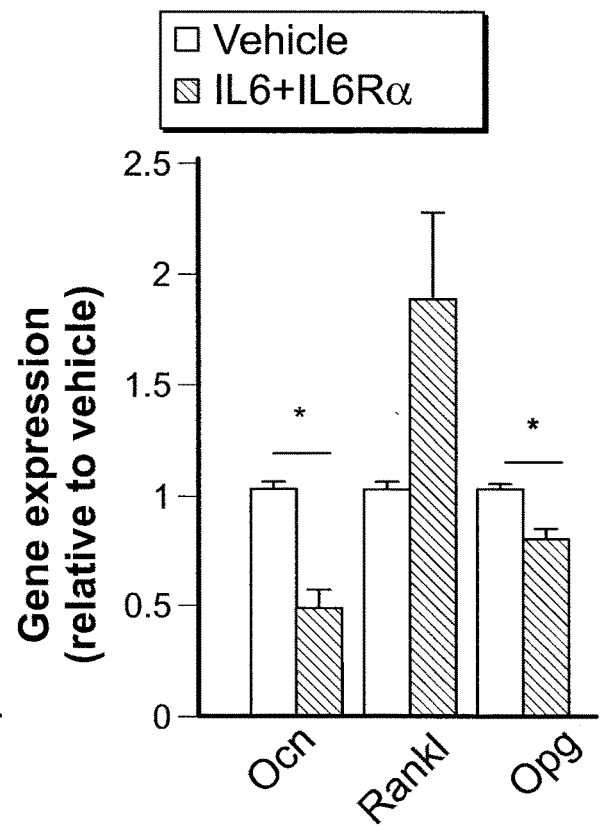
Figure 29G:
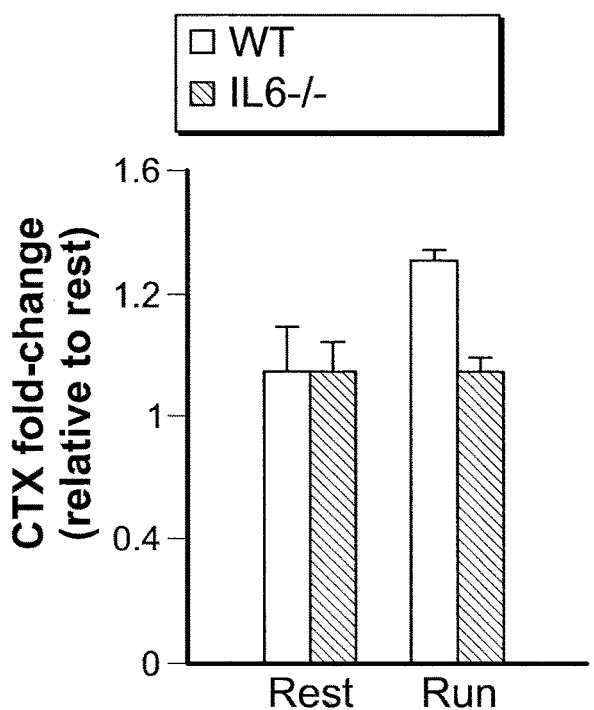
Figure 29H:
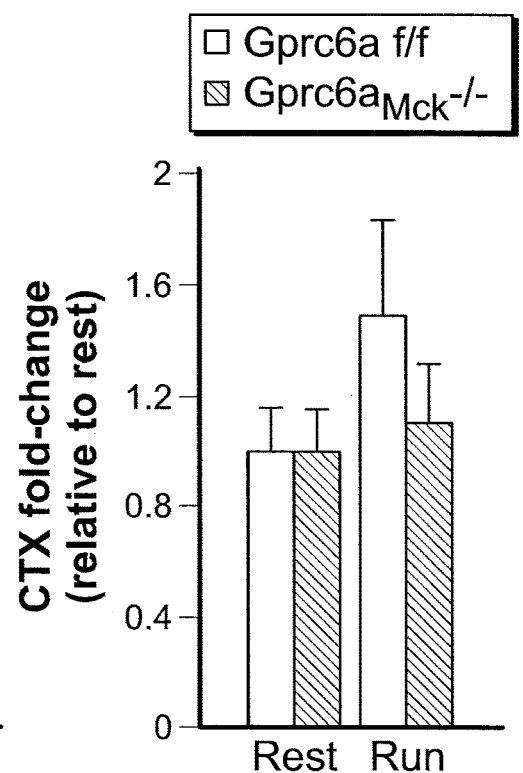

In view of these results, and since IL-6 can signal in bone cells (Li et al., 2008, Cytokine 43:165-173; Tamura et al., 1993, Proc. Natl. Acad. Sci. USA 90:11924-11928), whether IL-6 regulates the production of osteocalcin by osteoblasts and/or its activation by bone resorption was tested. It was observed that treating osteoblasts with IL-6 decreased expression of Osteocalcin, thereby explaining why the circulating levels of total (carboxylated and uncarboxylated forms) osteocalcin are increased in Il6-/- mice. More importantly, IL-6 increased the expression in osteoblasts of Rankl, a cytokine that favors osteoclast differentiation and decreased the expression of Osteoprotegerin (Opg), a decoy receptor for Rankl and an inhibitor of bone resorption (Karsenty and Wagner, 2002, Developmental Cell 2:389-406; Palmqvist et al., 2002, J. Immunol. 169:3353-3362). This observation is consistent with the fact that the circulating levels of the undercarboxylated and active form of osteocalcin are decreased in Il6-/- mice (FIG. 29E). The regulation of Il-6 expression by osteocalcin signaling in myofibers and of bone resorption by IL-6 also explains why circulating levels of CTX, a biomarker of bone resorption, were low after exercise in Il6-/- and Gprc6a$_{Mck}$-/- mice (FIG. 29G-H). These experiments reveal the existence of a feed-forward regulation between osteocalcin production in bone and IL-6 synthesis in muscle that is necessary for the increase in muscle function during exercise. This regulatory loop should synergize with the ability of IL-6 to favor liver gluconeogenesis and lipolysis, since these two other functions of IL-6 increase the pool of nutrients made available for myofibers during exercise.

Circulating Osteocalcin Levels Decline Steeply Before Mid-Life

The decrease in exercise capacity caused by the absence of osteocalcin signaling in myofibers bears similarities to the deleterious influence of aging on exercise capacity. To determine if a decrease in osteocalcin circulating levels could contribute to this deleterious consequence of aging, circulating osteocalcin levels in multiple species throughout life were measured.

Figure 30A:
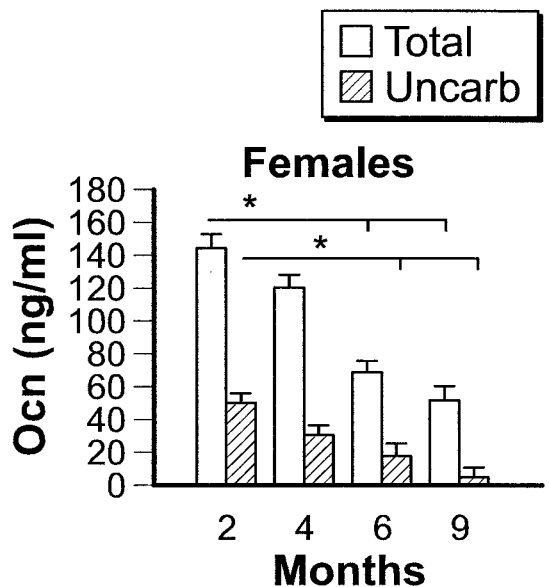
Figure 30B:
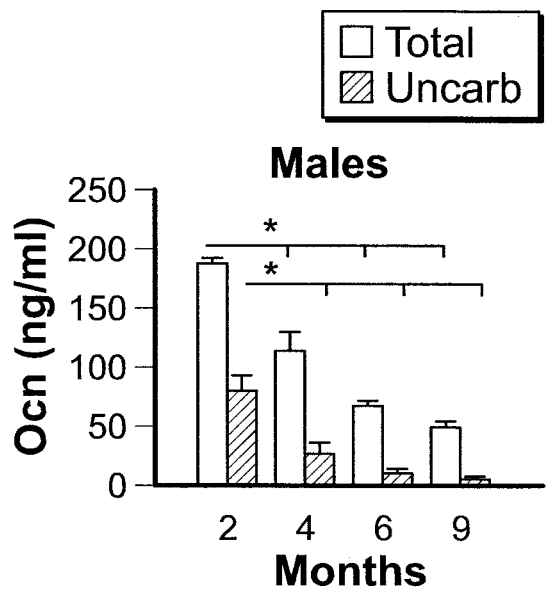
Figure 30C:
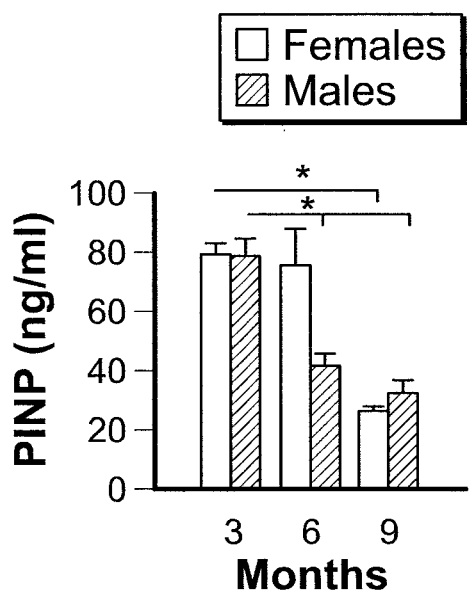
Figure 30D:
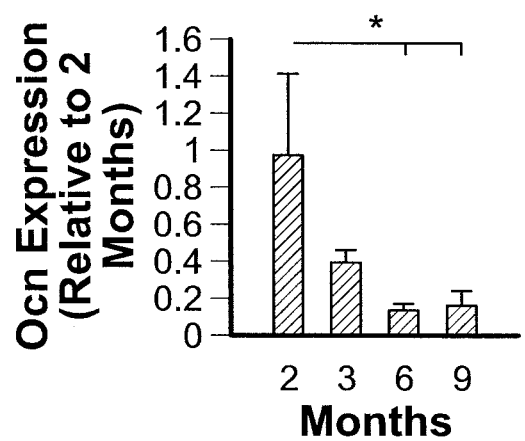
Figure 30E:
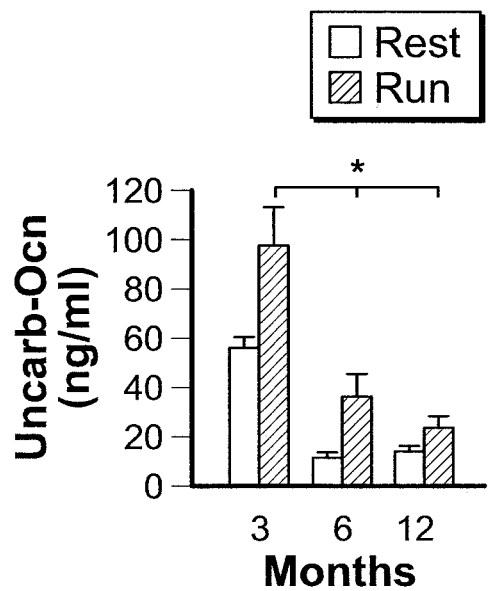
Figure 30F:
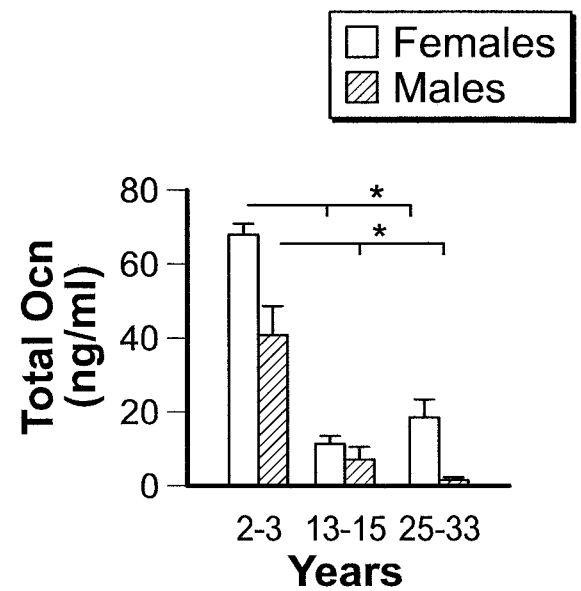
Figure 30G:
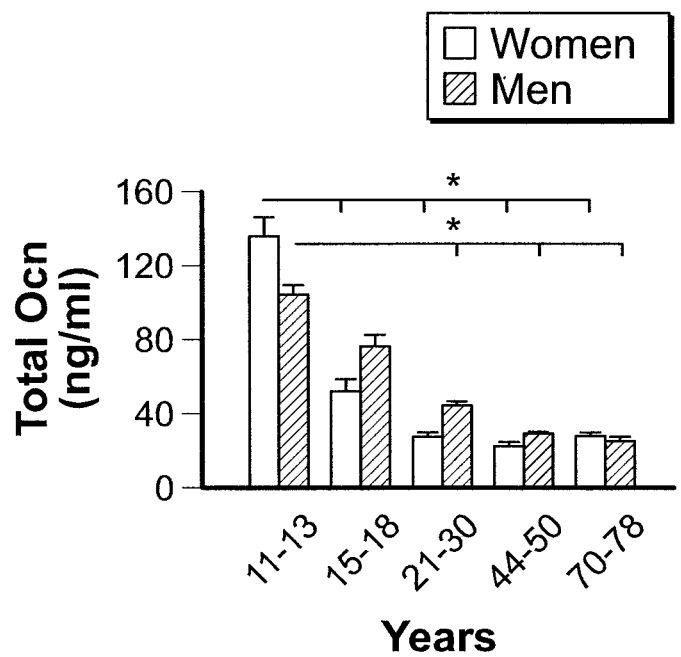

It was observed that the circulating levels of osteocalcin decreased by 70% in male and female mice between 2 and 9 months of age because of a marked decline in bone formation as measured by serum PINP levels and Osteocalcin expression (FIG. 30A-D). Of note, this decrease in circulating osteocalcin levels occurs at the time the ability of WT mice to perform exercise declines. It was also observed that circulating osteocalcin levels do not increase during exercise as much in 6 and 12 month-old mice as they do in 3 month-old mice. Circulating osteocalcin levels also decrease in male and female rhesus monkeys between young (2-3 years) and middle age (13-15 years) (FIG. 30F). Even more strikingly, in humans circulating osteocalcin levels reach their lowest point before 30 years of age in women, and before or at 50 years of age in men (FIG. 30G). Thus circulating osteocalcin levels reach their nadir before or around mid-life in all species analyzed when exercise capacity begins to decline.

Osteocalcin can Increase Exercise Capacity of Young and Older WT Mice

The regulation of muscle function during exercise by osteocalcin, the steep and early decrease of its circulating levels during life and the fact that these levels do not rise in older mice as they do in younger ones during exercise were reasons to ask whether exogenous osteocalcin could increase the exercise capacity of young and older WT mice.

Figure 31A:
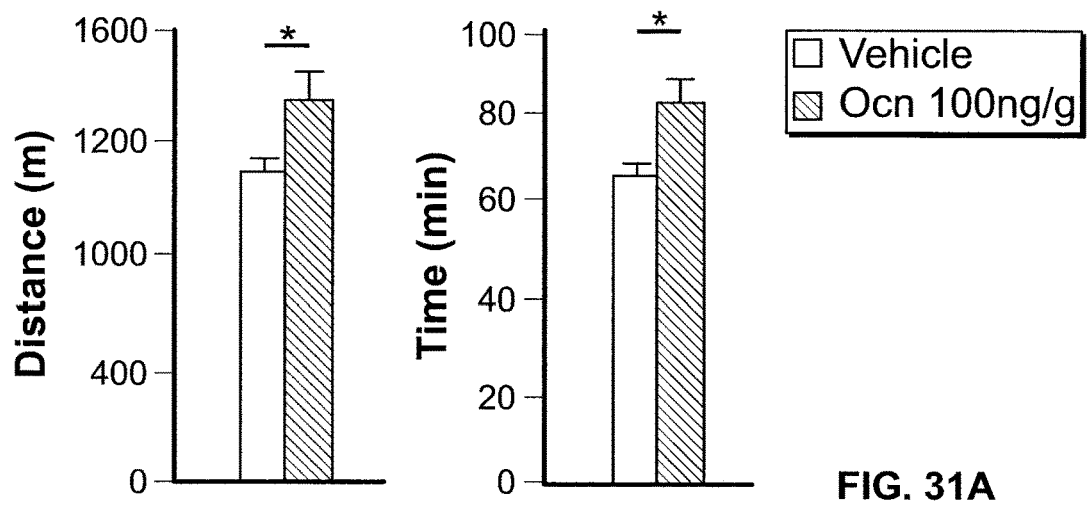
Figure 31B:
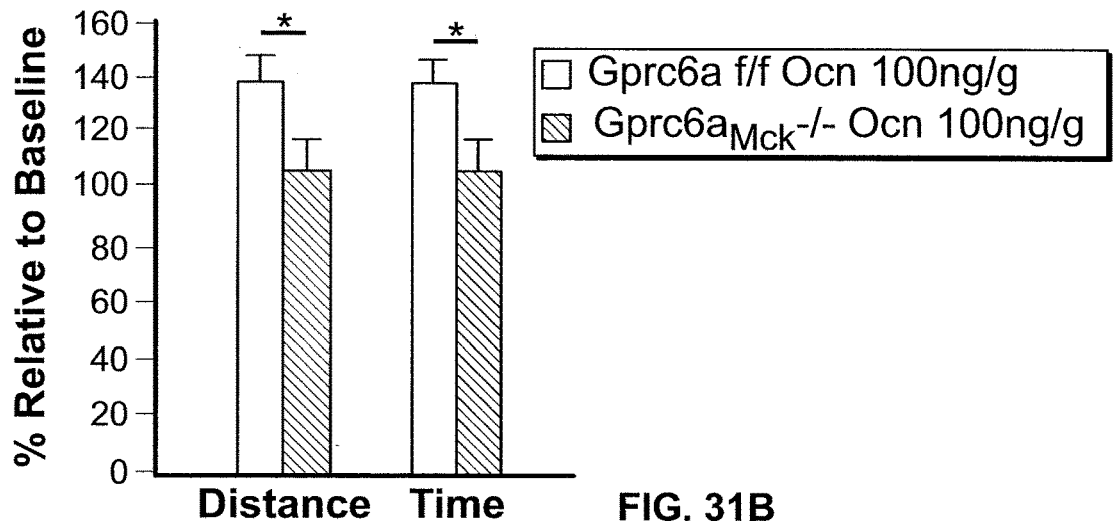
Figure 31C:
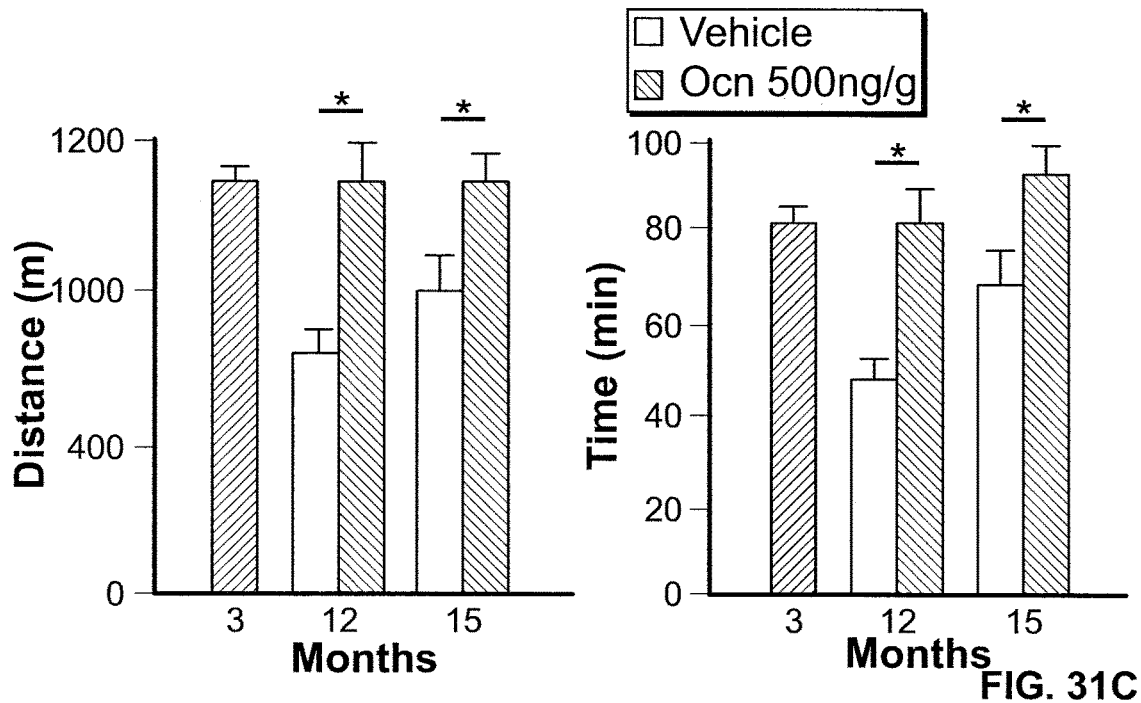
Figure 31D:
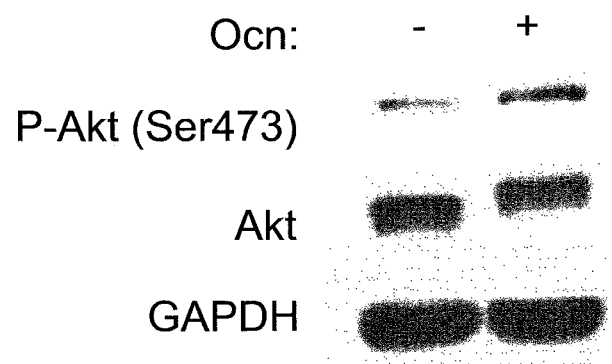
Figure 31E:
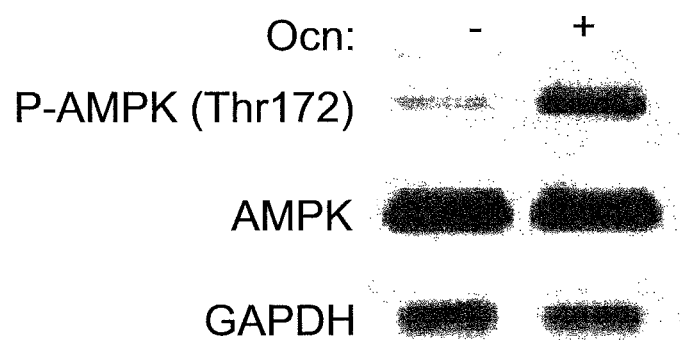
Figure 31F:
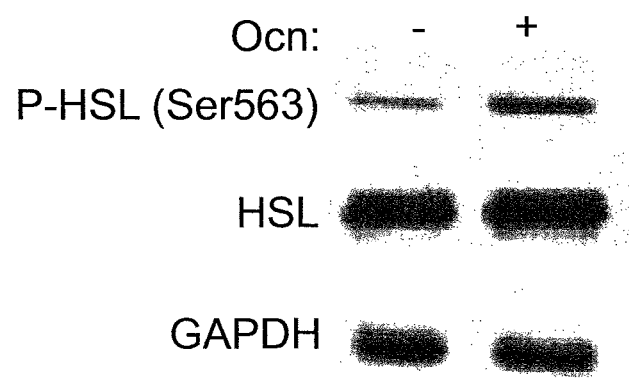

First, whether a single intraperitoneal injection of uncarboxylated mouse osteocalcin (osteocalcin) (100 ng/g of body weight) immediately before exercise would improve the exercise capacity of 3 month-old WT mice was tested. This injection increased circulating osteocalcin levels without affecting circulating insulin levels. It also increased the time and distance these mice run on the treadmill before exhaustion by over 20% (FIG. 31A). That osteocalcin did not improve muscle function in Gprc6a$_{Mck}$-/- mice demonstrated that osteocalcin needs to signal in myofibers to favor muscle function (FIG. 31B).

Figure 31G:
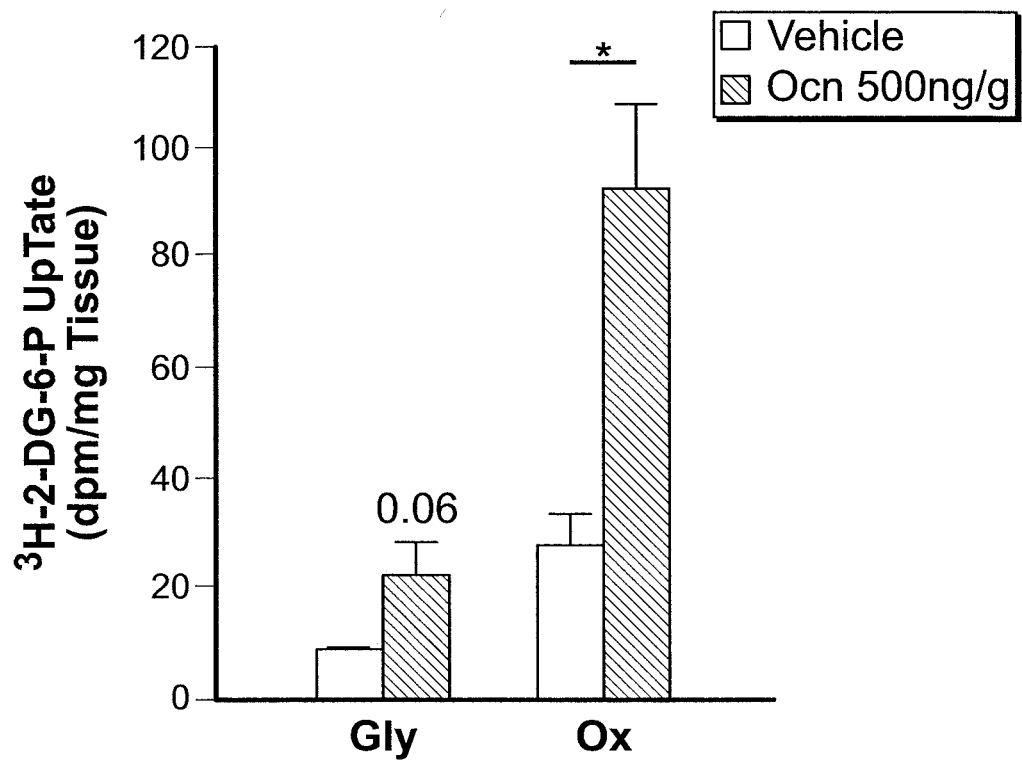
Figure 31H:
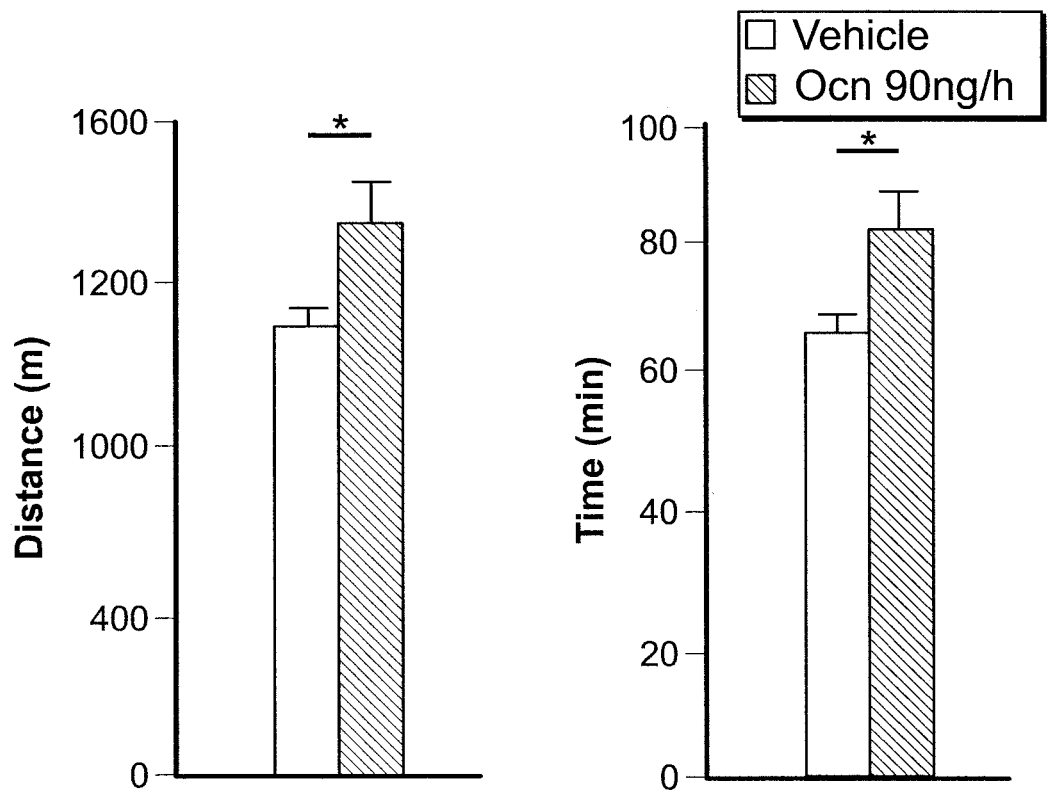
Figure 31I:
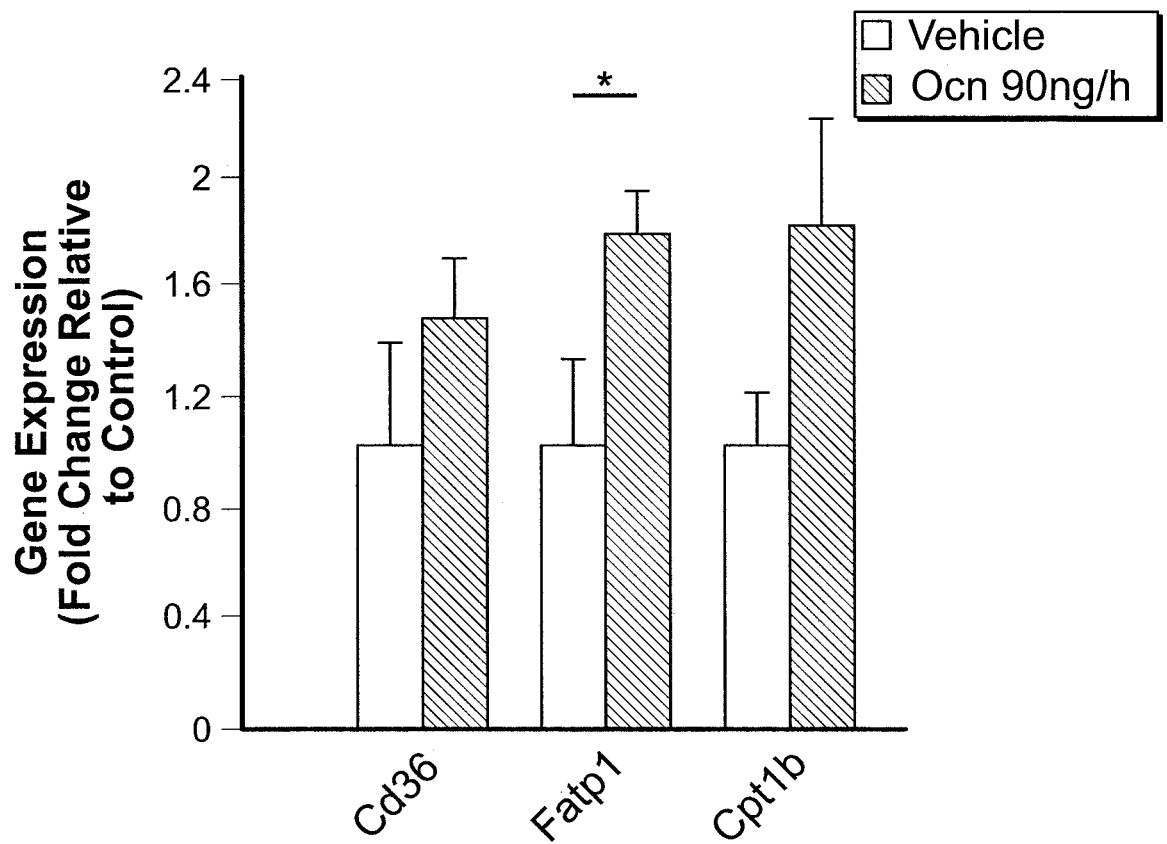
Figure 31J:
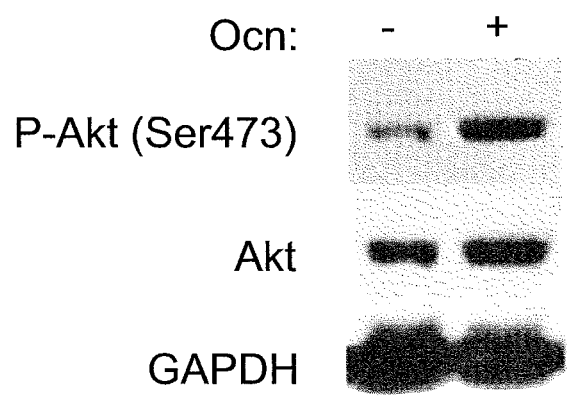

To determine if osteocalcin has the same ability in older mice, 12 and 15 month-old mice that have low circulating osteocalcin levels were injected prior to running with 500 ng/g of body weight of osteocalcin in order to raise their circulating levels substantially. This acute delivery of osteocalcin conferred to older mice the ability to run the same time and distance as 3 month-old untreated mice. This was due to an increase in the phosphorylation of Akt, AMPK and HSL, as well as in glucose uptake, that occurred to a greater extent in oxidative muscles that express Gprc6a at the highest level, than in glycolytic muscles (FIG. 31C-F). Whether chronic delivery of osteocalcin through minipumps (90 ng/hour) for 28 days would increase muscle function in 9 month old mice that have the lowest circulating osteocalcin levels was also tested. This mode of delivery increased circulating osteocalcin levels but did not affect those of insulin; it also resulted in a significant increase in the time and distance these mice run on the treadmill before exhaustion (FIG. 31G). This improved ability to perform exercise was caused in part by an increase in the expression in muscle of the fatty acid transporter Fatp1 and an activation of the Akt pathway (FIG. 31H-). Taken together, these results indicate that exogenous osteocalcin can improve exercise capacity of 3 to 15 month-old WT mice.

This study reveals that osteocalcin signaling in myofibers is necessary and sufficient to enhance muscle function and adaptation to exercise because it favors uptake and utilization of glucose and FAs. Osteocalcin signaling in myofibers during exercise also increases the expression of Il-6, a myokine that favors the production of nutrients and of bioactive osteocalcin. This study uncovers a regulatory pathway centered around a crosstalk between bone and muscle that determines adaptation to exercise.

Regulation of Muscle Function During Exercise by Osteocalcin

Whether and how osteocalcin could promote adaptation to exercise was tested. The analyses of various mutant mouse strains in which Osteocalcin or its receptor, Gprc6a, were inactivated in a cell-specific manner showed that osteocalcin signaling in myofibers through Gprc6a is needed for optimum muscle function during exercise and thereby to foster exercise capacity. The decrease in muscle function caused by the absence of osteocalcin signaling in myofibers does not appear before 3 months of age and is reproduced by a post-natal and osteoblast specific deletion of Osteocalcin, indicating that this function of osteocalcin reveals an influence of bone on muscle that is not of developmental origin. Additional genetic evidence ruled out that this function of osteocalcin was secondary to its signaling in the heart. Hence, osteocalcin is a systemic regulator of muscle function during exercise and therefore of the adaptation to exercise through it signaling via Gprc6a in myofibers.

Regulation of Nutrient Utilization by Osteocalcin Signaling in Myofibers

This investigation showed that osteocalcin signaling in myofibers enhances several aspects of nutrient uptake and utilization. First, by favoring the translocation of the glucose transporter GLUT4 to the plasma membrane, osteocalcin signaling in myofibers promotes glucose uptake in myofibers in an insulin-independent manner. Second, osteocalcin signaling in myofibers is needed for efficient mobilization of glycogen, an important source of glucose for contracting skeletal muscle during exercise; third, osteocalcin signaling promotes the activity of the TCA cycle and thereby the generation of ATP necessary for muscle contraction; fourth, osteocalcin signaling in myofibers increases the expression and accumulation of FA transporters and enhances FA utilization as determined by the accumulation of acylcarnitines in muscle of $Gprc6a_{Mck}-/-$ mice. The depletion of TCA cycle intermediates observed in muscles of $Gprc6a_{Mck}-/-$ mice after exercise, and the decreased utilization of FAs in these mutant muscles all support the notion that osteocalcin signaling in myofibers is necessary for the efficient oxidation of glucose and FAs in the mitochondria and to favor adaptation to exercise by increasing muscle function.

The Crosstalk Between Osteocalcin and Interleukin-6 and Adaptation to Exercise

An investigation was undertaken to look for genes whose expression in myofibers is regulated by osteocalcin and that could either mediate or hamper osteocalcin's ability to increase muscle function during exercise. This investigation identified IL-6, one the earliest characterized myokines, as an osteocalcin target gene. Importantly for muscle function during exercise, IL-6 also favors lipolysis in white adipose tissue and liver gluconeogenesis, i.e., the generation of nutrients for myofibers (Faldt et al., 2004, Endocrinol. 145:2680-2686). By showing that osteocalcin signaling in myofibers is responsible for over two thirds of the increase in circulating interleukin-6 levels that occurs during exercise, the results herein identify osteocalcin as a long sought-after regulator of Il-6 expression in muscle during exercise.

It was found that interleukin-6 signals in bone cells to exert several functions whose end result is to increase the production of active osteocalcin. Although interleukin-6 inhibits the expression of Osteocalcin, it favors osteoclast differentiation and bone resorption by stimulating the expression of Rankl. This latter function provides an explanation for the decrease in circulating levels of bioactive osteocalcin seen in Il6-/- mice and suggests that IL-6 and Osteocalcin cooperate to favor adaptation to exercise. On the one hand, by favoring glucose production in the liver and the generation of FAs through lipolysis, IL-6 favors the availability of nutrients for myofibers; on the other hand, IL-6 enhances the production of bioactive osteocalcin, which in turn favors uptake of these nutrients in myofibers (Pedersen and Febbraio, 2012, 2012, Nat. Rev. Endocrinol. 8:457-465). Hence, the crosstalk between osteocalcin and IL-6 is part of a more global mechanism allowing adaptation to exercise. This indicates that the metabolic functions of bone act in concert with those of other organs to favor adaptation to exercise.

Osteocalcin can Revert the Age Related Decline in Exercise Capacity

The results herein indicate that, whether osteocalcin is delivered acutely or chronically, osteocalcin signaling in myofibers is sufficient to increase the exercise capacity of 3 month-old WT mice and to confer to 15 month-old mice the exercise capacity of 3 month-old mice. These results are important from a biomedical point of view as they indicate that osteocalcin signaling could be harnessed to treat the decrease in muscle function that occurs with aging.

Osteocalcin circulating levels increase after exercise and decrease with aging. It has been observed that mice lacking osteocalcin or its receptor, gprc6a, present at 3 months of age a phenotype of muscle wasting that is seen in aged mice. This phenotype includes decreased muscle mass and decreased muscle performance, as judged by the ability of the mice to run on a treadmill. The same phenotype is observed in mice lacking gprc6a in myoblasts only. These mice do not have any of the metabolic perturbations seen in Osteocalcin$^{-/-}$ mice, which lack osteocalcin in all tissues.

It has been shown that in muscle osteocalcin favors glucose uptake, glycolysis, fatty acid oxidation, and protein synthesis.

A simple injection of osteocalcin in wild-type mice while they run on a treadmill apparatus increases the distance the mice run by 20%. Moreover, 12-15 month-old wild-type mice given injections of osteocalcin run like young mice.

The above observations indicate that administration of undercarboxylated/uncarboxylated osteocalcin to patients should provide beneficial effects on muscle wasting. In particular, administration of undercarboxylated/uncarboxylated osteocalcin to patients should provide beneficial effects on the muscle wasting that is part of the frailty complex associated with aging.

It has been found that the absence of osteocalcin or its receptor GPRC6A leads to bronchoconstriction, as seen in asthma, but without the local inflammation seen in asthma. Intracerebroventricular infusions of osteocalcin in Osteocalcin$^{-/-}$ mice do not correct their bronchoconstriction, indicating that it is not a consequence of the central functions of osteocalcin.

The level of acetylcholine, a neurotransmitter that causes bronchoconstriction, is increased in the lungs but not in the brains of Osteocalcin$^{-/-}$ and Gprc6a$^{-/-}$ mice. The delivery of osteocalcin by nebulization for two weeks in wild-type mice in which an asthma-like condition has been triggered by an allergen completely rescued their bronchoconstriction without affecting the local inflammation caused by the allergen.

GPRC6A, a receptor for osteocalcin, is expressed at high levels in the lungs. Osteocalcin and GPRC6A knockout mice (Osteocalcin$^{-/-}$, gprc6a$^{-/-}$, respectively) show increased airway resistance, more bronchoconstriction, and decreased airway diameters compared to wild-type mice. In contrast, an osteocalcin gain of function knockout mouse (Esp$^{-/-}$) showed increased airway diameters.

When metacholine is administered to the lungs of mice, the lung airways constrict. Osteocalcin$^{-/-}$ mice showed an exaggerated response to metacholine (more constriction) compared to wild-type mice. Wild-type mice were treated with an inflammation-increasing agent and developed asthma that included bronchoconstriction and signs of inflammation. When nebulized osteocalcin was administered to these mice, inflammatory signs were still observed but bronchoconstriction was not. Osteocalcin delivered to the brains of these mice did not show a similar effect.

In a mouse asthma model that involves intraperitoneal injection of albumin (to sensitize the mice) followed a week later by nebulized administration of albumin to the lungs of the mice, osteocalcin given by nebulization together with the nebulized albumin prevented the bronchoconstriction that would have otherwise been observed.

The above observations indicate that administration of undercarboxylated/uncarboxylated osteocalcin to patients should provide beneficial effects on lung disorders. In particular, administration of undercarboxylated/uncarboxylated osteocalcin to patients should provide beneficial effects on lung disorders that are part of the frailty complex associated with aging.

Undercarboxylated/uncarboxylated osteocalcin secreted by osteoblasts in bone is responsible for regulating various aspects of energy metabolism. For example, it increases pancreatic beta-cell proliferation, insulin secretion, insulin sensitivity, glucose tolerance, and serum adiponectin and decreases weight gain and fat mass. It also reduces the pathological effects of atherosclerosis. Undercarboxylated/uncarboxylated osteocalcin, as well as fragments and variants thereof, are useful to alleviate metabolic syndrome, type 1 and type 2 diabetes, atherosclerosis, and obesity.

Osteocalcin and reproductive biology in male mammals are linked by a biochemical pathway by which increased activity of osteocalcin leads to increased activity of enzymes involved in the synthesis of testosterone. This in turn leads to beneficial effects on male reproduction. Undercarboxylated/uncarboxylated osteocalcin, as well as fragments and variants thereof, are useful to alleviate disorders related to reproduction in male mammals. Such disorders include male infertility, low sperm count, impaired sperm motility, impaired sperm viability, low testosterone levels, reduced libido, erectile dysfunction, underdevelopment of testes, and excess apoptosis in testes.

Direct administration of undercarboxylated/uncarboxylated osteocalcin to the brains of adult Osteocalcin$^{-/-}$ mice (mice completely lacking osteocalcin expression) rescued defects in anxiety, depression, learning, and memory in the mice. In view of the observations described above, it may be concluded that osteocalcin regulates cognitive functions such as anxiety, depression, learning, and memory. Thus, certain aspects of the invention are directed to the therapeutic use of undercarboxylated/uncarboxylated osteocalcin, as well as fragments and variants thereof, to alleviate cognitive disorders that are part of the frailty complex associated with aging. It is known that aging is frequently associates with mild to severe cognitive impairment. Aging is also associated with loss of bone mass. Since bone osteoblasts are a major source of osteocalcin, the findings disclosed herein support the use of osteocalcin to alleviate cognitive disorders associated with frailty. In certain embodiments, the cognitive disorder is increased anxiety, increased depression, decreased memory, or decreased learning ability that occurs as a result of aging.

In certain embodiments, the methods of the present invention comprise the step of identifying a patient in need of therapy for frailty. Thus, the present invention provides a method comprising:

(a) identifying a patient in need of therapy for frailty;
(b) administering to the patient a therapeutically effective amount of undercarboxylated/uncarboxylated osteocalcin;

wherein the frailty is treated.

Gamma-carboxylase carboxylates osteocalcin, thereby producing carboxylated osteocalcin. This provides the opportunity to modulate the degree of carboxylation of osteocalcin by modulating the activity of gamma-carboxylase. In particular, this provides the opportunity to lower the degree of carboxylation of osteocalcin, thus providing undercarboxylated/uncarboxylated osteocalcin for treating frailty. Therefore, certain aspects of the invention are directed to the therapeutic use of agents that inhibit the activity of gamma-carboxylase to treat frailty in mammals.

OST-PTP activates gamma-carboxylase through dephosphorylation. As indicated above, activation of gamma-carboxylase leads to carboxylation of osteocalcin. This provides the opportunity to indirectly modulate the degree of carboxylation of osteocalcin by modulating the activity of OST-PTP (which will then modulate the activity of gamma-carboxylase). Therefore certain aspects of the invention are directed to the therapeutic use of agents that inhibit the activity of OST-PTP to treat frailty in mammals.

In humans, PTP-1B activates gamma-carboxylase through dephosphorylation. As indicated above, activation of gamma-carboxylase leads to carboxylation of osteocalcin. This provides the opportunity to indirectly modulate the degree of carboxylation of osteocalcin by modulating the activity of PTP-1B in humans (which will then modulate the activity of gamma-carboxylase). Therefore certain aspects of the invention are directed to the therapeutic use in humans of agents that inhibit the activity of PTP-1B to treat frailty in humans.

Other aspects of the invention are directed to diagnostic methods based on detection of the level of undercarboxylated/uncarboxylated osteocalcin in a patient, which level is associated with disorders related to frailty in mammals.

In one aspect, the method of diagnosing frailty in a patient comprises (i) determining a patient level of undercarboxylated/uncarboxylated osteocalcin in a biological sample taken from the patient (ii) comparing the patient level of undercarboxylated/uncarboxylated osteocalcin and a control level of undercarboxylated/uncarboxylated osteocalcin, and (iii) if the patient level is significantly lower than the control level, then diagnosing the patient as having, or being at risk for, frailty. A further step may then be to inform the patient or the patient's healthcare provider of the diagnosis.

Other aspects of the invention are directed to diagnostic methods based on detection of decreased ratios of undercarboxylated/uncarboxylated vs carboxylated osteocalcin. Such ratios may be associated with frailty in mammals. In one aspect, the method of diagnosing a disorder related to frailty in a patient comprises (i) determining a patient ratio of undercarboxylated/uncarboxylated vs. carboxylated osteocalcin in a biological sample taken from the patient (ii) comparing the patient ratio of undercarboxylated/uncarboxylated vs carboxylated osteocalcin and a control ratio of undercarboxylated/uncarboxylated vs carboxylated osteocalcin, and (iii) if the patient ratio is significantly lower than the control ratio, then the patient is diagnosed has having, or being at risk for, frailty. A further step may then be to inform the patient or the patient's healthcare provider of the diagnosis.

Pharmaceutical Compositions for Use in the Methods of the Invention

The present invention provides pharmaceutical compositions for use in the treatment of frailty in mammals comprising an agent for modulating the OST-PTP signaling pathway or for modulating the PTP-1B signaling pathway, which pathways involve gamma-carboxylase and osteocalcin. In particular embodiments, the agent inhibits OST-PTP phosphorylase activity, inhibits PTP-1B phosphorylase activity reduces gamma-carboxylase activity, and/or increases undercarboxylated/uncarboxylated osteocalcin. In particular embodiments, the agent decarboxylates osteocalcin. The agent may be selected from the group consisting of small molecules, polypeptides, antibodies, and nucleic acids. The pharmaceutical compositions of the invention provide an amount of the agent effective to treat frailty in mammals.

In certain embodiments, the pharmaceutical compositions for use in the methods of the invention may function to increase serum undercarboxylated/uncarboxylated osteocalcin serum levels.

In particular embodiments of the invention, therapeutic agents that may be administered in the methods of the present invention include undercarboxylated osteocalcin; uncarboxylated osteocalcin; or inhibitors that reduce the expression or activity of gamma-carboxylase, PTP-1B, or OST-PTP (e.g., antibodies, small molecules, antisense nucleic acids or siRNA). The pharmaceutical agents may also include agents that decarboxylate osteocalcin.

The therapeutic agents are administered in an amount sufficient to treat frailty.

In certain embodiments, the pharmaceutical compositions comprising undercarboxylated/uncarboxylated osteocalcin are administered together with another therapeutic agent. In some embodiments, the undercarboxylated/uncarboxylated osteocalcin and the other therapeutic agent are present in the same pharmaceutical composition. In other embodiments, the undercarboxylated/uncarboxylated osteocalcin and the other therapeutic agent are administered in separate pharmaceutical compositions.

In other embodiments, undercarboxylated/uncarboxylated osteocalcin is the only active pharmaceutical ingredient present in the pharmaceutical compositions.

Biologically active fragments or variants of the therapeutic agents are also within the scope of the present invention. By "biologically active" is meant capable of modulating the OST-PTP signaling pathway or the PTP-1B signaling pathway involving gamma-carboxylase and osteocalcin. "Biologically active" may also mean reducing the expression of OST-PTP or its ability to dephosphorylate gamma-carboxylase and reducing the expression of gamma-carboxylase or its ability to carboxylate osteocalcin, or decarboxylating carboxylated osteocalcin thereby leading to increased levels of undercarboxylated/uncarboxylated osteocalcin.

"Biologically active" also means reducing the expression of PTP-1B or its ability to dephosphorylate gamma-carboxylase and reducing the expression of gamma-carboxylase or its ability to carboxylate osteocalcin, or decarboxylating carboxylated osteocalcin thereby leading to increased levels of undercarboxylated/uncarboxylated osteocalcin.

"Biologically active" also refers to fragments or variants of osteocalcin that retain the ability of undercarboxylated/uncarboxylated osteocalcin to treat frailty in mammals.

Pharmaceutical Compositions Comprising Undercarboxylated/Uncarboxylated Osteocalcin In a specific embodiment of the invention, pharmaceutical compositions comprising undercarboxylated/uncarboxylated osteocalcin are provided for use in treating frailty in a mammal.

"Undercarboxylated osteocalcin" means osteocalcin in which one or more of the Glu residues at positions Glu17, Glu21, and Glu24 of the amino acid sequence of the mature human osteocalcin having 49 amino acids, or at the positions corresponding to Glu17, Glu21 and Glu24 in other forms of osteocalcin, are not carboxylated. Undercarboxylated osteocalcin includes "uncarboxylated osteocalcin," i.e., osteocalcin in which all three of the glutamic acid residues at positions 17, 21, and 24 are not carboxylated. Preparations of osteocalcin are considered to be "undercarboxylated osteocalcin" if more than about 10% of the total Glu residues at positions Glu17, Glu21, and Glu24 (taken together) in mature osteocalcin (or the corresponding Glu residues in other forms) of the preparation are not carboxylated. In particular preparations of undercarboxylated osteocalcin, more than about 20%, more than about 30%, more than about 40%, more than about 50%, more than about 60%, more than about 70%, more than about 80%, more than about 90%, more than about 95%, or more than about 99% of the total Glu residues at positions Glu17, Glu21, and Glu24 in mature osteocalcin (or the corresponding Glu residues in other forms) of the preparation are not carboxylated. In particularly embodiments, essentially all of the Glu residues at positions Glu17, Glu21 and Glu24 in mature osteocalcin (or the corresponding Glu residues in other forms) of the preparation are not carboxylated.

"Undercarboxylated/uncarboxylated osteocalcin" is used herein to refer collectively to undercarboxylated and uncarboxylated osteocalcin. "Uncarboxylated osteocalcin" is used herein to refer to a preparation of osteocalcin in which all of the Glu residues at positions Glu17, Glu21 and Glu24 in mature osteocalcin (or the corresponding Glu residues in other forms) of the preparation are not carboxylated.

Human osteocalcin cDNA (SEQ ID NO:1) encodes a mature osteocalcin protein represented by the last 49 amino acids of SEQ ID NO:2 (i.e., positions 52-100) with a predicted molecular mass of 5,800 kDa (Poser et al., 1980, J. Biol. Chem. 255:8685-8691). SEQ ID NO:2 is the pre-pro-sequence of human osteocalcin encoded by SEQ ID NO:1 and mature human osteocalcin (SEQ ID NO:12) is the processed product of SEQ ID NO:2. In this application, the amino acid positions of mature human osteocalcin are referred to. It will be understood that the amino acid positions of mature human osteocalcin correspond to those of SEQ ID NO:2 as follows: position 1 of mature human osteocalcin corresponds to position 52 of SEQ ID NO:2; position 2 of mature human osteocalcin corresponds to position 53 of SEQ ID NO:2, etc. In particular, positions 17, 21, and 24 of mature human osteocalcin correspond to positions 68, 72, and 75, respectively, of SEQ ID NO:2.

When positions in two amino acid sequences correspond, it is meant that the two positions align with each other when the two amino acid sequences are aligned with one another to provide maximum homology between them. This same concept of correspondence also applies to nucleic acids.

For example, in the two amino acid sequences AGLYSTVLMGRPS and GLVSTVLMGN, positions 2-11 of the first sequence correspond to positions 1-10 of the second sequence, respectively. Thus, position 2 of the first sequence corresponds to position 1 of the second sequence; position 4 of the first sequence corresponds to position 3 of the second sequence; etc. It should be noted that a position in one sequence may correspond to a position in another sequence, even if the positions in the two sequences are not occupied by the same amino acid.

"Osteocalcin" includes the mature protein and further includes biologically active fragments derived from full-length osteocalcin (SEQ ID NO:2) or the mature protein, including various domains, as well as variants as described herein.

In one embodiment of the present invention, the pharmaceutical compositions for use in the methods of the invention comprise a mammalian uncarboxylated osteocalcin. In a particular embodiment of the invention, the compositions for use in the methods of the invention comprise human uncarboxylated osteocalcin having the amino acid sequence of SEQ ID NO:2, or portions thereof, and encoded for by the nucleic acid of SEQ ID NO:1, or portions thereof. In some embodiments, the compositions for use in the methods of the invention may comprise one or more of the human osteocalcin fragments described herein.

In a particular embodiment of the invention, the compositions for use in the methods of the invention comprise human uncarboxylated osteocalcin having the amino acid sequence of SEQ ID NO:12.

In a specific embodiment, the present invention provides pharmaceutical compositions comprising human undercarboxylated osteocalcin which does not contain a carboxylated glutamic acid at one or more of positions corresponding to positions 17, 21, and 24 of mature human osteocalcin. A particular form of osteocalcin for use in the methods of the present invention is mature human osteocalcin wherein at least one of the glutamic acid residues at positions 17, 21, and 24 is not carboxylated. In certain embodiments, the glutamic acid residue at position 17 is not carboxylated. Preferably, all three of the glutamic acid residues at positions 17, 21, and 24 are not carboxylated. The amino acid sequence of mature human osteocalcin is shown in SEQ. ID. NO:12.

The primary sequence of osteocalcin is highly conserved among species and it is one of the ten most abundant proteins in the human body, suggesting that its function is preserved throughout evolution. Conserved features include 3 Gla residues at positions 17, 21, and 24 and a disulfide bridge between Cys23 and Cys29. In addition, most species contain a hydroxyproline at position 9. The N-terminus of osteocalcin shows highest sequence variation in comparison to other parts of the molecule. The high degree of conservation of human and mouse osteocalcin underscores the relevance of the mouse as an animal model for the human, in both healthy and diseased states, and validates the therapeutic and diagnostic use of osteocalcin to treat frailty in humans based on the experimental data derived from the mouse model disclosed herein.

The present invention also includes the use of polypeptide fragments of osteocalcin. Fragments can be derived from the full-length, naturally occurring amino acid sequence of osteocalcin (e.g., SEQ. ID. NO:2). Fragments may also be derived from mature osteocalcin (e.g., SEQ. ID. NO:12). The invention also encompasses fragments of the variants of osteocalcin described herein. A fragment can comprise an amino acid sequence of any length that is biologically active.

Particular fragments of osteocalcin include fragments containing Glu17, Glu21, and Glu24 of the mature protein. Other particular fragments are fragments of the mature protein missing the last 10 amino acids from the C-terminal end of the mature protein. Other particular fragments are fragments missing the first 10 amino acids from the N-terminal end of the mature protein. Another particular fragment is a fragment of the mature protein missing both the last 10 amino acids from the C-terminal end and the first 10 amino acids from the N-terminal end. Such a fragment comprises amino acids 62-90 of SEQ ID NO:2.

Other particular fragments of osteocalcin for the pharmaceutical compositions of the invention described herein include polypeptides comprising, consisting of, or consisting essentially of, the following sequences of amino acids:
positions 1-19 of mature human osteocalcin
positions 20-43 of mature human osteocalcin
positions 20-49 of mature human osteocalcin
positions 1-43 of mature human osteocalcin
positions 1-42 of mature human osteocalcin
positions 1-41 of mature human osteocalcin
positions 1-40 of mature human osteocalcin
positions 1-39 of mature human osteocalcin
positions 1-38 of mature human osteocalcin
positions 1-37 of mature human osteocalcin
positions 1-36 of mature human osteocalcin
positions 1-35 of mature human osteocalcin
positions 1-34 of mature human osteocalcin
positions 1-33 of mature human osteocalcin
positions 1-32 of mature human osteocalcin
positions 1-31 of mature human osteocalcin
positions 1-30 of mature human osteocalcin
positions 1-29 of mature human osteocalcin
positions 2-49 of mature human osteocalcin
positions 2-45 of mature human osteocalcin
positions 2-40 of mature human osteocalcin
positions 2-35 of mature human osteocalcin
positions 2-30 of mature human osteocalcin
positions 2-25 of mature human osteocalcin
positions 2-20 of mature human osteocalcin
positions 4-49 of mature human osteocalcin
positions 4-45 of mature human osteocalcin
positions 4-40 of mature human osteocalcin
positions 4-35 of mature human osteocalcin
positions 4-30 of mature human osteocalcin
positions 4-25 of mature human osteocalcin
positions 4-20 of mature human osteocalcin
positions 8-49 of mature human osteocalcin positions 8-45 of mature human osteocalcin
positions 8-40 of mature human osteocalcin
positions 8-35 of mature human osteocalcin
positions 8-30 of mature human osteocalcin
positions 8-25 of mature human osteocalcin
positions 8-20 of mature human osteocalcin
positions 10-49 of mature human osteocalcin
positions 10-45 of mature human osteocalcin
positions 10-40 of mature human osteocalcin
positions 10-35 of mature human osteocalcin
positions 10-30 of mature human osteocalcin
positions 10-25 of mature human osteocalcin
positions 10-20 of mature human osteocalcin
positions 6-34 of mature human osteocalcin
positions 6-35 of mature human osteocalcin
positions 6-36 of mature human osteocalcin
positions 6-37 of mature human osteocalcin
positions 6-38 of mature human osteocalcin
positions 7-34 of mature human osteocalcin
positions 7-35 of mature human osteocalcin
positions 7-36 of mature human osteocalcin
positions 7-37 of mature human osteocalcin
positions 7-38 of mature human osteocalcin
positions 7-30 of mature human osteocalcin
positions 7-25 of mature human osteocalcin
positions 7-23 of mature human osteocalcin
positions 7-21 of mature human osteocalcin
positions 7-19 of mature human osteocalcin
positions 7-17 of mature human osteocalcin
positions 8-30 of mature human osteocalcin
positions 8-25 of mature human osteocalcin
positions 8-23 of mature human osteocalcin
positions 8-21 of mature human osteocalcin
positions 8-19 of mature human osteocalcin
positions 8-17 of mature human osteocalcin
positions 9-30 of mature human osteocalcin
positions 9-25 of mature human osteocalcin
positions 9-23 of mature human osteocalcin
positions 9-21 of mature human osteocalcin
positions 9-19 of mature human osteocalcin
positions 9-17 of mature human osteocalcin One particular fragment is a fragment comprising positions 1-36 of mature human osteocalcin. Another particular fragment is a fragment comprising positions 20-49 of mature human osteocalcin. Other fragments can be designed to contain Pro13 to Tyr76 or Pro13 to Asn26 of mature human osteocalcin. Additionally, fragments containing the cysteine residues at positions 23 and 29 of mature human osteocalcin, and capable of forming a disulfide bond between those two cysteines, are useful.

Fragments can be discrete (not fused to other amino acids or polypeptides) or can be within a larger polypeptide. Further, several fragments can be comprised within a single larger polypeptide. In one embodiment, a fragment designed for expression in a host can have heterologous pre- and pro-polypeptide regions fused to the amino terminus of the osteocalcin fragment and/or an additional region fused to the carboxyl terminus of the fragment.

Also provided for use in the compositions and methods of the present invention are variants of osteocalcin and the osteocalcin fragments described above. "Variants" refers to osteocalcin peptides that contain modifications in their amino acid sequences such as one or more amino acid substitutions, additions, deletions and/or insertions but that are still biologically active. In some instances, the antigenic and/or immunogenic properties of the variants are not substantially altered, relative to the corresponding peptide from which the variant was derived. Such modifications may be readily introduced using standard mutagenesis techniques, such as oligonucleotide directed site-specific mutagenesis as taught, for example, by Adelman et al., 1983, DNA 2:183, or by chemical synthesis. Variants and fragments are not mutually exclusive terms. Fragments also include peptides that may contain one or more amino acid substitutions, additions, deletions and/or insertions such that the fragments are still biologically active.

One particular type of variant that is within the scope of the present invention is a variant in which one of more of the positions corresponding to positions 17, 21, and 24 of mature human osteocalcin is occupied by an amino acid that is not glutamic acid. In some embodiments, the amino acid that is not glutamic acid is also not aspartic acid. Such variants are versions of undercarboxylated osteocalcin because at least one of the three positions corresponding to positions 17, 21, and 24 of mature human osteocalcin is not carboxylated glutamic acid, since at least one of those positions is not occupied by glutamic acid.

In particular embodiments, the present invention provides osteocalcin variants comprising the amino acid sequence (SEQ. ID. NO: 13)
YLYQWLGAPV PYPDPLX$_1$PRR X$_2$VCX$_3$LNPDCD ELADHIGFQE

AYRRFYGPV wherein $X_1$, $X_2$ and $X_3$ are each independently selected from an amino acid or amino acid analog, with the proviso that if $X_1$, $X_2$ and $X_3$ are each glutamic acid, then $X_1$ is not carboxylated, or less than 50 percent of $X_2$ is carboxylated, and/or less than 50 percent of $X_3$ is carboxylated.

In certain embodiments, the osteocalcin variants comprise an amino acid sequence that is different from SEQ. ID. NO:13 at 1 to 7 positions other than $X_1$, $X_2$ and $X_3$.

In other embodiments, the osteocalcin variants comprise an amino acid sequence that includes one or more amide backbone substitutions.

Fully functional variants typically contain only conservative variation or variation in non-critical residues or in non-critical regions. Functional variants can also contain substitutions of similar amino acids, which results in no change, or an insignificant change, in function. Alternatively, such substitutions may positively or negatively affect function to some degree. The activity of such functional osteocalcin variants can be determined using assays such as those described herein.

Variants can be naturally-occurring or can be made by recombinant means, or chemical synthesis, to provide useful and novel characteristics for undercarboxylated/uncarboxylated osteocalcin. For example, the variant osteocalcin polypeptides may have reduced immunogenicity, increased serum half-life, increased bioavailability, and/or increased potency. In particular embodiments, serum half-life is increased by substituting one or more of the native Arg residues at positions 19, 20, 43, and 44 of mature osteocalcin with another amino acid or an amino acid analog, e.g., β-dimethyl-arginine. Such substitutions can be combined with the other changes in the native amino acid sequence of osteocalcin described herein.

Provided for use in the pharmaceutical compositions and methods of the present invention are variants that are also derivatives of the osteocalcin and osteocalcin fragments described above. Derivatization is a technique used in chemistry which transforms a chemical compound into a product of similar chemical structure, called derivative. Generally, a specific functional group of the compound participates in the derivatization reaction and transforms the compound to a derivate of different reactivity, solubility, boiling point, melting point, aggregate state, functional activity, or chemical composition. Resulting new chemical properties can be used for quantification or separation of the derivatized compound or can be used to optimize the derivatized compound as a therapeutic agent. The well-known techniques for derivatization can be applied to the above-described osteocalcin and osteocalcin fragments. Thus, derivatives of the osteocalcin and osteocalcin fragments described above will contain amino acids that have been chemically modified in some way so that they differ from the natural amino acids.

Provided also are osteocalcin mimetics. "Mimetic" refers to a synthetic chemical compound that has substantially the same structural and functional characteristics of a naturally or non-naturally occurring osteocalcin polypeptide, and includes, for instance, polypeptide- and polynucleotide-like polymers having modified backbones, side chains, and/or bases. Peptide mimetics are commonly used in the pharmaceutical industry as non-peptide drugs with properties analogous to those of the template peptide. Generally, mimetics are structurally similar (i.e., have the same shape) to a paradigm polypeptide that has a biological or pharmacological activity, but one or more polypeptide linkages are replaced. The mimetic can be either entirely composed of synthetic, non-natural analogues of amino acids or is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

By way of examples that can be adapted to osteocalcin by those skilled in the art: Cho et al., 1993, Science 261:1303-1305 discloses an "unnatural biopolymer" consisting of chiral aminocarbonate monomers substituted with a variety of side chains, synthesis of a library of such polymers, and screening for binding affinity to a monoclonal antibody. Simon et al., 1992, Proc. Natl. Acad. Sci. 89:9367-9371 discloses a polymer consisting of N-substituted glycines ("peptoids") with diverse side chains. Schumacher et al, 1996, Science 271:1854-1857 discloses D-peptide ligands identified by screening phage libraries of L-peptides against proteins synthesized with D-amino acids and then synthesizing a selected L-peptide using D-amino acids. Brody et al., 1999, Mol. Diagn. 4:381-8 describes generation and screening of hundreds to thousands of aptamers.

A particular type of osteocalcin variant within the scope of the invention is an osteocalcin mimetic in which one or more backbone amides is replaced by a different chemical structure or in which one or more amino acids are replaced by an amino acid analog. In a particular embodiment, the osteocalcin mimetic is a retroenantiomer of uncarboxylated human osteocalcin.

Osteocalcin, as well as its fragments and variants, is optionally produced by chemical synthesis or recombinant methods and may be produced as a modified osteocalcin molecule (i.e., osteocalcin fragments or variants) as described herein. Osteocalcin polypeptides can be produced by any conventional means (Houghten, 1985, Proc. Natl. Acad. Sci. USA 82:5131-5135). Simultaneous multiple peptide synthesis is described in U.S. Pat. No. 4,631,211 and can also be used. When produced recombinantly, osteocalcin may be produced as a fusion protein, e.g., a GST-osteocalcin fusion protein.

Undercarboxylated/uncarboxylated osteocalcin molecules that can be used in the methods of the invention include proteins substantially homologous to human osteocalcin, including proteins derived from another organism, i.e., an ortholog of human osteocalcin. One particular ortholog is mouse osteocalcin. Mouse osteocalcin gene 1 cDNA is SEQ ID NO:3; mouse osteocalcin gene 2 cDNA is SEQ ID NO:4; the amino acid sequence of mouse osteocalcin gene 1 and gene 2 is SEQ ID NO:5.

As used herein, two proteins are substantially homologous when their amino acid sequences are at least about 70-75% homologous. Typically the degree of homology is at least about 80-85%, and most typically at least about 90-95%, 97%, 98% or 99% or more.

"Homology" between two amino acid sequences or nucleic acid sequences can be determined by using the algorithms disclosed herein. These algorithms can also be used to determine percent identity between two amino acid sequences or nucleic acid sequences.

In a specific embodiment of the invention, the undercarboxylated/uncarboxylated osteocalcin is an osteocalcin molecule sharing at least 80% homology with the human osteocalcin of SEQ ID:2 or a portion of SEQ ID:2 that is at least 8 amino acids long. In another embodiment, the undercarboxylated/uncarboxylated osteocalcin is an osteocalcin molecule sharing at least 80%, at least 90%, at least 95%, or at least 97% amino acid sequence identity with the human osteocalcin of SEQ ID:2 or a portion of SEQ ID:2 that is at least 8 amino acids long. Homologous sequences include those sequences that are substantially identical. In particular embodiments, the homology or identity is over the entire length of mature human osteocalcin.

To determine the percent homology or percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). Preferably, the length of a reference sequence aligned for comparison purposes is at least 30%, preferably at least 40%, more preferably at least 50%, even more preferably at least 60%, and even more preferably at least 70%, 80%, or 90% or more of the length of the sequence that the reference sequence is compared to. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but which have sufficient similarity so as to perform one or more of the same functions performed by undercarboxylated/uncarboxylated osteocalcin. Similarity is determined by considering conserved amino acid substitutions. Such substitutions are those that substitute a given amino acid in a polypeptide by another amino acid of like characteristics. Conservative substitutions are likely to be phenotypically silent. Guidance concerning which amino acid changes are likely to be phenotypically silent may be found in Bowie et al., 1990, Science 247: 1306-1310.

Examples of conservative substitutions are the replacements, one for another, among the hydrophobic amino acids Ala, Val, Leu, and Ile; interchange of the hydroxyl residues Ser and Thr; exchange of the acidic residues Asp and Glu; substitution between the amide residues Asn and Gln; exchange of the basic residues Lys, His and Arg; replacements among the aromatic residues Phe, Trp and Tyr; exchange of the polar residues Gln and Asn; and exchange of the small residues Ala, Ser, Thr, Met, and Gly.

The comparison of sequences and determination of percent identity and homology between two osteocalcin polypeptides can be accomplished using a mathematical algorithm. See, for example, Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, HG, eds., Humana Press, New Jersey, 1994; Sequence Analysis in Molecular Biology, van Heinje, G, Academic Press, 1987; and Sequence Analysis Primer, Gribskov, M. and Devereux, J., eds., M Stockton Press, New York, 1991. A non-limiting example of such a mathematical algorithm is described in Karlin et al., 1993, Proc. Natl. Acad. Sci. USA 90:5873-5877.

The percent identity or homology between two osteocalcin amino acid sequences may be determined using the Needleman et al., 1970, J. Mol. Biol. 48:444-453 algorithm.

A substantially homologous osteocalcin, according to the present invention, may also be a polypeptide encoded by a nucleic acid sequence capable of hybridizing to the human osteocalcin nucleic acid sequence under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel et al., eds., 1989, Current Protocols in Molecular Biology, Vol. I, Green Publishing Associates, Inc., and John Wiley & sons, Inc., New York, at p. 2.10.3) and encoding a functionally equivalent gene product; or under less stringent conditions, such as moderately stringent conditions, e.g., washing in 0.2×SSC/0.1% SDS at 42° C. (Ausubel et al., 1989 supra), yet which still encodes a biologically active undercarboxylated/uncarboxylated osteocalcin.

A substantially homologous osteocalcin according to the present invention may also be a polypeptide encoded by a nucleic acid sequence capable of hybridizing to a sequence having at least 70-75%, typically at least about 80-85%, and most typically at least about 90-95%, 97%, 98% or 99% identity to the human osteocalcin nucleic acid sequence, under stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encoding a functionally equivalent gene product; or under less stringent conditions, such as moderately stringent conditions, e.g., washing in 0.2×SSC/0.1% SDS at 42° C. (Ausubel et al., 1989 supra), yet which still encodes a biologically active undercarboxylated/uncarboxylated osteocalcin.

It will be understood that a biologically active fragment or variant of human osteocalcin may contain a different number of amino acids than native human osteocalcin. Accordingly, the position number of the amino acid residues corresponding to positions 17, 21, and 24 of mature human osteocalcin may differ in the fragment or variant. One skilled in the art would easily recognize such corresponding positions from a comparison of the amino acid sequence of the fragment or variant with the amino acid sequence of mature human osteocalcin.

Peptides corresponding to fusion proteins in which full length osteocalcin, mature osteocalcin, or an osteocalcin fragment or variant is fused to an unrelated protein or polypeptide are also within the scope of the invention and can be designed on the basis of the osteocalcin nucleotide and amino acid sequences disclosed herein. Such fusion proteins include fusions to an enzyme, fluorescent protein, or luminescent protein which provides a marker function. In a particular embodiment of the invention, the fusion protein comprises fusion to a polypeptide capable of targeting the osteocalcin to a particular target cell or location in the body. For example, osteocalcin polypeptide sequences may be fused to a ligand molecule capable of targeting the fusion protein to a cell expressing the receptor for said ligand. In a particular embodiment, osteocalcin polypeptide sequences may be fused to a ligand capable of targeting the fusion protein to specific neurons in the brain of a mammal.

Osteocalcin can also be made as part of a chimeric protein for drug screening or use in making recombinant protein. These chimeric proteins comprise an osteocalcin peptide sequence linked to a heterologous peptide having an amino acid sequence not substantially homologous to the osteocalcin. The heterologous peptide can be fused to the N-terminus or C-terminus of osteocalcin or can be internally located. In one embodiment, the fusion protein does not affect osteocalcin function. For example, the fusion protein can be a GST-fusion protein in which the osteocalcin sequences are fused to the N- or C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant osteocalcin. In certain host cells (e.g., mammalian host cells), expression and/or secretion of a protein can be increased by using a heterologous signal sequence. Therefore, the fusion protein may contain a heterologous signal sequence at its N-terminus.

Those skilled in art would understand how to adapt well-known techniques for use with osteocalcin. For example, EP 0 464 533 discloses fusion proteins comprising various portions of immunoglobulin constant regions (Fc regions). The Fc region is useful in therapy and diagnosis and thus results, for example, in improved pharmacokinetic properties (see, e.g., EP 0 232 262). In drug discovery, for example, human proteins have been fused with Fc regions for the purpose of high-throughput screening assays to identify antagonists (Bennett et al., 1995, J. Mol. Recog. 8:52-58 and Johanson et al., 1995, J. Biol. Chem. 270:9459-9471). Thus, various embodiments of this invention also utilize soluble fusion proteins containing an osteocalcin polypeptide and various portions of the constant regions of heavy or light chains of immunoglobulins of various subclasses (e.g., IgG, IgM, IgA, IgE, IgB). A particular immunoglobulin is the constant part of the heavy chain of human IgG, particularly IgG1, where fusion takes place at the hinge region. For some uses, it is desirable to remove the Fc region after the fusion protein has been used for its intended purpose. In a particular embodiment, the Fc part can be removed in a simple way by a cleavage sequence, which is also incorporated and can be cleaved, e.g., with factor Xa.

A chimeric or fusion protein can be produced by standard recombinant DNA techniques. For example, DNA fragments coding for the different protein sequences can be ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., 1992, Current Protocols in Molecular Biology). Moreover, many expression vectors are commercially available that already encode a fusion moiety (e.g., a GST protein). An osteocalcin-encoding nucleic acid can be cloned into such an expression vector such that the fusion moiety is linked in-frame to osteocalcin.

Chimeric osteocalcin proteins can be produced in which one or more functional sites are derived from a different isoform, or from another osteocalcin molecule from another species. Sites also could be derived from osteocalcin-related proteins that occur in the mammalian genome but which have not yet been discovered or characterized.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art.

Accordingly, the osteocalcin polypeptides useful in the methods of the present invention also encompass derivatives which contain a substituted non-naturally occurring amino acid residue that is not one encoded by the genetic code, in which a substituent group is included, in which the mature polypeptide is fused with another compound, such as a compound to increase the half-life of the polypeptide (for example, polyethylene glycol), or in which the additional amino acids are fused to the osteocalcin polypeptide, such as a leader or secretory sequence or a sequence for purification of the osteocalcin polypeptide or a pro-protein sequence.

Undercarboxylated/uncarboxylated osteocalcin can be modified according to known methods in medicinal chemistry to increase its stability, half-life, uptake or efficacy. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

In a specific embodiment of the invention, modifications may be made to the osteocalcin to reduce susceptibility to proteolysis at residue Arg43 as a means for increasing serum half life. Such modifications include, for example, the use of retroenantio isomers, D-amino acids, or other amino acid analogs.

Acylation of the N-terminal amino group can be accomplished using a hydrophilic compound, such as hydroorotic acid or the like, or by reaction with a suitable isocyanate, such as methylisocyanate or isopropylisocyanate, to create a urea moiety at the N-terminus. Other agents can also be N-terminally linked that will increase the duration of action of the osteocalcin derivative.

Reductive amination is the process by which ammonia is condensed with aldehydes or ketones to form imines which are subsequently reduced to amines. Reductive amination is a useful method for conjugating undercarboxylated/uncarboxylated osteocalcin and its fragments or variants to polyethylene glycol (PEG). Covalent linkage of PEG to undercarboxylated/uncarboxylated osteocalcin and its fragments and variants may result in conjugates with increased water solubility, altered bioavailability, pharmacokinetics, immunogenic properties, and biological activities. See, e.g., Bentley et al., 1998, J. Pharm. Sci. 87:1446-1449.

Several particularly common modifications that may be applied to undercarboxylated/uncarboxylated osteocalcin and its fragments and variants such as glycosylation, lipid attachment, sulfation, hydroxylation and ADP-ribosylation are described in most basic texts, such as Proteins-Structure and Molecular Properties, 2nd ed., T. E. Creighton, W. H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al., 1990, Meth. Enzymol. 182:626-646 and Rattan et al., 1992, Ann. New York Acad. Sci. 663:48-62.

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods. Well-known techniques for preparing such non-linear polypeptides may be adapted by those skilled in the art to produce non-linear osteocalcin polypeptides.

Modifications can occur anywhere in the undercarboxylated/uncarboxylated osteocalcin and its fragments and variants, including the peptide backbone, the amino acid side-chains and the amino or carboxyl termini. Blockage of the amino or carboxyl group in a polypeptide, or both, by a covalent modification, is common in naturally-occurring and synthetic polypeptides and may be applied to the undercarboxylated/uncarboxylated osteocalcin or its fragments and variants used in the present invention. For instance, the amino terminal residue of polypeptides made in *E. coli*, prior to proteolytic processing, almost invariably will be N-formylmethionine. Thus, the use of undercarboxylated/uncarboxylated osteocalcin and its fragments and variants with N-formylmethionine as the amino terminal residue are within the scope of the present invention.

A brief description of various protein modifications that come within the scope of this invention are set forth in the table below:

TABLE 1

| Protein Modification | Description |
| --- | --- |
| Acetylation | Acetylation of N-terminus or ε-lysines. Introducing an acetyl group into a protein, specifically, the substitution of an acetyl group for an active hydrogen atom. |

TABLE 1-continued

| Protein Modification | Description |
|---|---|
| | A reaction involving the replacement of the hydrogen atom of a hydroxyl group with an acetyl group (CH$_3$CO) yields a specific ester, the acetate. Acetic anhydride is commonly used as an acetylating agent, which reacts with free hydroxyl groups. Acylation may facilitate addition of other functional groups. A common reaction is acylation of e.g., conserved lysine residues with a biotin appendage. |
| ADP-ribosylation | Covalently linking proteins or other compounds via an arginine-specific reaction. |
| Alkylation | Alkylation is the transfer of an alkyl group from one molecule to another. The alkyl group may be transferred as an alkyl carbocation, a free radical or a carbanion (or their equivalents). Alkylation is accomplished by using certain functional groups such as alkyl electrophiles, alkyl nucleophiles or sometimes alkyl radicals or carbene acceptors. A common example is methylation (usually at a lysine or arginine residue). |
| Amidation | Reductive animation of the N-terminus. Methods for amidation of insulin are described in U.S. Pat. No. 4,489,159. |
| Carbamylation | Nigen et al. describes a method of carbamylating hemoglobin. |
| Citrullination | Citrullination involves the addition of citrulline amino acids to the arginine residues of a protein, which is catalyzed by peptidylarginine deaminase enzymes (PADs). This generally converts a positively charged arginine into a neutral citrulline residue, which may affect the hydrophobicity of the protein (and can lead to unfolding). |
| Condensation of amines with aspartate or glutamate | Such reactions, may be used, e.g., to attach a peptide to other proteins labels. |
| Covalent attachment of flavin | Flavin mononucleotide (FAD) may be covalently attached to serine and/or threonine residues. May be used, e.g., as a light-activated tag. |
| Covalent attachment of heme moiety | A heme moiety is generally a prosthetic group that consists of an iron atom contained in the center of a large heterocyclic organic ring, which is referred to as a porphyrin. The heme moiety may be used, e.g., as a tag for the peptide. |
| Attachment of a nucleotide or nucleotide derivative | May be used as a tag or as a basis for further derivatising a peptide. |
| Cross-linking | Cross-linking is a method of covalently joining two proteins. Cross-linkers contain reactive ends to specific functional groups (primary amines, sulfhydryls, etc.) on proteins or other molecules. Several chemical groups may be targets for reactions in proteins and peptides. For example, Ethylene glycol bis[succinimidylsuccinate, Bis[2-(succinimidooxycarbonyloxy)ethyl]sulfone, and Bis[sulfosuccinimidyl] suberate link amines to amines. |
| Cyclization | For example, cyclization of amino acids to create optimized delivery forms that are resistant to, e.g., aminopeptidases (e.g., formation of pyroglutamate, a cyclized form of glutamic acid). |
| Disulfide bond formation | Disulfide bonds in proteins are formed by thiol-disulfide exchange reactions, particularly between cysteine residues (e.g., formation of cystine). |
| Demethylation | See, e.g., U.S. Pat. No. 4,250,088 (Process for demethylating lignin). |
| Formylation | The addition of a formyl group to, e.g., the N-terminus of a protein. See, e.g., U.S. Pat. Nos. 4,059,589, 4,801,742, and 6,350,902. |
| Glycylation | The covalent linkage of one to more than 40 glycine residues to the tubulin C-terminal tail. |
| Glycosylation | Glycosylation may be used to add saccharides (or polysaccharides) to the hydroxy oxygen atoms of serine and threonine side chains (which is also known as O-linked Glycosylation). Glycosylation may also be used to add saccharides (or polysaccharides) to the amide nitrogen of asparagine side chains (which is also known as N-linked Glycosylation), e.g., via oligosaccharyl transferase. |
| GPI anchor formation | The addition of glycosylphosphatidylinositol to the C-terminus of a protein. GPI anchor formation involves the addition of a hydrophobic phosphatidylinositol group - linked through a carbohydrate containing linker (e.g., glucosamine and mannose linked to phosphoryl ethanolamine residue) - to the C-terminal amino acid of a protein. |
| Hydroxylation | Chemical process that introduces one or more hydroxyl groups (—OH) into a protein (or radical). Hydroxylation reactions are typically catalyzed by hydroxylases. Proline is |

TABLE 1-continued

| Protein Modification | Description |
|---|---|
| | the principal residue to be hydroxylated in proteins, which occurs at the $C^\gamma$ atom, forming hydroxyproline (Hyp). In some cases, proline may be hydroxylated at its $C^\beta$ atom. Lysine may also be hydroxylated on its $C^\delta$ atom, forming hydroxylysine (Hyl). These three reactions are catalyzed by large, multi-subunit enzymes known as prolyl 4-hydroxylase, prolyl 3-hydroxylase and lysyl 5-hydroxylase, respectively. These reactions require iron (as well as molecular oxygen and α-ketoglutarate) to carry out the oxidation, and use ascorbic acid to return the iron to its reduced state. |
| Iodination | See, e.g., U.S. Pat. No. 6,303,326 for a disclosure of an enzyme that is capable of iodinating proteins. U.S. Pat. No. 4,448,764 discloses, e.g., a reagent that may be used to iodinate proteins. |
| ISGylation | Covalently linking a peptide to the ISG15 (Interferon-Stimulated Gene 15) protein, for, e.g., modulating immune response. |
| Methylation | Reductive methylation of protein amino acids with formaldehyde and sodium cyanoborohydride has been shown to provide up to 25% yield of N-cyanomethyl (—$CH_2CN$) product. The addition of metal ions, such as $Ni^{2+}$, which complex with free cyanide ions, improves reductive methylation yields by suppressing by-product formation. The N-cyanomethyl group itself, produced in good yield when cyanide ion replaces cyanoborohydride, may have some value as a reversible modifier of amino groups in proteins. (Gidley et al.) Methylation may occur at the arginine and lysine residues of a protein, as well as the N- and C-terminus thereof. |
| Myristoylation | Myristoylation involves the covalent attachment of a myristoyl group (a derivative of myristic acid), via an amide bond, to the alpha-amino group of an N-terminal glycine residue. This addition is catalyzed by the N-myristoyltransferase enzyme. |
| Oxidation | Oxidation of cysteines. Oxidation of N-terminal Serine or Threonine residues (followed by hydrazine or aminooxy condensations). Oxidation of glycosylations (followed by hydrazine or aminooxy condensations). |
| Palmitoylation | Palmitoylation is the attachment of fatty acids, such as palmitic acid, to cysteine residues of proteins. Palmitoylation increases the hydrophobicity of a protein. |
| (Poly)glutamylation | Polyglutamylation occurs at the glutamate residues of a protein. Specifically, the gamma-carboxy group of a glutamate will form a peptide-like bond with the amino group of a free glutamate whose alpha-carboxy group may be extended into a polyglutamate chain. The glutamylation reaction is catalyzed by a glutamylase enzyme (or removed by a deglutamylase enzyme). Polyglutamylation has been carried out at the C-terminus of proteins to add up to about six glutamate residues. Using such a reaction, Tubulin and other proteins can be covalently linked to glutamic acid residues. |
| Phosphopantetheinylation | The addition of a 4'-phosphopantetheinyl group. |
| Phosphorylation | A process for phosphorylation of a protein or peptide by contacting a protein or peptide with phosphoric acid in the presence of a non-aqueous apolar organic solvent and contacting the resultant solution with a dehydrating agent is disclosed e.g., in U.S. Pat. No. 4,534,894. Insulin products are described to be amenable to this process. See, e.g., U.S. Pat. No. 4,534,894. Typically, phosphorylation occurs at the serine, threonine, and tyrosine residues of a protein. |
| Prenylation | Prenylation (or isoprenylation or lipidation) is the addition of hydrophobic molecules to a protein. Protein prenylation involves the transfer of either a farnesyl (linear grouping of three isoprene units) or a geranyl-geranyl moiety to C-terminal cysteine(s) of the target protein. |
| Proteolytic Processing | Processing, e.g., cleavage of a protein at a peptide bond. |
| Selenoylation | The exchange of, e.g., a sulfur atom in the peptide for selenium, using a selenium donor, such as selenophosphate. |
| Sulfation | Processes for sulfating hydroxyl moieties, particularly tertiary amines, are described in, e.g., U.S. Pat. No. 6,452,035. A process for sulphation of a protein or peptide by contacting the protein or peptide with sulphuric acid in the presence of a non-aqueous apolar organic solvent and contacting the resultant solution with a dehydrating agent is disclosed. Insulin products are described to be amenable to this process. See, e.g., U.S. Pat. No. 4,534,894. |

TABLE 1-continued

| Protein Modification | Description |
| --- | --- |
| SUMOylation | Covalently linking a peptide a SUMO (small ubiquitin-related Modifier) protein, for, e.g., stabilizing the peptide. |
| Transglutamination | Covalently linking other protein(s) or chemical groups (e.g., PEG) via a bridge at glutamine residues |
| tRNA-mediated addition of amino acids (e.g., arginylation) | For example, the site-specific modification (insertion) of an amino acid analog into a peptide. |
| Ubiquitination | The small peptide ubiquitin is covalently linked to, e.g., lysine residues of a protein. The ubiquitin-proteasome system can be used to carryout such reaction. See, e.g., U.S. 2007-0059731. |

The present invention also encompasses the use of prodrugs of undercarboxylated/uncarboxylated osteocalcin or derivative or variant thereof that can be produced by esterifying the carboxylic acid functions of the undercarboxylated/uncarboxylated osteocalcin or derivative or variant thereof with a lower alcohol, e.g., methanol, ethanol, propanol, isopropanol, butanol, etc. The use of prodrugs of the undercarboxylated/uncarboxylated osteocalcin or derivative or variant thereof that are not esters is also contemplated. For example, pharmaceutically acceptable carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters of the undercarboxylated/uncarboxylated osteocalcin or derivative or variant thereof are also contemplated. In some embodiments, the prodrugs will contain a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Guidance for the preparation of prodrugs of the undercarboxylated/uncarboxylated osteocalcin or derivative or variant thereof disclosed herein can be found in publications such as *Design of Prodrugs*, Bundgaard, A. Ed., Elsevier, 1985; *Design and Application of Prodrugs, A Textbook of Drug Design and Development*, Krosgaard-Larsen and H. Bundgaard, Ed., 1991, Chapter 5, pages 113-191; and Bundgaard, H., Advanced Drug Delivery Review, 1992, 8, pages 1-38.

To practice the methods of the present invention, it may be desirable to recombinantly express osteocalcin, e.g., by recombinantly expressing a cDNA sequence encoding osteocalcin. The cDNA sequence and deduced amino acid sequence of human osteocalcin is represented in SEQ ID NO:1 and SEQ ID NO:2. Osteocalcin nucleotide sequences may be isolated using a variety of different methods known to those skilled in the art. For example, a cDNA library constructed using RNA from a tissue known to express osteocalcin can be screened using a labeled osteocalcin probe. Alternatively, a genomic library may be screened to derive nucleic acid molecules encoding osteocalcin. Further, osteocalcin nucleic acid sequences may be derived by performing a polymerase chain reaction (PCR) using two oligonucleotide primers designed on the basis of known osteocalcin nucleotide sequences. The template for the reaction may be cDNA obtained by reverse transcription of mRNA prepared from cell lines or tissue known to express osteocalcin.

While the osteocalcin polypeptides and peptides can be chemically synthesized (e.g., see Creighton, 1983, Proteins: Structures and Molecular Principles, W.H. Freeman & Co., N.Y), large polypeptides derived from osteocalcin and the full length osteocalcin itself may be advantageously produced by recombinant DNA technology using techniques well known in the art for expressing a nucleic acid. Such methods can be used to construct expression vectors containing the osteocalcin nucleotide sequences and appropriate transcriptional and translational control signals. These methods include, for example, in vitro recombinant DNA techniques, synthetic techniques, and in vivo genetic recombination. See, for example, the techniques described in Ausubel et al., 1989, supra.

A variety of host-expression vector systems may be utilized to express the osteocalcin nucleotide sequences. In a particular embodiment, the osteocalcin peptide or polypeptide is secreted and may be recovered from the culture media.

Appropriate expression systems can be chosen to ensure that the correct modification, processing and subcellular localization of the osteocalcin protein occurs. To this end, bacterial host cells are useful for expression of osteocalcin, as such cells are unable to carboxylate osteocalcin.

The isolated osteocalcin can be purified from cells that naturally express it, e.g., osteoblasts, or purified from cells that naturally express osteocalcin but have been recombinantly modified to overproduce osteocalcin, or purified from cells that that do not naturally express osteocalcin but have been recombinantly modified to express osteocalcin. In a particular embodiment, a recombinant cell has been manipulated to activate expression of the endogenous osteocalcin gene. For example, International Patent Publications WO 99/15650 and WO 00/49162 describe a method of expressing endogenous genes termed random activation of gene expression (RAGE), which can be used to activate or increase expression of endogenous osteocalcin. The RAGE methodology involves non-homologous recombination of a regulatory sequence to activate expression of a downstream endogenous gene. Alternatively, International Patent Publications WO 94/12650, WO 95/31560, and WO 96/29411, as well as U.S. Pat. Nos. 5,733,761 and 6,270,985, describe a method of increasing expression of an endogenous gene that involves homologous recombination of a DNA construct that includes a targeting sequence, a regulatory sequence, an exon, and a splice-donor site. Upon homologous recombination, a downstream endogenous gene is expressed. The methods of expressing endogenous genes described in the foregoing patents are hereby expressly incorporated by reference herein.

In certain embodiments of methods of the present invention where the therapeutic agent is undercarboxylated/uncarboxylated osteocalcin or a derivative or variant thereof, the undercarboxylated/uncarboxylated osteocalcin or a derivative or variant thereof is administered to a patient in a dosage range of from about 0.5 µg/kg/day to about 100 mg/kg/day, from about 1 µg/kg/day to about 90 mg/kg/day, from about 5 µg/kg/day to about 85 mg/kg/day, from about 10 µg/kg/day to about 80 mg/kg/day, from about 20 µg/kg/ day to about 75 mg/kg/day, from about 50 µg/kg/day to about 70 mg/kg/day, from about 150 µg/kg/day to about 65 mg/kg/day, from about 250 µg/kg/day to about 50 mg/kg/day, from about 500 µg/kg/day to about 50 mg/kg/day, from about 1 mg/kg/day to about 50 mg/kg/day, from about 5 mg/kg/day to about 40 mg/kg/day, from about 10 mg/kg/day to about 35 mg/kg/day, from about 15 mg/kg/day to about 30 mg/kg/day, from about 5 mg/kg/day to about 16 mg/kg/day, or from about 5 mg/kg/day to about 15 mg/kg/day.

In certain embodiments of methods of the present invention where the therapeutic agent is undercarboxylated/uncarboxylated osteocalcin or a derivative or variant thereof, the undercarboxylated/uncarboxylated osteocalcin or a derivative or variant thereof is administered to a patient in a dosage range of from about 0.5 µg/kg/day to about 100 µg/kg/day, from about 1 ag/kg/day to about 80 µg/kg/day, from about 3 µg/kg/day to about 50 µg/kg/day, or from about 3 g/kg/day to about 30 µg/kg/day.

In certain embodiments of methods of the present invention where the therapeutic agent is undercarboxylated/uncarboxylated osteocalcin or a derivative or variant thereof, the undercarboxylated/uncarboxylated osteocalcin or a derivative or variant thereof is administered to a patient in a dosage range of from about 0.5 ng/kg/day to about 100 ng/kg/day, from about 1 ng/kg/day to about 80 ng/kg/day, from about 3 ng/kg/day to about 50 ng/kg/day, or from about 3 ng/kg/day to about 30 ng/kg/day.

Compositions Comprising Inhibitors of Gamma-Carboxylase, PTP-1B, and/or OST-PTP

In certain embodiments of the invention, the pharmaceutical compositions useful in the method of the invention comprise an inhibitor that reduces the expression or activity of gamma-carboxylase, PTP-1B, or OST-PTP. Preferably, the biological activity of gamma-carboxylase, PTP-1B, or OST-PTP is inhibited. The inhibitors may be antibodies (monoclonal or polyclonal) or fragments of antibodies, small molecules, polypeptides or proteins, or nucleic acids (e.g., antisense DNA or RNA, siRNA).

In certain embodiments, the inhibitors reduce the activity of OST-PTP having the amino acid sequence of SEQ ID NO:11. In other embodiments, the inhibitors reduce the activity of an OST-PTP having an amino acid sequence that is substantially homologous or substantially identical, as previously described, to the amino acid sequence of SEQ ID NO:11.

In certain embodiments, the inhibitors reduce the activity of human PTP-1B having the amino acid sequence of SEQ ID NO:17. In other embodiments, the inhibitors reduce the activity of a PTP-1B having an amino acid sequence that is substantially homologous or substantially identical, as previously described, to the amino acid sequence of SEQ ID NO:17.

In certain embodiments, the inhibitors reduce the activity of human gamma-carboxylase having the amino acid sequence of SEQ ID NO:7. In other embodiments, the inhibitors reduce the activity of a gamma-carboxylase having an amino acid sequence that is substantially homologous or identical to SEQ ID NO:7.

Small Molecule Inhibitors of OST-PTP, PTP-1B, and Gamma-Carboxylase

In certain embodiments, the agent is a small molecule. By "small molecule" is meant organic compounds of molecular weight of more than 100 and less than about 2,500 daltons, and preferably less than 500 daltons. Such small molecules inhibit the biological activity of OST-PTP, PTP-1B, or gamma-carboxylase.

The small molecule inhibitors may comprise agents that act as inhibitors of vitamin K. Warfarin and other vitamin K inhibitors, including Coumadin and other derivatives, may be administered to patients who would benefit from inhibition of gamma-carboxylase in order to treat frailty in mammals. In a specific embodiment of the invention, the small molecule warfarin may be used to inhibit the activity of gamma-carboxylase. Warfarin derivatives are exemplified by acenocoumarol, phenprocoumon and phenindione. Warfarin and other Coumadin derivatives block vitamin K-dependent gamma-carboxylation of osteocalcin, thus increasing the level of undercarboxylated/uncarboxylated osteocalcin.

Other inhibitors include thiol specific inhibitors of gamma-carboxylase. Cys and His residues of gamma-carboxylase are implicated in the carboxylase mechanism of gamma-carboxylase and it is observed that the enzyme is inhibited by thiol-specific inhibitors, such as N-ethylmaleimide (NEM) and mercurials such asp-hydroxymurcuribenzoate (pHMB). Additional non-limiting examples of these inhibitors include 5,5-dithiobis-(2-nitrobenzoic acid) (DTNB), 2-nitro-5-thiocyanobenzoic acid (NTCB), iodoacetamide (IA), N-phenylmaleimide (PheM), N-(1-pyrenyl) maleimide (PyrM), naphthalene-1,5-dimaleimide (NDM), N,N'-(1,2-phenylene) dimaleimide (oPDM), N,N'-1,4-phenylene dimaleimide (pPDM), N,N'-1,3-phenylene dimaleimide (mPDM), 1,1-(methylenedi-4,1-phenylene)bismaleimide (BM), 4-(N-maleimido)phenyltrimethylammonium (MPTM), N,N'-bis(3-maleimidopropionyl)-2-hydroxy-1,3-propanediamine (BMP), N-succinimidyl 3-(2-pyridyldithio) propionate, diethyl pyrocarbonate, p-chloromercuribenzene sulphonic acid and thiosulfinates. These inhibitors may also be provided as conjugate or derivative, such as with, e.g., BSA or aminodextran.

Antibody Inhibitors of OST-PTP, PTP-1B, and Gamma-Carboxylase

The present invention also provides compositions comprising an antibody or antibodies, as well as biologically active fragments or variants thereof, that are capable of binding to an epitope of OST-PTP, PTP-1B, or gamma-carboxylase polypeptides and inhibiting the activity of OST-PTP, PTP-1B, or gamma-carboxylase.

An antibody against OST-PTP that decreases its activity can be used therapeutically. In certain embodiments, the antibody against OST-PTP binds to the extracellular domain of OST-PTP.

In certain embodiments, the antibody against OST-PTP binds to an epitope in the mouse OST-PTP of SEQ ID NO:11 or an OST-PTP having an amino acid sequence that is substantially homologous or identical to SEQ ID NO:11. In other embodiments, the antibody against OST-PTP binds to an epitope in an OST-PTP having an amino acid sequence that is at least 70% homologous or identical to SEQ ID NO:11.

Human OST-PTP can be obtained by isolating the human ortholog of mouse OST-PTP (SEQ ID NO:10) or rat OST-PTP (SEQ ID NO:14) by methods known in the art. For example, one could prepare a cDNA library from human osteoblasts and identify human OST-PTP cDNA by hybridizing the cDNA clones from the library to a mouse probe. The mouse probe could be based on a portion of mouse OST-PTP (SEQ ID NO: 10). Alternatively, PCR, using primers based on the mouse sequence, can be used to obtain the human OST-PTP gene.

An antibody against human PTP-1B that decreases its activity can be used therapeutically in the methods of the present invention. In certain embodiments, the antibody against human PTP-1B binds to the extracellular domain of human PTP-1B.

In certain embodiments, the antibody against human PTP-1B binds to an epitope in the human PTP-1B of SEQ ID NO:17 or an OST-PTP having an amino acid sequence that is substantially homologous or identical to SEQ ID NO:17. In other embodiments, the antibody against human PTP-1B binds to an epitope in a human PTP-1B having an amino acid sequence that is at least 70% homologous or identical to SEQ ID NO:17.

Gamma-carboxylase is an intracellular protein, so antibodies or fragments of antibodies against it are preferably used therapeutically when combined with technologies for delivering the antibodies, fragments or variants into the interior of target cells expressing gamma-carboxylase, e.g., osteoblasts. Antibodies or antibody fragments or variants against osteocalcin similarly can be used with technologies for delivering the antibodies or fragments into the interior of target cells and can also be used in diagnostics and drug screening assays.

In a particular embodiment, the present invention provides antibodies, fragments or variants of antibodies that recognize an epitope in OST-PTP that includes the amino acid at position 1316 of mouse OST-PTP or the corresponding position of human OST-PTP. In certain embodiments, these antibodies, fragments or variants of antibodies block or inhibit the ability of OST-PTP to activate gamma-carboxylase. In certain embodiments, use of these antibodies or fragments results in OST-PTP losing 50%, 60%, 70%, 80%, 90%, 95%, or essentially all of its ability to activate gamma-carboxylase.

The term "epitope" refers to an antigenic determinant on an antigen to which an antibody binds. Epitopes usually consist of chemically active surface groupings of molecules such as amino acids or sugar side chains, and typically have specific three-dimensional structural characteristics, as well as specific charge characteristics. Epitopes generally have at least five contiguous amino acids but some epitopes are formed by discontinuous amino acids that are brought together by the folding of the protein that contains them.

The terms "antibody" and "antibodies" include polyclonal antibodies, monoclonal antibodies, humanized or chimeric antibodies, single chain Fv antibody fragments, Fab fragments, and F(ab')$_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful in the present invention.

Antibody fragments that have specific binding affinity for the polypeptide of interest (e.g., OST-PTP, PTP-1B, or gamma-carboxylase) can be generated by known techniques. Such antibody fragments include, but are not limited to, F(ab')$_2$ fragments that can be produced by pepsin digestion of an antibody molecule, and Fab fragments that can be generated by reducing the disulfide bridges of F(ab')$_2$ fragments. Alternatively, Fab expression libraries can be constructed. See, for example, Huse et al., 1989, Science 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

Once produced, antibodies or fragments thereof can be tested for recognition of the target polypeptide by standard immunoassay methods including, for example, enzyme-linked immunosorbent assay (ELISA) or radioimmunoassay assay (RIA). See, Short Protocols in Molecular Biology eds. Ausubel et al., Green Publishing Associates and John Wiley & Sons (1992).

The immunoassays, immunohistochemistry, RIA, IRMAs used herein are based on the generation of various antibodies, including those that specifically bind to osteocalcin, OST-PTP, PTP-1B, gamma-carboxylase, vitamin K, or their fragments or variants. Antibodies and methods of using antibodies to quantitate the amount of osteocalcin, in particular, in a sample are also described in U.S. Pat. No. 5,681,707. U.S. Pat. No. 5,681,707 discloses antibodies that bind to the N-terminal 20 amino acids, or the C-terminal 14 amino acids of osteocalcin. Anti-OST-PTP antibodies are commercially available.

In one embodiment, antibodies against OST-PTP, PTP-1B, or gamma-carboxylase that reduce its activity are useful in the treatment of a patient having frailty.

Nucleic Acid Inhibitors of OST-PTP, PTP-1B, and Gamma-Carboxylase

Other embodiments of the present invention are directed to the use of antisense nucleic acids or small interfering RNA (siRNA) to reduce or inhibit expression and hence the biological activity of osteocalcin, OST-PTP, PTP-1B, and/or gamma-carboxylase. cDNA sequences encoding osteocalcin, OST-PTP, PTP-1B, and/or gamma-carboxylase are set forth herein. Based on these sequences, antisense DNA or RNA that hybridize sufficiently to the respective gene or mRNA encoding osteocalcin, OST-PTP, PTP-1B, and/or gamma-carboxylase to turn off or reduce expression can be readily designed and engineered, using methods known in the art.

In a specific embodiment of the invention, antisense or siRNA molecules for use in the methods of the present invention include those that bind under stringent conditions to the human gamma-carboxylase nucleic acid sequence of SEQ ID NO:6. In yet another embodiment of the invention, the antisense or siRNA molecules are those that that bind under stringent conditions to the OST-PTP nucleic acid sequence of SEQ ID NO:10, or sequences that are substantially homologous to SEQ ID NO:10.

In a specific embodiment of the invention, antisense or siRNA molecules for use in the methods of the present invention include those that bind under stringent conditions to the human PTP-1B nucleic acid sequence of SEQ ID NO:16, or sequences that are substantially homologous to SEQ ID NO:16.

Antisense-RNA and anti-sense DNA have been used therapeutically in mammals to treat various diseases. See for example Agrawal & Zhao, 1998, Curr. Opin. Chemical Biol. 2: 519-528; Agrawal & Zhao, 1997, CIBA Found. Symp. 209:60-78; and Zhao et al., 1998, Antisense Nucleic Acid Drug Dev. 8:451-458; the entire contents of which are hereby incorporated by reference as if fully set forth herein. Antisense oligodeoxyribonucleotides (antisense-DNA), oligoribonucleotides (antisense-RNA), and other polymeric antisense compounds (e.g., oligonucleotides composed of naturally-occurring nucleobases, sugars and covalent internucleoside linkages and non-naturally-occurring portions which function similarly) can base pair with a gene or its transcript. Anderson et al., 1996, Antimicrobiol. Agents Chemother. 40:2004-2011 and U.S. Pat. No. 6,828,151 describe methods for making and using antisense nucleic acids and their formulation, the entire contents of which are hereby incorporated by reference as if fully set forth herein. The disclosures of the foregoing publications can be adapted by those skilled in the art for use in the methods of the present invention.

Methods of making antisense nucleic acids are well known in the art. Further provided by the present invention are methods of modulating the expression of OST-PTP, PTP1B, and gamma-carboxylase genes and mRNA in cells or tissues by contacting the cells or tissues with one or more antisense compounds or compositions in order to treat frailty in mammals. As used herein, the term "target nucleic acid" encompasses DNA encoding osteocalcin, OST-PTP, PTP-1B, or gamma-carboxylase and RNA (including pre-mRNA and mRNA) transcribed from such DNA. The specific hybridization of a nucleic acid oligomeric compound with its target nucleic acid interferes with the normal function of the target nucleic acid. This modulation of function of a target nucleic acid by compounds which specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, and catalytic activity which may be engaged in or facilitated by the RNA. The overall effect of such interference with target nucleic acid function is modulation of the expression of the protein encoded by the DNA or RNA. In the context of the present invention, "modulation" means reducing or inhibiting the expression of the gene or mRNA for osteocalcin, OST-PTP and/or gamma-carboxylase. DNA is the preferred antisense nucleic acid.

The targeting process includes determination of a site or sites within the target DNA or RNA encoding the osteocalcin, OST-PTP, PTP-1B, and/or gamma-carboxylase for the antisense interaction to occur such that the desired inhibitory effect is achieved. Within the context of the present invention, a particular intragenic site is the region encompassing the translation initiation or termination codon of the open reading frame (ORF) of the mRNA for osteocalcin, OST-PTP, PTP-1B, or gamma-carboxylase, preferably human osteocalcin, OST-PTP, PTP-1B, or gamma-carboxylase. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUQ 5'-UUG or 5'-CUQ and 5'-AUA, 5'-ACG and 5'-CUG have been shown to function in vivo. Thus, the terms "translation initiation codon" and "start codon" can encompass many codon sequences, even though the initiator amino acid in each instance is typically methionine in eukaryotes. It is also known in the art that eukaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene. Routine experimentation will determine the optimal sequence of the antisense or siRNA.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene.

It is also known in the art that variants can be produced through the use of alternative signals to start or stop transcription and that pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, nucleic acids are chosen which are sufficiently complementary to the target, i.e., hybridize sufficiently well and with sufficient specificity, to give the desired effect of inhibiting gene expression and transcription or mRNA translation.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of a nucleic acid is capable of hydrogen bonding with a nucleotide at the same position of a DNA or RNA molecule, then the nucleic acid and the DNA or RNA are considered to be complementary to each other at that position. The nucleic acid and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the nucleic acid and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of function, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense nucleic acids have been employed as therapeutic moieties in the treatment of disease states in animals and man. Antisense nucleic acid drugs, including ribozymes, have been safely and effectively administered to humans in numerous clinical trials. It is thus established that nucleic acids can be useful therapeutic modalities that can be configured to be useful in treatment regimes for treatment of cells, tissues and animals, especially humans, for example to regulate expression of osteocalcin, OST-PTP, PTP-1B, and/or gamma-carboxylase.

Nucleic acids in the context of this invention include "oligonucleotides," which refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense nucleic acids are a preferred form of antisense compound, the present invention comprehends other oligomeric antisense compounds, including but not limited to oligonucleotide mimetics. The antisense compounds in accordance with this invention preferably comprise from about 8 to about 50 nucleobases (i.e., from about 8 to about 50 linked nucleosides). Particularly preferred antisense compounds are antisense nucleic acids comprising from about 12 to about 30 nucleobases. Antisense compounds include ribozymes, external guide sequence (EGS) nucleic acids (oligozymes), and other short catalytic RNAs or catalytic nucleic acids which hybridize to the target nucleic acid and modulate its expression.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare nucleic acids such as the phosphorothioates and alkylated derivatives.

The antisense compounds of the present invention can be utilized for diagnostics, therapeutics, and prophylaxis and as research reagents and kits. For therapeutics, an animal, preferably a human, suspected of having frailty, is treated by administering antisense compounds in accordance with this invention. The compounds useful in the methods of the invention can be formulated into pharmaceutical compositions by adding an effective amount of an antisense compound to a suitable pharmaceutically acceptable diluent or carrier. The antisense compounds and methods of the invention are also useful to retard the progression of frailty.

The present invention also encompasses the use of siRNA to treat frailty in mammals. U.S. Patent Application Publication No. 2004/0023390 (the entire contents of which are hereby incorporated by reference as if fully set forth herein) teaches that double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shut-down of protein synthesis and even cell death through apoptosis. Recent work shows that RNA fragments are the sequence-specific mediators of RNAi (Elbashir et al., 2001, Nature 411:494-498). Interference of gene expression by these small interfering RNA (siRNA) is now recognized as a naturally occurring strategy for silencing genes in *C. elegans, Drosophila*, plants, and in mouse embryonic stem cells, oocytes and early embryos (Baulcombe, 1996, Plant Mol Biol. 32:79-88; Timmons & Fire, 1998, Nature 395: 854; Wianny and Zernicka-Goetz, 2000, Nat Cell Biol. 2:70-75; Svoboda et al., 2000, Development 127:4147-4156).

In mammalian cell culture, a siRNA-mediated reduction in gene expression has been accomplished by transfecting cells with synthetic RNA nucleic acids (Elbashir et al., 2001, Nature 411:494-498). U.S. Patent Application Publication No. 2004/0023390, the entire contents of which are hereby incorporated by reference as if fully set forth herein, provides exemplary methods using a viral vector containing an expression cassette containing a pol II promoter operably-linked to a nucleic acid sequence encoding a small interfering RNA molecule (siRNA) targeted against a gene of interest.

As used herein, RNAi is the process of RNA interference. A typical mRNA produces approximately 5,000 copies of a protein. RNAi is a process that interferes with or significantly reduces the number of protein copies made by an mRNA, preferably encoding osteocalcin, OST-PTP, PTP-1B, or gamma-carboxylase. For example, a double-stranded short interfering RNA (siRNA) molecule is engineered to complement and match the protein-encoding nucleotide sequence of the target mRNA to be interfered with. In certain embodiments of the present invention, following intracellular delivery, the siRNA molecule associates with an RNA-induced silencing complex (RISC) and binds the target mRNA (such as mRNA encoding osteocalcin, gamma-carboxylase, PTP-1B or OST-PTP) through a base-pairing interaction and degrades it. The RISC remains capable of degrading additional copies of the targeted mRNA. Other forms of RNA such as short hairpin RNA and longer RNA molecules can be used in the methods of the present invention. Longer molecules cause cell death, for example by instigating apoptosis and inducing an interferon response. Cell death was the major hurdle to achieving RNAi in mammals because dsRNAs longer than 30 nucleotides activated defense mechanisms that resulted in non-specific degradation of RNA transcripts and a general shutdown of the host cell. Using from about 20 to about 29 nucleotide siRNAs to mediate gene-specific suppression in mammalian cells has apparently overcome this obstacle. These siRNAs are long enough to cause gene suppression but not of a length that induces an interferon response. In a specific embodiment of the present invention, the targets for suppression are osteocalcin mRNA, OST-PTP mRNA, PTP-1B mRNA, or gamma-carboxylase mRNA. siRNA molecules useful in the methods of the present invention include those sequences that bind under stringent conditions to the human PTP-1B sequence of SEQ ID:16, the human gamma-carboxylase sequence of SEQ ID:6, or the mouse OST-PTP sequence of SEQ ID NO:10. siRNA molecules useful in the methods of the present invention also include those sequences that bind under stringent conditions to nucleic acids that are 80%, 85%, 90%, or 95% homologous to SEQ ID NO:16, SEQ ID NO:6 or SEQ ID NO:10.

Formulation and Administration of Pharmaceutical Compositions

The present invention encompasses the use of the polypeptides, nucleic acids, antibodies, small molecules and other therapeutic agents described herein formulated in pharmaceutical compositions to administer to a subject. The therapeutic agents (also referred to as "active compounds") can be incorporated into pharmaceutical compositions suitable for administration to a subject, e.g., a human. Such compositions typically comprise the polypeptides, nucleic acids, antibodies, small molecules and a pharmaceutically acceptable carrier. Preferably, such compositions are non-pyrogenic when administered to humans.

The pharmaceutical compositions of the invention are administered in an amount sufficient to modulate the OST-PTP signaling pathway or the PTP-1B signaling pathway involving gamma-carboxylase and osteocalcin.

As used herein the language "pharmaceutically acceptable carrier" is intended to include any and all solvents, binders, diluents, disintegrants, lubricants, dispersion media, coatings, antibacterial and antifungal agents, isotonic and absorption delaying agents, and the like, compatible with pharmaceutical administration. The use of such media and agents for pharmaceutically active substances is well known in the art. As long as any conventional media or agent is compatible with the active compound, such media can be used in the compositions of the invention. Supplementary active compounds or therapeutic agents can also be incorporated into the compositions. A pharmaceutical composition of the invention is formulated to be compatible with its intended route of administration. Examples of routes of administration include parenteral, e.g., intravenous, intradermal, intranasal, subcutaneous, oral, inhalation, transdermal (topical), transmucosal, and rectal administration.

The term "administer" is used in its broadest sense and includes any method of introducing the compositions of the present invention into a subject. This includes producing polypeptides or polynucleotides in vivo as by transcription or translation of polynucleotides that have been exogenously introduced into a subject. Thus, polypeptides or nucleic acids produced in the subject from the exogenous compositions are encompassed in the term "administer."

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diamine tetra acetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where the therapeutic agents are water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.) or phosphate buffered saline (PBS). In all cases, the composition must be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., undercarboxylated/uncarboxylated osteocalcin protein or anti-OST-PTP antibody) in the required amount in an appropriate solvent with one or a combination of the ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient plus any additional desired ingredient from a previously sterile-filtered solution thereof.

Oral compositions generally include an inert diluent or an edible carrier. They can be enclosed in gelatin capsules or compressed into tablets. Depending on the specific conditions being treated, pharmaceutical compositions of the present invention for treatment of frailty in mammals can be formulated and administered systemically or locally. Techniques for formulation and administration can be found in "Remington: The Science and Practice of Pharmacy" (20$^{th}$ edition, Gennaro (ed.) and Gennaro, Lippincott, Williams & Wilkins, 2000). For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL®, or corn starch; a lubricant such as magnesium stearate or STEROTES®; a glidant such as colloidal silicon dioxide; a sweetening agent such as sucrose or saccharin; or a flavoring agent such as peppermint, methyl salicylate, or orange flavoring.

For administration by inhalation, the compounds may be delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

If appropriate, the compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to particular cells with, e.g., monoclonal antibodies) can also be used as pharmaceutically acceptable carriers. These can be prepared according to methods known to those skilled in the art, for example, as described in U.S. Pat. No. 4,522,811.

It is especially advantageous to formulate oral or parenteral compositions in unit dosage form for ease of administration and uniformity of dosage. "Unit dosage form" as used herein refers to physically discrete units suited as unitary dosages for the subject to be treated; each unit containing a predetermined quantity of active compound calculated to produce the desired therapeutic effect in association with the required pharmaceutical carrier. The specification for the unit dosage forms of the invention are dictated by and directly dependent on the unique characteristics of the active compound and the particular therapeutic effect to be achieved, and the limitations inherent in the art of compounding such an active compound for the treatment of individuals.

As previously noted, the agent may be administered continuously by pump or frequently during the day for extended periods of time. In certain embodiments, the agent may be administered at a rate of from about 0.3-100 ng/hour, preferably about 1-75 ng/hour, more preferably about 5-50 ng/hour, and even more preferably about 10-30 ng/hour. The agent may be administered at a rate of from about 0.1-100 µg/hr, preferably about 1-75 µg/hr, more preferably about 5-50 µg/hr, and even more preferably about 10-30 µg/hr. It will also be appreciated that the effective dosage of antibody, protein, or polypeptide used for treatment may increase or decrease over the course of a particular treatment. Changes in dosage may result and become apparent from monitoring the level of undercarboxylated/uncarboxylated osteocalcin in a biological sample, preferably blood or serum.

In an embodiment of the invention, the agent can be delivered by subcutaneous, long-term, automated drug delivery using an osmotic pump to infuse a desired dose of the agent for a desired time. Insulin pumps are widely available and are used by diabetics to automatically deliver insulin over extended periods of time. Such insulin pumps can be adapted to deliver the agent for use in the methods of the present invention. The delivery rate of the agent can be readily adjusted through a large range to accommodate changing requirements of an individual (e.g., basal rates and bolus doses). New pumps permit a periodic dosing manner, i.e., liquid is delivered in periodic discrete doses of a small fixed volume rather than in a continuous flow manner. The overall liquid delivery rate for the device is controlled and adjusted by controlling and adjusting the dosing period. The pump can be coupled with a continuous monitoring device and remote unit, such as a system described in U.S. Pat. No. 6,560,471, entitled "Analyte Monitoring Device and Methods of Use." In such an arrangement, the hand-held remote unit that controls the continuous blood monitoring device could wirelessly communicate with and control both the blood monitoring unit and the fluid delivery device delivering therapeutic agents for use in the methods of the present invention.

In some embodiments of the present invention, routine experimentation may be used to determine the appropriate dosage value for each patient by monitoring the effect of the therapeutic agent on serum undercarboxylated/uncarboxylated osteocalcin levels. The agent can be administered once or multiple times per day. Serum undercarboxylated/uncarboxylated osteocalcin levels can be monitored before and during therapy to determine the appropriate amount of therapeutic agent to administer to raise serum undercarboxylated/uncarboxylated osteocalcin levels or bring serum undercarboxylated/uncarboxylated osteocalcin levels to normal and to maintain normal levels over extended periods of time. In a particular embodiment, a patient is tested to determine if his serum undercarboxylated/uncarboxylated osteocalcin levels are significantly lower than normal levels (about 25% below) before administering treatment with the therapeutic agent. The frequency of administration may vary from a single dose per day to multiple doses per day. Particular routes of administration include oral, intravenous and intraperitoneal, but other forms of administration may be chosen as well.

A "therapeutically effective amount" of a protein or polypeptide, small molecule, antibody, or nucleic acid is an amount that achieves the desired therapeutic result. For example, if a therapeutic agent is administered to treat frailty in mammals, a therapeutically effective amount is an amount that alleviates one or more symptoms related to muscle wasting or a lung disorder while at the same time alleviating one or more symptoms related to a metabolic disorder, a male reproductive disorder, or a cognitive disorder.

A therapeutically effective amount of protein or polypeptide, small molecule or nucleic acid for use in the present invention typically varies and can be an amount sufficient to achieve serum therapeutic agent levels typically of between about 1 nanogram per milliliter and about 10 micrograms per milliliter in the subject, or an amount sufficient to achieve serum therapeutic agent levels of between about 1 nanogram per milliliter and about 7 micrograms per milliliter in the subject. Other particular serum therapeutic agent levels include about 0.1 nanogram per milliliter to about 3 micrograms per milliliter, about 0.5 nanograms per milliliter to about 1 microgram per milliliter, about 1 nanogram per milliliter to about 750 nanograms per milliliter, about 5 nanograms per milliliter to about 500 nanograms per milliliter, and about 5 nanograms per milliliter to about 100 nanograms per milliliter.

The amount of therapeutic agent disclosed herein to be administered to a patient in the methods of the present invention can be determined by those skilled in the art through routine methods and may range from about 1 mg/kg/day to about 1,000 mg/kg/day, from about 5 mg/kg/day to about 750 mg/kg/day, from about 10 mg/kg/day to about 500 mg/kg/day, from about 25 mg/kg/day to about 250 mg/kg/day, from about 50 mg/kg/day to about 100 mg/kg/day, or other suitable amounts.

The amount of therapeutic agent disclosed herein to be administered to a patient in the methods of the present invention also may range from about 1 µg/kg/day to about 1,000 µg/kg/day, from about 5 µg/kg/day to about 750 µg/kg/day, from about 10 µg/kg/day to about 500 µg/kg/day, from about 25 µg/kg/day to about 250 µg/kg/day, or from about 50 µg/kg/day to about 100 µg/kg/day.

The amount of therapeutic agent disclosed herein to be administered to a patient in the methods of the present invention also may range from about 1 ng/kg/day to about 1,000 ng/kg/day, from about 5 ng/kg/day to about 750 ng/kg/day, from about 10 ng/kg/day to about 500 ng/kg/day, from about 25 ng/kg/day to about 250 ng/kg/day, or from about 50 ng/kg/day to about 100 ng/kg/day.

The skilled artisan will appreciate that certain factors may influence the dosage required to effectively treat a subject, including but not limited to the severity of the condition, previous treatments, the general health and/or age of the subject, and other disorders or diseases present.

Treatment of a subject with a therapeutically effective amount of a protein, polypeptide, nucleotide or antibody can include a single treatment or, preferably, can include a series of treatments.

In certain embodiments, treatment of a subject with undercarboxylated/uncarboxylated osteocalcin leads to undercarboxylated/uncarboxylated osteocalcin being about 10%, about 15%, about 20%, about 25%, about 30%, about 35%, about 40%, about 45%, or about 50% of the total osteocalcin in the blood of the patient.

It is understood that the appropriate dose of a small molecule agent depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, and the effect which the practitioner desires the small molecule to have. It is furthermore understood that appropriate doses of a small molecule depend upon the potency of the small molecule with respect to the expression or activity to be modulated. When one or more of these small molecules is to be administered to a mammal (e.g., a human) in order to modulate expression or activity of OST-PTP, PTP-1B, or gamma-carboxylase, a relatively low dose may be prescribed at first, with the dose subsequently increased until an appropriate response is obtained. In addition, it is understood that the specific dose level for any particular subject will depend upon a variety of factors including the activity of the specific compound employed, the age, body weight, general health, and diet of the subject, the time of administration, the route of administration, the rate of excretion, whether other drugs are being administered to the patient, and the degree of expression or activity to be modulated.

For treatment, a suitable subject can be a mammal suspected of having, has been diagnosed as having, or is at risk of developing, frailty.

Suitable routes of administration of the pharmaceutical compositions useful in the methods of the present invention can include oral, intestinal, parenteral, transmucosal, transdermal, intramuscular, subcutaneous, transdermal, rectal, intramedullary, intrathecal, intravenous, intraventricular, intraatrial, intraaortal, intraarterial, or intraperitoneal administration. The pharmaceutical compositions useful in the methods of the present invention can be administered to the subject by a medical device, such as, but not limited to, catheters, balloons, implantable devices, biodegradable implants, prostheses, grafts, sutures, patches, shunts, or stents. In one particular embodiment, the therapeutic agent (e.g., undercarboxylated/uncarboxylated osteocalcin) can be coated on a stent for localized administration to the target area. In this situation a slow release preparation of undercarboxylated/uncarboxylated osteocalcin, for example, may be employed.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations and that may be consulted by those skilled in the art for techniques useful for practicing the present invention include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

While uncarboxylated osteocalcin crosses the blood-brain barrier, certain derivatives, variants, or modified forms of osteocalcin may not. In embodiments of the invention utilizing a form of osteocalcin that does not cross the blood-brain barrier, one may take advantage of methods known in the art for transporting substances across the blood-brain barrier. For example, the methods disclosed in U.S. Patent Application Publication No. 2013/0034590 or U.S. Patent Application Publication No. 2013/0034572 may be used. The human insulin or transferrin receptor can be utilized by targeting these receptors with a monoclonal antibody-modified osteocalcin conjugate (Pardridge, 2007, Pharm. Res. 24:1733-1744; Beduneau et al., 2008, J. Control. Release 126:44-49). Surfactant coated poly(butylcyanoacrylate) nanoparticles containing modified osteocalcin may be used (Kreuter et al., 2003, Pharm. Res. 20:409-416). Alternatively, cationic carriers such as cationic albumin conjugated to pegylated nanoparticles containing modified osteocalcin may be used to deliver modified osteocalcin to the brain (Lu et al., 2006, Cancer Res. 66:11878-11887).

In yet another aspect of the invention, undercarboxylated/uncarboxylated osteocalcin is administered as a pharmaceutical composition with a pharmaceutically acceptable excipient. Exemplary pharmaceutical compositions for undercarboxylated/uncarboxylated osteocalcin include injections as solutions or injections as injectable self-setting or self-gelling mineral polymer hybrids.

Undercarboxylated/uncarboxylated osteocalcin may be administered using a porous crystalline biomimetic bioactive composition of calcium phosphate. See U.S. Pat. Nos. 5,830,682; 6,514,514; and 6,511,958 and U.S. Patent Application Publications Nos. 2006/0063699; 2006/0052327; 2003/199615; 2003/0158302; 2004/0157864; 2006/0292670; 2007/0099831 and 2006/0257492, all of which are incorporated herein in their entirety by reference.

Methods of Treatment

The present invention provides methods for modulating the level of undercarboxylated/uncarboxylated osteocalcin in mammals through modulating the OST-PTP signaling pathway or the PTP-1B signaling pathway for treating frailty in mammals. In particular, the methods are used to inhibit OST-PTP phosphorylase activity, inhibit PTP-1B phosphorylase activity, reduce gamma-carboxylase activity, and/or increase undercarboxylated/uncarboxylated osteocalcin. According to the invention, the methods provide an amount of an agent effective to treat frailty. The agent may be selected from the group consisting of small molecules, antibodies and nucleic acids.

In certain embodiments, the methods comprise identifying a patient in need of treatment of frailty and then applying the methods disclosed herein to the patient.

In one embodiment of the invention, the method of treatment comprises administering to a patient in need thereof a therapeutically effective amount of undercarboxylated/uncarboxylated osteocalcin sufficient to raise the patient's blood level of undercarboxylated/uncarboxylated osteocalcin compared to the pretreatment patient level. Since undercarboxylated/uncarboxylated osteocalcin can cross the blood/brain barrier, this can lead to therapeutically effective levels of undercarboxylated/uncarboxylated osteocalcin in target areas of the brain. Preferably, the patient is a human. In another embodiment, the method of treatment comprises administering to a patient in need thereof a therapeutically effective amount of undercarboxylated/uncarboxylated osteocalcin sufficient to raise the ratio of undercarboxylated/uncarboxylated osteocalcin to total osteocalcin in the patient's blood compared to the pretreatment patient ratio.

In another aspect of the invention, a method is provided for treating frailty in a mammal comprising administering to a mammal in need thereof undercarboxylated/uncarboxylated osteocalcin in a therapeutically effective amount such that the frailty is treated. Preferably, the mammal is a human.

In an embodiment of the invention, a method is provided for treating frailty in a mammal comprising administering to a mammal in need of such treatment a therapeutically effective amount of an agent that reduces OST-PTP expression or activity in osteoblasts, or reduces PTP-1B expression or activity in osteoblasts, such that the frailty is treated. Preferably, the patient is a human.

The present invention is directed to methods (i) for treating frailty in a mammal comprising administering to a mammal in need of such treatment in a therapeutically effective amount an agent that reduces gamma-carboxylase expression or activity in osteoblasts such that the frailty is treated comprising administering to the mammal in need of such treatment a therapeutically effective amount an agent that reduces gamma-carboxylase expression or activity in osteoblasts. Preferably, the mammal is a human. In an embodiment of the invention, the agent is an isolated nucleic acid that is selected from the group consisting of cDNA, antisense DNA, antisense RNA, and small interfering RNA, which nucleic acid is sufficiently complementary to the gene or mRNA encoding gamma-carboxylase to permit specific hybridization to the gene or mRNA, and wherein the hybridization prevents or reduces expression of gamma-carboxylase in osteoblasts. In another embodiment of the invention, the nucleic acid is conjugated to a phosphate group or other targeting ligand to facilitate uptake by osteoblasts.

In the methods described herein, it will be understood that "treating" or "alleviating" a disease or disorder encompasses not only improving the disease or disorder or its symptoms but also retarding the progression of the disease or disorder or ameliorating the deleterious effects of the disease or disorder.

The present invention also encompasses the use of gene therapy for treatment of frailty in mammals. This can be accomplished by introducing a gene encoding osteocalcin or a biologically active fragment or variant thereof into a vector, and transfecting or infecting cells from a mammal afflicted with frailty or at a high risk of developing frailty with the vector, according to various methods known in the art. The cells may be transfected or infected by ex vivo or by in vivo methods.

Methods of gene therapy known in the art can be adapted for use in the methods of the present invention. Adeno-associated virus (AAV) is one of the most promising vectors for gene therapy and may be used in the methods of the present invention. Conventional methods of gene transfer and gene therapy are described in, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996. AAV is an attractive vector system for human gene therapy because it is non-pathogenic for humans, it has a high frequency of integration, and it can infect non-dividing cells, thus making it useful for delivery of genes into mammalian cells both in tissue culture and in whole animals. See, e.g., Muzyczka, 1992, Curr. Top. Microbiol. Immunol., 158:97-129. Recent studies have demonstrated AAV to be a potentially useful vector for gene delivery. LaFace et al., 1998, Virology, 162:483-486; Zhou et al., 1993, Exp. Hematol. (NY), 21:928-933; Flotte et al., 1993, Proc. Natl. Acad. Sci. USA 90:10613-10617; and Walsh et al., 1994, Blood 84:1492-1500. Recombinant AAV vectors have been used successfully for in vitro and in vivo transduction of marker genes (Kaplitt et al., 1994, Nature Genetics, 8:148-154; Lebkowski et al., 1988, Mol. Cell. Biol. 8:3988-3996; Samulski et al., 1989, J. Virol., 63:3822-3828; Shelling & Smith, 1994, Gene Therapy 1:165-169; Yoder et al., 1994, Blood, 82:suppl. 1:347A; Zhou et al., 1994, J. Exp. Med., 179:1867-1875; Hermonat & Muzyczka, 1984, Proc. Natl. Acad. Sci. USA., 81:6466-6470; Tratschin et al., 1984, Mol. Cell. Biol., 4:2072-2081; McLaughlin et al., 1988, J. Virol., 62:1963-1973) as well as genes involved in human diseases (Flotte et al., 1992, Am. J. Respir. Cell Mol. Biol. 7:349-356; Luo et al., 1994, Blood, 82:suppl. 1,303A; Ohi et al., 1990, Gene, 89:279-282; Walsh et al., 1992, Proc. Natl. Acad. Sci. USA 89:7257-7261; Wei et al., 1994, Gene Therapy, 1:261-268).

In certain other embodiments, the gene of interest (e.g., osteocalcin) can be transferred into a target cell using a retroviral vector. Retroviruses refer to viruses that belong to the Retroviridae family, and include oncoviruses, foamy viruses (Russell & Miller, 1996, J. Virol. 70:217-222; Wu et al., 1999, J. Virol. 73:4498-4501, and lentiviruses (for example, HIV-1 (Naldini et al., 1996, Science 272:263-267; Poeschla et al., 1996, Proc. Natl. Acad. Sci. USA 93:11395-11399; Srinivasakumar et al., 1997, J. Virol. 71:5841-5848; Zufferey et al., 1997, Nat. Biotechnol. 15:871-875; Kim et al., 1998, J. Virol. 72:811-816) and feline immunodeficiency virus (Johnston et al., 1999, J. Virol. 73:4991-5000; Johnston & Power, 1999, Virol. 73:2491-2498; Poeschla et al., 1998, Nat. Med. 4:354-357). The disclosures of these publications may be adapted for use in the methods of the present invention. Numerous gene therapy methods that take advantage of retroviral vectors for treating a wide variety of diseases are well-known in the art and can be adapted for use in the methods of the present invention (see, e.g., U.S. Pat. Nos. 4,405,712 and 4,650,764; Friedmann, 1989, Science, 244:1275-1281; Mulligan, 1993, Science, 260:926-932; Crystal, 1995, Science 270:404-410, and U.S. Pat. No. 6,899,871, each of which are incorporated herein by reference in their entirety). An increasing number of these methods are currently being applied in human clinical trials (Morgan, 1993, BioPharm, 6:32-35; see also The Development of Human Gene Therapy, Theodore Friedmann, Ed., Cold Spring Harbor Laboratory Press, Cold Spring Harbor, N.Y, 1999. ISBN 0-87969-528-5, which is incorporated herein by reference in its entirety).

Efficacy of the methods of treatment described herein can be monitored by determining whether the methods ameliorate any of the symptoms of the disease or disorder being treated. Alternatively, one can monitor the level of serum undercarboxylated/uncarboxylated osteocalcin (either in absolute terms or as a ratio of undercarboxylated/uncarboxylated osteocalcin/total osteocalcin), which levels should increase in response to therapy.

Diagnostics

The present invention provides methods and compositions for diagnosing frailty in mammals based on decreased levels of undercarboxylated/uncarboxylated osteocalcin. In a specific embodiment of the invention, a method is provided for diagnosing a patient having or at risk of developing frailty, comprising: (i) determining a patient level of undercarboxylated/uncarboxylated osteocalcin in a biological sample taken from the patient and a control level of undercarboxylated/uncarboxylated osteocalcin in a biological sample taken from a subject that does not have the disorder, (ii) comparing the patient and control levels, and (iii) diagnosing the patient as having or as being at risk of developing frailty if the patient level is lower than the control level.

"Biological samples" include solid and fluid body samples. The biological samples of the present invention may include tissue, organs, cells, protein or membrane extracts of cells, blood or biological fluids such as blood, serum, ascites fluid or brain fluid (e.g., cerebrospinal fluid). Preferably, the biological sample is blood or cerebrospinal fluid.

In another embodiment of the invention, a method is provided for diagnosing a patient having or at risk of developing frailty, comprising: (i) determining a patient level of undercarboxylated/uncarboxylated osteocalcin in a biological sample taken from the patient; and (ii) comparing the patient level to a standard level; where, if the patient level is lower than the standard level, diagnosing the patient as having or at risk of developing frailty. In instances where the method is practiced on humans, the standard level can be a level of undercarboxylated/uncarboxylated osteocalcin that has been previously determined to be the normal range for humans who are not at risk of developing the disorder. In particular embodiments, the biological sample is blood, serum, plasma, cerebrospinal fluid, urine, a cell sample, or a tissue sample.

A "standard level" of undercarboxylated/uncarboxylated osteocalcin in humans can include values of 0.1 ng/ml to 10 ng/ml, preferably 0.2 ng/ml to 7.5 ng/ml, more preferably 0.5 ng/ml to 5 ng/ml, and even more preferably 1 ng/ml to 5 ng/ml of undercarboxylated/uncarboxylated osteocalcin. A standard level of undercarboxylated/uncarboxylated osteocalcin in humans can also include about 0.1 ng/ml, about 0.5 ng/ml, about 1 ng/ml, about 2 ng/ml, about 3 ng/ml, about 4 ng/ml, about 5 ng/ml, about 6 ng/ml, about 7 ng/ml, or about 10 ng/ml of undercarboxylated/uncarboxylated osteocalcin.

In another embodiment of the invention, a method is provided for diagnosing a patient having or at risk of developing frailty, comprising: (i) determining the ratio of undercarboxylated/uncarboxylated osteocalcin to total osteocalcin in a biological sample taken from the patient; and (ii) comparing the ratio to a standard ratio; where, if the patient ratio is lower than the standard ratio, diagnosing the patient as having or being at risk of developing frailty. In certain embodiments, the standard ratio is 5%-10%, 10%-15%, 15%-20%, 20%-25%, 25%-30%, or 30%-35%. In certain embodiments, the standard ratio is about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35%. Preferably, the patient is a human. In particular embodiments, the biological sample is blood, serum, plasma, cerebrospinal fluid, urine, a cell sample, or a tissue sample.

Assays for detecting the levels of protein expression, e.g., osteocalcin expression, are well known to those of skill in the art. Such assays include, for example, antibody-based immunoassays. Methods for using antibodies as disclosed herein are particularly applicable to the cells, tissues and other biological samples from mammal with frailty that differentially express osteocalcin, OST-PTP, PTP-1B, or gamma-carboxylase. The methods use antibodies that selectively bind to the protein of interest and its fragments or variants.

The amount of osteocalcin in a biological sample may be determined by an assay such as a radioimmunoassay, an immunoradiometric assay, and/or an enzyme immunoassay. A "radioimmunoassay" is a technique for detecting and measuring the concentration of an antigen using a labeled (e.g., radioactively labeled) form of the antigen. Examples of radioactive labels for antigens include $^{3}H$, $^{14}C$, and $^{125}I$. The concentration of antigen (e.g., osteocalcin) in a biological sample may be measured by having the antigen in the sample compete with a labeled (e.g., radioactively, fluorescently) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed *S. aureus*. Yet another method for separating the antigen-antibody complex from the free antigen is by performing a "solid-phase radioimmunoassay" where the antibody is linked (e.g., covalently) to Sepharose® beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "Immunoradiometric Assay" (IRMA) is an immunoassay in which the antibody reagent is radioactively labeled. An IRMA requires the production of a multivalent antigen conjugate, by techniques such as conjugation to a protein, e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

The most common enzyme immunoassay is the "Enzyme-Linked Immunosorbent Assay (ELISA)." The "Enzyme-Linked Immunosorbent Assay (ELISA)" is a technique for detecting and measuring the concentration of an antigen using a labeled (e.g., enzyme linked) form of the antibody. In a "sandwich ELISA," an antibody (e.g., to osteocalcin) is linked to a solid phase (e.g., a microtiter plate) and exposed to a biological sample containing antigen (e.g., osteocalcin). The solid phase is then washed to remove unbound antigen. A labeled (e.g., enzyme linked) antibody is then bound to the bound-antigen (if present) forming an antibody-antigen-antibody sandwich. Examples of enzymes that can be linked to the antibody include alkaline phosphatase, horseradish peroxidase, luciferase, urease, and p-galactosidase. The enzyme linked antibody reacts with a substrate to generate a colored reaction product that can be assayed.

In a "competitive ELISA," antibody is incubated with a sample containing antigen (e.g., osteocalcin). The antigen-antibody mixture is then contacted with an antigen-coated solid phase (e.g., a microtiter plate). The more antigen present in the sample, the less free antibody that will be available to bind to the solid phase. A labeled (e.g., enzyme linked) secondary antibody is then added to the solid phase to determine the amount of primary antibody bound to the solid phase.

In an "immunohistochemistry assay," a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or β-galactosidase), or chemical methods (e.g., DAB/Substrate chromagen).

In addition to detecting levels of protein expression, the diagnostic assays of the invention may employ methods designed to detect the level of RNA expression. Levels of RNA expression may be determined using methods well known to those of skill in the art, including, for example, the use of northern blots, RT-PCR or in situ hybridizations.

Carboxylation of osteocalcin confers a greater affinity for hydroxyapatite. Total osteocalcin may be measured by immunoassay followed by incubation with hydroxyapatite and centrifugation. The supernatant, which contains osteocalcin that has not adsorbed to hydroxyapatite is then measured using the same immunoassay. The results of this procedure can be expressed either as absolute concentrations or as a ratio of undercarboxylated to carboxylated osteocalcin.

Another procedure uses monoclonal antibodies that distinguish the carboxylation state of all or some of the Glu/Gla residues of osteocalcin. For example, GluOC4-5 (TaKaRa catalog no. M171) reacts with human osteocalcin with glutamic acid residues (decarboxylated) at positions 21 and 24, and does not react with react with Gla-type osteocalcin.

For a review of osteocalcin measurement methods, see Lee et al., 2000, Ann. Clin. Biochem. 37:432-446.

Drug Screening and Assays

Cell-based and non-cell based methods of drug screening are provided to identify candidate agents that reduce OST-PTP, PTP-1B, or gamma-carboxylase activity or expression, and/or increase the level of undercarboxylated/uncarboxylated osteocalcin activity or expression. Such agents find use in treating frailty in mammals.

Non-cell based screening methods are provided to identify compounds that bind to OST-PTP, PTP-1B, gamma-carboxylase or osteocalcin and thereby modulate the activity of these proteins.

Such non-cell based methods include a method to identify, or assay for, an agent that binds to OST-PTP, the method comprising the steps of: (i) providing a mixture comprising OST-PTP or a fragment or variant thereof, (ii) contacting the mixture with a candidate agent, (iii) determining whether the candidate agent binds to the OST-PTP, wherein if the agent binds to the OST-PTP or a fragment or variant thereof (iv) determining whether the agent reduces the ability of OST-PTP to dephosphorylate gamma-carboxylase and (v) administering the agent to a patient in need of treatment for frailty in mammals. In certain embodiments, the mixture comprises membrane fragments comprising OST-PTP or a fragment or variant thereof.

A screening method is provided to identify or assay for an agent that binds to the phosphatase 1 domain of OST-PTP, the method comprising the steps of: (i) providing a mixture comprising the phosphatase 1 domain of OST-PTP or a fragment or variant thereof, (ii) contacting the mixture with an agent, (iii) determining whether the agent binds to the phosphatase 1 domain of OST-PTP, wherein if the agent binds to the phosphatase 1 domain of OST-PTP or a fragment or variant thereof (iv) determining whether the agent inhibits the phosphatase 1 domain of OST-PTP and, if the agent inhibits the phosphatase 1 domain of OST-PTP (v) administering the agent to a patient in need of treatment for frailty in mammals.

A screening method is provided to identify or assay for an agent that binds to PTP-1B, the method comprising the steps of: (i) providing a mixture comprising PTP-1B or a fragment or variant thereof, (ii) contacting the mixture with a candidate agent, (iii) determining whether the candidate agent binds to the PTP-1B, wherein if the agent binds to the PTP-1B or a fragment or variant thereof (iv) determining whether the agent reduces the ability of PTP-1B to dephosphorylate gamma-carboxylase and (v) administering the agent to a patient in need of treatment for frailty in mammals. In certain embodiments, the mixture comprises membrane fragments comprising PTP-1B or a fragment or variant thereof.

A screening method is provided to identify, or assay for, an agent that binds to gamma-carboxylase, the method comprising the steps of: (i) providing a mixture comprising the gamma-carboxylase or a fragment or variant thereof, (ii) contacting the mixture with an agent, (iii) determining whether the agent binds to the gamma-carboxylase, wherein if the agent binds to the gamma-carboxylase or a fragment or variant thereof (iv) administering the agent to a mammal in need of treatment for frailty. The method may further comprise the step of determining whether the agent reduces gamma-carboxylase activity.

The binding of the agent to the target molecule in the above-described assays may be determined through the use of competitive binding assays. The competitor is a binding moiety known to bind to the target molecule. Under certain circumstances, there may be competitive binding as between the agent and the binding moiety, with the binding moiety displacing the agent or the agent displacing the binding moiety.

Either the agent or the competitor may be labeled. Either the agent, or the competitor is added first to the protein for a time sufficient to allow binding. Incubations may be performed at any temperature which facilitates optimal binding, typically between 4° C. and 40° C. Incubation periods may also be chosen for optimum binding, but may also optimized to facilitate rapid high throughput screening. Typically, between 0.1 and 1 hour will be sufficient. Excess agent and competitor are generally removed or washed away.

Using such assays, the competitor may be added first, followed by the agent. Displacement of the competitor is an indication that the agent is binding to the target molecule and thus is capable of binding to, and potentially modulating, the activity of the target molecule. In this embodiment, either component can be labeled. Thus, for example, if the competitor is labeled, the presence of label in the wash solution indicates displacement by the agent.

In another example, the agent is added first, with incubation and washing, followed by the competitor. The absence of binding by the competitor may indicate that the agent is bound to the target molecule with a higher affinity than the competitor. Thus, if the agent is labeled, the presence of the label on the target molecule, coupled with a lack of competitor binding, may indicate that the agent is capable of binding to the target molecule.

The method may comprise differential screening to identify agents that are capable of modulating the activity of the target molecule. In such an instance, the methods comprise combining the target molecule and a competitor in a first sample. A second sample comprises an agent, the target molecule, and a competitor. Addition of the agent is performed under conditions which allow the modulation of the activity of the target molecule. The binding of the competitor is determined for both samples, and a change, or difference in binding between the two samples indicates the presence of an agent capable of binding to the target molecule and potentially modulating its activity. That is, if the binding of the competitor is different in the second sample relative to the first sample, the agent is capable of binding to the target molecule.

Positive controls and negative controls may be used in the assays. Preferably, all control and test samples are performed in at least triplicate to obtain statistically significant results. Incubation of all samples is for a time sufficient for the binding of the agent to the target molecule. Following incubation, all samples are washed free of non-specifically bound material and the amount of bound, generally labeled agent determined. For example, where a radiolabel is employed, the samples may be counted in a scintillation counter to determine the amount of bound agent.

A variety of other reagents may be included in the screening assays. These include reagents like salts, neutral proteins, e.g. albumin, detergents, etc. which may be used to facilitate optimal protein-protein binding and/or reduce non-specific or background interactions. Also, reagents that otherwise improve the efficiency of the assay, such as protease inhibitors, nuclease inhibitors, anti-microbial agents, etc., may be used. The mixture of components may be added in any order that provides for the requisite binding.

Thus, in one example, the methods comprise combining a sample comprising OST-PTP, PTP-1B, or gamma-carboxylase and an agent, and evaluating the effect on OST-PTP, PTP-1B, or gamma-carboxylase enzyme activity. By enzyme activity, specifically OST-PTP, PTP-1B, or gamma-carboxylase enzyme activity, is meant one or more of the biological activities associated with the enzyme. For OST-PTP and PTP-1B, this activity is preferably the dephosphorylation of gamma-carboxylase; for gamma-carboxylase, it is the carboxylation of osteocalcin. The screening assays are designed to find agents that reduce OST-PTP, PTP-1B, or gamma-carboxylase activity, and/or increase levels of undercarboxylated/uncarboxylated osteocalcin.

Specifically, a screening method is provided to identify an agent that reduces OST-PTP activity, the method comprising the steps of: (a) providing a control mixture comprising OST-PTP or a fragment or variant thereof and a test mixture comprising OST-PTP or a fragment or variant thereof, (b) contacting the test mixture with an agent, (c) determining the level of activity of OST-PTP in the test mixture and in the control mixture, (d) identifying the agent as an agent that reduces OST-PTP activity if the level of OST-PTP activity in the test mixture is lower than the level of OST-PTP activity in the control mixture, and (e) administering the identified agent to a mammal in need of treatment for frailty.

A screening method is provided to identify an agent that reduces PTP-1B activity, the method comprising the steps of: (a) providing a control mixture comprising PTP-1B or a fragment or variant thereof and a test mixture comprising PTP-1B or a fragment or variant thereof, (b) contacting the test mixture with an agent, (c) determining the level of activity of PTP-1B in the test mixture and in the control mixture, (d) identifying the agent as an agent that reduces PTP-1B activity if the level of PTP-1B activity in the test mixture is lower than the level of PTP-1B activity in the control mixture, and (e) administering the identified agent to a mammal in need of treatment for frailty.

A screening method is provided to identify an agent that reduces gamma-carboxylase activity, the method comprising the steps of: (a) providing a control mixture comprising gamma-carboxylase or a fragment or variant thereof and a test mixture comprising gamma-carboxylase or a fragment or variant thereof, (b) contacting the test mixture with an agent, (c) determining the level of activity of gamma-carboxylase in the test mixture and in the control mixture, (d) identifying the agent as an agent that reduces gamma-carboxylase activity if the level of gamma-carboxylase activity in the test mixture is lower than the level of gamma-carboxylase activity in the control mixture, and (e) administering the identified agent to a mammal in need of treatment for frailty.

The present invention also provides a screening method to identify an agent that decarboxylates osteocalcin, the method comprising the steps of: (a) providing a control mixture comprising carboxylated osteocalcin and a test mixture comprising carboxylated osteocalcin, (b) adding to the test mixture an agent, (c) determining the level of carboxylated osteocalcin in the test mixture and in the control mixture, (d) identifying the agent as an agent that decarboxylates osteocalcin if the level of carboxylated osteocalcin in the test mixture is lower than the level of carboxylated osteocalcin in the control mixture, and (e) administering the identified agent to a mammal in need of treatment for frailty.

A cell-based method is provided for identifying an agent that increases osteocalcin gene expression, the method comprising steps: (a) determining a first expression level of osteocalcin in a cell, (b) determining a second expression level of osteocalcin after contact with a test agent; and (c) comparing the first expression level with the second expression level, wherein if the first expression level is lower than the second expression level the agent is identified as an agent that increases osteocalcin gene expression, and (e) administering the identified agent to a mammal in need of treatment for frailty. The level of osteocalcin gene expression may be determined by measuring the amount of osteocalcin mRNA made or the amount of osteocalcin protein made. In certain embodiments, the cell is an osteoblast.

Gamma carboxylase catalyzes the posttranslational modification of specific glutamic acid residues within osteocalcin to form γ-carboxyglutamic acid residues. In an embodiment of the assays described herein, the level of gamma carboxylase activity or decarboxylase activity is determined by measuring the level of osteocalcin carboxylation.

Cells to be used in the screening or assaying methods described herein include cells that naturally express OST-PTP, the phosphatase 1 domain of OST-PTP, PTP-1B, gamma-carboxylase, or osteocalcin as well as cells that have been genetically engineered to express (or overexpress) OST-PTP, the phosphatase 1 domain of OST-PTP, PTP-1B gamma-carboxylase, or osteocalcin. Such cells include transformed osteoblasts that overexpress OST-PTP, the phosphatase 1 domain of OST-PTP, PTP-1B, or gamma-carboxylase.

A method is provided for identifying an agent useful for treating frailty in mammals comprising: (a) providing a mammal that has frailty, (b) determining the amount of undercarboxylated/uncarboxylated osteocalcin in a pre-administration biological sample taken from the mammal, (c) administering an agent to the mammal, (d) determining the amount of undercarboxylated/uncarboxylated osteocalcin in a post-administration biological sample taken from the mammal, and (e) identifying the agent as useful for treating frailty in mammals if the amount of undercarboxylated/uncarboxylated osteocalcin in the post-administration biological sample is higher than the amount of undercarboxylated/uncarboxylated osteocalcin in the pre-administration biological sample.

The term "agent" as used herein includes any molecule, e.g., protein, oligopeptide, small organic molecule, polysaccharide, polynucleotide, lipid, etc., or mixtures thereof. Some of the agents can be used therapeutically. An agent may be OST-PTP, PTP-1B, gamma-carboxylase, osteocalcin, or fragments thereof.

Generally, in the assays described herein, a plurality of assay mixtures is run in parallel with different agent concentrations to obtain a differential response to the various concentrations. Typically, one of these concentrations serves as a negative control, i.e., is at zero concentration or below the level of detection.

Agents for use in screening encompass numerous chemical classes, though typically they are organic molecules, preferably small organic compounds having a molecular weight of more than 100 and less than about 2,500 daltons, preferably less than about 500 daltons. Agents comprise functional groups necessary for structural interaction with proteins, particularly hydrogen bonding, and typically include at least an amine, carbonyl, hydroxyl or carboxyl group, preferably at least two of these functional chemical groups. The agents often comprise cyclical carbon or heterocyclic structures and/or aromatic or polyaromatic structures substituted with one or more of the above functional groups. Agents are also found among biomolecules including peptides, saccharides, fatty acids, steroids, purines, pyrimidines, derivatives, structural analogs or combinations thereof. Particularly preferred biomolecules are peptides.

Libraries of high-purity small organic ligands and peptides that have well-documented pharmacological activities are available from numerous sources for use in the assays herein. One example is an NCI diversity set which contains 1,866 drug-like compounds (small, intermediate hydrophobicity). Another is an Institute of Chemistry and Cell Biology (ICCB; maintained by Harvard Medical School) set of known bioactives (467 compounds) which includes many extended, flexible compounds. Some other examples of the ICCB libraries are: Chem Bridge DiverSet E (16,320 compounds); Bionet 1 (4,800 compounds); CEREP (4,800 compounds); Maybridge 1 (8,800 compounds); Maybridge 2 (704 compounds); Maybridge HitFinder (14,379 compounds); Peakdale 1 (2,816 compounds); Peakdale 2 (352 compounds); ChemDiv Combilab and International (28,864 compounds); Mixed Commercial Plate 1 (352 compounds); Mixed Commercial Plate 2 (320 compounds); Mixed Commercial Plate 3 (251 compounds); Mixed Commercial Plate 4 (331 compounds); ChemBridge Microformat (50,000 compounds); Commercial Diversity Set1 (5,056 compounds). Other NCI Collections are: Structural Diversity Set, version 2 (1,900 compounds); Mechanistic Diversity Set (879 compounds); Open Collection 1 (90,000 compounds); Open Collection 2 (10,240 compounds); Known Bioactives Collections: NINDS Custom Collection (1,040 compounds); ICCB Bioactives 1 (489 compounds); SpecPlus Collection (960 compounds); ICCB Discretes Collections. The following ICCB compounds were collected individually from chemists at the ICCB, Harvard, and other collaborating institutions: ICCB1 (190 compounds); ICCB2 (352 compounds); ICCB3 (352 compounds); ICCB4 (352 compounds). Natural Product Extracts: NCI Marine Extracts (352 wells); Organic fractions—NCI Plant and Fungal Extracts (1,408 wells); Philippines Plant Extracts 1 (200 wells); ICCB-ICG Diversity Oriented Synthesis (DOS) Collections; DDS1 (DOS Diversity Set) (9600 wells). Compound libraries are also available from commercial suppliers, such as ActiMol, Albany Molecular, Bachem, Sigma-Aldrich, TimTec, and others.

Known and novel pharmacological agents identified in screens may be further subjected to directed or random chemical modifications, such as acylation, alkylation, esterification, or amidification to produce structural analogs.

When screening, designing, or modifying compounds, other factors to consider include the Lipinski rule-of-five (not more than 5 hydrogen bond donors (OH and NH groups); not more than 10 hydrogen bond acceptors (notably N and O); molecular weight under 500 g/mol; partition coefficient log P less than 5), and Veber criteria, which are recognized in the pharmaceutical art and relate to properties and structural features that make molecules more or less drug-like.

The agent may be a protein. By "protein" in this context is meant at least two covalently attached amino acids, and includes proteins, polypeptides, oligopeptides and peptides. The protein may be made up of naturally occurring amino acids and peptide bonds, or synthetic peptidomimetic structures. Thus "amino acid," or "peptide residue," as used herein means both naturally occurring and synthetic amino acids. For example, homo-phenylalanine, citrulline and nor-leucine are considered amino acids for the purposes of the invention. "Amino acids" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

The agent may be a naturally occurring protein or fragment or variant of a naturally occurring protein. Thus, for example, cellular extracts containing proteins, or random or directed digests of proteinaceous cellular extracts, may be used. In this way, libraries of prokaryotic and eukaryotic proteins may be made for screening against one of the various proteins. Libraries of bacterial, fungal, viral, and mammalian proteins, with the latter being preferred, and human proteins being especially preferred, may be used.

Agents may be peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "random" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized agent bioactive proteinaceous agents.

The library may be fully randomized, with no sequence preferences or constants at any position. Alternatively, the library may be biased. That is, some positions within the sequence are either held constant, or are selected from a limited number of possibilities. For example, the nucleotides or amino acid residues are randomized within a defined class, for example, of hydrophobic amino acids, hydrophilic residues, sterically biased (either small or large) residues, towards the creation of cysteines, for cross-linking, prolines for SH3 domains, serines, threonines, tyrosines or histidines for phosphorylation sites, etc., or to purines, etc.

The agent may be an isolated nucleic acid, preferably antisense, siRNA, or cDNA that binds to either the gene encoding the protein of interest, or its mRNA, to block gene expression or mRNA translation, respectively. By "nucleic acid" or "oligonucleotide" or grammatical equivalents herein means at least two nucleotides covalently linked together. Such nucleic acids will generally contain phosphodiester bonds, although in some cases, as outlined below, nucleic acid analogs are included that may have alternate backbones, comprising, for example, phosphoramide (Beaucage et al., 1993, Tetrahedron 49:1925 and references therein; Letsinger, 1970, J. Org. Chem. 35:3800; Sprinzl et al., 1977, Eur. J. Biochem. 81:579; Letsinger et al., 1986, Nucl. Acids Res. 14:3487; Sawai et al, 1984, Chem. Lett. 805; Letsinger et al., 1988, J. Am. Chem. Soc. 110:4470; and Pauwels et al., 1986, Chemica Scripta 26:141); phosphorothioate (Mag et al., 1991, Nucleic Acids Res. 19:1437; and U.S. Pat. No. 5,644,048), phosphorodithioate (Briu et al., 1989, J. Am. Chem. Soc. 111:2321); O-methylphophoroamidite linkages (see Eckstein, Oligonucleotides and Analogues: A Practical Approach, Oxford University Press), and peptide nucleic acid backbones and linkages (see Egholm, 1992, J. Am. Chem. Soc. 114:1895; Meier et al., 1992, Chem. Int. Ed. Engl. 31:1008; Nielsen, 1993, Nature, 365:566; Carlsson et al., 1996, Nature 380:207); all of which publications are incorporated by reference and may be consulted by those skilled in the art for guidance in designing nucleic acid agents for use in the methods described herein.

Other analog nucleic acids include those with positive backbones (Denpcy et al., 1995, Proc. Natl. Acad. Sci. USA 92:6097); non-ionic backbones (U.S. Pat. Nos. 5,386,023; 5,637,684; 5,602,240; 5,216,141; and U.S. Pat. No. 4,469,863; Kiedrowshi et al., 1991, Angew. Chem. Intl. Ed. English 30:423; Letsinger et al., 1988, J. Am. Chem. Soc. 110:4470; Letsinger et al., 1994, Nucleoside & Nucleoside 13:1597; Chapters 2 and 3, ASC Symposium Series 580, "Carbohydrate Modifications in Antisense Research," Ed. Y S. Sanghui and P. Dan Cook; Mesmaeker et al., 1994, Bioorganic & Medicinal Chem. Lett. 4:395; Jeffs et al., 1994, J. Biomolecular NMR 34:17); and non-ribose backbones, including those described in U.S. Pat. Nos. 5,235,033 and 5,034,506, and Chapters 6 and 7, ASC Symposium Series 580, "Carbohydrate Modifications in antisense Research," Ed. Y S. Sanghui and P. Dan Cook. Nucleic acids containing one or more carbocyclic sugars are also included within the definition of nucleic acids that may be used as agents as described herein. Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring acids and analogs can be made. Alternatively, mixtures of different nucleic acid analogs, and mixtures of naturally occurring nucleic acids and analogs may be made. The nucleic acids may be single stranded or double stranded, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc.

As described above generally for proteins, nucleic acid agents may be naturally occurring nucleic acids, random nucleic acids, or "biased" random nucleic acids. For example, digests of prokaryotic or eukaryotic genomes may be used as outlined above for proteins.

The agents may be obtained from combinatorial chemical libraries, a wide variety of which are available in the literature. By "combinatorial chemical library" herein is meant a collection of diverse chemical compounds generated in a defined or random manner, generally by chemical synthesis. Millions of chemical compounds can be synthesized through combinatorial mixing.

The determination of the binding of the agent to one of the various proteins such as OST-PTP, PTP-1B, or gamma-carboxylase may be done in a number of ways. In a preferred embodiment, the agent is labeled, and binding determined directly. For example, this may be done by attaching all or a portion of one of the various proteins to a solid support, adding a labeled agent (for example an agent comprising a radioactive or fluorescent label), washing off excess reagent, and determining whether the label is present on the solid support. Various blocking and washing steps may be utilized as is known in the art.

By "labeled" herein is meant that the agent is either directly or indirectly labeled with a label which provides a detectable signal, e.g. a radioisotope (such as $^3$H, $^{14}$C, $^{32}$P, $^{33}$P, $^{35}$S, or $^{125}$I), a fluorescent or chemiluminescent compound (such as fluorescein isothiocyanate, rhodamine, or luciferin), an enzyme (such as alkaline phosphatase, beta-galactosidase or horseradish peroxidase), antibodies, particles such as magnetic particles, or specific binding molecules, etc. Specific binding molecules include pairs, such as biotin and streptavidin, digoxin and antidigoxin, etc. For the specific binding members, the complementary member would normally be labeled with a molecule which provides for detection, in accordance with known procedures, as outlined above. The label can directly or indirectly provide a detectable signal. Only one of the components may be labeled. Alternatively, more than one component may be labeled with different labels.

Transgenic mice, including knock in and knock out mice, and isolated cells from them (especially osteoblasts) that over or under express the nucleic acids disclosed herein (e.g., cDNA for Esp, PTP-1B, osteocalcin, gamma-carboxylase) can be made using routine methods known in the art. In certain instances, nucleic acids are inserted into the genome of the host organism operably connected to and under the control of a promoter and regulatory elements (endogenous or heterogeneous) that will cause the organism to over express the nucleic acid gene or mRNA. One example of an exogenous/heterogeneous promoter included in the transfecting vector carrying the gene to be amplified is alpha 1(I) collagen. Many such promoters are known in the art.

Human osteoblasts can be transfected with vectors carrying the cDNA for human Esp, human PTP-1B, or human osteocalcin (or fragments or variants thereof) operably linked to known promoters and regulatory elements that cause the transfected human osteoblast to overexpress osteocalcin (or fragments or variants thereof).

Disclosed herein are transgenic mice and mouse cells, and transfected human cells overexpressing osteocalcin (or fragments or variants thereof), OST-PTP, PTP-1B, or gamma-carboxylase. Also disclosed herein are double mutant mice that have deletions of one or both alleles for osteocalcin, Esp, and gamma-carboxylase, and various combinations of double mutants.

Also disclosed herein are vectors carrying the cDNA or mRNA encoding the proteins for insertion into the genome of a target animal or cell. Such vectors can optionally include promoters and regulatory elements operably linked to the cDNA or mRNA. By "operably linked" is meant that promoters and regulatory elements are connected to the cDNA or mRNA in such a way as to permit expression of the cDNA or mRNA under the control of the promoters and regulatory elements.

Antisense and small interfering RNAs for use in reducing expression of OST-PTP, PTP-1B, and/or gamma-carboxylase, thereby treating frailty in a mammal can be made that specifically hybridize to the gene and/or mRNA encoding OST-PTP, PTP-1B, or gamma-carboxylase, respectively. The sequence for mouse (OST-PTP, Ptprv) cDNA is set forth in SEQ ID NO:10. The amino acid sequence for OST-PTP, Ptprv) protein is set forth in SEQ ID NO:11. This cDNA, or antisense and small interfering RNAs based on this cDNA, will hybridize with mRNA for OST-PTP and thereby interfere with its translation. Reducing OST-PTP expression will increase the level of undercarboxylated/uncarboxylated osteocalcin, thereby providing a therapeutic benefit with respect to disorders related to cognition in mammals. The sequence for human PTP-1B cDNA is set forth in SEQ ID NO: 16. The amino acid sequence for human PTP-1B protein is set forth in SEQ ID NO:17. This cDNA, or antisense and small interfering RNAs based on this cDNA, will hybridize with mRNA for human PTP-1B and thereby interfere with its translation. Reducing human PTP-1B expression will increase the level of undercarboxylated/uncarboxylated osteocalcin, thereby providing a therapeutic benefit with respect to frailty in mammals. The cDNA for mouse gamma-carboxylase is identified by SEQ ID NO:8, and its amino acid sequence is SEQ ID NO:9. This cDNA, or antisense and small interfering RNAs based on this cDNA, will hybridize with mRNA for gamma-carboxylase and thereby interfere with its translation and is a preferred embodiment. The cDNA for human gamma-carboxylase is identified by SEQ ID NO:6, and the amino acid sequence is SEQ ID NO:7. Human gamma-carboxylase cDNA can be used therapeutically to reduce gamma-carboxylase expression to treat frailty in humans.

The invention is illustrated herein by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

EXAMPLES

Example 1—Osteocalcin-Deficient Mice

"Osteocalcin-deficient mice" or "Osteocalcin$^{-/-}$" mice refers to a strain of mice in which both osteocalcin alleles are deleted. Generation of Osteocalcin$^{-/-}$ mice was previously reported (Ducy et al., 1996, Nature 382:448-452). Exon 4 of osteocalcin gene 1 (OG1) coding for the mature protein, and the entire osteocalcin gene 2 (OG2) sequence were deleted, while osteocalcin-related gene (ORG) was left in place. Correct targeting resulted in the replacement of the entire mature osteocalcin protein-coding sequences by the pGK-Neo selection cassette.

Osteocalcin$^{-/-}$ mice had higher blood glucose and lower insulin serum levels than WT mice. Insulin secretion and sensitivity as well as glucose tolerance analyzed by GSIS, GTT and ITT were all decreased in Osteocalcin$^{-/-}$ mice, as was energy expenditure. Accordingly, the expression of genes involved in insulin action was decreased in skeletal muscle and liver while Pepck expression was increased. Islet size and number, beta-cell mass, pancreas insulin content and insulin immunoreactivity were all markedly decreased in Osteocalcin$^{-/-}$ mice. Beta-cell proliferation measured by Ki67 immunostaining was decreased two fold in Osteocalcin$^{-/-}$ pancreas in P5 pups and at 3 months of age. Accompanying this marked decrease in beta-cell proliferation, insulin secretion and sensitivity, was an increase in fat pad mass, adipocyte number (WT, 93.2+/−10.7×10$^3$ adipocytes/fat pad (n=5); Osteocalcin$^{-/-}$, 125.6+/−10.6×10$^3$ adipocytes/fat pad (n=3)) and serum triglyceride levels. Adiponectin expression and serum levels were significantly lower in Osteocalcin$^{-/-}$ than in WT mice, especially considering their increased fat pad mass, while expression of other adipokines was not affected. Expression of molecular targets of adiponectin action was decreased in Osteocalcin$^{-/-}$ mice. However, Osteocalcin$^{+/-}$ mice were undistinguishable from WT littermates. The cDNA sequence for mouse adiponectin is SEQ ID NO:8; and it is identified also by amino acid SEQ ID NO:9. The cDNA sequence for human adiponectin is SEQ ID NO:6; and it is identified also by amino acid SEQ ID NO:7.

Example 2—GTG Induced Obesity

For GTG-induced obesity, male and female 4 week-old wild-type (WT) and Osteocalcin$^{-/-}$ mice (n=10 per group) were injected with 0.5 mg/kg of GTG Example 3—Metabolic Studies For glucose tolerance test (GTT), glucose (2 g/kg body weight (BW)) was injected intraperitoneally (IP) after an overnight fast and blood glucose was monitored using blood glucose strips and the Accu-Check glucometer (Roche) at indicated times.

Example 4—Recombinant Osteocalcin

Recombinant osteocalcin was bacterially produced and purified on glutathione beads according to standard procedures. Osteocalcin was then cleaved from the GST subunit using thrombin digestion. Thrombin contamination was removed using an affinity column. The purity of the product was qualitatively assessed by SDS-PAGE.

Example 5—Administration of Uncarboxylated Osteocalcin Decreases Glycemia

An in vivo experiment was conducted in which the effect of undercarboxylated osteocalcin on glycemia was monitored. Wild type mice were infused with 3 different amounts of mouse recombinant undercarboxylated osteocalcin or placebo (PBS) subcutaneously for 28 days (0.3, 1 and 3 ng/hour). Compared to the control animal infused with placebo, all three doses of undercarboxylated osteocalcin decreased glycemia in vivo over the 28 day period (FIG. 1).

Figure 2:
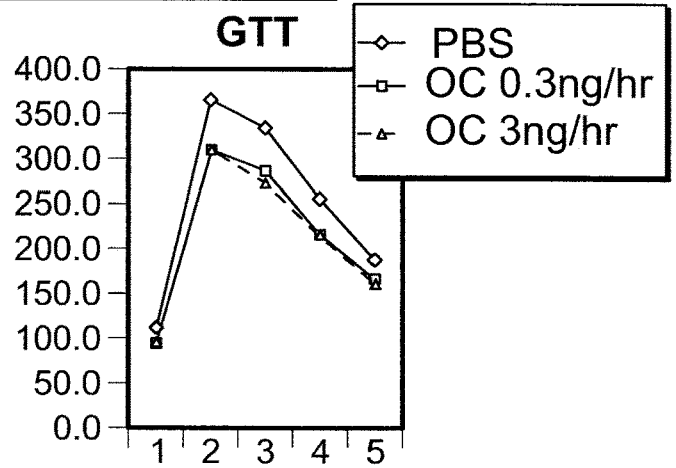
FIG. 2. Osteocalcin subcutaneous infusion increases glucose tolerance in wild-type mice. Wild-type mice were infused subcutaneously with indicated doses of recombinant osteocalcin or PBS for 14 days before receiving a single injection of glucose. Blood glucose was measured thereafter at indicated times.

Example 6—Administration of Uncarboxylated Osteocalcin Increases Glucose Tolerance In another in vivo experiment, the effect of uncarboxylated osteocalcin on glucose tolerance was investigated. Wild type mice were infused subcutaneously with either 0.3 or 3 ng/hour doses of recombinant uncarboxylated osteocalcin or PBS for 14 days before receiving a single injection of glucose. Blood glucose was measured thereafter at the indicated times. The results show that both doses of uncarboxylated osteocalcin increased glucose tolerance above control levels over the 120 minute time period following the glucose injection (FIG. 2).

Figure 3:
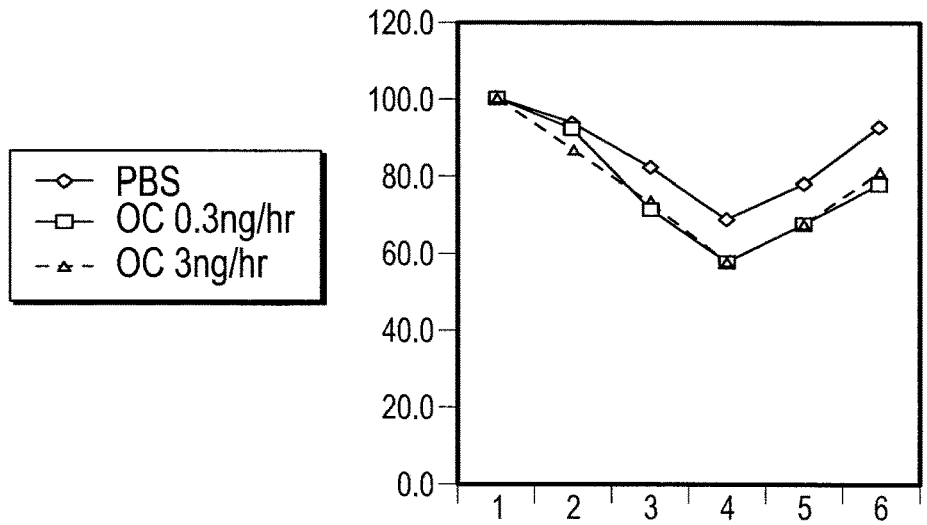
FIG. 3. Osteocalcin subcutaneous infusion increases insulin sensitivity in wild-type mice. Wild-type mice were infused subcutaneously with indicated doses of recombinant osteocalcin or PBS for 18 days before receiving a single injection of insulin. Blood glucose was measured thereafter at indicated times.

Example 7—Administration of Uncarboxylated Osteocalcin Increases Insulin Sensitivity The effect of uncarboxylated osteocalcin on insulin sensitivity was also examined. Wild type mice were infused subcutaneously with 0.3 or 3 ng/hour doses of recombinant osteocalcin or PBS for 18 days before receiving a single injection of insulin. Blood glucose was measured thereafter at the indicated times from 0-120 minutes after injection. The results show that insulin sensitivity was increased by both doses of uncarboxylated osteocalcin (FIG. 3).

Example 8—Administration of Uncarboxylated Osteocalcin Increases Fat Mass

Figure 4A:
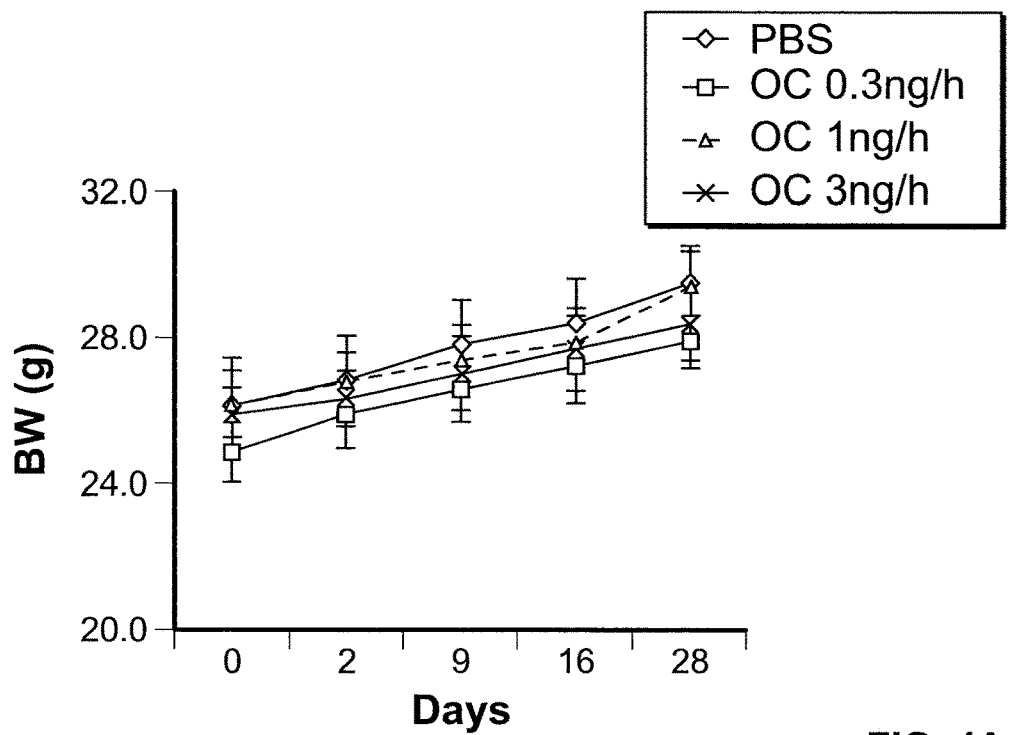
FIG. 4. Osteocalcin subcutaneous infusion decreases fat mass in wild-type mice. (A) Indicated doses of recombinant osteocalcin or PBS were infused subcutaneously for 28 days in wild-type mice. Body weight was recorded at indicated days. (B) Gonadal fat pad mass was measured after 28 days.
Figure 4B:
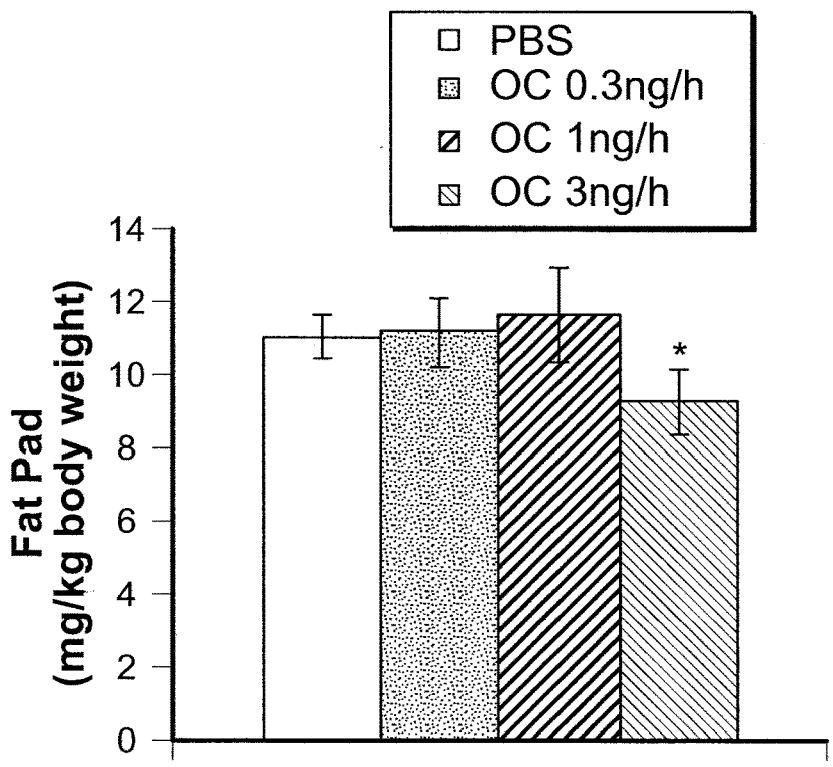

In another in vivo experiment, the effect of uncarboxylated osteocalcin on body weight and fat pad mass was monitored (FIG. 4). Wild type mice were infused subcutaneously for 28 days with PBS or uncarboxylated osteocalcin at 0.3, 1 or 3 ng/hour. The results show that body weight was slightly reduced by uncarboxylated osteocalcin with the highest dose being the most effective (FIG. 4). Gonadal fat pad mass, measured after 28 days, decreased by about %18 with 3 ng/hour uncarboxylated osteocalcin treatment. The other doses did not significantly decrease fat pad mass in that period.

Figure 5:
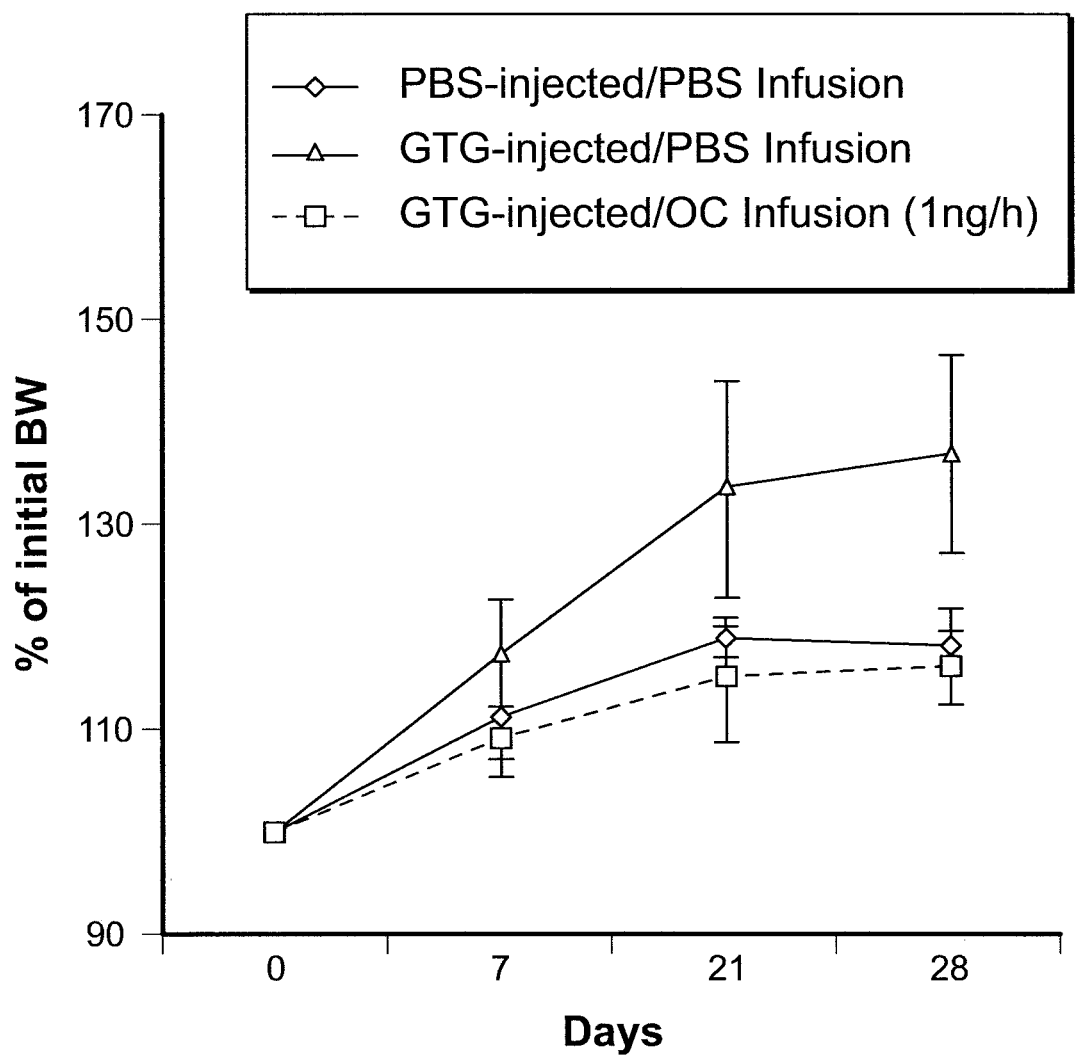
FIG. 5. Osteocalcin subcutaneous infusion alleviates GTG-induced obesity in wild-type mice. Wild-type mice were injected with gold thioglucose (GTG) or vehicle to induce hyperphagia and obesity. Two weeks later they were implanted with subcutaneous osmotic pumps infusing 1n/hr of recombinant osteocalcin or PBS for 28 days before. Body weight gain was recorded thereafter at indicated days.

Example 9—Administration of Uncarboxylated Osteocalcin Decreases GTG-Induced Obesity The effect of uncarboxylated osteocalcin on GTG-induced obesity was investigated (FIG. 5). Wild type mice were injected with gold thioglucose (GTG) to induce hyperphagia and obesity or vehicle. Two weeks later they were implanted with subcutaneous osmotic pumps infusing 1 ng/hr of recombinant uncarboxylated osteocalcin or PBS for 28 days. Body weight gain was significantly reduced with both doses of uncarboxylated osteocalcin by the first time point checked, 7 days, and remained lower than controls for the entire 28 day period. At 28 days, body weight was reduced by about 15% with uncarboxylated osteocalcin treatment.

Example 10—Male Osteocalcin-Deficient Mice have Decreased Fertility

Figure 6A:
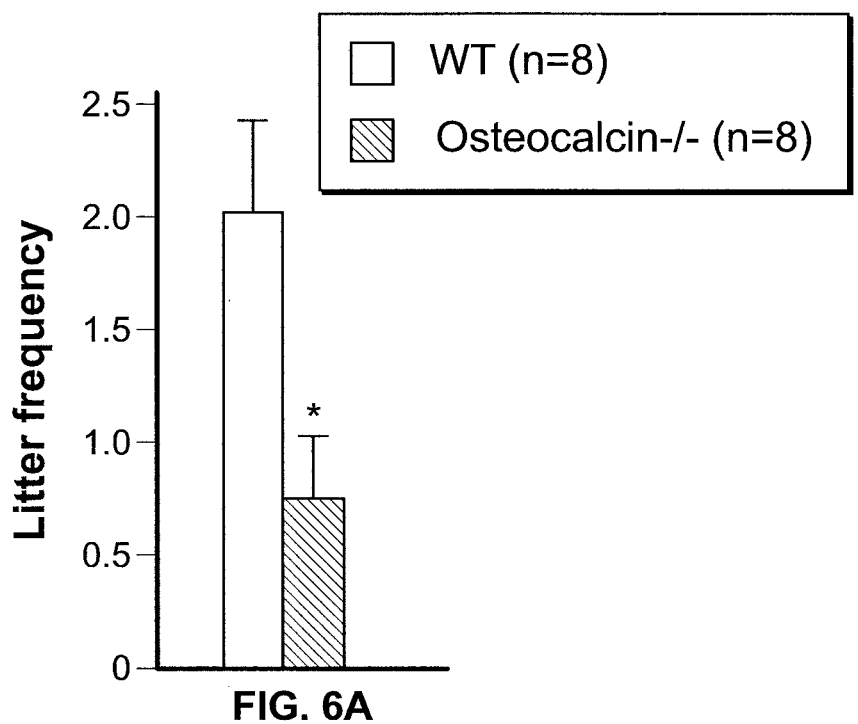
FIG. 6. Comparison between the average litter frequency (A) and size (B) generated by Osteocalcin$^{-/-}$ and wild type (WT) male mice crossed with WT females (breedings were tested from 6 weeks to 4 months of age).
Figure 6B:
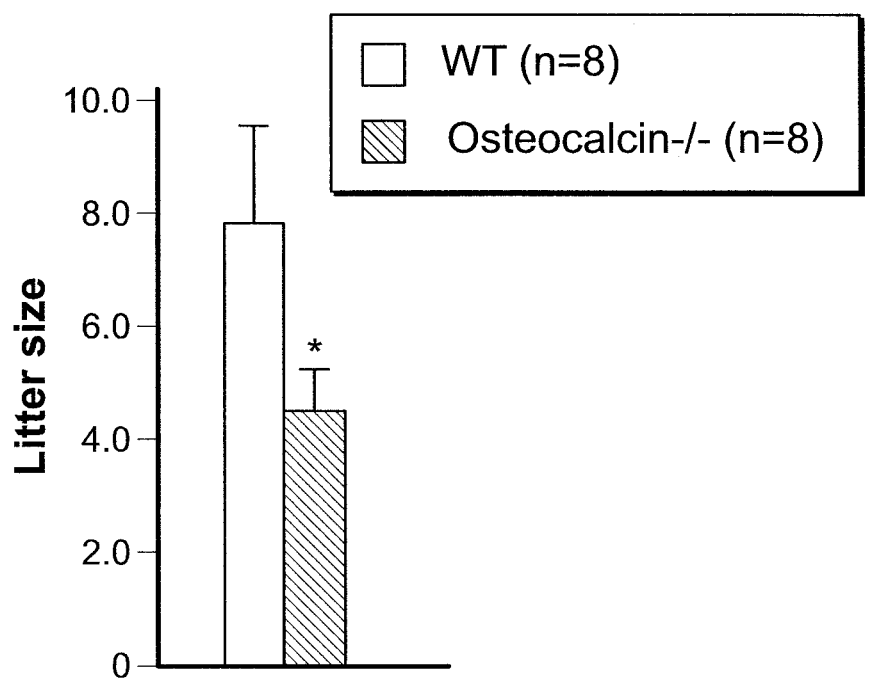

Male mice in which both alleles of osteocalcin were disrupted and non-functional (Osteocalcin$^{-/-}$ mice) that were crossed with wild-type (WT) littermates show impaired fertility. Whether the Osteocalcin-mutation was on the C57B1/6J or on the 129sv/ev genetic background, very few litters were obtained over the course of 3 months. Moreover, the litters were of significantly smaller size than those obtained when crossing WT male mice with WT female mice. When 8 Osteocalcin$^{-/-}$ male mice were placed with 2 WT female mice each from 6 to 12 weeks of age, only 17 pups were obtained and the litter size was 4.25 pups per litter. In contrast, when 8 WT male mice were placed with 2 WT female mice each for the same period of time, 63 pups were obtained and the litter size was also significantly larger (7.93 pups per litter) (FIG. 6). Furthermore, it was observed that after 6 months of age, and unlike what is the case for WT mice, male Osteocalcin$^{-/-}$ mice were totally infertile. This reproduction phenotype was not observed in Osteocalcin$^{-/-}$ mice (mice having a single allele of osteocalcin disrupted).

Example 11—Abnormal Spermatogenesis in the Absence of Osteocalcin

Figure 7A:
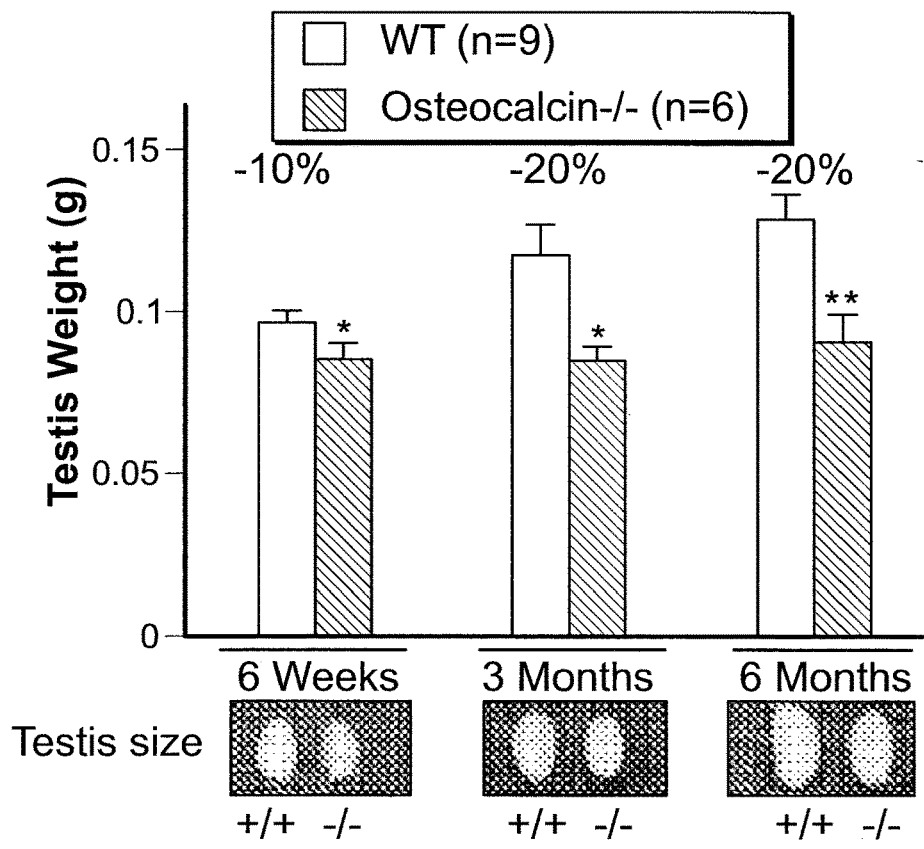
FIG. 7. Analysis of testicular weight (A), size (lower panel in A) and sperm count (B) of Osteocalcin$^{-/-}$ and wild-type ($^{+/+}$) littermate mice at 6 weeks, 3 months, and 6 months of age.
Figure 7B:
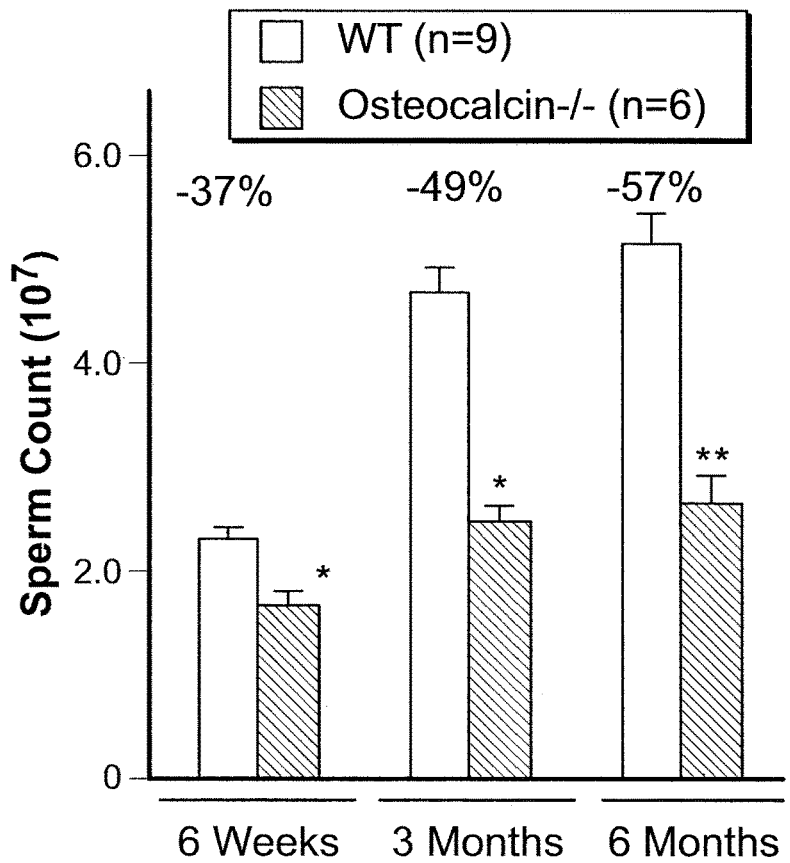
Figure 8A:
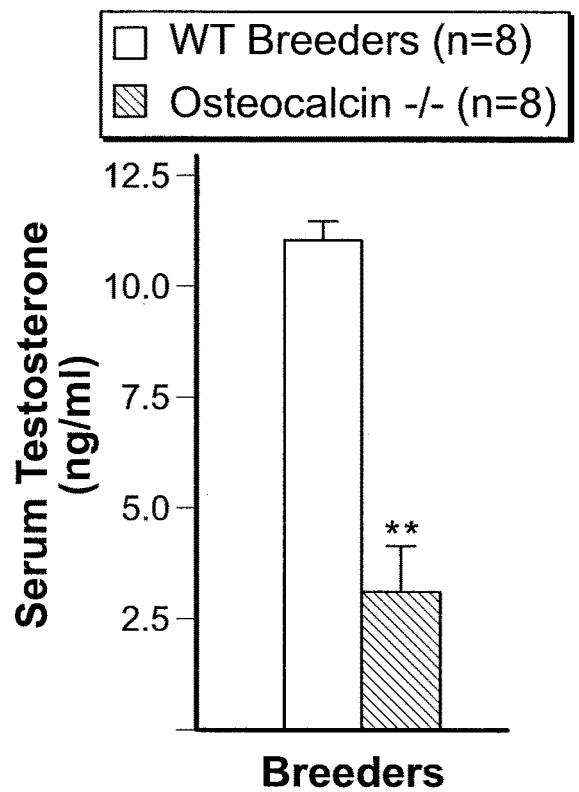
FIG. 8. Analysis of testosterone serum levels in Osteocalcin$^{-/-}$ and WT littermate breeder mice at 3 months of age (A). Analysis of testosterone serum level of Esp$^{-/-}$ and WT littermate non-breeder mice (B) at 3 months of age.
Figure 8B:
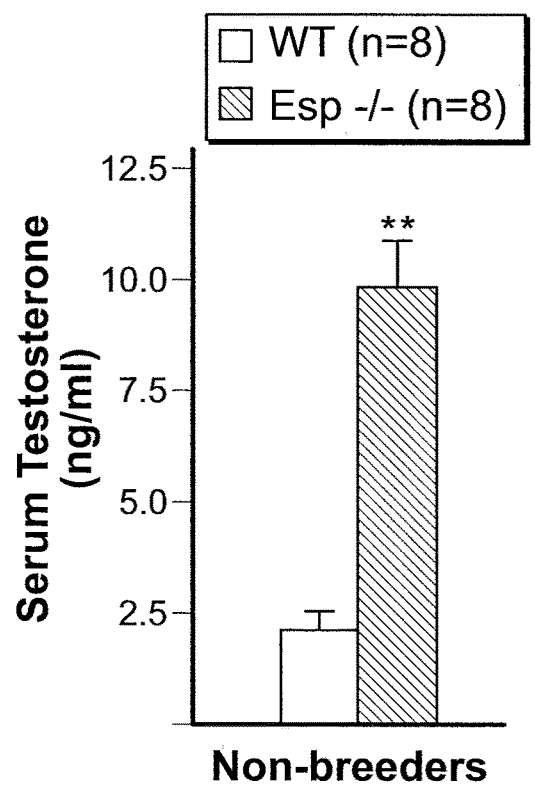
Figure 10A:
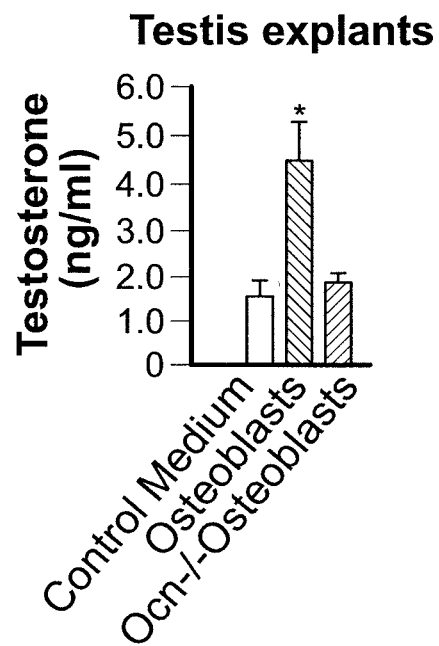
FIG. 10. Osteocalcin favors male fertility by increasing testosterone production by Leydig cells. (A-B) Testosterone production by testis explants (A) or primary Leydig cells (B) cultured in the presence of supernatants of wild type (WT) or Osteocalcin$^{-/-}$ osteoblast cultures. (C-D) Testosterone production by testis explants (C) or primary Leydig cells (D) following stimulation with increasing doses of recombinant uncarboxylated osteocalcin (0, 0.3, 1, 3, 10, 100 ng/ml of culture medium). (E) Circulating testosterone levels in WT mice 1 hour, 4 hours, and 8 hours after vehicle or recombinant uncarboxylated osteocalcin (3 ng/g of body weight) injection. (F-G) Comparison between the average litter size (F) and frequency (G) generated by WT, Osteocalcin$^{-/-}$, or Esp$^{-/-}$ male littermate mice crossed with WT females (breeding was tested from 6 to 16 weeks of age). (H-L) Testis size (H), testis weight (I), epididymides weight (J), seminal vesicles weight (K), and sperm count (L) in Osteocalcin$^{-/-}$ and Esp$^{-/-}$ compared to WT littermate mice. (M) Circulating steroid sex hormone levels in Osteocalcin$^{-/-}$ and Esp$^{-/-}$ compared to WT littermate mice. The analyses were performed on breeder and non-breeder mice. Error bars represent SEM. Student's t test (*) P<0.05, (**) P<0.001.
Figure 10B:
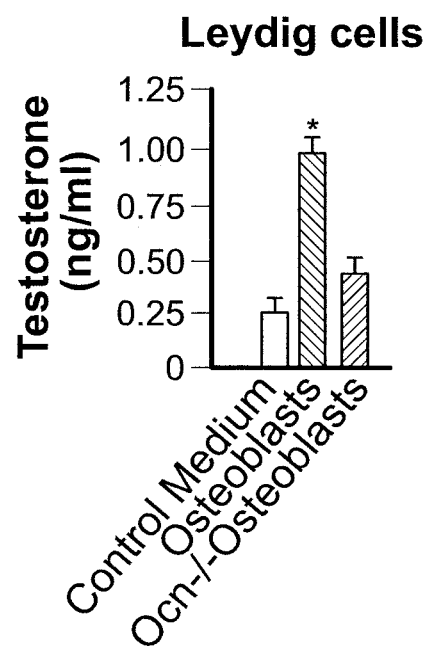
Figure 10C:
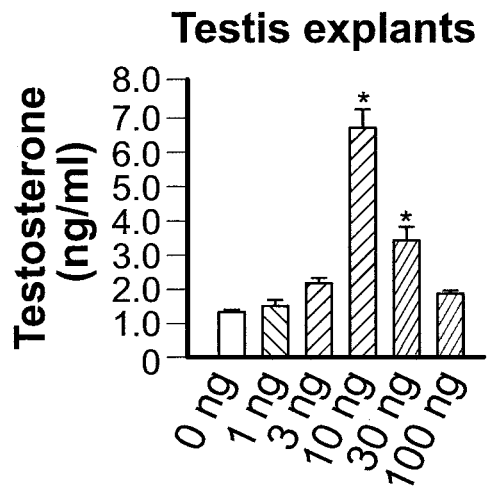
Figure 10D:
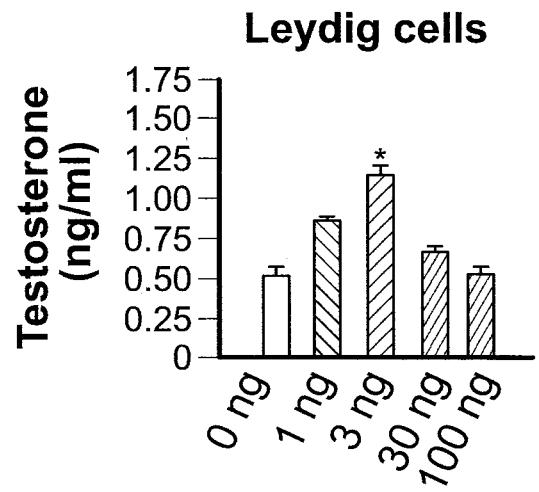
Figure 10E:
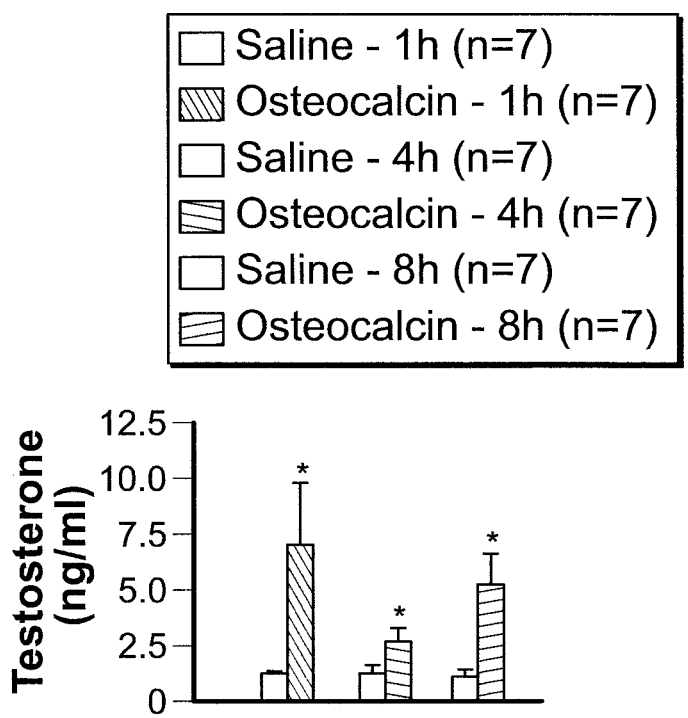
Figure 10F:
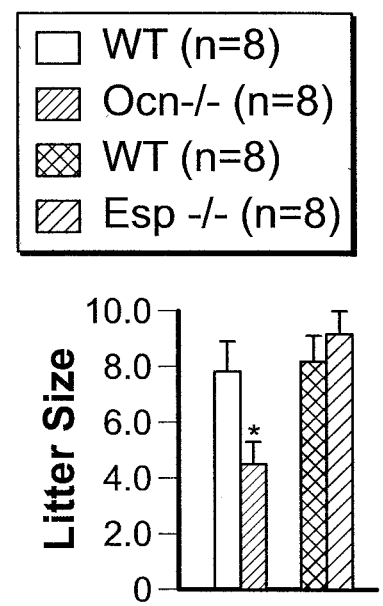

Testis weight was measured at different ages in male Osteocalcin-deficient mice. As early as at 6 weeks of age, male Osteocalcin$^{-/-}$ mice had significantly smaller testes than their WT littermates and this phenotype progressively worsened over time (FIG. 7A). Sperm count in the seminal fluid of Osteocalcin$^{-/-}$ and WT littermate male mice was also measured. It was found that sperm count was already decreased by 37% in 6 weeks old Osteocalcin$^{-/-}$ mice and that this decrease reached 60% of the sperm count in WT mice at 6 months of age (FIG. 7B).

Example 12—Gprc6a$^{-/-}$ Mice

Gprc6a$^{-/-}$ mice were generated as in Oury et al., 2011, Cell 144:796-809.

Example 13—Osteocalcin Delivery to Pregnant Mice

For osteocalcin delivery to pregnant mice, IP injections (240 ng/day) were performed as soon as a plug was present daily until delivery (E0.5-E18.5). For osteocalcin or leptin infusion in adult Osteocalcin$^{-/-}$ or ob/ob mice, pumps (Alzet micro-osmotic pump, Model 1002) delivering osteocalcin (300 ng/hr), leptin (50 ng/hr), or vehicle were surgically installed subcutaneously in the backs of 3-month old mice. For the postnatal rescue of cognitive functions in Osteocalcin$^{-/-}$ mice, osteocalcin (10 ng/hour) or vehicle were delivered intrasubventricularly (icv) as previously described (Ducy et al., 2000, Cell 100:197-207). Leptin and osteocalcin content in sera and tissues were determined by ELISA.

Example 14—Histology

All dissections were performed in ice-cold PBS 1× under a Leica MZ8 dissecting light microscope. Brainstems were isolated from the cerebellum and the hypothalamus was removed from the midbrain during collection. All parts of the brain isolated were flash frozen in liquid nitrogen and kept at −80° C. until use.

Example 15—Immunofluorescence, Cresyl Violet Statining, and Apoptosis

Immunofluorescence of whole adult and embryonic brains was performed on 20 m coronal cryostat slices of tissue fixed with 4% PFA, embedded in cryomatrix (Tissue-Tek) and stored at −80° C. Sections were allowed to dry at room temperature, post-fixed in 4% PFA followed by permeabilization with 0.1% Triton detergent. After room temperature blocking with donkey serum, sections were incubated with anti-Neun antibody (Millipore) overnight at 4° C. Slides were mounted with Fluorogel (Electron Microscopy Sciences).

Cresyl violet staining to visualize brain morphology was carried out by incubating 20 µm cryosections defatted with 1:1 chloroform:ethanol in cresyl violet acetate (1 g/L) overnight. The stain was differentiated using ethanol and xylene and mounted using DPX mounting medium for histology (Sigma).

To assess apoptosis in WT and Osteocalcin$^{-/-}$ brains, 20 µm cryostat sections were processed using the APOPTAG® Fluorescein Direct In Situ Apoptosis Detection Kit (Millipore) according to manufacturer's protocol. Images were obtained using Leica DM 4000B, and Image J was used to quantify cell number and intensity of staining.

Example 16—Physiological Measurements

Physical activity, including ambulatory activity (xamb) and total activity (xtot) was measured using infrared beams connected to the Oxymax system as previously described (Ferron et al, 2012, Bone 50:568-575).

Example 17—Tail Suspension Test (TST)

Tail suspension testing was performed as previously described (Mayorga et al., 2001, J. Pharmacology Exper. Therapeutics 298:1101-1107; Steru et al., 1985, Psychopharmacology 85:367-370). Mice were transported a short distance from the holding facility to the testing room and left there undisturbed for at least 1 hour. Mice were individually suspended by the tail (distance from floor was 35 cm) using adhesive tape (distance from tip of tail was 2 cm). Typically, mice demonstrated several escape-oriented behaviors interspersed with temporally increasing bouts of immobility. The parameter recorded was the number of seconds spent immobile. Mice were scored by a highly trained observer, over a 5 min period, blind to the genotype of the mice.

Example 18—Open Field Paradigm Test (OFT)

Anxiety and locomotor activity of mice were measured using the open field test (David et al., 2009, Neuron 62:479-493). Each animal was placed in a 43×43 cm open field chamber, and tested for 30 min. Mice were monitored throughout each test session by video tracking and analyzed using Matlab software. Mice were placed individually into the center of the open-field arena and allowed to explore freely. The overall motor activity was quantified as the total distance travelled. The anxiety was quantified measuring the number of rearings and the time and distance spent in the center versus periphery of the open field chamber (in %).

Example 19—Elevated Plus Maze Test (EPMT)

Each mouse was allowed to explore the apparatus for 5 min. Global activity was assessed by measuring the number of entries into the open arms (David et al, 2009, Neuron 62:479-493). Anxiety was assessed by comparing the time spent in the open arms.

Example 20—Mouse Forced Swim Test (FST)

The forced swimming test was carried out according to the method described by David et al., 2009, Neuron 62:479-493. Briefly, mice were dropped individually into glass cylinders (height: 25 cm, diameter: 10 cm) containing 10 cm water height., maintained at 23-25° C. Animals were tested for a total of 6 min. The total duration of immobility time was recorded. Mice were considered immobile when they made no attempts to escape with the exception of the movements necessary to keep their heads above the water. Mice were scored by an observer blind to their genotypes.

Example 21—Light and Dark Test

The test was performed in a quiet, darkened room. Mice were individually housed in cages containing a handful of bedding from their home cage and acclimated to the room at least 1 h before the test. Naïve mice were placed individually in the testing chamber in the dark compartment. The test was 5 min in duration, and time spent and number of entries in light compartments were recorded a highly trained observer, blind to the genotype of the mice.

Example 22—Morris Water Maze Test

Spatial memory was assessed with Morris water maze (MWM) setup (Morris, 1981, Nature 297:681-683) using a training protocol adapted for mice (D'Hooge et al., 2005, J. Soc. Neurosci. 25:6539-6549). The maze had a diameter of 150 cm and contained water (23° C.) that was made opaque with non-toxic white paint. The pool was located in a brightly lit room with distal visual cues, including computer, tables and posters with geometric figures attached to the walls. Spatial learning is assessed across repeated trials (4 trials/day for 10 days).

During trials, a small platform (diameter 10 cm) was hidden beneath the surface at a fixed position. Mice were placed in the water at the border of the maze and had to reach the platform after which they were transported back to their home cage. Mice that did not reach the platform within 2 min were gently guided towards the platform and were left on it for 10 s before being placed back in their cages. Four of such daily training trials (inter trial interval: 5 min) were given on 10 subsequent days. Starting positions in the pool varied between four fixed positions (0°, 90°, 180° and 270°) so that each position was used. Since a decrease in latency to find the platform was already present on the second acquisition day, the first acquisition day is also reported.

Example 23—Osteocalcin Affects Several Types of Behavior

Osteocalcin$^{-/-}$ mice demonstrate broad cognitive impairments, as demonstrated by subjecting Osteocalcin$^{-/-}$, Osteocalcin$^{+/-}$, Esp$^{-/-}$, and Gprc6a$^{-/-}$ mice to a battery of behavioral tests. As controls in these experiments, WT littermates and Tph2$^{+/-}$ mice that demonstrated a decrease in serotonin and dopamine content similar to that one observed in Osteocalcin$^{-/-}$ mice were used.

Figure 11E:
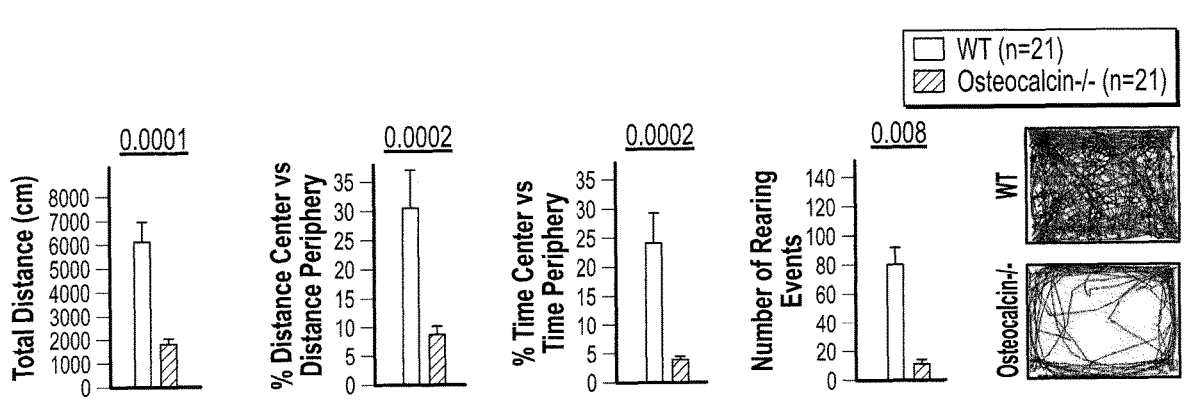
FIG. 11. Osteocalcin affects anxiety, depression, memory, and learning. (A-L) Behavioral analysis of (A, C, E, G, I and K) Osteocalcin$^{-/-}$ (n=21), (B, D, F, H, J and L) Gprc6a$^{-/-}$ (n=16) and WT (n=21 and n=15) littermate mice. (A-B) Light and Dark test (L/DT): The latency (Sec=seconds) to enter in the lit compartment, number of transitions between compartments, and amount of time spent in the lit compartment were measured. (C-D) Elevated Plus Maze test (EPMT): Number of entries and amount of time spent (Sec=seconds) in the open arms were scored. (E-F) Open field test (OFT): Total distance (cm), % of the distance traveled, and time spent in the center versus periphery as well as number of rearing events were measured. The video tracking of each group of mice are represented on the right panel. (G-J) Representation of the time spent (seconds) immobile during the (G-H) forced swim test and the (I-J) Tail suspension test. Both tests assess depression-like behavior. (K-L) Morris Water Maze test performed over 10 days. The graphic shows the time (seconds) needed for each group of mice to locate a submerged platform in the swimming area. The video trackings on the left panel are the representations of the standards obtained for each group analyzed. Error bars represent SEM. Student's T-test is represented on the top of the bars.
Figure 11F:
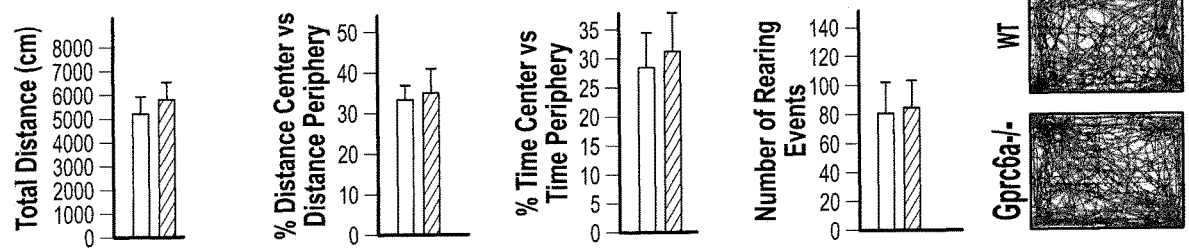

Anxiety-like behavior was analyzed through three conflict-based tests. The first, the dark/light transition test (DLT), is based on the innate aversion of rodents to brightly illuminated areas and on their spontaneous exploratory behavior to avoid the light (Crawley et al., 1985, Neuroscience and Biobehavorial Reviews 9:37-44; David et al., 2009, Neuron 62:479-493). The test apparatus consists of a dark, safe compartment and an illuminated, aversive one. Mice are tested for 6 min each and three parameters recorded: (i) latency to enter the lit compartment, (ii) time spent in the lit compartment, and (iii) number of transitions between compartments. In Osteocalcin$^{-/-}$ mice, there was an increase in the latency to enter in the lit compartment and a decrease of time spent in the lit compartment, two indications of anxiety-related behavior. There was also a decrease in the number of transitions between compartments, another indication of anxiety-related behavior and of motor-exploratory activity (FIG. 11A-B). Conversely, the opposite was true in Esp$^{-/-}$ mice. The elevated plus maze (EPM) test (Lira et al., 2003, Biological Psychiatry 54:960-971; Holmes et al., 2000, Physiology and Behavior 71:509-516) that exploits the aversion of rodents to open spaces was also used. The EPM is comprised of two open and two enclosed arms, each with an open roof elevated 60 cm from the floor. Testing takes place in bright ambient light conditions. Animals are placed onto the central area facing one closed arm and allowed to explore the EPM for 5 min. The total number of arm entries and time spent in open arms measure general activity. A decrease in the proportion of time spent and in the number of entries into the open arms indicates an increase in anxiety. This is exactly what was seen in Osteocalcin$^{-/-}$ mice, while Esp$^{-/-}$ mice demonstrated less anxiety-like behaviors and more exploratory drive than WT littermates (FIG. 11C-D). Lastly, we used the open field paradigm test (OFT) in which a novel environment evokes anxiety and exploration (David et al., 2009, Neuron 62:479-493; Sahay et al., 2011, Nature 472:466-470). Animals are placed in the center of an open field box and video-tracked under normal light conditions over 30 min. Osteocalcin$^{-/-}$ mice demonstrated a drastic decrease in the distance moved, in time spent in the center, and in vertical activity compared to WT littermates, all features indicative of increased anxiety (FIG. 11E-F).

Figure 11G:
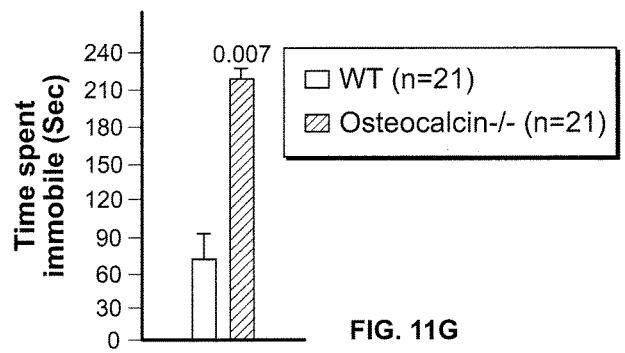
Figure 11H:
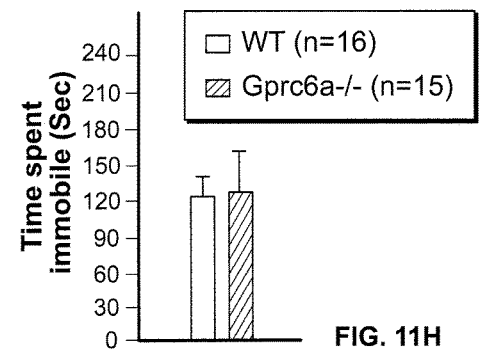
Figure 11I:
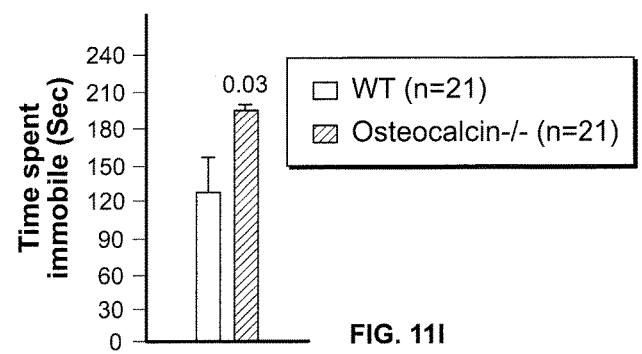
Figure 11J:
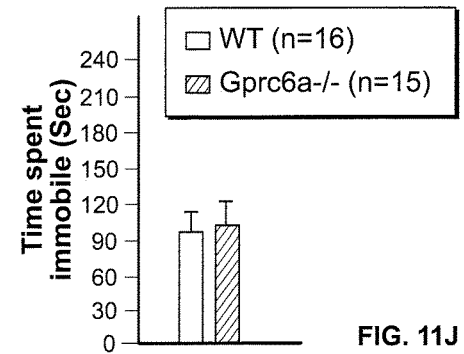
Figure 12D:
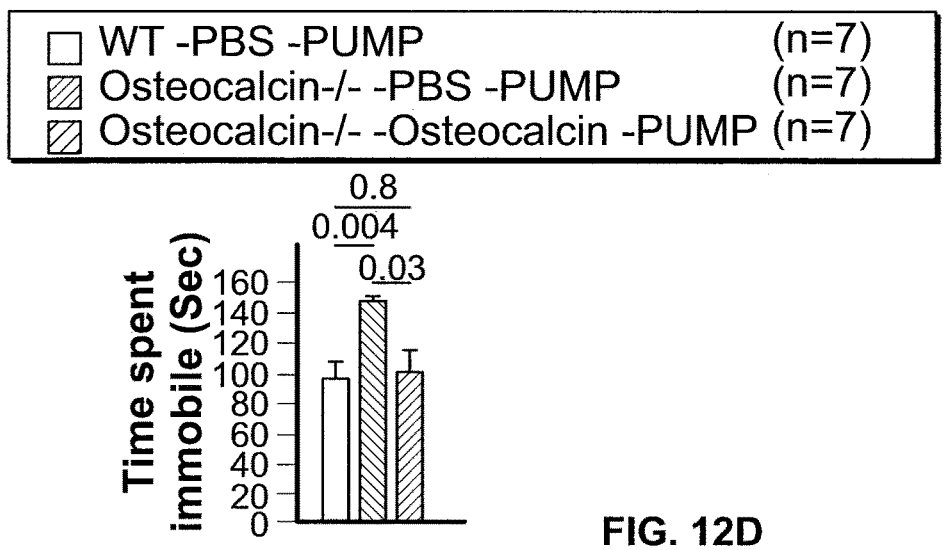
FIG. 12. Administration of osteocalcin alleviates anxiety and depression. (A-E) Behavioral analyses of adult Osteocalcin$^{-/-}$ mice receiving recombinant uncarboxylated osteocalcin through intracerebro-ventricular (ICV) infusions. (A) Light and Dark test, (B) Elevated plus maze test, (C) Open field test, (D) Forced swim test, and (E) Tail suspension test performed in a cohort of WT (n=7) and Osteocalcin$^{-/-}$ infused with vehicle or recombinant uncarboxylated osteocalcin (10 ng/hour). In each set of three bars, the rightmost bar represents the results following administration of osteocalcin.
Figure 12E:
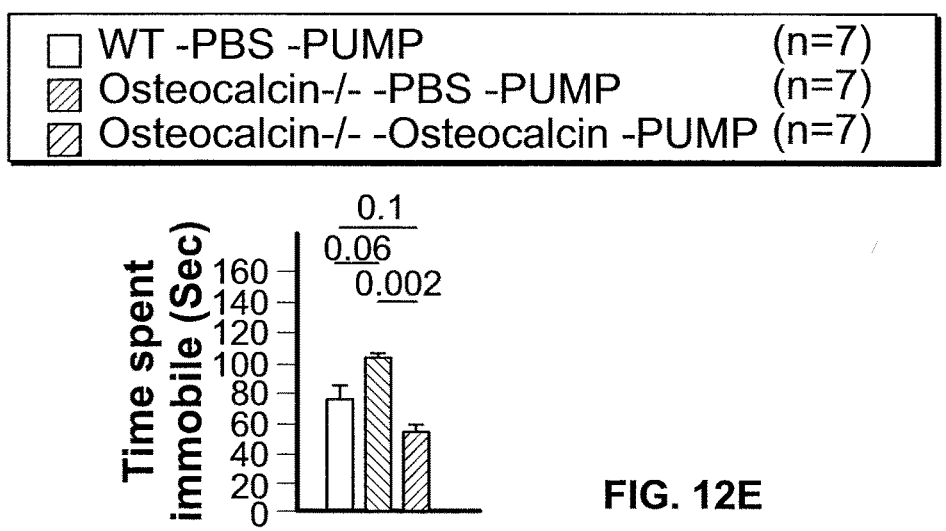

Anxiety is often accompanied by depression. This was assessed by the tail suspension test (TST), in which animals are subjected to the short-term, inescapable stress of being suspended by their tails, to which they respond by developing an immobile posture (Cryan et al., 2005, Neurosci. Behaviorial Rev. 20:571-625; Crowley et al., 2006; Neuropsychopharmacology 29:571-576; David et al., 2009, Neuron 62:479-493). In this test, the more time mice remain immobile, the more depressed they are. This is what was observed in Osteocalcin$^{-/-}$ mice (FIG. 11G-H). In the forced swim test (FST), mice are subjected to two trials during which they are forced to swim in a glass cylinder filled with water from which they cannot escape. The first trial lasts 15 minutes. Twenty-four hours later, a second trial is performed that lasts 6 minutes. Over time, mice cease their attempts to escape and float passively, indicative of a depression-like state. Consistent with the other behavioral tests, Osteocalcin$^{-/-}$ mice spent 45% more time floating than WT mice (FIG. 11I-J).

To assess memory and spatial learning behavior, Osteocalcin$^{-/-}$ and Osteocalcin$^{+/-}$ mice were subjected to the Morris water maze (MWMT) task. This test relies on the ability of mice to learn distance cues and to navigate around the perimeter of an open swimming arena to locate a submerged platform to escape the water. Spatial learning is assessed across repeated trials (4 trials/day for 12 days). Osteocalcin$^{+/-}$ and Osteocalcin$^{-/-}$ mice showed a delayed and a complete inability to learn, respectively (FIG. 11K-L).

As noted for neurotransmitter content and for gene expression in the brain, Gprc6a$^{-/-}$ mice were indistinguishable from WT littermates in all these tests. Collectively, these tests indicate that osteocalcin alleviates anxiety and depression, and enhances exploratory behavior, memory, and learning.

Example 24—Administration of Osteocalcin Corrects Cognitive Defects

The pharmacological relevance of this ability of osteocalcin to signal in neurons was established by delivering uncarboxylated osteocalcin through intracerebro-ventricular (ICV) infusions (10 ng/hour) in WT and Osteocalcin$^{-/-}$ mice. The localization of the cannula was verified by administering methylene blue through these pumps. The dye labeled all ventricles, indicating that osteocalcin was probably diffusing throughout the brain. Moreover, measurements of osteocalcin in the blood of infused Osteocalcin$^{-/-}$ mice showed that there was no leakage of the centrally delivered hormone into the general circulation. This weeklong treatment with uncarboxylated osteocalcin corrected the anxiety and depression features noted in Osteocalcin$^{-/-}$ mice (FIG. 12A-E). Collectively, the results described herein indicate that osteocalcin alleviates anxiety and depression in the mouse by acting directly in the brain.

Example 25—Maternal Osteocalcin Favors Spatial Memory and Learning in Adult Offspring The influence of maternally-derived osteocalcin on fetal brain development raised the question of whether osteocalcin has any influence on cognitive functions in the offspring later in life. To address this question, three month-old Osteocalcin$^{-/-}$ mice born from either Osteocalcin$^{-/-}$ or Osteocalcin$^{+/-}$ mothers were subjected to behavioral tests. While the anxiety and depression-like phenotypes were equally severe in Osteocalcin$^{-/-}$ mice regardless of the genotype of their mothers, the deficit in learning and memory was significantly more severe in Osteocalcin$^{-/-}$ mice born from Osteocalcin$^{-/-}$ mothers than in those born from Osteocalcin$^{+/-}$ mothers (FIG. 13A-F). This result indicated that maternal osteocalcin is needed for the acquisition of spatial learning and memory in adult offspring.

Figure 13A:
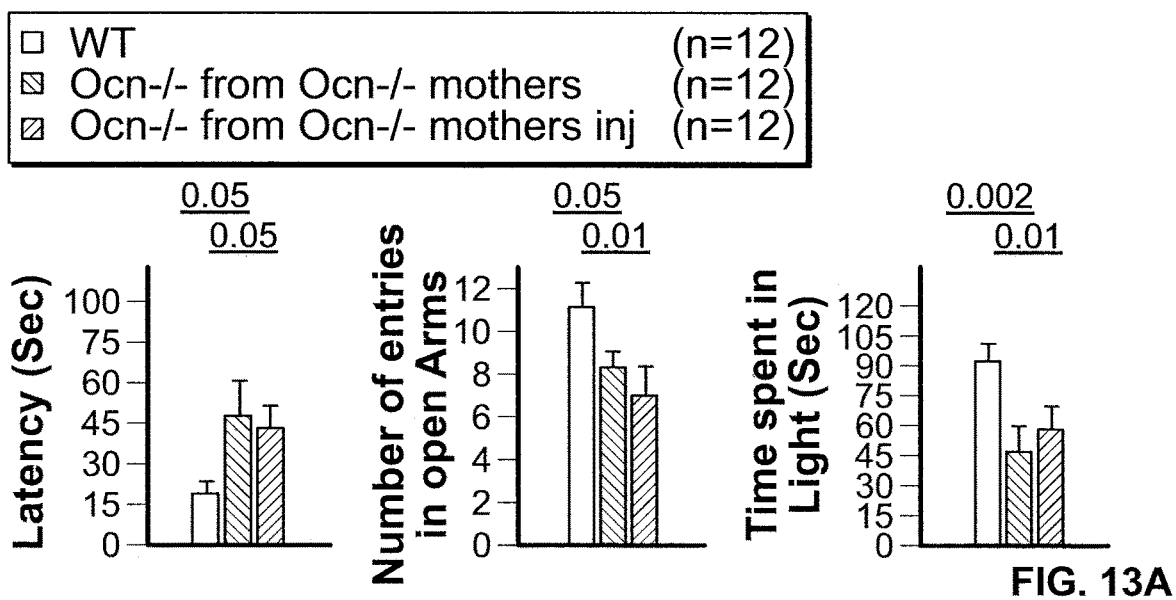
FIG. 13. Maternal osteocalcin determines spatial learning and memory in adult offspring. (A-F) DLT (A), EPMT (B), OFT (C), FST (D), TST (E), and MWMT (F) performed in 3-month-old Osteocalcin$^{-/-}$ mice born from Osteocalcin$^{-/-}$ mothers injected once a day with vehicle or recombinant uncarboxylated osteocalcin (240 ng/day) during pregnancy compared to WT mice. (G) Surface of the lateral ventricle over brain area (%) of E18.5 hippocampi coronal sections of WT embryos originating from WT mothers and Osteocalcin$^{-/-}$ embryos originating from osteocalcin-injected Osteocalcin$^{-/-}$ mothers. (H) Number of apoptotic cells (stained by TUNEL assay) of E18.5 hippocampi coronal sections of WT embryos originating from WT mothers and Osteocalcin$^{-/-}$ embryos originating from Osteocalcin$^{-/-}$ mothers injected with osteocalcin (240 ng/day). (I) Cresyl violet, NeuN immunofluorescence, and dentate gyrus area (% versus WT) of WT and Osteocalcin$^{-/-}$ embryos originating from osteocalcin-injected Osteocalcin$^{-/-}$ mothers. Scale bars=0.5 mm.
Figure 13B:
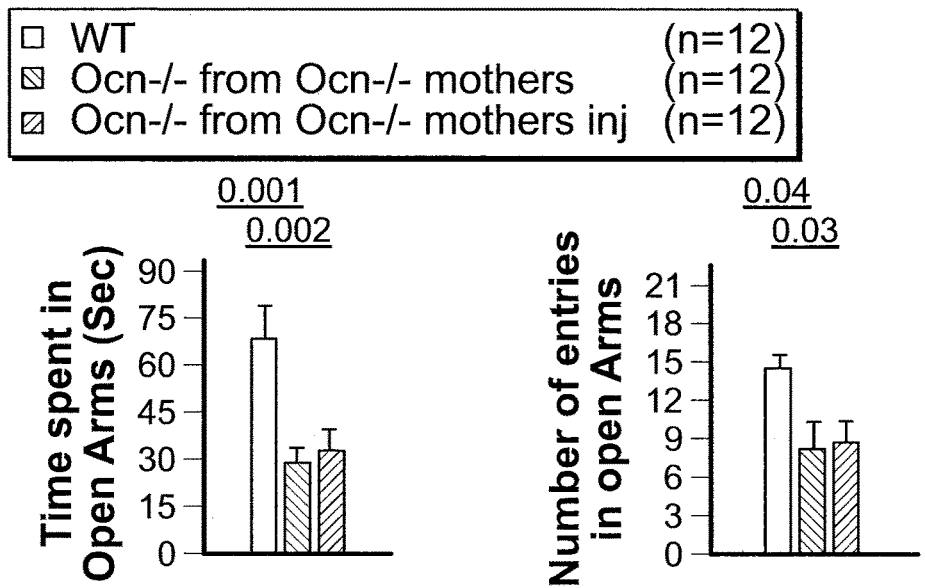
Figure 13C:
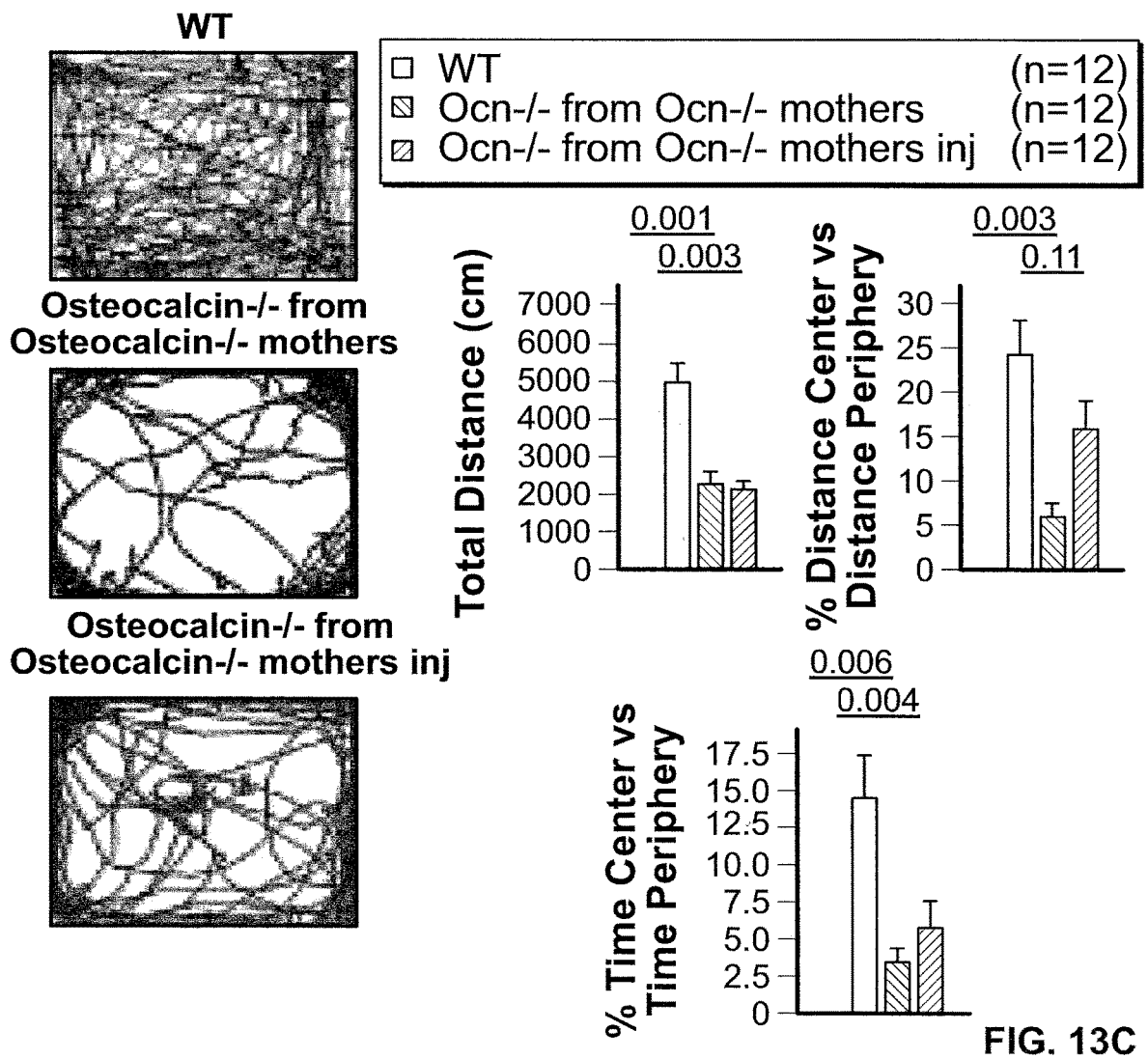
Figure 13H:
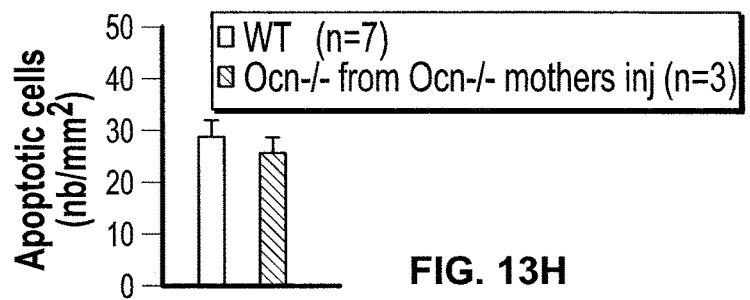
Figure 13I:
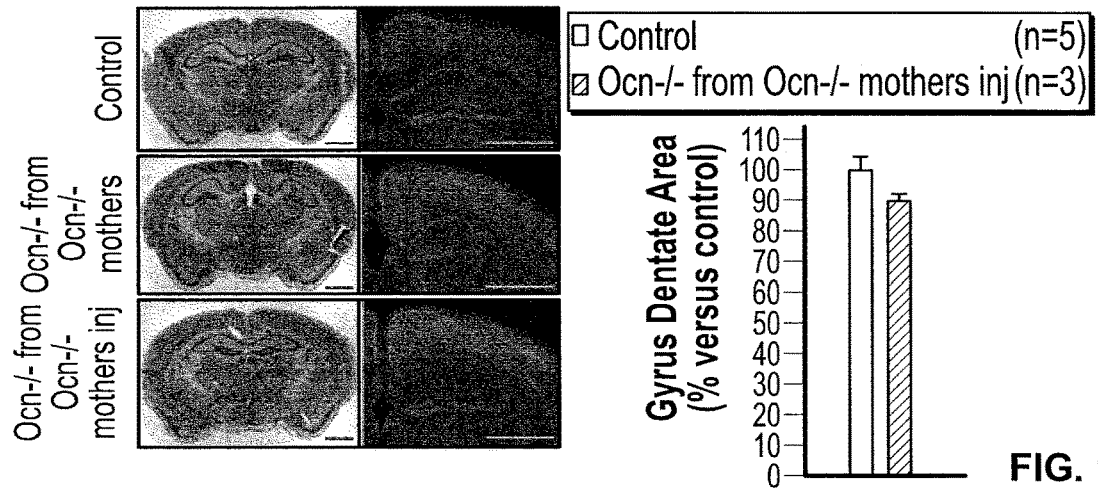
Figure 13J:
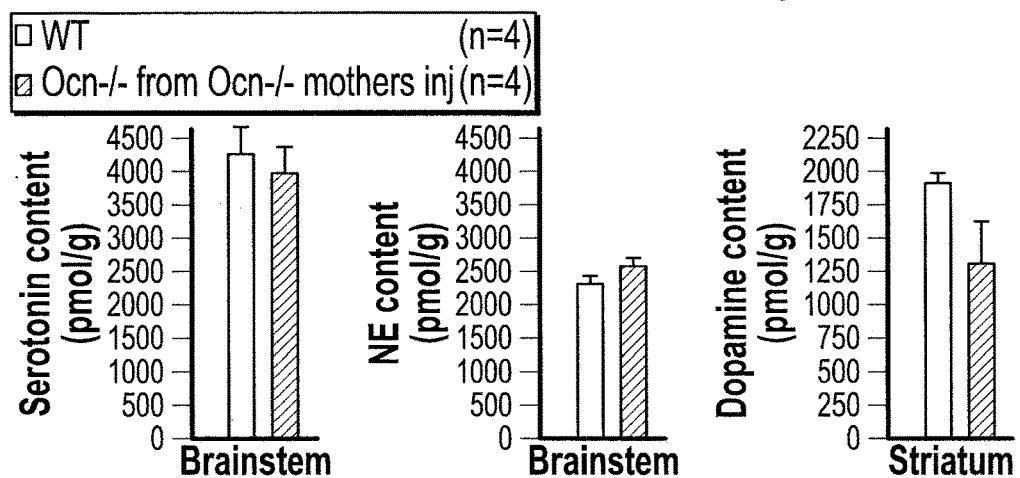
Figure 13K:
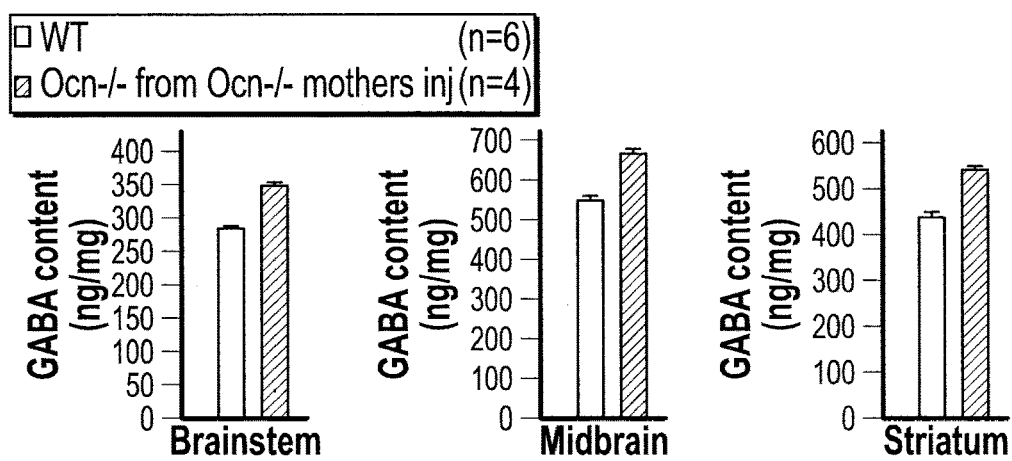

To further evaluate the importance of maternal osteocalcin for the acquisition of spatial learning and memory in adult offspring, pregnant Osteocalcin$^{-/-}$ mothers from E0.5 to E18.5 were treated with injections, once a day, of osteocalcin (240 ng/day). Osteocalcin was never injected in these females or their pups after delivery. This pregnancy-only treatment did not have any beneficial effect on the anxiety or depression phenotypes of the Osteocalcin$^{-/-}$ mice but rescued over two third of their deficit in learning and memory, indicating that this phenotype is, to a large extent, of developmental origin (FIG. 13A-G). Consistent with this observation, cresyl violet staining of histological sections showed a rescue of the cerebral ventricle enlargement in the brains of E18.5 Osteocalcin$^{-/-}$ embryos after injection of the pregnant Osteocalcin$^{-/-}$ mothers (FIG. 13H). Likewise, the number of apoptotic cells was reduced and the number of NeuN positive cells was increased compared to Osteocalcin$^{-/-}$ embryos originating from Osteocalcin$^{-/-}$ mothers that were not injected (FIG. 13I-J). This staining also showed a rescue of the thickness defect in the CA3 and CA4 regions of the hippocampus in adult Osteocalcin$^{-/-}$ originating from Osteocalcin$^{-/-}$ mothers (FIG. 13H). Lastly, a Western blot analysis showed a decrease in Caspase-3 cleaved protein level in the hippocampus of Osteocalcin$^{-/-}$ E18.5 embryos originating from Osteocalcin$^{-/-}$ mothers injected compare to the ones originating from Osteocalcin$^{-/-}$ mothers that were not injected (FIG. 13K).

Figure 14A:
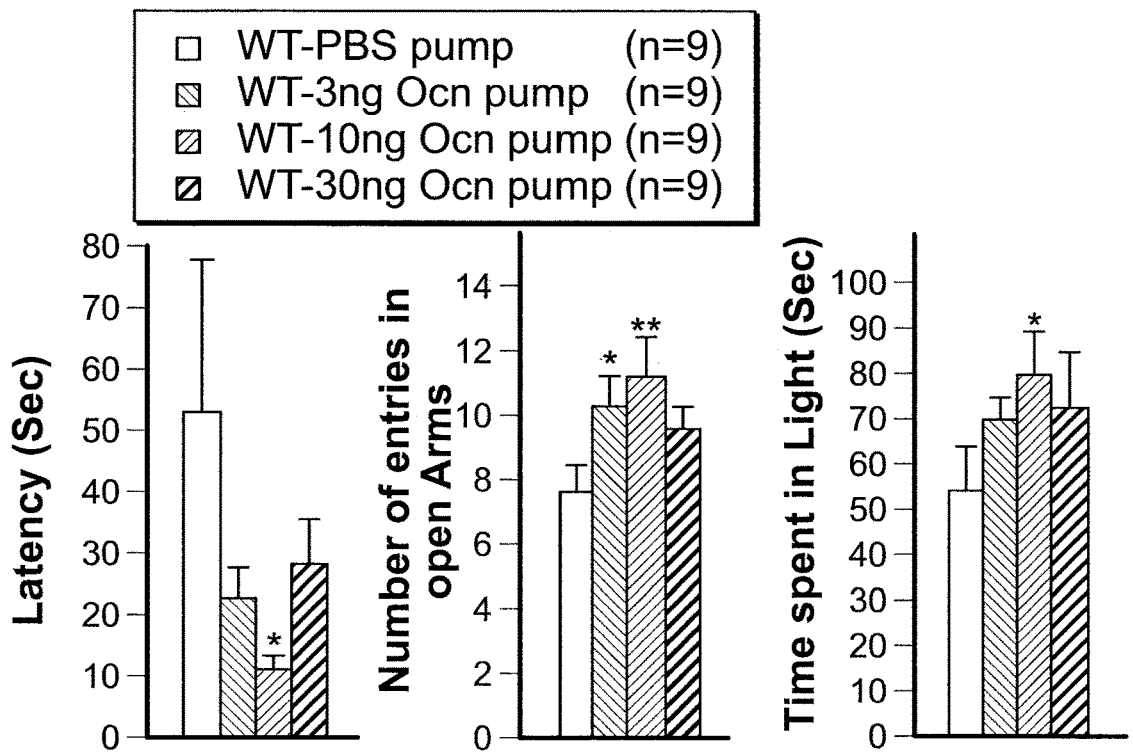
FIG. 14. Osteocalcin improves cognitive function in adult wild-type (WT) mice. Results from dark and light (DLT) and elevated plus maze tests (EPMT) performed in 3-month old WT mice infused ICV with vehicle (PBS) or recombinant uncarboxylated osteocalcin (Ocn) (3, 10, 30 ng/hour) are shown. (A) DLT measuring the latency to enter, the number of entries, and the time spend in lit compartment. (B) EPMT measuring the number of entries into open arms and the time spend in lit compartments.
Figure 14B:
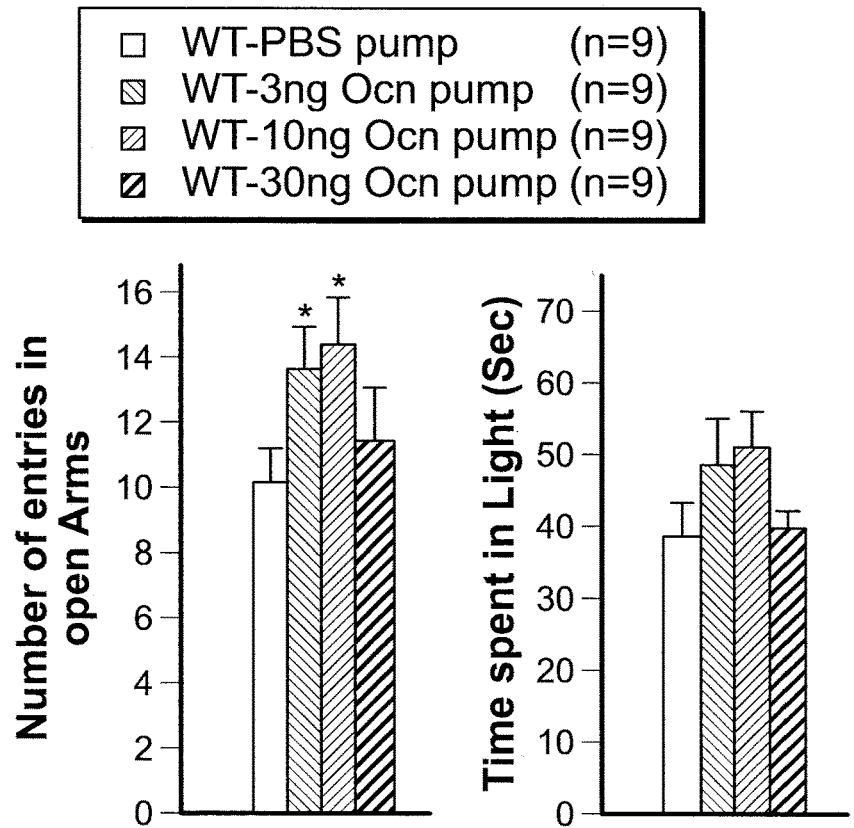

Example 26—Direct Delivery of Osteocalcin to the Brain Improves Cognitive Function in Wild-Type (WT) Adult Mice in a Dose Dependent Manner To determine if osteocalcin is sufficient to improve cognitive function in adult mice, WT 2-month old mice were implanted with ICV pumps delivering vehicle (PBS), or 3, 10, or 30 ng/hr recombinant uncarboxylated full-length mouse osteocalcin for a period of one month. After one month of infusion, animals were subjected to behavioral testing. Based on their performance in the dark to light transition (D/LT) test and the elevated plus maze (EPMT) test, animals receiving 3 or 10 ng/hour of recombinant uncarboxylated full-length mouse osteocalcin showed a decrease in anxiety-like behavior. This improvement is evidenced by an increase in the exploration of the lit compartment and open arms in the D/LT and EMP tests, respectively (FIG. 14A-B).

Figure 15:
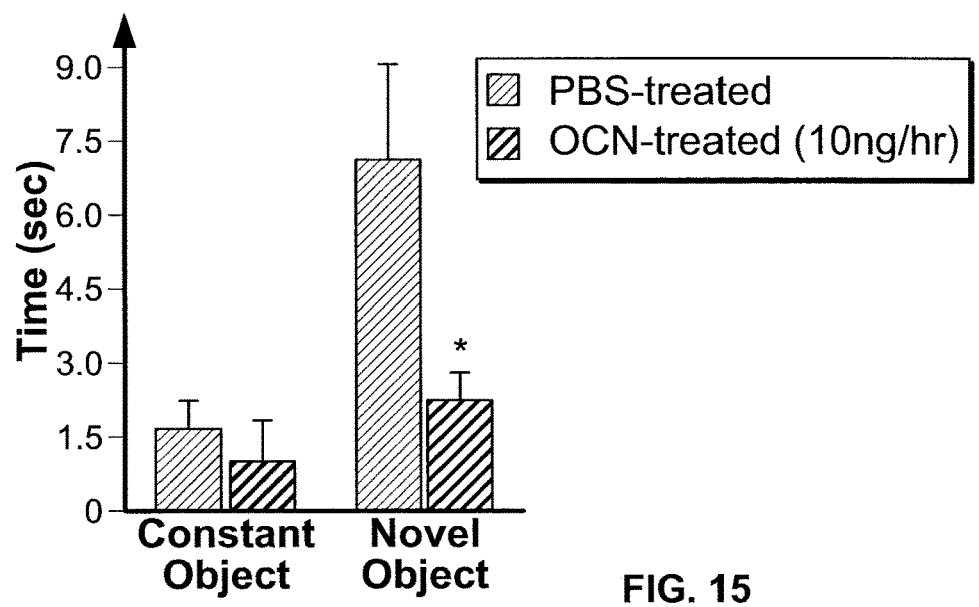
FIG. 15. Osteocalcin improves hippocampal function in aged wild-type (WT) mice. Constant and novel object investigation in the Novel Object Recognition test in 17 month old mice treated for 1 month with vehicle or 10 ng/hr recombinant uncarboxylated osteocalcin.
Figure 16A:
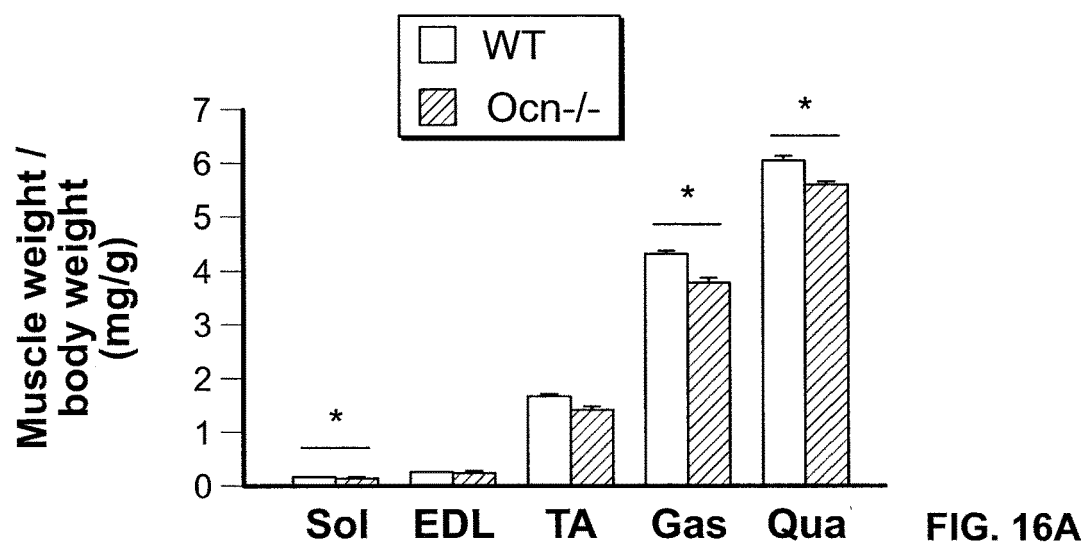
FIG. 16. Decreased muscle mass and functions in young mice lacking osteocalcin. (A) Ratio of muscle weight to body weight for various muscles in 3-month old wild-type (WT) and Osteocalcin$^{-/-}$ mice for various muscle types (Sol; EDL; TA; Gas=gastrocnemius; Qua=quadriceps). (B) Comparison of distances run by 3-month old wild-type (WT) and Osteocalcin$^{-/-}$ mice. (C) Comparison of running times for 3-month old wild-type (WT) and Osteocalcin$^{-/-}$ mice.
Figure 16B:
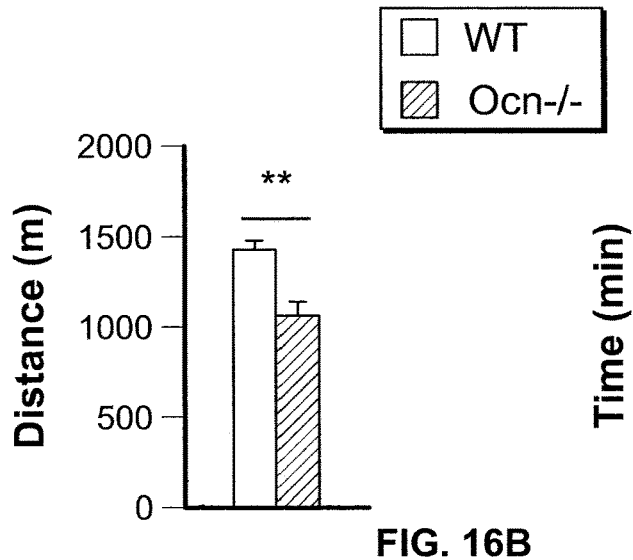
Figure 16C:
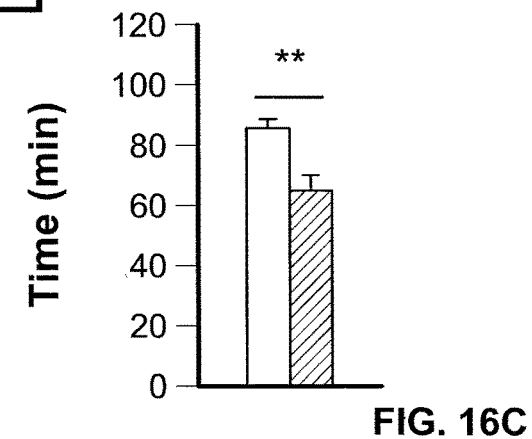
Figure 21:
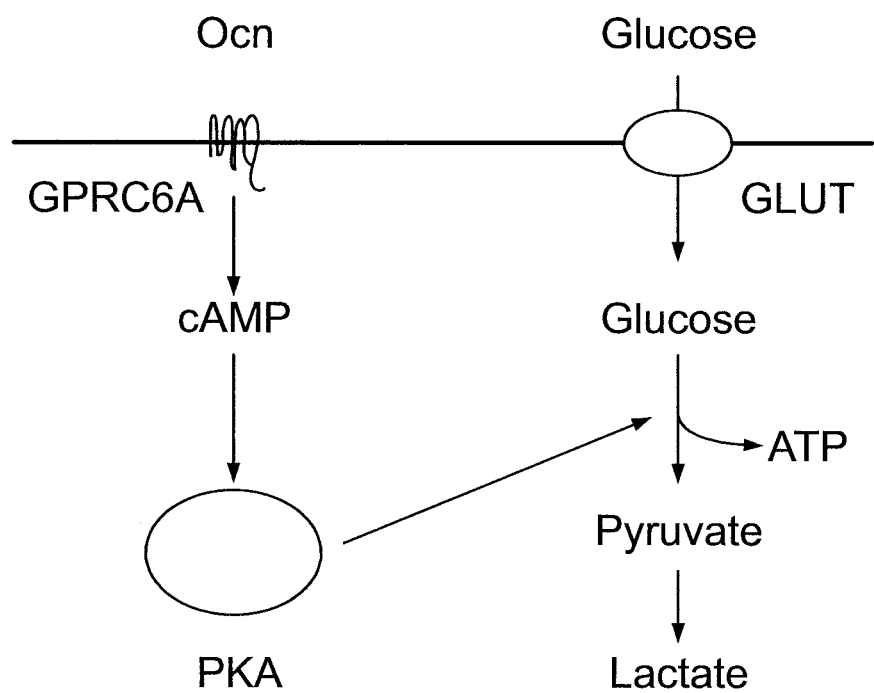
FIG. 21. Generic mode of action of osteocalcin and glucose.
Figure 22A:
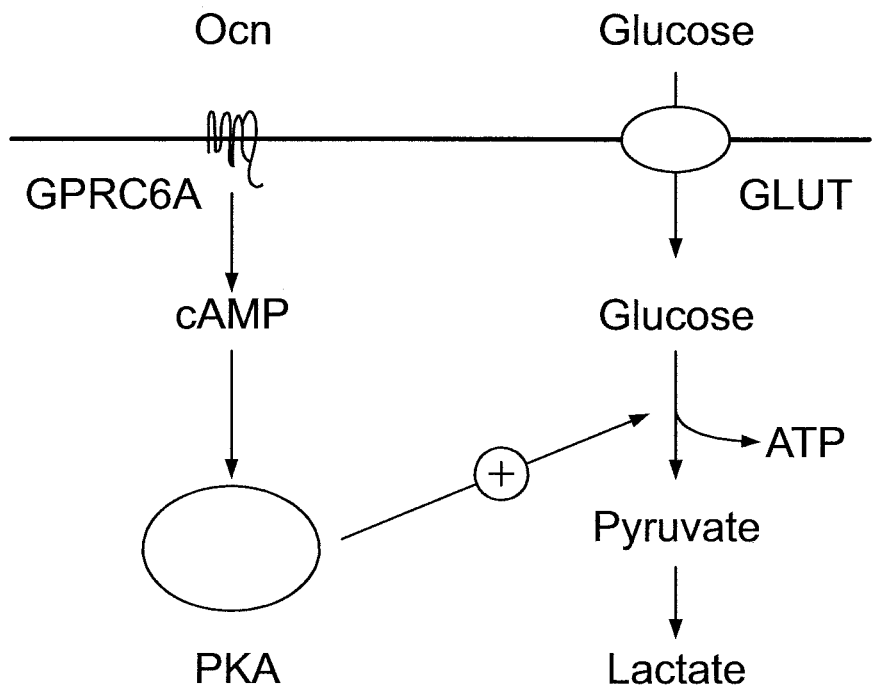
FIG. 22. Regulation of glycolysis by osteocalcin is mediated by PKA. (A) Schematic of how osteocalcin might positively regulate glycolysis. (B) Effect of uncarboxylated osteocalcin on extracellular acidification rate (ECAR) in the presence and absence of KT5720 (an inhibitor of protein kinase A (PKA)).
Figure 22B:
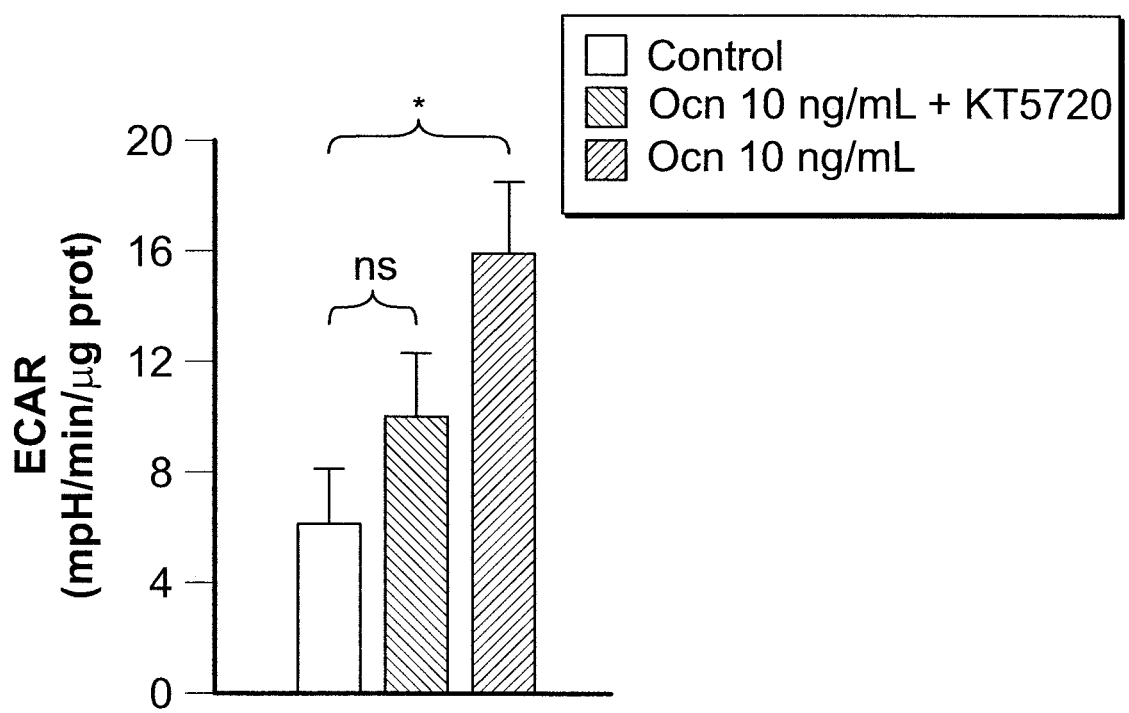
Figure 24:
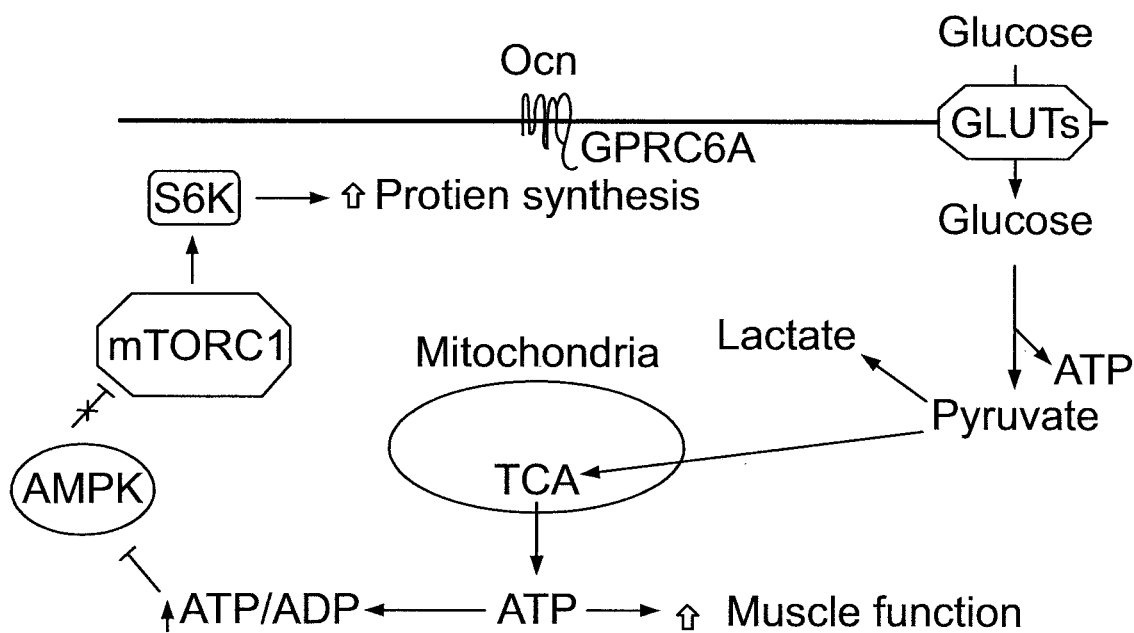
FIG. 24. Schematic of possible mechanism of action for osteocalcin in muscle.

Example 27—Direct Delivery of Osteocalcin to the Brain of Aged Wild Type (WT) Mice Improves Hippocampal Functions ICV pumps delivering (10 ng/hr) recombinant uncarboxylated full-length mouse osteocalcin were implanted in 16 month old WT mice. After an infusion period of one month, the mice were subjected to a modified version of the Novel Object Recognition test, to assay memory and hippocampal function. Briefly, mice were given five 5 minute exposures, with 3 minute resting intervals between exposures, to a novel arena containing two objects. During exposures 1-4, mice were habituated to these two objects, which elicited equal amounts of exploration. In the fifth exposure, one of the objects was replaced with a novel object. Aged mice receiving either PBS or recombinant uncarboxylated full-length mouse osteocalcin were both able to discriminate between the novel and constant objects. However, FIG. 15 shows that mice which had received osteocalcin treatment spent less time exploring the novel object than mice treated with vehicle alone, indicating improved efficiency in hippocampal context encoding and/or acquisition efficiency (Denny et al., 2012, Hippocampus 22:1188-1201).

Example 28—Osteocalcin Deficiency Leads to Muscle Wasting

FIGS. 16-24 Show that the absence of osteocalcin signaling has deleterious consequences on muscle mass and function. Young Osteocalcin$^{-/-}$ mice, lacking both copies of Osteocalcin, have a phenotype reminiscent of muscle wasting in old mice. These mice have a lower ratio of muscle weight to body weight than wild-type mice (FIG. 16A) and are unable to run as far (FIG. 16B) or as long (FIG. 16C) as wild-type mice.

Example 29—Animal and Human Studies

Rhesus monkeys (*Macaca mulatta*) were housed individually in standard nonhuman primate caging on a 12 h light/12 h dark cycle, room temperature 78±2 degrees, humidity at 60±20% at the NIH Animal Center, Poolesville, Md. Ocn−/− mice were maintained on 129-Sv genetic background. Gprc6a$_{Mck}$−/−, Gprc6a$_{Myh}$6−/−, Ocn+/−; Gprc6a$_{Mck}$+/− and Gprc6a$_{Mck}$+/−; Creb$_{Mck}$+/− mice were maintained on 129-Sv/C57/BL6 mixed genetic background. Control littermates were used in all experiments. Mice genotypes were determined by PCR. Generation of Osteocalcin conditional and Gprc6a conditional alleles has been described previously (Oury et al., 2013, Cell 155:228-241; Oury et al., 2011, Cell 144:796-809).

For exercise studies, all mice were trained before the tests to run on a treadmill (Harvard apparatus) for three days (10 minutes/day). The day of the test, mice were acclimated to the treadmill for 5 minutes followed by 10 minutes running at a constant speed of 17 cm/s, then a gradual increase in the speed up to 30 cm/s. Next, mice were run until exhaustion as defined by the number of times a mouse fell off to the electric grid during one minute (>15). Measurements of muscle strength were carried out using a grip strength meter (Columbus instruments). Values are expressed as the average of five single measurements, taken one minute apart from each other. For all biochemical and metabolic analyses performed, blood/tissues were collected and processed either at rest or at the end of a 40 min run (30 cm/s).

Human healthy volunteers were used to assay osteocalcin (Elecsys, Roche Diagnosis) across lifespan.

Example 30—Energy Metabolism Studies

Glucose and insulin tolerance tests were performed as previously described (Lee et al., 2007, Cell 130:456-469). For in vivo glucose uptake, a bolus of 2-deoxy-d-[$^3$H] glucose ($^3$H-2-DG, Perkin Elmer) (10 µCi) was administered before an endurance run. $^3$H-2-DG and $^3$H-2-DG-6-P content in muscle was determined by liquid scintillation counter and normalized to muscle weight. Glucose uptake and fatty acid oxidation assays in myotubes were performed as previously described (Sebastian et al., 2007, Am. J. Physiol. Endocrinol. Metab. 292:E667-686). GLUT4 translocation was determined by flow cytometry using an antibody against the extracellular domain of the GLUT4 protein (Santa Cruz, Sc-1606). Measurements of oxygen consumption rates (OCR) in isolated myofibers were performed using a XF24 Seahorse Analyzer® (Seahorse Biosciences). To analyze mitochondrial function, myofibers were treated with three compounds in succession (oligomycin 10 µg/ml, FCCP 200 µM, rotenone 0.2 µM) and OCR was recorded following administration of each of them.

Metabolite profiling was done at the Einstein Stable Isotope and Metabolomics Core Facility (Bronx, N.Y.). Metabolites from freeze-clamped skeletal muscles were extracted, derivatized with a two-step procedure, and run for GC-TOFMS analysis (Qiu et al., 2014, J. Am. Assn. Cancer Res. 20:2136-2146). LC/MS/MS (Waters Xevo TQ) analysis was used for quantitation of glycolytic and TCA cycle metabolites as per Serasinghe et al., 2015, Molecular Cell 57:521-536. The Biocrates AbsoluteIDQ p180 kit (Wang-Sattler et al., 2012, Molecular Systems Biology 8:615) was used to quantitate amino acids, biogenic amines, acylcarnitines and phospholipids by LC/MS/MS (Waters Xevo TQ) for both plasma and muscle. Echocardiography was performed using a Visualsonics Vevo Model 2100 under light anesthesia with isoflurane.

ADP and ATP analyses were performed using commercial kits from Sigma (MAK033) and Abcam (ab83355) respectively following manufacturer's instructions.

Example 31—Biochemistry and Molecular Biology

Serum osteocalcin, PINP, CTX, and insulin levels were measured using ELISA assays. Blood glucose level was measured using an Accu-Check glucometer. Urine 3-MHT was measured as previously described (Aranibar et al., 2011, Anal. Biochem. 410:84-91). Determination of cAMP accumulation was performed using a commercial kit (R&D). For gene expression, 1 µg of total RNA was reverse transcribed into cDNA. qPCR analyses were performed using a SYBER green master mix (Applied Biosciences) and a CFX-Connect real time PCR (Bio-Rad). Relative expression levels of each gene were normalized to that of Hprt or Gapdh. For in situ hybridization, muscle was frozen in liquid $N_2$-cooled methylbutane. Samples were sectioned at 10 µm using a cryostat. In situ hybridization was performed with a DIG-labeled riboprobe as previously described (Oury et al., 2011, Cell 144:796-809).

Example 32—Muscle Histomorphometry

Mitochondria histomorphometry, muscle enzyme histochemistry and hematoxylin/eosin staining were performed following standard protocols.

Example 33—Culture of Myoblasts and Myofibers

Culture of skeletal muscle myoblasts from 7 day-old mice was performed as described (Gharaibeh et al., 2008, Nature Protocols 3:1501-1509). Myoblasts were differentiated into myotubes for 3-4 days in a medium containing 5% horse serum. Muscle fibers were isolated from flexor digitorum brevis muscle. Muscles were dissected with DMEM 2% collagenase for 2 hours at 37° C., in a 5% $CO_2$ incubator. Muscle fibers were disaggregated from the tissue using a wide bore pipet and plated in matrigel-coated plates at approximately 50% confluence. After overnight incubation, isolated myofibers were used.

Contractile measurements were performed on fast twitch muscle Extensor digitorum longus (EDL) and slow twitch muscle Soleus. Both muscles were dissected from hind limbs and placed in chilled Krebs solution (in mM: 119 NaCl, 4.7 KCl, 2.5 $CaCl_2$, 1.2 $KH_2PO_4$, 1.2 $MgSO_4$, 20 $NaHCO_3$, bubbled with 95% $O_2$-5% $CO_2$ (pH 7.4). The tendons of the muscles were tied to a force transducer (400A, Aurora Scientific) and an adjustable hook using nylon sutures. The muscles were immersed in a stimulation chamber containing the Krebs solution continuously bubbled ($O_2$ 95/$CO_2$ 5%) (at 28° C.). The muscle was stimulated to contract using an electrical field between two platinum electrodes (Aurora Scientific 1200A—in vitro System).

The muscle length (Lo) was first adjusted to yield the maximum force. The force-frequency relationships were determined by triggering contraction using incremental stimulation frequencies (0.5 ms pulses at 10-120 Hz for 350 ms at supra-threshold current). Between stimulations the muscle was allowed to rest for ~1 min. Fatigability of the muscles was assessed by measuring the loss of force in response to repeated stimuli (30 Hz, 300 ms duration) at 1 Hz over 10 min. After the measurements of contractile properties were completed, muscles were measured at Lo, dried to remove the buffer, and weighed. The muscle cross-sectional area was determined by dividing muscle weight by its length and tissue density (1.056 g/cm3). Force production was then normalized to the muscle cross-sectional area to determine the specific force.

Example 34—Statistics

All data are presented as mean±standard error of mean. Statistical analyses were performed using unpaired, two-tailed Student's t test for comparison between two groups and ANOVA test for experiments involving more than two groups. For all experiments, * denotes P≤0.05, # denotes P≤0.005.

NUCLEOTIDE AND AMINON ACID SEQUENCES

SEQUENCE ID NO: 1
Human Osteocalcin cDNA
cgcagccacc gagacaccat gagagccctc acactcctcg ccctattggc cctggccgca ctttgcatcg ctggccaggc
aggtgcgaag cccagcggtg cagagtccag caaaggtgca gcctttgtgt ccaagcagga gggcagcgag gtagtgaaga
gacccaggcg ctacctgtat caatggctgg gagcccagt cccctacccg gatcccctgg agcccaggag ggaggtgtgt
gagctcaatc cggactgtga cgagttgct gaccacatcg gctttcagga ggcctatcgg cgcttctacg gcccggtcta
gggtgtcgct ctgctggcct ggccggcaac cccagttctg ctcctctcca ggcacccttc tttcctcttc cccttgccct
tgccctgacc tcccagccct atggatgtgg ggtccccatc atcccagctg ctcccaaata aactccagaa gaggaatctg
aaaaaaaaaa aaaaaaaa SEQUENCE ID NO: 2
Human Osteocalcin amino acid sequence
MRALTLLALL ALAALCIAGQ AGAKPSGAES SKGAAFVSKQ EGSEVVKRPR RYLYQWLGAP VPYPDPLEPR REVCELNPDC
DELADHIGFQ EAYRRFYGPV SEQUENCE ID NO: 3
Mouse osteocalcin gene 1 cDNA
agaacagaca agtcccacac agcagcttgg cccagaccta gcagacacca tgaggaccat ctttctgctc actctgctga
ccctggctgc gctctgtctc tctgacctca cagatgccaa gccagcggc cctgagtctg acaaagcctt catgtccaag
caggagggca ataaggtagt gaacagactc cggcgctacc ttggagcctc agtccccagc ccagatcccc tggagcccac
ccgggagcag tgtgagctta accctgcttg tgacgagcta tcagaccagt atggcttgaa gaccgcctac aaacgcatct
atggtatcac tatttaggac ctgtgctgcc ctaaagccaa actctggcag ctcggctttg gctgctctcc gggacttgat
cctccctgtc ctctctctct gccctgcaag tatggatgtc acagcagctc caaaataaag ttcagatgag gaagtgcaaa
aaaaaaaaaa aaaa SEQUENCE ID NO: 4
Mouse osteocalcin gene 2 cDNA
gaacagacaa gtcccacaca gcagcttggt gcacacctag cagacaccat gaggaccctc tctctgctca ctctgctggc
cctggctgcg ctctgtctct ctgacctcac agatcccaag cccagcgcc ctgagtctga caaagccttc atgtccaagc
aggagggcaa taaggtagtg aacagactcc ggcgctacct tggagcctca gtccccagcc cagatcccct ggagcccacc
cgggagcagt gtgagcttaa ccctgcttgt gacgagctat cagaccagta tggcttgaag accgcctaca aacgcatcta
cggtatcact atttaggacc tgtgctgccc taaagccaaa ctctggcagc tcggctttgc tgctctccg ggacttgatc
ctccctgtcc tctctctctg ccctgcaagt atggatgtca cagcagctcc aaaataaagt tcagatgagg SEQUENCE ID NO: 5
Mouse osteocalcin gene 1 and 2 amino acid sequence
MRTLSLLTLL ALAALCLSDL TDPKPSGPES DKAFMSKQEG NKVVNRLRRY LGASVPSPDP LEPTREQCEL NPACDELSDQ
YGLKTAYKRI YGITI SEQUENCE ID NO: 6
Human gamma-carboxylase cDNA
gtgacccacc tgcctcctcc gcagagcaat ggcggtgtct gccgggtccg cgcggacctc gcccagctca gataaagtac
agaaagacaa ggctgaactg atctcagggc ccaggcagga cagccgaata gggaaactct gggttttga gtggacagat
ttgtccagtt ggcggaggct ctgaatcgac caacggaccc tgcaagctta gctgtctttc gttttctttt tgggttcttg
atggtgctag acattcccca ggagcgggg ctcagctctc tggacagcaa gggctggatg tgtgccgctt ccccttgctg
gatgccctac gccactgcc atgtatcttg tctacaccat catgtttctg ggggcactgg gcatgatgct taccggataa
gctgtgtgtt attcctgctg ccatactggt atgtgtttct cctggacaag acatcatgga caaccactc ctatctgtat
gggttgttgg cctttcagct gatgcaaacc actactggtc tgtggacggt ctgctgaatg cccataggag gtgccccttt
ggaactatgc agtgctccgt ggccagatct tcattgtgta cttcattgcg ggtgtgaaaa agctggatgc agactgggtt
gaaggctatt ccatggaata tttgtcccgg cactgctct tcagtccctt caaactgctg ttgtctgagg agctgactag
cctgctggtc gtgcactggg gtgggctgct gcttggacctc tcagctggtt tcctgctctt ttttgatgtc tcaagatcca
ttggcctgtt ctttgtgtcc tacttccact gcatgaattc cagctttc agcattggta tgttctccta cgtcatgctg
gccagcagcc tctccttctg ctccccctga agcctcggaa agtggtgtc ctactgcccc cgaaggttgc aacaactgtt
gcccctcaag gcagcccctc agcccagtgt ttcctgctgt tataagagga gccgggcaa aagtggccag aagccagggc
tgcgccatca gctgggagct gccttcaccc tgctctacct cctggagcag ctattcctgc cctattctca ttttctcacc
cagggctata caactggac aaatgggctg tatggctatt cctgggacat gatggtgcac tcccgctccc accagcacgt
gaagatcacc taccgtgatg gccgcactgg cgaactgggc taccttaacc ctgggggtatt tacacagagt cggcgatgga
aggatcatgc agacatgctg aagcaatatg ccacttgcct gagccgcctg cttcccaagt ataatgtcac tgagcccag
atctactttg atatttgggt ctccatcaat gaccgctcc agcagaggat ttttgacccct cgtgtggaca tcgtgccaggc
cgcttggtca ccctttcagc gcacatcctg ggtgcaacca ctcttgatgg acctgtctcc ctggagggcc aagttacagg
aaatcaagag cagcctagac aaccacactg aggtggtctt cattgcagat ttccctggac tgcacttgga gaattttgtg
agtgaagcc tgggcaacac tagcatccag ctgctgcagg gggaagtgac tgtggagctt gtggcagaac agaagaacca
gactcttcga gagggagaaa aaatgcagtt gcctgctggt gagtaccata aggtgtatac gacatcacct agcccttctt
gctacatgta cgtctatgtc aacactacag agcttgcact ggagcaagac ctggcatatc tgcaagaatt aaaggaaaag
gtggagaatg aagtgaaac agggcctcta cccccagagc tgcagcctct gttggaaggg gaagtaaaag ggggccctga
gccaacacct ctggttcaga cctttcttag acgccaacaa aggctccagg agattgaacg ccggcgaaat atcctttcc
atgagcgatt cttccgcttc ttgttgcgaa agctctatgt cttttcgcgc agcttcctga tgacttgtat ctcacttcga
aatctgatat taggccgtcc ttccctggag cagctggccc aggaggtgac ttatgcaaac ttgagaccct tgaggcagt
tggagaactg aatccctcaa acacggattc ttcacattct aatcctcctg agtcaaatcc tgatcctgtc cactcagagt
tctgaagggg gccagatgtt gggtgcagat gtagaagcag ccagtcacag accccattcta tgcaatggac atttatttga
aaaaaattct caaagttttt ttttttttttt ttgggggggc ggggttcta agctgttttt aactccgaga ttacaactta
gaggaaccaa ggaaataaag caaataagat ttaacaaccc aagattaaga ggccaggaag aggttagacg caatgtgaaa
ctgtcctcct aggataaggt ttaaagtggc ttttggggg ctgggtgccg tggctcacgc ctgtaatccc agcatttgg
gaggctgagg tgggcagatc acttgaggcc aggagttcga gaccaggcct ggccaacatg caaaaccct tctctactaa
aaatacaaaa attagccaga cgtggtggtg ggtgcctgta atcccactac ccagaggctc gaggcatgag aatcgcttgg
gcccaggagg tggaggttgc agtgagccga gatcgagcca ctgcactcct gggcaacaga gcaagacttc gtctcaaat
aaataaataa agtggctctt ggggaaaagc aatttaatgt accacgatga atagctaact gttccaagt gtttgctatg
tgcaacacac cgcgtgagca gtgttacctg cattattaca ttaggctgag aggtaaaata atttgcccga agacatacag
ctagtgacga atgagctgat ggtttgaact taacgtctat ttgacttaag gtcctgcacc ctgccactgg taattttcag

| NUCLEOTIDE AND AMINON ACID SEQUENCES |
|---|

```
aatcactgat aatctgaaat aatgcagctt aaaacatgtt ttcttaatta aaagtataaa aaaaaaaaaa aaaaaaaaa
aaaaaaaaaa aaaaaaaaaa aaaaaaaaaa aaaaaaaaaa aaaaaaaaaa aaaaaa SEQUENCE ID NO.: 7
Human gamma-carboxylase amino acid sequence
MAVSAGSART SPSSDKVQKD KAELISGPRQ DSRIGKLLGF EWTDLSSWRR LVTLLNRPTD PASLAVFRFL FGFLMVLDIP
QERGLSSLDR KYLDGLDVCR FPLLDALRPL PLDWMYLVYT IMFLGALGMM LGLCYRISCV LFLLPYWYVF LLDKTSWNNH
SYLYGLLAFQ LTFMDANHYW SVDGLLNAHR RNAHVPLWNY AVLRGQIFIV YFIAGVKKLD ADWVEGYSME YLSRHWLFSP
FKLLLSEELT SLLVVHWGGL LLDLSAGFLL FFDVSRSIGL FFVSYFHCMN SQLFSIGMFS YVMLASSPLF CSPEWPRKLV
SYCPRRLQQL LPLKAAPQPS VSCVYKRSRG KSGQKPGLRH QLGAAFTLLY LLEQLFLPYS HFLTQGYNNW TNGLYGYSWD
MMVHSRSHQH VKITYRDGRT GELGYLNPGV FTQSRRWKDH ADMLKQYATC LSRLLPKYNV TEPQIYFDIW VSINDRFQQR
IFDPRVDIVQ AAWSPFQRTS WVQPLLMDLS PWRAKLQEIK SSLDNHTEVV FIADFPGLHL ENFVSEDLGN TSIQLLQGEV
TVELVAEQKN QTLREGEKMQ LPAGEYHKVY TTSPSPSCYM YVYVNTTELA LEQDLAYLQE LKEKVENGSE TGPLPPELQP
LLEGEVKGGP EPTPLVQTFL RRQQRLQEIE RRRNTPFHER FFRFLLRKLY VFRRSFLMTC ISLRNLILGR PSLEQLAQEV
TYANLRPFEA VGELNPSNTD SSHSNPPESN PDPVHSEF SEQUENCE ID NO: 8
Mouse gamma-carboxylase cDNA
agacagcaag tctaagtctg gaggttccac tgggtccgac ctggctgcag agaggctcac ctgtccctgc agtcatggct
gtgcaccgcg gctccgcact ggttgctccc gcctcagata aagtacagaa aaacaagtct gcacagacat caggactgaa
acagggcagc cgaatggaga aaattttagg gtttgaatgg acagatttat ctagctggca gagtgtcgtg accctgctta
acaaaccaac ggaccctgca aacctggctg tctttcgttt tctcttttgct ttcttgatgc tgctggacat tcccagaa
cgcggcctta gctccctgga ccgaaaatac ttggatgggc tggatgtgtg ccgtttcccc ttgctggatg ccttgcgccc
actgccactg gactggatgt atcttgtcta caccatcatg tttctggggg cactgggcat gatgctgggg ctatgctacc
ggctaagctg tgtgttattc ctgctaccgt actggtacgt gtttctcctg gacaagactt cgtggaacaa tcactcctat
ctgtatggtt tgttggcctt tcagttgaca ttcatggatg caaaccacta ctggtctgtg gatggcttgc tgaatgcccg
aaagaagaat gctcacgtgc cccttttgaa ctacacagtt ctgcgtggcc agatcttcat cgtgtacttc atcgcgggtg
tgaagaagct cgatgctgac tgggttgggg gctactccat ggagcacctg tcccggcact ggctcttcag tccctcaag
ctggtgttgt cggaggagtc gacaagcctg ctggtagtac actggtgtgg gcttctcctt gacctctcgg ctggcttcct
gctcttcttt gatgcctcca gaccgtcgg cctgttcttc gtgtcctact tcactgcat gaactcgcag ctcttcagca
tcgggatgtt tccctatgtc atgctggcca gcagccctct cttctgctca gctgaatggc ctcggaagtt ggtagcccga
tgcccgaaaa ggctgcaaga gctgctgccc accaaagccg ctctccggcc tagtgcttcc tgtgtgtata agaggtcccg
gggcaaagct ggcccgaagc ccggggctgcg ccaccagtc ggagccatct tcaccctgta cctactccta gagcagctct
tcctgcccta ttcccacttc ctgacccagg gttacaataa ctggacaaat gggctgtatg gctattcctg ggacatgatg
gtgcactccc gctcccacca gcacgtaaag atcacctacc gcgacggcct cacgggcgag ctaggctacc ttaacccgtgg
ggtattcaca cagagccggc gatggaagga tcatgcagac atgctgaagc aatatgccac ttgcctgagc ctcctgcttc
ccaagtacaa tgtcactgag ccccagatct actttgatat ttggtctcc atcaatgacc gcttccagca gaggcttttt
gaccctcgtg tggacatcgt gcaggctgtc tggtcccct tccagcgcac accttgggtg cagccactct tgatggattt
atctccctgg aggaccaagt tacaggatat taagagcagt ctggacaacc acaccgaggt ggtcttcatt gcagatttcc
ctgggcttca cttggagaat tttgtgagtg aagacctggg caacactagc atccagctgc tgcaggaga agtcaccgtg
gaattggtgg cagaacgaaa aaatcagact cttcaagaag gagagaaaat gcagttgcct gctggagagt accataaagt
ctatactgta tcatctagtc cttcctgcta catgtacgtc tatgtcaaca ctacagagtt cgcactgtag caagacctag
catatctgca agaattaaag gagaaggtgg agaacgaag tgaaacaggg cccctgcctc cagaacttca gcctcttttg
gaagggggaag taaagggggg ccctgagcca cacctctgg tccaaacttt tctcagacga cagaggaagc tccaagaaat
tgaacgcagg cgaaatagcc cttttccatga gcgatttctc cgcttcgtgc tgcgaaagct ctacgtcttt cgacgcagct
tcctgatgac tcgaatttca ctccgaaacc tgctattagg ccgcccttcc ctagagcaac tagcccaaga ggtgacatat
gcaaacttgc gaccatttga accagttgat gagtcaagtg cttcaaacac agattcttca aatcacccgt cagagccaga
ttctgagcat gttcactctg agttctgagg gatgtacaga tgctctgtgc agatgtgggg gcagcctgtt ataggcttat
tgtctacgca aagaacatat tttttggagaa aaatgatatg gacaggcttt tcacagtacc gcccaggctg gcctcaaact
catggttggt ccctctgctt cagcctgttt tgtaattaca tagtatcacc aaacctagtt gcttttccct ttacattttt
tccccttata agttctttaa aattatagct tacatttttt ctttttttct ttttttttttt ttgtatttt tctttgtcaa
gacaggtctc tctctgtgta gcactggctg tcctggaact cactctgtag tccaggctgg cctccaactc agaaattctc
ctgcctctgc ctcccaagtg ctgggattaa aggtgtgtgc caccacgcc cactgggctt tagttttta tagacaagat
ttctccatgt agaccagaca agctctctg agtgctgaaa ttaaaggcac gggacatcac tacctggctt tcttattaaa
cttgttttag tggtctcaac aaaaa SEQUENCE ID NO: 9
Mouse gamma-carboxylase amino acid sequence
MAVHRGSALV APASDKVQKN KSAQTSGLKQ GSRMEKILGF EWTDLSSWQS VVTLLNKPTD PANLAVFRFL FAFLMLLDIP
QERGLSSLDR KYLDGLDVCR FPLLDALRPL PLDWMYLVYT IMFLGALGMM LGLCYRLSCV LFLLPYWYVF LLDKTSWNNH
SYLYGLLAFQ LTFMDANHYW SVDGLLNARK KNAHVPLWNY TVLRGQIFIV YFIAGQVKKLD ADWVGGYSME HLSRHWLFSP
FKLVLSEELT SLLVVHWCGL LLDLSAGFLL FFDASRPVGL FFVSYFHCMN SQLFSIGMFP YVMLASSPLF CSAEWPRKLV
ARCPKRLQEL LPTKAAPRPS ASCVYKRSRG KAGPKPGLRH QLGAIFTLLY LLEQLFLPYS HFLTQGYNNW TNGLYGYSWD
MMVHSRSHQH VKITYRDGLT GELGYLNPGV FTQSRRWKDH ADMLKQYATC LSLLLPKYNV TEPQIYFDIW VSINDRFQQR
LFDPRVDIVQ AVWSPFQRTP WVQPLLMDLS PWRTKLQDIK SSLDNHTEVV FIADFPGLHL ENFVSEDLGN TSIQLLQGEV
TVELVAEQKN QTLQEGEKMQ LPAGEYHKVY TVSSSPSCYM YVYVNTTEVA LEQDLAYLQE LKEKVENGSE TGPLPPELQP
LLEGEVKGGP EPTPLVQTFL RRQRKLQEIE RRRNSPFHER FLRFVLRKLY VFRRSFLMTR ISLRNLLLGR PSLEQLAQEV
TYANLRPFEP VDESSASNTD SSNHPSEPDS EHVHSEF SEQUENCE ID NO: 10
Mouse Esp (OST-PTP, Ptprv) cDNA
ggctgtggga gagcagaaga gagcagccta caacagctgt cggggaggac cagggctagt tcacacttgg
aagctgggat gccaggaccg gcctcctgc ctctctcggt ctccatcggc tcctggtca gctcactcca cactgagacg
attctgaagt aagatgctcc tggctcctca cagactctgc tacaagagac agagtcgaagt gtcccagg ctcagagcct
ttgactctgc tccttccctt cccacgctg agttggcaca ggagcacctg ggtgagctgc accagactta agaagatgag
gcccctgatt ctgttagctg ccctcctctg gctccaggac tctttggccc aggaagatgt atgctcatcc ttggatggga
gcccagacag gcagggtgga ggtccacctc tgagtgtgaa cgtcagcagc gcggaaagc ctacagccct gtttctgagc
```

-continued

NUCLEOTIDE AND AMINON ACID SEQUENCES

```
tgggtagctg cagagccagg tggatttgac tatgccctct gcctcagggc tatgaacttg tcgggttttc cagaagggca
acagctccaa gctcatacca acgagtccag ctttgagttc catggcctgg tgccaggag tcgctaccag ctggaactga
ctgtcctaag accctgttgg cagaatgtca caattaccct cactgctcga actgcccta cagtggtccg tggactgcaa
ctgcatagca ctgggagccc agccagcctg gaagcctcat ggagcgatgc ctctgggat caagacagct atcaacttct
cctctaccac ccggaatccc acactctggc atgtaatgtc tctgtgtccc ctgacaccct gtcttacaat tttggtgacc
tcttgccagg tagtcagtat gtcttggagg ttatcacctg gctggcagt ctccatgcga agactagcat cctccaatgg
acagagcctg tccctcctga tcacctaaca ctgcgtgcct tgggtaccag tagcctgcaa gccttctgga acagtctga
agggggccacc tggtttcacc tgatacttac agacctccta gagggtacca acctgaccaa agtggtcaga caaggcatct
caacccacac cttccttcgc ctgtctccgg gtacaccta ccagctgaag atctgtgctg ctgctgggcc ccaccagatt
tggggaccca atgccactga gtggacctat ccctcttacc catctgacct ggtgctgacc cccttatgga atgagctctg
ggcaagctgg aaggcagggc agggagcccg ggatggctat gtactgaagt taagtgggcc agtggagaat acaactactc
tgggtcctga ggagtgcaac gctgtcttcc caggggcccct cctccagga cactacactt tggggctgag ggttctagct
ggaccttatg atgcctgggt agagggcagt atctggctgg ctgaatctgc tgctcgtccc atggaggtcc ctggtgccag
actgtggcta gaaggactgg aagctactaa gcaacctggg agacgggcgc tgctctattc tgttgatgcc ccaggcctcc
tagggaacat ctctgtgtct tctggtgcca ctcatgtcac cttctgtggc ttggtacccg agcgcacta cagggtggac
attgcctcat ccatgggaga catcactcag agcctcacag agcctacaag tccctgcca ccacagtctc tggagatcat
cagccggaac agcccatctg acctgactat cggttgggct ccagcaccag ggcagatgga aggttataag gtcacctgc
atcaggatgg cagccagagg tcacctggcg accttgttga cttgggccct gacatttcga gcctgactct gaaatctctg
gtacctggtt cctgctacac cgtgtcagca tgggcctggt ctgggaacct cagctctgac tctcagaaga ttcacagttg
caccgtccc gctcctccca ccaacctgag cctgggcttt gcccaccagc ctgcaaccact gaggcttcc tggtgtcacc
caccgggtgg cagggatgcc tttcagttac ggctttacag gctgaggccc ctgacactgg aaagtgagaa gatcctatcc
caggaggccc agaactctc ctgggcccag ctgcctgcag gctatgaatt ccaggtacag ctgtctacct tgtggggtc
ggaggagagc ggcagtgcca acaccacagg ctggacaccc cctcagctc ctacattggt aaatgtgacc agtgaagccc
ccacccagct ccacgtatcc tgggtccacg ctgtggggca ccggagcagc taccaagtga ccctatacca ggagagcact
cggacagcca ccagcattgt ggggcccaag gcagacagca caagcttttg gggttgact cctggcacta agtacaaggt
ggaagccatc tcctgggctg ggcccctta cactgcagca gccaacgttt ctgcttggac ctacccactc acacccaatg
agctgctcgc ctctatgcag gcaggcagtg ctgtggttaa cctggcctgg cccagtggtc ccttggggca agggacatgc
catgccaac tctcagatgc tggacaccct tcatggagc aaccgctgtc gctaggccaa gacctcctca tgctaaggaa
tcttatacca ggacatacgg tttcattgtc tgtgaagtgt cgggcaggac cactccagcc ctccactcac cccctggtgc
tgtctgtaga gcctggccct gtggaagatg tgttctgtca acctgaggcc acctacctgt ccctgaactg gacgatgcct
actgagatg tggctgtctg tctggtggag gtagagcagc tggtgccagg agggagcgct cattttgtct tccaggtcaa
cacctcggag gatgcacttc tgctgccaa cttgacgccc accactcttt accgcctag cctcactgtg ctgggtggga
atcgccagtg gagccgggcg gttacctgc tgtgcactac ttctgctgag gtttggcacc ccccagagct agctgaggcc
ccccaggtgg agctggggac agggatgggt gtgacagtca cacgtggcat gtttggtaaa gatgacgggc agatccagtg
gtatggcata attgccacca tcaacatgac actgggccag ccttcccagg aagccatcaa ccacacatgg tatgaccact
actatagagg acatgactcc tacctggctc tcctgttccc aaacccctc tacccagagc cttgggctgt gccaagatcc
tggacagtac ctgtgggtac agaggactgt gacaacaccc aggagatatg caactgagat ctcaagccag gcttccagta
taggttcagc attgcagcct ttagtaggct cagctctcca gagaccatcc tggccttctc cgccttctca gagcctcagg
ctagcatctc tctggtggcc atgccctga cagttatgat ggggactgtg gtgggctgca tcatcattgt gtgtgcagtg
ctatgcttgt tgtgccggcg cgcctgaag ggaccaaggt cagagaagaa tggcttttcc caggagttga tgccttacaa
cctgtggcgg acccatcggc ccatagcttc cggcagagct atgaggccaa gagtgcacgt gcacaccagg
ccttcttcca ggaatttgag gagctgaagg aggtgggcaa ggaccagccc agactagagg ctgagcatcc tgccaacatc
accaagaacc ggtacccaca cgtgctacct tatgaccact ccagggtcag gctgaccag ctatcaggag agcctcattc
tgactacatc aatgccaact tcatcccagg ctatagccac ccacaggaga tcattgccac ccaggggcct ctcaaaaga
cggtcgagga cttctgcgg ttggtgtggg agcagcaagt ccacgtgatc atcatgctaa ctgtgggcat ggagaatggg
cgggtactgt gtgagcacta ctggccagtc aactccacg ctgtcaccca cggtcacatc accaccaccc tcctgccaga
ggaatctgag gacgagtgga ccaggaggga attccagctg cagcacggtg cagagcaaaa acagaggcgc gtgaagcagc
tgcagttcac gacctggcca gaccacagtg tccccgaggc tcccagctct ctgctcgctt tgtggaact ggtgcaggag
gaggtgaagg caactcaggg caaggggccc atcctggtgc attgcagtgc gggtgtgggc aggacaggca cctttgtggc
tctcttaccg gctgttcgac aactagagga agaacaggtg gtcgatgtgt tcaacactgt gtacactc cggctgcacc
ggcccctcat gatccagacc ttgagtcaat acatcttcct gcacagctgc ctgctgaaca agattctgga agggccctct
gacgcctcag actccggccc catccctgtg atgaattttg cacaagcttg tgccaagagg cagccaatg ccaatgccgg
tttcttgaag gagtacaggc tcctgaagca ggccatcaag gatgagcatg gctctctgct gccctctcct gactataatc
agaacagcat cgcctcctgt catcattctc aggagcagtt ggccctggtg gaggagagcc ctgctgataa catgctggca
gcctcgctct tccctggtgg gccgtctggt cgcgaccatg tggtgctgac tggctcggcc ggaccaaagg aactctggga
aatggtgtgg gaacatggcg cctatgtgct tgtctccctg ggtctgcctg ataccaagga gaagccacaa gacatctggc
caatggagat gcagcctatt gtcacagaca tggtgacagt gcacagagtg gctgagacaa acagctgg ctggcccagt
accctcatca gagttataca tggggacagt gggacggaaa ggcaggttca atgcctgcag tttccacact gcgagactgg
gagtgagctc ccagctaaca ccctactgac cttccttgat gctgctgggcc agtgctgctc ccggggcaat agcaagaagc
cagggaccct gctcagtcac tccagcaagg tcacaaacca gctgagcacc ttcttggcta tgaacagct gctacagcaa
gcagggaccg agccacagt ggatgtcttc agtgtggccc tgaagcagac acaggcctgt ggcttaaga ccccaacgct
ggagcagtat atctacctct acaactgtct gaacagcgca ttgaggaaca ggctgccccg agctaggaag tgaccttgcc
ctgctaggca tcacgttcca gcaatccacc caggcctggc ttccccagga gaacagatct attcggcctc acgctgtcaa
agggcagagt ctgggaataa agggtaaatc tcgag
```

SEQUENCE ID NO: 11
Mouse Esp (OST-PTP, Ptprv) amino acid sequence
MRPLILLAAL LWLQDSLAQE DVCSSLDGSP DRQGGGPPLS VNVSSRGKPT SLFLSWVAAE PGGFDYALCL RAMNLSGFPE
GQQLQAHTNE SSFEHGLVP GSRYQLELTV LRPCWQNVTI TLTARTAPTV VRGLQLHSTG SPASLEASWS DASGDQDSYQ
LLLYHPESHT LACNVSVSPD TLSYNFGDLL PGSQYVLEVI TWAGSLHAKT SILQWTEPVP PDHLTLRALG TSSLQAFWNS
SEGATWFHLI LTDLLEGTNL TKVVRQGIST HTFLRLSPGT PYQLKICAAA GPHQIWGPNA TEWTYPSYPS DLVLTPLWNE
LWASWKAGQG ARDGYVLKLS GPVENTTTLG PEECNAVFPG PLPPGHYTLG LRVLAGPYDA WVEGSIWLAE SAARPMEVPG
ARLWLEGLEA TKQPGRRALL YSVDAPGLLG NISVSSGATH VTFCGLVPGA HYRVDIASSM GDITQSLTGY TSPLPPQSLE
IISRNSPSDL TIGWAPAPGQ MEGYKVTWHQ DGSQRSPGDL VDLGPDISSL TLKSLVPGSC YTVSAWAWSG NLSSDSQKIH
SCTRPAPPTN LSLGFAHQPA TLRASWCHPP GGRDAFQLRL YRLRPLTLES EKILSQEAQN FSWAQLPAGY EFQVQLSTLW
GSEESGSANT TGWTPPSAPT LVNVTSEAPT QLHVSWVHAA GDRSSYQVTL YQESTRTATS IVGPKADSTS FWGLTPGTKY
KVEAISWAGP LYTAAANVSA WTYPLTPNEL LASMQAGSAV VNLAWPSGPL GQGTCHAQLS DAGHLSWEQP LSLGQDLLML -continued

NUCLEOTIDE AND AMINON ACID SEQUENCES

```
RNLIPGHTVS LSVKCRAGPL QASTHPLVLS VEPGPVEDVF CQPEATYLSL NWTMPTGDVA VCLVEVEQLV PGGSAHFVFQ
VNTSEDALLL PNLTPTTSYR LSLTVLGGNR QWSRAVTLVC TTSAEVWHPP ELAEAPQVEL GTGMGVTVTR GMFGKDDGQI
QWYGIIATIN MTLAQPSQEA INHTWYDHYY RGHDSYLALL FPNPFYPEPW AVPRSWTVPV GTEDCDNTQE ICNGHLKPGF
QYRFSIAAFS RLSSPETILA FSAFSEPQAS ISLVAMPLTV MMGTVVGCII IVCAVLCLLC RRRLKGPRSE KNGFSQELMP
YNLWRTHRPI PSHSFRQSYE AKSARAHQAF FQEFEELKEV GKDQPRLEAE HPANITKNRY PHVLPYDHSR VRLTQLSGEP
HSDYINANFI PGYSHPQEII ATQGPLKKTV EDFWRLVWEQ QVHVIIMLTV GMENGRVLCE HYWPVNSTPV THGHITTHLL
AEESEDEWTR REFQLQHGAE QKQRRVKQLQ FTTWPDHSVP EAPSSLLAFV ELVQEEVKAT QGKGPILVHC SAGVGRTGTF
VALLPAVRQL EEEQVVDVFN TVYILRLHRP LMIQTLSQYI FLHSCLLNKI LEGPSDASDS GPIPVMNFAQ ACAKRAANAN
AGFLKEYRLL KQAIKDETGS LLPSPDYNQN SIASCHHSQE QLALVEESPA DNMLAASLFP GGPSGRDHVV LTGSAGPKEL
WEMVWEHGAY VLVSLGLPDT KEKPQDIWPM EMQPIVTDMV TVHRVAESNT AGWPSTLIRV IHGDSGTERQ VQCLQFPHCE
TGSELPANTL LTFLDAVGQC CSRGNSKKPG TLLSHSSKVT NQLSTFLAME QLLQQAGTER TVDVFSVALK QTQACGLKTP
TLEQYIYLYN CLNSALRNRL PRARK

SEQUENCE ID NO: 12
Mature human osteocalcin amino acid sequence
YLYQWLGAPV PYPDPLEPRR EVCELNPDCD ELADHIGFQE AYRRFYGPV SEQUENCE ID NO: 13
human osteocalcin variant amino acid sequence
YLYQWLGAPV PYPDPLX₁PRR X₂VCX₃LNPDCD ELADHIGFQE AYRRFYGPV SEQUENCE ID NO: 14
Rat Esp (OST-PTP, Ptprv) cDNA
   1 agaacagcct acaacagctg ccttccggga gggaccaggc tagttcacac ttggaagttg
  61 ggatgccagg agcagccttc tgtcttccga ggccttcctg ggtctcctgg tcagctcatt
 121 ccacactgag atgattctaa agaaagatcc tcacacagac tctgctggaa gaaacaaagt
 181 gaagtgtccc cagactttat caggatgagg cccctgattc tgttagctgc cctcctctgg
 241 ctccagggct ttttggccga ggacgacgca tgctcatcct tggaagggag cccagacagg
 301 cagggtggag gtccacttct gagtgtgaac gtcagtagcc atggaaagtc taccagcctg
 361 tttctgagct gggtagctgc agagctgggc ggatttgact atgccctcag cctcaggagt
 421 gtgaactcct caggttctcc agaagggcaa cagctccagg ctcacacaaa tgagtccggc
 481 tttgagttcc atggcctggt gccagggagt cgctaccagc taaaactgac tgtcctaaga
 541 ccctgttggc agaatgtcac aattaccctc actgcccgaa ctgcccccgac agtggtccgt
 601 ggactgcagc tgcatagcgc tgggagccca gccaggctgg aagcctcgtg gagtgatgcc
 661 cctggagatc aagacagcta ccaacttctc ctctaccacc tggaatccca aactctggca
 721 tgcaatgtct ctgtgtcccc tgcaccctg tcttacagtt ttggcgacct tttgccaggt
 781 actcagtatg tcttggaggt tatcacctgg gctggcagtc tccatgcgaa gactagtatc
 841 ctccagtgga cagagcctgt ccctcctgat cacctagcac tacgtgcctt gggtaccagt
 901 agcctgcaag ccttctggaa cagctctgaa ggggccacct cgtttcacct gatgctcaca
 961 gacctcctcg gggcaccaa cacgactgcg gtgatcagac aaggggtctc gacccacacc
1021 tttcttcacc tatctccggg tacacctcat gagctgaaga tttgtgcttc tgctgggccc
1081 caccagatct ggggacccag tgccaccgag tggacctatc cctcttaccc atctgacctg
1141 gtgctgactc ccttacggaa tgagctctgg gccagctgga aggcagggct gggagcccgg
1201 gacggctatg tactgaagtt aagtgggcca atggagagta cgtctaccct gggcccggaa
1261 gagtgcaatg cagtcttccc agggccctg cctccgggac actacacttt gcagctgaag
1321 gttctagctg gaccttatga tgcctggggt gagggcagta cctggctggc tgaatctgct
1381 gcccttccca gggaggtccc tggtgccaga ctgtggctag atggactgga agcttccaag
1441 cagcctggga gacgggcgct actctattct gacgatgccc aggctccct agggaacatc
1501 tctgtgccct ctggtgccac tcacgtcatt ttctgtgcc tggtacctgg agccactat
1561 agggtggaca ttgcctcatc cacgggggac atctctcaga gcatctcagg ctatacaagt
1621 cccctgccac cgcagtcact ggaggtcatc agcaggagca gccatctga cctgactatt
1681 gcttggggtc cagcaccagg gcagctgaa ggttataagg ttacctggca tcaggatggc
1741 agccagaggt ctcctggcga ccttgttgac ttgggccctg acactttgag cctgactctg
1801 aaatctctgg tacccggctc ctgctacacc gtgtcagcat gggcctgggc cgggaacctc
1861 gactctgact tcagaagat tcacagctgc acccgcccg ctcctcccac caacctgagt
1921 ctgggctttg cccaccagcc tgcggcactg aaggcttcct ggtatcaccc accgggtggc
1981 agggatgcct ttcacttacg gctttacagg ctgaggcctc tgacactgga aagtgagaag
2041 gtcctacctc gggaggccca gaacttctcc tgggcccagc tgactgcagg ctgtgagttc
2101 caggtacagc tgtctacctt gtgggggtct gagagaagca gcagtgccaa cgccacaggc
2161 tggacacccc cttcagctcc tacactggta aacgtgacca gcgatgctcc tacccagctc
2221 caagtatcct gggcccacgt tcctgggggc cggagccgct accaagtgac cctataccag
2281 gagagtaccc ggacagccac cagcatcatg gggcccaagg aagatggcac gagcttttg
2341 ggtttgactc ctggcactaa gtacaaggtg gaagtcatct cctgggctgg gcccctctac
2401 actgcagcag ccaacgtttc tgcctggacc tacccactca tacccaatga gctgctcgtg
2461 tcaatgcagg caggcagtgc tgtggttaac ctggcctggc ccagtggtcc cctggggcaa
2521 ggggcatgcc acgcccaact ctcagatgct ggacacctct catggagcca accctgaaa
2581 ctaggccaag agctcttcat gctaaggat ctcacaccag gacataccat ctcgatgtca
2641 gtgaggtgtc gggcagggcc gctccaggcc tctacgcacc ttgtggtgct gtctgtggag
2701 cctgccctg tggaagatgt gctctgtcat ccagaggcca cctacctggc cctgaactgg
2761 acgatgcctc tggagacgt ggatgtctgt ctggtggtgg tagagcggct ggtgccggga
2821 gggggcactc atttgtctt ccaggtcaac acctcagggg atgctcttct gttgcccaac
2881 ttgatgccca ccacttctta ccgcttagc ctcaccgttc tgggcaggaa tagtcggtgg
2941 agccggggcg tttcccctgg tgtgcagtact tctgctgagg cttggcaccc cccagagcta
3001 gctgagcccc ccaggtggga gctggggaca gggatgggtg tgacagtcat gcgtggcatg
3061 tttggtaaag atgacgggca gatccagtgg tatggcataa ttgccaccat caacatgacg
3121 ctgcccagc cttccggga agcatcaat tacacatggt atgaccacta ctatagagga
3181 tgtgagtcct tcctggctct cctgttccca aaccccttct cccagagcc ttgggctggg
```

| NUCLEOTIDE AND AMINON ACID SEQUENCES |
|---|
| 3241 ccaagatcct ggacagtacc tgtgggtact gaggactgtg acaacaccca agagatatgc
3301 aatgggcgtc tcaagtcagg cttccagtat aggttcagcg ttgtggcctt tagtaggctc
3361 aacactccag agaccatcct cgccttctcg gccttctcag agccccggcc cagcatctct
3421 ctggcgatca ttcccctgac agttatgctg gggctgtgg tggcagcat tgtcattgtg
3481 tgtcagtgc tatgcttgct ccgctggcgg tgcctgaagg gaccaagatc agagaaggat
3541 ggcttttcca aggagctgat gccttacaac ctgtggcgga cccatcggcc tatccccatc
3601 catagcttcc ggcagagcta tgaggccaag agcgcacatg cacaccagac cttcttccag
3661 gaatttgagg agttgaagga ggtaggcaag gaccagcccc gactagaggc tgagcatccg
3721 gacaacatca tcaagaaccg gtacccacac gtgctgccct atgaccactc cagggtcagg
3781 ctgacccagc taccaggaga gcctcattct gactacatca atgccaactt catcccaggc
3841 tatagccaca cacaggagat cattgccacc caggggcctc tcaaaaagac gctagaggac
3901 ttctggcggt tggtatggga gcagcaagtc cacgtgatca tcatgctgac tgtgggcatg
3961 gagaacgggc gggtactgtg tgagcactac tggccagcca actccacgcc tgttactcac
4021 ggtcacatca ccatccacct cctggcagag gagcctgagg atgagtggac caggagggaa
4081 ttccagctgc agcacggtac cgagcaaaaa cagaggcgag tgaagcagct gcagttcact
4141 acctggccag accacagtgt cccggaggct cccagctctc tgctcgcttt tgtagaactg
4201 gtacaggagc aggtgcaggc cactcagggc aagggaccca tcctggtgca ttgcagtgct
4261 ggcgtgggga ggacaggcac cttttgtggct ctcttgcggc tactgcgaca actagaggaa
4321 gagaaggtgg ccgatgtgtt caacactgtg tacatactcc ggttgcaccg gcccctcatg
4381 atccagaccc tgagtcaata catcttcctg cacagttgcc tgctgaacaa gattctggaa
4441 gggccccctg acagctccga ctccggcccc atctctgtga tggattttgc acaggcttgt
4501 gccaagaggg cagccaacgc caatgctggt ttcttgaagg agtacaagct cctgaagcag
4561 gccatcaagg atgggactgg ctctctgctg cccctcctg actacaatca gaacagcatt
4621 gtctcccgtc gtcattctca ggagcagttc gccctggtgg aggagtgccc tgaggatagc
4681 atgctggaag cctcactctt ccctggtggt ccgtctggtt gtgatcatgt ggtgctgact
4741 ggctcagccg gaccaaagga actctgggaa atggtgtggg agcatgatgt ccatgtgctc
4801 gtctccctgg gcctgcctga taccaaggag aagccaccag acatctggcc agtggagatg
4861 cagccctattg tcacagacat ggtgacagtg cacagtgt ctgagagcaa cacaacaact
4921 ggctggccca gcaccctctt cagagtcata cacggggaga gtggaaagga aaggcaggtt
4981 caatgcctgc aatttccatg ctctgagtct gggtgtgagc tcccagctaa caccctactg
5041 accttccttg atgctgtggg ccagtgctgc ttccggggca agagcaagaa gccagggacc
5101 ctgctcagcc actccagcaa aaacacaaac cagctgggca ccttcttggc tatggaacag
5161 ctgttacagc aagcagggac agagcgcaca gtggacgtct tcaatgtggc cctgaagcag
5221 tcacaggcct gcgggcttat gaccccaaca ctggagcagt atatctacct ctacaactgt
5281 ctgaacagcg cactgctgaa cgggctgccc agagctggga agtggcctgc gccctgctag
5341 gcgtcatgtt ccagcaaatc cacccaggcc tgacttccct aggagagtgg atccaccggg
5401 cctcacactg tccaagggca gagtccagga ataaagagac atggtc |

SEQUENCE ID NO: 15
Rat Esp (OST-PTP, Ptprv) amino acid sequence
MRPLILLAALLWLQGFLAEDDACSSLEGSPDRQGGGPLLSVNVSSHGKSTSLFLSWVAAELGGFDYALSLRSVNSSGSPEGQQLQAH
TNESGFEFHGLVPGSRYQLKLTVLRPCWQNVTITLTARTAPTVVRGLQLHSAGSPARLEASWSDAPGDQDSYQLLLYHLESQTLACN
VSVSPDTLSYSFGDLLPGTQYVLEVITWAGSLHAKTSILQWTEPVPPDHLALRALGTSSLQAFWNSSEGATSFHLMLTDLLGGTNTT
AVIRQGVSTHTFLHLSPGTPHELKICASAGPHQIWGPSATEWTYPSYPSDLVLTPLRNELWASWKAGLGARDGYVLKLSGPMESTST
LGPEECNAVFPGPLPPGHYTLQLKVLAGPYDAWVEGSTWLAESAALPREVPGARLWLDGLEASKQPGRRALLYSDDAPGSLGNISVP
SGATHVIFCGLVPGAHYRVDIASSTGDISQSISGYTSPLPPQSLEVISRSSPSDLTIAWGPAPGQLEGYKVTWHQDGSQRSPGDLVD
LGPDTLSLTLKSLVPGSCYTVSAWAWAGNLDSDSQKIHSCTRPAPPTNLSLGFAHQPAALKASWYHPPGGRDAFHLRLYRLRPLTLE
SEKVLPREAQNFSWAQLTAGCEFQVQLSTLWGSERSSSANATGWTPPSAPTLVNVTSDAPTQLQVSWAHVPGGRSRYQVTLYQESTR
TATSIMGPKEDGTSFLGLTPGTKYKVEVISWAGPLYTAAANVSAWTYPLIPNELLVSMQAGSAVVNLAWPSGPLGQGACHAQLSDAG
HLSWEQPLKLGQELFMLRDLTPGHTISMSVRCRAGPLQASTHLVVLSVEPGPVEDVLCHPEATYLALNWTMPAGDVDVCLVVVERLV
PGGGTHFVFQVNTSGDALLLPNLMPTTSYRLSLTVLGRNSRWSRAVSLVCTSAEAWHPPELAEPPQVELGTGMGVTVMRGMFGKDDG
QIQWYGIIATINMTLAQPSREAINYTWYDHYYRGCESFLALLFPNPFYPEPWAGPRSWTVPVGTEDCDNTQEICNGRLKSGFQYRFS
VVAFSRLNTPETILAFSAFSEPRASISLAIIPLTVMLGAVVGSIVVCAVLCLLRWRCLKGPRSEKDGFSKELMPYNLWRTHTPIPI
HSFRQSYEAKSAHAHQTFFQEFEELKEVGKDQPRLEAEHPDNIIKNRYPHVLPYDHSRVRLTQLPGEPHSDYINANFIPGYSHTQEI
IATQGPLKKTLEDFWRLVWEQQVHVIIMLTVGMENGRVLCEHYWPANSTPVTHGHITIHLLAEEPEDEWTRREFQLQHGTEQKQRRV
KQLQFTTWPDHSVPEAPSSLLAFVELVQEQVQATQGKGPILVHCSAGVGRTGTFVALLRLLRQLEEEKVADVFNTVYILRLHRPLMI
QTLSQYIFLHSCLLNKILEGPPDSSDSGPISVMDFAQACAKRAANANAGFLKEYKLLKQAIKDGTGSLLPPPDYNQNSIVSRRHSQE
QFALVEECPEDSMLEASLFPGGPSGCDHVVLTGSAGPKELWEMVWEHDAHVLVSLGLPDTKEKPPDIWPVEMQPIVTDMVTVHRVSE
SNTTTGWPSTLFRVIHGESGKERQVQCLQFPCSESGCELPANTLLTFLDAVGQCCFRGKSKKPGTLLSHSSKNTNQLGTFLAMEQLL
QQAGTERTVDVFNVALKQSQACGLMTPTLEQYIYLYNCLNSALLNGLPRAGKWPAPC SEQUENCE ID NO: 16
Human PTP-1B cDNA
GenBank HUMPTPBX Accession no. M31724

| 1 gggcgggcct cggggctaag agcgcgacgc ctagagcggc agacggcgca gtgggccgag
61 aaggaggcgc agcagccgcc ctggcccgtc atggagatgg aaaaggagtt cgagcagatc
121 gacaagtccg ggagctgggc ggccatttac caggatatcc gacatgaagc cagtgacttc
181 ccatgtagag tggccaagct tcctaagaac aaaaaccgaa ataggtacag agacgtcagt
241 ccccttgacc atagtcggat taaactacat caagaagata tgactatat caacgctagt
301 ttgataaaaa tggaagaagc ccaaaggagt tacattctta cccagggccc tttgcctaac
361 acatcgggtc acttttggga gatggtgtgg gagcagaaaa gcagggtgt cgtcatgctc
421 aacagagtga tggagaacga ttcgttaaaa tgcgcacaat actggccaca aaaagaagaa
481 aaagagatga tctttgaaga cacaaatttg aaattaacat tgatctctga agatatcaag
541 tcatattata cagtgcgaca gctagaattg gaaaacctta caccccaaga aactcgagag
601 atcttacatt tccactatac cacatggcct gactttggag tccctgaatc accagcctca
661 ttcttgaact tctttttcaa agtccgagag tcagggtcac tcagcccgga gcacgggccc
721 gttgtggtgc actgcagtgc aggcatcggc aggtctggaa ccttctgtct ggctgatacc |

NUCLEOTIDE AND AMINON ACID SEQUENCES

```
 781 tgcctcctgc tgatggacaa gaggaaagac ccttcttccg ttgatatcaa gaaagtgctg
 841 ttagaaatga ggaagtttcg gatggggttg atccagacag ccgaccagct gcgcttctcc
 901 tacctggctg tgatcgaagg tgccaaattc atcatggggg actcttccgt gcaggatcag
 961 tggaaggagc tttcccacga ggacctggag cccccacccg agcatatccc cccacctccc
1021 cggccaccca aacgaatcct ggagccacac aatgggaaat gcaggagtt cttcccaaat
1081 caccagtggg tgaaggaaga gacccaggag gataaagact gccccatcaa ggaagaaaaa
1141 ggaagcccct taaatgccgc accctacggc atcgaaagca tgagtcaaga cactgaagtt
1201 agaagtcggg tcgtgggggg aagtcttcga ggtgcccagg ctgcctcccc agccaaaggg
1261 gagccgtcac tgcccgagaa ggacgaggac catgcactga gttactggaa gcccttcctg
1321 gtcaacatgt gcgtggctac ggtcctcacg gccggcgctt acctctgcta caggttcctg
1381 ttcaacagca acacatagcc tgaccctcct ccactccacc tccacccact gtccgcctct
1441 gcccgacagg cccacgcccg actacgggcc atgccgcggt aggtaagggc cgccggaccg
1501 cgtagagagc cgggccccgg acggacgttg gttctgcact aaaacccatc ttccccggat
1561 gtgtgtctca cccctcatcc ttttactttt tgcccctttcc actttgagta ccaaatccac
1621 aagccattt ttgaggagag tgaaagagag taccatgctg gcggcgcaga gggaaggggc
1681 ctacaccgt cttgggggctc gccccaccca gggctcctc ctggagcatc ccaggcggcg
1741 cacgccaaca gccccccct tgaatctgca gggagcaact ctccactcca tatttattta
1801 aacaattttt tccccaaagg catccatagt gcactagcat tttcttgaac caataatgta
1861 ttaaaatttt ttgatgtcag ccttgcatca agggctttat caaaaagtac aataataaat
1921 cctcaggtag tactgggaat ggaaggcttt gccatgggcc tgctgcgtca gaccagtact
1981 gggaaggagg acggttgtaa gcagttgtta tttagtgata ttgtgggtaa cgtgagaaga
2041 tagaacaatg ctataatata taatgaacac gtgggtattt aataagaaac atgatgtgag
2101 attactttgt cccgcttatt ctcctccctg ttatctgcta gatctagttc tcaatcactg
2161 ctccccgtg tgtattagaa tgcatgtaag gtcttcttgt gtcctgatga aaaatatgtg
2221 cttgaaatga gaaactttga tctctgctta ctaatgtgcc ccatgtccaa gtccaacctg
2281 cctgtgcatg acctgatcat tacatggctg tggttcctaa gctgttgct gaagtcattg
2341 tcgctcagca atagggtgca gttttccagg aataggcatt tgctaattcc tggcatgaca
2401 ctctagtgac ttcctggtga gcccagcct gtcctggtac agcaggtct tgctgtaact
2461 cagacattcc aagggtatgg gaagccatat tcacacctca cgctctggac atgatttagg
2521 gaagcaggga caccccccgc ccccaccctt gggatcagc ctccgccatt ccaagtcaac
2581 actcttcttg agcagaccgt gatttggaag agaggcacct gctggaaacc acacttcttg
2641 aaacagcctg ggtgacggtc cttaggcag cctgccgccg tctctgtccc ggttcacctt
2701 gccgagagag gcgcgtctgc cccacccctca aaccctgtgg ggcctgatgg tgctcacgac
2761 tcttcctgca aagggaactg aagacctcca cattaagtgg ctttttaaca tgaaaaacac
2821 ggcagctgta gctcccgagc tactctcttg ccagcatttt cacattttgc ctttctcgtg
2881 gtagaagcca gtacagagaa attctgtggt gggaacattc gaggtgtcac cctgcagagc
2941 tatggtgagg tgtggataag gcttaggtgc caggctgtga gcattctgag ctggcttgtt
3001 gttttttaagt cctgtatatg tatgtagtag tttgggtgtg tatatatagt agcatttcaa
3061 aatgggacgta ctggttaac ctcctatcct tggagagcag ctggctctcc accttgttac
3121 acattatgtt agagaggtag cgagctgctc tgctatatgc cttaagccaa tatttactca
3181 tcaggtcatt attttttaca atgggccatgg aataaaccat ttttacaaaa ataaaaacaa
3241 aaaaagc
```

SEQUENCE ID NO: 17
Human PTP-1B amino acid sequence
GenBank HUMPTPBX Accession no. M31724
MEMEKEFEQIDKSGSWAAIYQDIRHEASDFPCRVAKLPKNKNRNRYRDVSPFDHSRIKLHQEDNDYINASLIKMEEAQRSYILTQGP
LPNTCGHFWEMVWEQKSRGVVMLNRVMEKGSLKCAQYWPQKEEKEMIFEDTNLKLTLISEDIKSYYTVRQLELENLTTQETREILHF
HYTTWPDFGVPESPASFLNFLFKVRESGSLSPEHGPVVVHCSAGIGRSGTFCLADTCLLLMDKRKDPSSVDIKKVLLEMRKFRMGLI
QTADQLRFSYLAVIEGAKFIMGDSSVQDQWKELSHEDLEPPPEHIPPPPRPPKRILEPHNGKCREFFPNHQWVKEETQEDKDCPIKE
EKGSPLNAAPYGIESMSQDTEVRSRVVGGSLRGAQAASPAKGEPSLPEKDEDHALSYWKPFLVNMCVATVLTAGAYLCYRFLFNSNT

TABLE 2

| | SEQ ID NO: | | GenBank Accession No: |
|---|---|---|---|
| | cDNA | Amino Acid | |
| Human Osteocalcin cDNA | 1 | 2 | NM_199173 |
| Mouse osteocalcin gene 1 | 3 | 5 | NM_007541 |
| Mouse osteocalcin gene 2 | 4 | 5 | NM_001032298 |
| Human Gamma-glutamyl carboxylase | 6 | 7 | NM_000821 |
| Mouse Gamma-glutamyl carboxylase | 8 | 9 | NM_019802 |
| Mouse Esp (OST-PTP, Ptprv) | 10 | 11 | NM_007955 |
| Rat (OST-PTP, Ptprv) | 14 | 15 | L36884 |
| Human PTP-1B | 16 | 17 | M31724 |

What is claimed is:

1. A method of treating loss of skeletal muscle function, comprising administering to a patient suffering from loss of skeletal muscle function a pharmaceutical composition comprising a therapeutically effective amount of undercarboxylated/uncarboxylated osteocalcin and a pharmaceutically acceptable carrier or excipient,
wherein the undercarboxylated/uncarboxylated osteocalcin is a polypeptide selected from a group consisting of:
(a) a fragment comprising mature human osteocalcin of SEQ ID NO: 12 missing the last 10 amino acids from the C-terminal end,
(b) a fragment comprising mature human osteocalcin of SEQ ID NO: 12 missing the first 10 amino acids from the N-terminal end,
(c) a fragment comprising amino acids 62-90 of SEQ ID NO:2,
(d) a fragment comprising amino acids 1-36 of mature human osteocalcin of SEQ ID NO:12,
(e) a fragment comprising amino acids 13-26 of mature human osteocalcin of SEQ ID NO:12, and
(f) a fragment comprising amino acids 13-46 of mature human osteocalcin of SEQ ID NO:12,
wherein the administering also alleviates asthma.

2. A method of treating loss of skeletal muscle function, comprising:
administering to a patient suffering from loss of skeletal muscle function a pharmaceutical composition comprising a therapeutically effective amount of undercarboxylated/uncarboxylated osteocalcin and a pharmaceutically acceptable carrier or excipient,
wherein the administering also alleviates at least asthma and at least one of a metabolic disorder selected from the group consisting of metabolic syndrome, glucose intolerance, type 1 diabetes, type 2 diabetes, and obesity, a male reproductive disorder selected from the group consisting of low sperm count, impaired sperm motility, impaired sperm viability, low testosterone levels, and excessive apoptosis in testes, or a cognitive disorder selected from the group consisting of anxiety, depression and memory loss.

3. The method of claim 1, wherein the administering further alleviates a metabolic disorder selected from the group consisting of metabolic syndrome, glucose intolerance, type 1 diabetes, type 2 diabetes, and obesity.

4. The method of claim 1, wherein the administering further a male reproductive disorder selected from the group consisting of low sperm count, impaired sperm motility, impaired sperm viability, low testosterone levels, and excessive apoptosis in testes.

5. The method of claim 1, wherein the administering further alleviates a cognitive disorder selected from the group consisting of anxiety, depression and memory loss.

6. The method of claim 1, wherein the administering further alleviates muscle wasting.

7. The method of claim 1, wherein the administering further alleviates muscle wasting as well as at least one of a metabolic disorder selected from the group consisting of metabolic syndrome, glucose intolerance, type 1 diabetes, type 2 diabetes, and obesity, a male reproductive disorder selected from the group consisting of low sperm count, impaired sperm motility, impaired sperm viability, low testosterone levels, and excessive apoptosis in testes, or a cognitive disorder selected from the group consisting of anxiety, depression and memory loss.

8. The method of claim 1, wherein the administering further alleviates muscle wasting as well as a metabolic disorder selected from the group consisting of metabolic syndrome, glucose intolerance, type 1 diabetes, type 2 diabetes, and obesity.

9. The method of claim 1, wherein the administering further alleviates muscle wasting and a male reproductive disorder selected from the group consisting of low sperm count, impaired sperm motility, impaired sperm viability, low testosterone levels, and excessive apoptosis in testes.

10. The method of claim 1, wherein the administering further alleviates muscle wasting and a cognitive disorder selected from the group consisting of anxiety, depression and memory loss.

11. The method of claim 1, wherein the administering further alleviates muscle wasting a metabolic disorder selected from the group consisting of metabolic syndrome, glucose intolerance, type 1 diabetes, type 2 diabetes, and obesity, a male reproductive disorder selected from the group consisting of low sperm count, impaired sperm motility, impaired sperm viability, low testosterone levels, and excessive apoptosis in testes, and a cognitive disorder selected from the group consisting of anxiety, depression and memory loss.

12. The method of claim 1, wherein the patient is a human who is at least 55 years of age.

13. The method of claim 1, wherein the osteocalcin is human osteocalcin.

14. The method of claim 13, wherein the osteocalcin is completely uncarboxylated human osteocalcin.

15. The method of claim 1, wherein the patient suffers from frailty.

16. The method of claim 1, wherein the patient suffers from sarcopenia.

17. The method of claim 2, wherein the cognitive disorder is memory loss due to neurodegeneration.

18. The method of claim 2, wherein the cognitive disorder is memory loss.

19. The method of claim 18, wherein the cognitive disorder is at least one of short term memory loss or long term memory loss.

20. The method of claim 2, wherein the cognitive disorder comprises temporary or permanent loss of an ability to learn, memorize, solve problems, process information, reason correctly, or recall information, and wherein the temporary or permanent loss is at least one of total or partial.

21. The method of claim 2, wherein the cognitive disorder is anxiety.

22. The method of claim 2, wherein the cognitive disorder is depression.

23. A method of treating loss of skeletal muscle function, comprising: administering to a patient suffering from loss of skeletal muscle function a pharmaceutical composition which comprises a therapeutically effective amount of undercarboxylated/uncarboxylated osteocalcin and a pharmaceutically acceptable carrier or excipient, wherein the administering also alleviates asthma.

24. The method of claim 23, wherein the administering improves a distance and/or a time that the patient achieves before exhaustion in an endurance exercise.

* * * * *

SEQUENCE LISTING

<160> NUMBER OF SEQ ID NOS: 17

<210> SEQ ID NO 1
<211> LENGTH: 498

```
<212> TYPE: DNA
<213> ORGANISM: Human

<400> SEQUENCE: 1
cgcagccacc gagacaccat gagagccctc acactcctcg ccctattggc cctggccgca      60
ctttgcatcg ctggccaggc aggtgcgaag cccagcggtg cagagtccag caaaggtgca     120
gcctttgtgt ccaagcagga gggcagcgag gtagtgaaga cccaggcg ctacctgtat      180
caatggctgg agccccagt ccctacccg atcccctgg agcccaggag ggaggtgtgt        240
gagctcaatc cggactgtga cgagttggct gaccacatcg gctttcagga ggcctatcgg     300
cgcttctacg cccggtcta gggtgtcgct ctgctggcct ggccggcaac ccagttctg       360
ctcctctcca ggcaccctc tttcctcttc cccttgccct tgccctgacc tcccagccct      420
atggatgtgg ggtccccatc atcccagctg ctcccaaata aactccagaa gaggaatctg     480
aaaaaaaaaa aaaaaaaa                                                   498

<210> SEQ ID NO 2
<211> LENGTH: 100
<212> TYPE: PRT
<213> ORGANISM: Human

<400> SEQUENCE: 2

Met Arg Ala Leu Thr Leu Leu Ala Leu Leu Ala Leu Ala Ala Leu Cys
1               5                   10                  15

Ile Ala Gly Gln Ala Gly Ala Lys Pro Ser Gly Ala Glu Ser Ser Lys
            20                  25                  30

Gly Ala Ala Phe Val Ser Lys Gln Glu Gly Ser Glu Val Val Lys Arg
        35                  40                  45

Pro Arg Arg Tyr Leu Tyr Gln Trp Leu Gly Ala Pro Val Pro Tyr Pro
    50                  55                  60

Asp Pro Leu Glu Pro Arg Arg Glu Val Cys Glu Leu Asn Pro Asp Cys
65                  70                  75                  80

Asp Glu Leu Ala Asp His Ile Gly Phe Gln Glu Ala Tyr Arg Arg Phe
                85                  90                  95

Tyr Gly Pro Val
            100

<210> SEQ ID NO 3
<211> LENGTH: 493
<212> TYPE: DNA
<213> ORGANISM: Mouse

<400> SEQUENCE: 3
agaacagaca agtcccacac agcagcttgg cccagaccta gcagacacca tgaggaccat      60
ctttctgctc actctgctga ccctggctgc gctctgtctc tctgacctca cagatgccaa     120
gcccagcggc cctgagtctg acaaagcctt catgtccaag caggagggca ataaggtagt     180
gaacagactc ggcgctacct tggagcctca gtccccagcc cagatcccct ggagcccacc     240
cgggagcagt gtgagcttaa ccctgcttgt gacgagctat cagaccagta tggcttgaag     300
accgcctaca aacgcatcta tggtatcact atttaggacc tgtgctgccc taaagccaaa     360
ctctggcagc tcggctttgg ctgctctccg ggacttgatc ctccctgtcc tctctctctg     420
ccctgcaagt atggatgtca cagcagctcc aaaataaagt tcagatgagg aagtgcaaaa     480
aaaaaaaaaa aaa                                                        493
```

-continued

```
<210> SEQ ID NO 4
<211> LENGTH: 470
<212> TYPE: DNA
<213> ORGANISM: Mouse

<400> SEQUENCE: 4
gaacagacaa gtcccacaca gcagcttggt gcacacctag cagacaccat gaggaccctc      60
tctctgctca ctctgctggc cctggctgcg ctctgtctct ctgacctcac agatcccaag     120
cccagcggcc ctgagtctga caaagccttc atgtccaagc aggagggcaa taaggtagtg     180
aacagactcc ggcgctacct tggagcctca gtccccagcc cagatcccct ggagcccacc     240
cgggagcagt gtgagcttaa ccctgcttgt gacgagctat cagaccagta tggcttgaag     300
accgcctaca aacgcatcta cggtatcact atttaggacc tgtgctgccc taaagccaaa     360
ctctggcagc tcggctttgg ctgctctccg ggacttgatc ctccctgtcc tctctctctg     420
ccctgcaagt atggatgtca gcagctcc aaaataaagt tcagatgagg                  470

<210> SEQ ID NO 5
<211> LENGTH: 95
<212> TYPE: PRT
<213> ORGANISM: Mouse

<400> SEQUENCE: 5

Met Arg Thr Leu Ser Leu Leu Thr Leu Leu Ala Leu Ala Ala Leu Cys
 1               5                  10                  15

Leu Ser Asp Leu Thr Asp Pro Lys Pro Ser Gly Pro Glu Ser Asp Lys
                20                  25                  30

Ala Phe Met Ser Lys Gln Glu Gly Asn Lys Val Val Asn Arg Leu Arg
            35                  40                  45

Arg Tyr Leu Gly Ala Ser Val Pro Ser Pro Asp Pro Leu Glu Pro Thr
        50                  55                  60

Arg Glu Gln Cys Glu Leu Asn Pro Ala Cys Asp Glu Leu Ser Asp Gln
65                  70                  75                  80

Tyr Gly Leu Lys Thr Ala Tyr Lys Arg Ile Tyr Gly Ile Thr Ile
                85                  90                  95

<210> SEQ ID NO 6
<211> LENGTH: 3176
<212> TYPE: DNA
<213> ORGANISM: Human

<400> SEQUENCE: 6
gtgacccacc tgcctcctcc gcagagcaat ggcggtgtct gccgggtccg cgcggacctc      60
gcccagctca gataaagtac agaaagacaa ggctgaactg atctcagggc ccaggcagga    120
cagccgaata gggaaactct tgggttttga gtggacagat ttgtccagtt ggcggaggct    180
ctgaatcgac caacggaccc tgcaagctta gctgtctttc gttttctttt tgggttcttg    240
atggtgctag acattcccca ggagcggggg ctcagctctc tggaccggaa gggctggatg    300
tgtgccgctt cccccttgctg gatgccctac gcccactgcc atgtatcttg tctacaccat    360
catgtttctg ggggcactgg gcatgatgct taccggataa gctgtgtgtt attcctgctg    420
ccatactggt atgtgtttct cctggacaag acatcatgga caaccactc ctatctgtat     480 gggttgttgg cctttcagct gatgcaaacc actactggtc tgtggacggt ctgctgaatg    540
cccataggag gtgcccctttt ggaactatgc agtgctccgt ggccagatct tcattgtgta    600
cttcattgcg ggtgtgaaaa agctggatgc agactgggtt gaaggctatt ccatggaata    660
```

-continued

| | |
|---|---|
| tttgtcccgg cactggctct tcagtccctt caaactgctg ttgtctgagg agctgactag | 720 |
| cctgctggtc gtgcactggg gtgggctgct gcttgacctc tcagctggtt tcctgctctt | 780 |
| ttttgatgtc tcaagatcca ttggcctgtt ctttgtgtcc tacttccact gcatgaattc | 840 |
| ccagcttttc agcattggta tgttctccta cgtcatgctg gccagcagcc ctctcttctg | 900 |
| ctcccctgag tggcctcgga agctggtgtc ctactgcccc cgaaggttgc aacaactgtt | 960 |
| gcccctcaag gcagcccctc agcccagtgt ttcctgtgtg tataagagga gccggggcaa | 1020 |
| aagtggccag aagccagggc tgcgccatca gctgggagct gccttcaccc tgctctacct | 1080 |
| cctggagcag ctattcctgc cctattctca ttttctcacc cagggctata caactggac | 1140 |
| aaatgggctg tatggctatt cctgggacat gatggtgcac tcccgctccc accagcacgt | 1200 |
| gaagatcacc taccgtgatg gccgcactgg cgaactgggc taccttaacc ctggggtatt | 1260 |
| tacacagagt cggcgatgga aggatcatgc agacatgctg aagcaatatg ccacttgcct | 1320 |
| gagccgcctg cttcccaagt ataatgtcac tgagccccag atctactttg atatttgggt | 1380 |
| ctccatcaat gaccgcttcc agcagaggat ttttgaccct cgtgtggaca tcgtgcaggc | 1440 |
| cgcttggtca ccctttcagc gcacatcctg ggtgcaacca ctcttgatgg acctgtctcc | 1500 |
| ctggagggcc aagttacagg aaatcaagag cagcctagaa aaccacactg aggtggtctt | 1560 |
| cattgcagat ttccctggac tgcacttgga aattttgtg agtgaagacc tgggcaacac | 1620 |
| tagcatccag ctgctgcagg gggaagtgac tgtggagctt gtggcagaac agaagaacca | 1680 |
| gactcttcga gagggagaaa aaatgcagtt gcctgctggt gagtaccata aggtgtatac | 1740 |
| gacatcacct agcccttctt gctacatgta cgtctatgtc aacactacag agcttgcact | 1800 |
| ggagcaagac ctggcatatc tgcaagaatt aaaggaaaag gtggagaatg aagtgaaac | 1860 |
| agggcctcta cccccagagc tgcagcctct gttggaaggg gaagtaaaag ggggccctga | 1920 |
| gccaacacct ctggttcaga ccttttcttag acgccaacaa aggctccagg agattgaacg | 1980 |
| ccggcgaaat actcctttcc atgagcgatt cttccgcttc ttgttgcgaa agctctatgt | 2040 |
| cttttcgccgc agcttcctga tgacttgtat ctcacttcga aatctgatat taggccgtcc | 2100 |
| ttccctggag cagctggccc aggaggtgac ttatgcaaac ttgagaccct ttgaggcagt | 2160 |
| tggagaactg aatccctcaa acacggattc ttcacattct aatcctcctg agtcaaatcc | 2220 |
| tgatcctgtc cactcagagt tctgaagggg gccagatgtt gggtgcagat gtagaagcag | 2280 |
| ccagtcacag acccattcta tgcaatggac atttatttga aaaaaattct caaaagtttt | 2340 |
| tttttttttt ttgggggggc ggggttctaa agctgttttt aactccgaga ttacaactta | 2400 |
| gaggaaccaa ggaaataaag caaataagat ttaacaaccc aagattaaga ggccaggaag | 2460 |
| aggttagacg caatgtgaaa ctgtcctcct aggataaggt ttaaagtggc tttttggggg | 2520 |
| ctgggtgccg tggctcacgc ctgtaatccc agcattttgg gaggctgagg tgggcagatc | 2580 |
| acttgaggcc aggagttcga gaccagcctg gccaacatgg caaacccct tctctactaa | 2640 |
| aaatacaaaa attagccaga cgtggtggtg ggtgcctgta atccaactac ccaggaggct | 2700 |
| gaggcatgag aatcgcttgg gcccaggagg tggaggttgc agtgagccga gatcgagcca | 2760 |
| ctgcactcct gggcaacaga gcaagacttc gtctcaaaat aaataaataa agtggctctt | 2820 |
| ggggaaaagc aatttaatgt accacgatga atagctaact gttcccaagt gtttgctatg | 2880 |
| tgcaacacac cgcgtgagca gtgttacctg cattattaca ttaggctgag aggtaaaata | 2940 |
| atttgcccga agacatacag ctagtgacga atggactgat ggtttgaact taacgtctat | 3000 |
| ttgacttaag gtcctgcacc ctgccacttg taattttcag aatcactgat aatctgaaat | 3060 |

```
aatgcagctt aaaacatgtt ttcttaatta aaagtataaa aaaaaaaaaa aaaaaaaaaa    3120
aaaaaaaaaa aaaaaaaaaa aaaaaaaaaa aaaaaaaaaa aaaaaaaaaa aaaaa         3176
```

<210> SEQ ID NO 7
<211> LENGTH: 758
<212> TYPE: PRT
<213> ORGANISM: Human

<400> SEQUENCE: 7

```
Met Ala Val Ser Ala Gly Ser Ala Arg Thr Ser Pro Ser Ser Asp Lys
1               5                   10                  15

Val Gln Lys Asp Lys Ala Glu Leu Ile Ser Gly Pro Arg Gln Asp Ser
            20                  25                  30

Arg Ile Gly Lys Leu Leu Gly Phe Glu Trp Thr Asp Leu Ser Ser Trp
        35                  40                  45

Arg Arg Leu Val Thr Leu Leu Asn Arg Pro Thr Asp Pro Ala Ser Leu
    50                  55                  60

Ala Val Phe Arg Phe Leu Phe Gly Phe Leu Met Val Leu Asp Ile Pro
65                  70                  75                  80

Gln Glu Arg Gly Leu Ser Ser Leu Asp Arg Lys Tyr Leu Asp Gly Leu
                85                  90                  95

Asp Val Cys Arg Phe Pro Leu Leu Asp Ala Leu Arg Pro Leu Pro Leu
            100                 105                 110

Asp Trp Met Tyr Leu Val Tyr Thr Ile Met Phe Leu Gly Ala Leu Gly
        115                 120                 125

Met Met Leu Gly Leu Cys Tyr Arg Ile Ser Cys Val Leu Phe Leu Leu
130                 135                 140

Pro Tyr Trp Tyr Val Phe Leu Leu Asp Lys Thr Ser Trp Asn Asn His
145                 150                 155                 160

Ser Tyr Leu Tyr Gly Leu Leu Ala Phe Gln Leu Thr Phe Met Asp Ala
                165                 170                 175

Asn His Tyr Trp Ser Val Asp Gly Leu Leu Asn Ala His Arg Arg Asn
            180                 185                 190

Ala His Val Pro Leu Trp Asn Tyr Ala Val Leu Arg Gly Gln Ile Phe
        195                 200                 205

Ile Val Tyr Phe Ile Ala Gly Val Lys Lys Leu Asp Ala Asp Trp Val
    210                 215                 220

Glu Gly Tyr Ser Met Glu Tyr Leu Ser Arg His Trp Leu Phe Ser Pro
225                 230                 235                 240

Phe Lys Leu Leu Leu Ser Glu Glu Leu Thr Ser Leu Leu Val Val His
                245                 250                 255

Trp Gly Leu Leu Leu Asp Leu Ser Ala Gly Phe Leu Leu Phe Phe
            260                 265                 270

Asp Val Ser Arg Ser Ile Gly Leu Phe Phe Val Ser Tyr Phe His Cys
        275                 280                 285

Met Asn Ser Gln Leu Phe Ser Ile Gly Met Phe Ser Tyr Val Met Leu
    290                 295                 300

Ala Ser Ser Pro Leu Phe Cys Ser Pro Glu Trp Pro Arg Lys Leu Val
305                 310                 315                 320

Ser Tyr Cys Pro Arg Arg Leu Gln Gln Leu Leu Pro Leu Lys Ala Ala
                325                 330                 335

Pro Gln Pro Ser Val Ser Cys Val Tyr Lys Arg Ser Arg Gly Lys Ser
            340                 345                 350
```

```
Gly Gln Lys Pro Gly Leu Arg His Gln Leu Gly Ala Ala Phe Thr Leu
        355                 360                 365
Leu Tyr Leu Leu Glu Gln Leu Phe Leu Pro Tyr Ser His Phe Leu Thr
    370                 375                 380
Gln Gly Tyr Asn Asn Trp Thr Asn Gly Leu Tyr Gly Tyr Ser Trp Asp
385                 390                 395                 400
Met Met Val His Ser Arg Ser His Gln His Val Lys Ile Thr Tyr Arg
                405                 410                 415
Asp Gly Arg Thr Gly Glu Leu Gly Tyr Leu Asn Pro Gly Val Phe Thr
            420                 425                 430
Gln Ser Arg Arg Trp Lys Asp His Ala Asp Met Leu Lys Gln Tyr Ala
        435                 440                 445
Thr Cys Leu Ser Arg Leu Leu Pro Lys Tyr Asn Val Thr Glu Pro Gln
    450                 455                 460
Ile Tyr Phe Asp Ile Trp Val Ser Ile Asn Asp Arg Phe Gln Gln Arg
465                 470                 475                 480
Ile Phe Asp Pro Arg Val Asp Ile Val Gln Ala Ala Trp Ser Pro Phe
                485                 490                 495
Gln Arg Thr Ser Trp Val Gln Pro Leu Leu Met Asp Leu Ser Pro Trp
            500                 505                 510
Arg Ala Lys Leu Gln Glu Ile Lys Ser Ser Leu Asp Asn His Thr Glu
        515                 520                 525
Val Val Phe Ile Ala Asp Phe Pro Gly Leu His Leu Glu Asn Phe Val
    530                 535                 540
Ser Glu Asp Leu Gly Asn Thr Ser Ile Gln Leu Leu Gln Gly Glu Val
545                 550                 555                 560
Thr Val Glu Leu Val Ala Glu Gln Lys Asn Gln Thr Leu Arg Glu Gly
                565                 570                 575
Glu Lys Met Gln Leu Pro Ala Gly Glu Tyr His Lys Val Tyr Thr Thr
            580                 585                 590
Ser Pro Ser Pro Ser Cys Tyr Met Tyr Val Tyr Val Asn Thr Thr Glu
        595                 600                 605
Leu Ala Leu Glu Gln Asp Leu Ala Tyr Leu Gln Glu Leu Lys Glu Lys
    610                 615                 620
Val Glu Asn Gly Ser Glu Thr Gly Pro Leu Pro Pro Glu Leu Gln Pro
625                 630                 635                 640
Leu Leu Glu Gly Glu Val Lys Gly Gly Pro Glu Thr Pro Leu Val
                645                 650                 655
Gln Thr Phe Leu Arg Arg Gln Gln Arg Leu Gln Glu Ile Glu Arg Arg
            660                 665                 670
Arg Asn Thr Pro Phe His Glu Arg Phe Phe Arg Phe Leu Leu Arg Lys
        675                 680                 685
Leu Tyr Val Phe Arg Arg Ser Phe Leu Met Thr Cys Ile Ser Leu Arg
    690                 695                 700
Asn Leu Ile Leu Gly Arg Pro Ser Leu Glu Gln Leu Ala Gln Glu Val
705                 710                 715                 720
Thr Tyr Ala Asn Leu Arg Pro Phe Glu Ala Val Gly Glu Leu Asn Pro
                725                 730                 735
Ser Asn Thr Asp Ser Ser His Ser Asn Pro Pro Glu Ser Asn Pro Asp
            740                 745                 750
Pro Val His Ser Glu Phe
        755
```

<210> SEQ ID NO 8
<211> LENGTH: 2905
<212> TYPE: DNA
<213> ORGANISM: Mouse

<400> SEQUENCE: 8

| | | | | | |
|---|---|---|---|---|---:|
| agacagcaag | tctaagtctg | gaggttccac | tgggtccgac | ctggctgcag agaggctcac | 60 |
| ctgtccctgc | agtcatggct | gtgcaccgcg | gctccgcact | ggttgctccc gcctcagata | 120 |
| aagtacagaa | aaacaagtct | gcacagacat | caggactgaa | acagggcagc cgaatggaga | 180 |
| aaatttagg | gtttgaatgg | acagatttat | ctagctggca | gagtgtcgtg accctgctta | 240 |
| acaaaccaac | ggaccctgca | aacctggctg | tctttcgttt | tctctttgct ttcttgatgc | 300 |
| tgctggacat | tccccaggaa | cgcggcctta | gctccctgga | ccgaaaatac ttggatgggc | 360 |
| tggatgtgtg | ccgtttcccc | ttgctggatg | ccttgcgccc | actgccactg gactggatgt | 420 |
| atcttgtcta | caccatcatg | tttctggggg | cactgggcat | gatgctgggg ctatgctacc | 480 |
| ggctaagctg | tgtgttattc | ctgctaccgt | actggtacgt | gtttctcctg acaagactt | 540 |
| cgtggaacaa | tcactcctat | ctgtatggtt | tgttggcctt | tcagttgaca ttcatggatg | 600 |
| caaaccacta | ctggtctgtg | gatggcttgc | tgaatgcccg | aaagaagaat gctcacgtgc | 660 |
| cccttggaa | ctacacagtt | ctgcgtggcc | agatcttcat | cgtgtacttc atcgcgggtg | 720 |
| tgaagaagct | cgatgctgac | tgggttgggg | gctactccat | ggagcacctg tcccggcact | 780 |
| ggctcttcag | tcccttcaag | ctggtgttgt | cggaggagct | gacaagcctg ctggtagtac | 840 |
| actggtgtgg | gcttctcctt | gacctctcgg | ctggcttcct | gctcttcttt gatgcctcca | 900 |
| gacccgtcgg | cctgttcttc | gtgtcctact | ttcactgcat | gaactcgcag ctcttcagca | 960 |
| tcgggatgtt | tccctatgtc | atgctggcca | gcagccctct | cttctgctca gctgaatggc | 1020 |
| ctcggaagtt | ggtagcccga | tgcccgaaaa | ggctgcaaga | gctgctgccc accaaagccg | 1080 |
| ctcctcggcc | tagtgcttcc | tgtgtgtata | agaggtcccg | gggcaaagct ggcccgaagc | 1140 |
| ccgggctgcg | ccaccagctg | ggagccatct | tcaccctgct | ctacctccta gagcagctct | 1200 |
| tcctgcccta | ttcccacttc | ctgacccagg | gttacaataa | ctggacaaat gggctgtatg | 1260 |
| gctattcctg | ggacatgatg | gtgcactccc | gctcccacca | gcacgtaaag atcacctacc | 1320 |
| gcgacggcct | cacgggcgag | ctaggctacc | ttaaccctgg | ggtattcaca cagagccggc | 1380 |
| gatgaagga | tcatgcagac | atgctgaagc | aatatgccac | ttgcctgagc ctcctgcttc | 1440 |
| ccaagtacaa | tgtcactgag | ccccagatct | actttgatat | tgggtctcc atcaatgacc | 1500 |
| gcttccagca | gaggcttttt | gaccctcgtg | tggacatcgt | gcaggctgtc tggtcccct | 1560 |
| tccagcgcac | accttgggtg | cagccactct | tgatggattt | atctccctgg aggaccaagt | 1620 |
| tacaggatat | taagagcagt | ctggacaacc | acaccgaggt | ggtcttcatt gcagatttcc | 1680 |
| ctgggcttca | cttggagaat | tttgtgagtg | aagacctggg | caacactagc atccagctgc | 1740 |
| tgcagggaga | agtcaccgtg | gaattggtgg | cagaacagaa | aaatcagact cttcaagaag | 1800 |
| gagagaaaat | gcagttgcct | gctggagagt | accataaagt | ctatactgta tcatctagtc | 1860 |
| cttcctgcta | catgtacgtc | tatgtcaaca | ctacagaggt | cgcactggag caagacctgg | 1920 |
| catatctgca | agaattaaag | gagaaggtgg | agaacgaag | tgaaacaggg ccctgcctc | 1980 |
| cagaacttca | gcctcttttg | gaaggggaag | taaaggggg | ccctgagcca cacctctgg | 2040 |
| tccaaacttt | tctcagacga | cagaggaagc | tccaagaaat | tgaacgcagg cgaaatagcc | 2100 |
| cttttccatga | gcgatttctc | cgcttcgtgc | tgcgaaagct | ctacgtcttt cgacgcagct | 2160 |

-continued

```
tcctgatgac tcgaatttca ctccgaaacc tgctattagg ccgcccttcc ctagagcaac      2220
tagcccaaga ggtgacatat gcaaacttgc gaccatttga accagttgat gagtcaagtg      2280
cttcaaacac agattcttca aatcacccgt cagagccaga ttctgagcat gttcactctg      2340
agttctgagg gatgtacaga tgctctgtgc agatgtgggg gcagcctgtt ataggcttat      2400
tgtctacgca agaacatat ttttggagaa aaatgatatg ggacaggctt tcacagtaca       2460
gcccaggctg gcctcaaact catggttggt ccctctgctt cagcctgttt tgtaattaca      2520
tagtatcacc aaacctagtt gcttttccct ttacattttt tccccttata agttctttaa      2580
aattatagct tacattttt cttttttctt tttttttttt ttgtattttt tctttgtcaa       2640
gacaggtctc tctctgtgta gcactggctg tcctggaact cactctgtag tccaggctgg      2700
cctccaactc agaaattctc ctgcctctgc ctcccaagtg ctgggattaa aggtgtgtgc      2760
caccacgccc cactgggctt ttagttttta tagacaagat ttctccatgt agaccagacc      2820
agctctcctg agtgctgaaa ttaaaggcac gggacatcac tacctggctt tcttattaaa      2880
cttgttttag tggtctcaac aaaaa                                            2905
```

<210> SEQ ID NO 9
<211> LENGTH: 757
<212> TYPE: PRT
<213> ORGANISM: Mouse

<400> SEQUENCE: 9

```
Met Ala Val His Arg Gly Ser Ala Leu Val Ala Pro Ala Ser Asp Lys
1               5                   10                  15

Val Gln Lys Asn Lys Ser Ala Gln Thr Ser Gly Leu Lys Gln Gly Ser
            20                  25                  30

Arg Met Glu Lys Ile Leu Gly Phe Glu Trp Thr Asp Leu Ser Ser Trp
        35                  40                  45

Gln Ser Val Val Thr Leu Leu Asn Lys Pro Thr Asp Pro Ala Asn Leu
    50                  55                  60

Ala Val Phe Arg Phe Leu Phe Ala Phe Leu Met Leu Leu Asp Ile Pro
65                  70                  75                  80

Gln Glu Arg Gly Leu Ser Ser Leu Asp Arg Lys Tyr Leu Asp Gly Leu
                85                  90                  95

Asp Val Cys Arg Phe Pro Leu Leu Asp Ala Leu Arg Pro Leu Pro Leu
            100                 105                 110

Asp Trp Met Tyr Leu Val Tyr Thr Ile Met Phe Leu Gly Ala Leu Gly
        115                 120                 125

Met Met Leu Gly Leu Cys Tyr Arg Leu Ser Cys Val Leu Phe Leu Leu
    130                 135                 140

Pro Tyr Trp Tyr Val Phe Leu Leu Asp Lys Thr Ser Trp Asn Asn His
145                 150                 155                 160

Ser Tyr Leu Tyr Gly Leu Leu Ala Phe Gln Leu Thr Phe Met Asp Ala
                165                 170                 175

Asn His Tyr Trp Ser Val Asp Gly Leu Leu Asn Ala Arg Lys Lys Asn
            180                 185                 190

Ala His Val Pro Leu Trp Asn Tyr Thr Val Leu Arg Gly Gln Ile Phe
        195                 200                 205

Ile Val Tyr Phe Ile Ala Gly Val Lys Lys Leu Asp Ala Asp Trp Val
    210                 215                 220

Gly Gly Tyr Ser Met Glu His Leu Ser Arg His Trp Leu Phe Ser Pro
225                 230                 235                 240
```

```
Phe Lys Leu Val Leu Ser Glu Glu Leu Thr Ser Leu Leu Val Val His
                245                 250                 255

Trp Cys Gly Leu Leu Leu Asp Leu Ser Ala Gly Phe Leu Leu Phe Phe
                260                 265                 270

Asp Ala Ser Arg Pro Val Gly Leu Phe Phe Val Ser Tyr Phe His Cys
                275                 280                 285

Met Asn Ser Gln Leu Phe Ser Ile Gly Met Phe Pro Tyr Val Met Leu
290                 295                 300

Ala Ser Ser Pro Leu Phe Cys Ser Ala Glu Trp Pro Arg Lys Leu Val
305                 310                 315                 320

Ala Arg Cys Pro Lys Arg Leu Gln Glu Leu Leu Pro Thr Lys Ala Ala
                325                 330                 335

Pro Arg Pro Ser Ala Ser Cys Val Tyr Lys Arg Ser Arg Gly Lys Ala
                340                 345                 350

Gly Pro Lys Pro Gly Leu Arg His Gln Leu Gly Ala Ile Phe Thr Leu
                355                 360                 365

Leu Tyr Leu Leu Glu Gln Leu Phe Leu Pro Tyr Ser His Phe Leu Thr
                370                 375                 380

Gln Gly Tyr Asn Asn Trp Thr Asn Gly Leu Tyr Gly Tyr Ser Trp Asp
385                 390                 395                 400

Met Met Val His Ser Arg Ser His Gln His Val Lys Ile Thr Tyr Arg
                405                 410                 415

Asp Gly Leu Thr Gly Glu Leu Gly Tyr Leu Asn Pro Gly Val Phe Thr
                420                 425                 430

Gln Ser Arg Arg Trp Lys Asp His Ala Asp Met Leu Lys Gln Tyr Ala
                435                 440                 445

Thr Cys Leu Ser Leu Leu Pro Lys Tyr Asn Val Thr Glu Pro Gln
450                 455                 460

Ile Tyr Phe Asp Ile Trp Val Ser Ile Asn Asp Arg Phe Gln Gln Arg
465                 470                 475                 480

Leu Phe Asp Pro Arg Val Asp Ile Val Gln Ala Val Trp Ser Pro Phe
                485                 490                 495

Gln Arg Thr Pro Trp Val Gln Pro Leu Leu Met Asp Leu Ser Pro Trp
                500                 505                 510

Arg Thr Lys Leu Gln Asp Ile Lys Ser Ser Leu Asp Asn His Thr Glu
                515                 520                 525

Val Val Phe Ile Ala Asp Phe Pro Gly Leu His Leu Glu Asn Phe Val
530                 535                 540

Ser Glu Asp Leu Gly Asn Thr Ser Ile Gln Leu Leu Gln Gly Glu Val
545                 550                 555                 560

Thr Val Glu Leu Val Ala Glu Gln Lys Asn Gln Thr Leu Gln Glu Gly
                565                 570                 575

Glu Lys Met Gln Leu Pro Ala Gly Glu Tyr His Lys Val Tyr Thr Val
                580                 585                 590

Ser Ser Ser Pro Ser Cys Tyr Met Tyr Val Tyr Val Asn Thr Thr Glu
                595                 600                 605

Val Ala Leu Glu Gln Asp Leu Ala Tyr Leu Gln Glu Leu Lys Glu Lys
                610                 615                 620

Val Glu Asn Gly Ser Glu Thr Gly Pro Leu Pro Glu Leu Gln Pro
625                 630                 635                 640

Leu Leu Glu Gly Glu Val Lys Gly Gly Pro Glu Pro Thr Pro Leu Val
                645                 650                 655

Gln Thr Phe Leu Arg Arg Gln Arg Lys Leu Gln Glu Ile Glu Arg Arg
```

```
                  660                 665                 670
Arg Asn Ser Pro Phe His Glu Arg Phe Leu Arg Phe Val Leu Arg Lys
            675                 680                 685

Leu Tyr Val Phe Arg Arg Ser Phe Leu Met Thr Arg Ile Ser Leu Arg
        690                 695                 700

Asn Leu Leu Leu Gly Arg Pro Ser Leu Glu Gln Leu Ala Gln Glu Val
705                 710                 715                 720

Thr Tyr Ala Asn Leu Arg Pro Phe Glu Pro Val Asp Glu Ser Ser Ala
                725                 730                 735

Ser Asn Thr Asp Ser Ser Asn His Pro Ser Glu Pro Asp Ser Glu His
                740                 745                 750

Val His Ser Glu Phe
        755

<210> SEQ ID NO 10
<211> LENGTH: 5555
<212> TYPE: DNA
<213> ORGANISM: Mouse

<400> SEQUENCE: 10
ggctgtggga gagcagaaga ggagctggaa gagcagccta aacagctgt cgggagggac      60 cagggctagt tcacacttgg aagctgggat gccaggaccg gccctcctgc ctctctcggt    120
ctccatcggc ctcctggtca gctcactcca cactgagacg attctgaagt aagatgctcc    180
tggctcctca cagactctgc tacaagagac agagtgaagt gtccccaggg ctcagagcct    240
ttgactctgc tccttccctt cccacggctg agttggcaca ggagcacctg ggtgagctgc    300
accagactta agaagatgag gccctgatt ctgttagctg ccctcctctg gctccaggac     360
tctttggccc aggaagatgt atgctcatcc ttggatggga gcccagacag gcagggtgga    420
ggtccacctc tgagtgtgaa cgtcagcagc gcggaaagc ctaccagcct gtttctgagc     480
tgggtagctg cagagccagg tggatttgac tatgccctct gcctcagggc tatgaacttg    540
tcgggttttc agaagggca acagctccaa gctcatacca acgagtccag cttgagttc      600 catggcctgg tgccagggag tcgctaccag ctggaactga ctgtcctaag accctgttgg    660
cagaatgtca caattaccct cactgctcga actgcccta cagtggtccg tggactgcaa     720
ctgcatagca ctgggagccc agccagcctg aagcctcat ggagcgatgc ctctggggat     780
caagacagct atcaacttct cctctaccac ccggaatccc acactctggc atgtaatgtc    840
tctgtgtccc ctgacacccct gtcttacaat tttggtgacc tcttgccagg tagtcagtat    900
gtcttggagg ttatcacctg gctggcagt tccatgcga agactagcat cctccaatgg      960
acagagcctg tccctcctga tcacctaaca ctgcgtgcct tgggtaccag tagcctgcaa   1020
gccttctgga acagctctga aggggccacc tggtttcacc tgatacttac agacctccta   1080
gagggtacca acctgaccaa agtggtcaga caaggcatct caacccacac cttccttcgc   1140
ctgtctccgg gtacaccta ccagctgaag atctgtgctg ctgctgggcc ccaccagatt    1200
tggggaccca atgccactga gtggacctat ccctcttacc catctgacct ggtgctgacc   1260
cccttatgga atgagctctg ggcaagctgg aaggcagggc agggagcccg ggatggctat   1320
gtactgaagt taagtgggcc agtggagaat acaactactc tgggtcctga ggagtgcaac   1380
gctgtcttcc cagggcccct gcctccagga cactacactt ggggctgag gttctagct    1440 ggaccttatg atgcctggt agagggcagt atctggctgg ctgaatctgc tgctcgtccc    1500
atggaggtcc ctggtgccag actgtggcta gaaggactgg aagctactaa gcaacctggg   1560
```

```
agacgggcgc tgctctattc tgttgatgcc ccaggcctcc tagggaacat ctctgtgtct   1620
tctggtgcca ctcatgtcac cttctgtggc ttggtacccg agcgcactac agggtggac    1680 attgcctcat ccatgggaga catcactcag agcctcacag gctacacaag tccctgcca    1740 ccacagtctc tggagatcat cagccggaac agcccatctg acctgactat cggttgggct   1800
ccagcaccag ggcagatgga aggttataag gtcacctggc atcaggatgg cagccagagg   1860
tcacctggcg accttgttga cttgggccct gacatttcga gcctgactct gaaatctctg   1920
gtacctggtt cctgctacac cgtgtcagca tgggcctggt ctgggaacct cagctctgac   1980
tctcagaaga ttcacagttg cacccgtccc gctcctccca ccaacctgag cctgggcttt   2040
gcccaccagc ctgcaacact gagggcttcc tggtgtcacc caccgggtgg cagggatgcc   2100
tttcagttac ggctttacag gctgaggccc ctgacactgg aaagtgagaa gatcctatcc   2160
caggaggccc agaacttctc ctgggcccag ctgcctgcag gctatgaatt ccaggtacag   2220
ctgtctacct tgtgggggtc ggaggagagc ggcagtgcca acaccacagg ctggacaccc   2280
ccctcagctc ctacattggt aaatgtgacc agtgaagccc ccacccagct ccacgtatcc   2340
tgggtccacg ctgctgggga ccggagcagc taccaagtga ccctatacca ggagagcact   2400
cggacagcca ccagcattgt ggggcccaag gcagacagca caagctttg gggtttgact    2460 cctggcacta agtacaaggt ggaagccatc tcctgggctg gcccctttta cactgcagca   2520
gccaacgttt ctgcttggac ctacccactc acacccaatg agctgctcgc tctctatgcag  2580 gcaggcagtg ctgtggttaa cctggcctgg cccagtggtc ccttggggca agggacatgc   2640
catgcccaac tctcagatgc tggacacctt tcatgggagc aaccgctgtc gctaggccaa   2700
gacctcctca tgctaaggaa tcttatacca ggacatacgg tttcattgtc tgtgaagtgt   2760
cgggcaggac cactccaggc ctccactcac cccctggtgc tgtctgtaga gcctggccct   2820
gtggaagatg tgttctgtca acctgaggcc acctacctgt ccctgaactg gacgatgcct   2880
actggagatg tggctgtctg tctggtggag gtagagcagc tggtgccagg agggagcgct   2940
cattttgtct tccaggtcaa cacctcggag gatgcacttc tgctgcccaa cttgacgccc   3000
accacttctt accgccttag cctcactgtg ctgggtggga atcgccagtg gagccgggcg   3060
gttaccctgg tgtgcactac ttctgctgag gtttggcacc cccagagct agctgaggcc    3120 cccaggtgg agctggggac agggatgggt gtgacagtca cacgtggcat gtttggtaaa    3180
gatgacgggc agatccagtg gtatggcata attgccacca tcaacatgac actggcccag   3240
ccttcccagg aagccatcaa ccacacatgg tatgaccact actatagagg acatgactcc   3300
tacctggctc tcctgttccc aaaccccttc tacccagagc cttgggctgt gccaagatcc   3360
tggacagtac ctgtgggtac agaggactgt gacaacaccc aggagatatg caatgggcat   3420
ctcaagccag gcttccagta taggttcagc attgcagcct ttagtaggct cagctctcca   3480
gagaccatcc tggccttctc cgccttctca gagcctcagg ctagcatctc tctggtggcc   3540
atgcccctga cagttatgat ggggactgtg gtgggctgca tcatcattgt gtgtgcagtg   3600
ctatgcttgt tgtgccggcg cgcgcctgaag ggaccaaggt cagagaagaa tggcttttcc   3660
caggagttga tgccttacaa cctgtggcgg acccatcggc catccccag ccatagcttc    3720 cggcagagct atgaggccaa gagtgcacgt gcacaccagg ccttcttcca ggaatttgag   3780
gagctgaagg aggtgggcaa ggaccagccc agactagagg ctgagcatcc tgccaacatc   3840
accaagaacc ggtacccaca cgtgctacct tatgaccact ccagggtcag gctgacccag   3900
```

-continued

| | |
|---|---|
| ctatcaggag agcctcattc tgactacatc aatgccaact tcatcccagg ctatagccac | 3960 |
| ccacaggaga tcattgccac ccaggggcct ctcaaaaaga cggtcgagga cttctggcgg | 4020 |
| ttggtgtggg agcagcaagt ccacgtgatc atcatgctaa ctgtgggcat ggagaatggg | 4080 |
| cgggtactgt gtgagcacta ctggccagtc aactccacgc ctgtcaccca cggtcacatc | 4140 |
| accacccacc tcctggcaga ggaatctgag gacgagtgga ccaggaggga attccagctg | 4200 |
| cagcacggtg cagagcaaaa acagaggcgc gtgaagcagc tgcagttcac gacctggcca | 4260 |
| gaccacagtg tccccgaggc tcccagctct ctgctcgctt ttgtggaact ggtgcaggag | 4320 |
| gaggtgaagg caactcaggg caaggggccc atcctggtgc attgcagtgc gggtgtgggc | 4380 |
| aggacaggca cctttgtggc tctcttaccg gctgttcgac aactagagga agaacaggtg | 4440 |
| gtcgatgtgt tcaacactgt gtacatactc cggctgcacc ggcccctcat gatccagacc | 4500 |
| ttgagtcaat acatcttcct gcacagctgc ctgctgaaca agattctgga agggccctct | 4560 |
| gacgcctcag actccggccc catccctgtg atgaattttg cacaagcttg tgccaagagg | 4620 |
| gcagccaatg ccaatgccgg tttcttgaag gagtacaggc tcctgaagca ggccatcaag | 4680 |
| gatgagactg gctctctgct gccctctcct gactataatc agaacagcat cgcctcctgt | 4740 |
| catcattctc aggagcagtt ggccctggtg gaggagagcc ctgctgataa catgctggca | 4800 |
| gcctcgctct tccctggtgg gccgtctggt cgcgaccatg tggtgctgac tggctcggcc | 4860 |
| ggaccaaagg aactctggga atggtgtgg gaacatggcg cctatgtgct tgtctccctg | 4920 |
| ggtctgcctg ataccaagga gaagccacaa gacatctggc caatggagat gcagcctatt | 4980 |
| gtcacagaca tggtgacagt gcacagagtg gctgagagca cacagcctgg ctggcccagt | 5040 |
| accctcatca gagttataca tggggacagt gggacggaaa ggcaggttca atgcctgcag | 5100 |
| tttccacact gcgagactgg gagtgagctc ccagctaaca ccctactgac cttccttgat | 5160 |
| gctgtgggcc agtgctgctc ccggggcaat agcaagaagc cagggaccct gctcagtcac | 5220 |
| tccagcaagg tcacaaacca gctgagcacc ttcttggcta tggaacagct gctacagcaa | 5280 |
| gcagggaccg agcgcacagt ggatgtcttc agtgtggccc tgaagcagac acaggcctgt | 5340 |
| ggccttaaga ccccaacgct ggagcagtat atctacctct acaactgtct gaacagcgca | 5400 |
| ttgaggaaca ggctgccccg agctaggaag tgaccttgcc ctgctaggca tcacgttcca | 5460 |
| gcaatccacc caggcctggc ttccccagga gaacagatct attcggcctc acgctgtcaa | 5520 |
| agggcagagt ctgggaataa agggtaaatc tcgag | 5555 |

<210> SEQ ID NO 11
<211> LENGTH: 1705
<212> TYPE: PRT
<213> ORGANISM: Mouse

<400> SEQUENCE: 11

Met Arg Pro Leu Ile Leu Leu Ala Ala Leu Leu Trp Leu Gln Asp Ser
1               5                   10                  15

Leu Ala Gln Glu Asp Val Cys Ser Ser Leu Asp Gly Ser Pro Asp Arg
            20                  25                  30

Gln Gly Gly Gly Pro Pro Leu Ser Val Asn Val Ser Ser Arg Gly Lys
        35                  40                  45

Pro Thr Ser Leu Phe Leu Ser Trp Val Ala Ala Glu Pro Gly Gly Phe
    50                  55                  60

Asp Tyr Ala Leu Cys Leu Arg Ala Met Asn Leu Ser Gly Phe Pro Glu
65                  70                  75                  80

```
Gly Gln Gln Leu Gln Ala His Thr Asn Glu Ser Ser Phe Glu Phe His
                85                  90                  95

Gly Leu Val Pro Gly Ser Arg Tyr Gln Leu Glu Leu Thr Val Leu Arg
            100                 105                 110

Pro Cys Trp Gln Asn Val Thr Ile Thr Leu Thr Ala Arg Thr Ala Pro
            115                 120                 125

Thr Val Val Arg Gly Leu Gln Leu His Ser Thr Gly Ser Pro Ala Ser
        130                 135                 140

Leu Glu Ala Ser Trp Ser Asp Ala Ser Gly Asp Gln Asp Ser Tyr Gln
145                 150                 155                 160

Leu Leu Leu Tyr His Pro Glu Ser His Thr Leu Ala Cys Asn Val Ser
                165                 170                 175

Val Ser Pro Asp Thr Leu Ser Tyr Asn Phe Gly Asp Leu Leu Pro Gly
            180                 185                 190

Ser Gln Tyr Val Leu Glu Val Ile Thr Trp Ala Gly Ser Leu His Ala
        195                 200                 205

Lys Thr Ser Ile Leu Gln Trp Thr Glu Pro Val Pro Pro Asp His Leu
    210                 215                 220

Thr Leu Arg Ala Leu Gly Thr Ser Ser Leu Gln Ala Phe Trp Asn Ser
225                 230                 235                 240

Ser Glu Gly Ala Thr Trp Phe His Leu Ile Leu Thr Asp Leu Leu Glu
                245                 250                 255

Gly Thr Asn Leu Thr Lys Val Val Arg Gln Gly Ile Ser Thr His Thr
            260                 265                 270

Phe Leu Arg Leu Ser Pro Gly Thr Pro Tyr Gln Leu Lys Ile Cys Ala
        275                 280                 285

Ala Ala Gly Pro His Gln Ile Trp Gly Pro Asn Ala Thr Glu Trp Thr
    290                 295                 300

Tyr Pro Ser Tyr Pro Ser Asp Leu Val Leu Thr Pro Leu Trp Asn Glu
305                 310                 315                 320

Leu Trp Ala Ser Trp Lys Ala Gly Gln Gly Ala Arg Asp Gly Tyr Val
                325                 330                 335

Leu Lys Leu Ser Gly Pro Val Glu Asn Thr Thr Thr Leu Gly Pro Glu
            340                 345                 350

Glu Cys Asn Ala Val Phe Pro Gly Pro Leu Pro Pro Gly His Tyr Thr
        355                 360                 365

Leu Gly Leu Arg Val Leu Ala Gly Pro Tyr Asp Ala Trp Val Glu Gly
    370                 375                 380

Ser Ile Trp Leu Ala Glu Ser Ala Ala Arg Pro Met Glu Val Pro Gly
385                 390                 395                 400

Ala Arg Leu Trp Leu Glu Gly Leu Glu Ala Thr Lys Gln Pro Gly Arg
                405                 410                 415

Arg Ala Leu Leu Tyr Ser Val Asp Ala Pro Gly Leu Leu Gly Asn Ile
            420                 425                 430

Ser Val Ser Ser Gly Ala Thr His Val Thr Phe Cys Gly Leu Val Pro
        435                 440                 445

Gly Ala His Tyr Arg Val Asp Ile Ala Ser Ser Met Gly Asp Ile Thr
    450                 455                 460

Gln Ser Leu Thr Gly Tyr Thr Ser Pro Leu Pro Gln Ser Leu Glu
465                 470                 475                 480

Ile Ile Ser Arg Asn Ser Pro Ser Asp Leu Thr Ile Gly Trp Ala Pro
                485                 490                 495

Ala Pro Gly Gln Met Glu Gly Tyr Lys Val Thr Trp His Gln Asp Gly
```

```
                500             505             510
Ser Gln Arg Ser Pro Gly Asp Leu Val Asp Leu Gly Pro Asp Ile Ser
            515             520             525

Ser Leu Thr Leu Lys Ser Leu Val Pro Gly Ser Cys Tyr Thr Val Ser
            530             535             540

Ala Trp Ala Trp Ser Gly Asn Leu Ser Ser Asp Ser Gln Lys Ile His
545             550             555             560

Ser Cys Thr Arg Pro Ala Pro Thr Asn Leu Ser Leu Gly Phe Ala
            565             570             575

His Gln Pro Ala Thr Leu Arg Ala Ser Trp Cys His Pro Gly Gly
            580             585             590

Arg Asp Ala Phe Gln Leu Arg Leu Tyr Arg Leu Arg Pro Leu Thr Leu
            595             600             605

Glu Ser Glu Lys Ile Leu Ser Gln Glu Ala Gln Asn Phe Ser Trp Ala
            610             615             620

Gln Leu Pro Ala Gly Tyr Glu Phe Gln Val Gln Leu Ser Thr Leu Trp
625             630             635             640

Gly Ser Glu Glu Ser Gly Ser Ala Asn Thr Thr Gly Trp Thr Pro Pro
            645             650             655

Ser Ala Pro Thr Leu Val Asn Val Thr Ser Glu Ala Pro Thr Gln Leu
            660             665             670

His Val Ser Trp Val His Ala Ala Gly Asp Arg Ser Ser Tyr Gln Val
            675             680             685

Thr Leu Tyr Gln Glu Ser Thr Arg Thr Ala Thr Ser Ile Val Gly Pro
            690             695             700

Lys Ala Asp Ser Thr Ser Phe Trp Gly Leu Thr Pro Gly Thr Lys Tyr
705             710             715             720

Lys Val Glu Ala Ile Ser Trp Ala Gly Pro Leu Tyr Thr Ala Ala Ala
                725             730             735

Asn Val Ser Ala Trp Thr Tyr Pro Leu Thr Pro Asn Glu Leu Leu Ala
                740             745             750

Ser Met Gln Ala Gly Ser Ala Val Val Asn Leu Ala Trp Pro Ser Gly
            755             760             765

Pro Leu Gly Gln Gly Thr Cys His Ala Gln Leu Ser Asp Ala Gly His
            770             775             780

Leu Ser Trp Glu Gln Pro Leu Ser Leu Gly Gln Asp Leu Leu Met Leu
785             790             795             800

Arg Asn Leu Ile Pro Gly His Thr Val Ser Leu Ser Val Lys Cys Arg
            805             810             815

Ala Gly Pro Leu Gln Ala Ser His Pro Leu Val Leu Ser Val Glu
            820             825             830

Pro Gly Pro Val Glu Asp Val Phe Cys Gln Pro Glu Ala Thr Tyr Leu
            835             840             845

Ser Leu Asn Trp Thr Met Pro Thr Gly Asp Val Ala Val Cys Leu Val
            850             855             860

Glu Val Glu Gln Leu Val Pro Gly Gly Ser Ala His Phe Val Phe Gln
865             870             875             880

Val Asn Thr Ser Glu Asp Ala Leu Leu Leu Pro Asn Leu Thr Pro Thr
            885             890             895

Thr Ser Tyr Arg Leu Ser Leu Thr Val Leu Gly Gly Asn Arg Gln Trp
            900             905             910

Ser Arg Ala Val Thr Leu Val Cys Thr Thr Ser Ala Glu Val Trp His
            915             920             925
```

```
Pro Pro Glu Leu Ala Glu Ala Pro Gln Val Glu Leu Gly Thr Gly Met
    930                 935                 940

Gly Val Thr Val Thr Arg Gly Met Phe Gly Lys Asp Asp Gly Gln Ile
945                 950                 955                 960

Gln Trp Tyr Gly Ile Ile Ala Thr Ile Asn Met Thr Leu Ala Gln Pro
                965                 970                 975

Ser Gln Glu Ala Ile Asn His Thr Trp Tyr Asp His Tyr Arg Gly
            980                 985                 990

His Asp Ser Tyr Leu Ala Leu Leu Phe Pro Asn Pro Phe Tyr Pro Glu
        995                1000                1005

Pro Trp Ala Val Pro Arg Ser Trp Thr Pro Val Gly Thr Glu
    1010                1015                1020

Asp Cys Asp Asn Thr Gln Glu Ile Cys Asn Gly His Leu Lys Pro
    1025                1030                1035

Gly Phe Gln Tyr Arg Phe Ser Ile Ala Ala Phe Ser Arg Leu Ser
    1040                1045                1050

Ser Pro Glu Thr Ile Leu Ala Phe Ser Ala Phe Ser Glu Pro Gln
    1055                1060                1065

Ala Ser Ile Ser Leu Val Ala Met Pro Leu Thr Val Met Met Gly
    1070                1075                1080

Thr Val Val Gly Cys Ile Ile Ile Val Cys Ala Val Leu Cys Leu
    1085                1090                1095

Leu Cys Arg Arg Arg Leu Lys Gly Pro Arg Ser Glu Lys Asn Gly
    1100                1105                1110

Phe Ser Gln Glu Leu Met Pro Tyr Asn Leu Trp Arg Thr His Arg
    1115                1120                1125

Pro Ile Pro Ser His Ser Phe Arg Gln Ser Tyr Glu Ala Lys Ser
    1130                1135                1140

Ala Arg Ala His Gln Ala Phe Phe Gln Glu Phe Glu Glu Leu Lys
    1145                1150                1155

Glu Val Gly Lys Asp Gln Pro Arg Leu Glu Ala Glu His Pro Ala
    1160                1165                1170

Asn Ile Thr Lys Asn Arg Tyr Pro His Val Leu Pro Tyr Asp His
    1175                1180                1185

Ser Arg Val Arg Leu Thr Gln Leu Ser Gly Glu Pro His Ser Asp
    1190                1195                1200

Tyr Ile Asn Ala Asn Phe Ile Pro Gly Tyr Ser His Pro Gln Glu
    1205                1210                1215

Ile Ile Ala Thr Gln Gly Pro Leu Lys Lys Thr Val Glu Asp Phe
    1220                1225                1230

Trp Arg Leu Val Trp Glu Gln Gln Val His Val Ile Ile Met Leu
    1235                1240                1245

Thr Val Gly Met Glu Asn Gly Arg Val Leu Cys Glu His Tyr Trp
    1250                1255                1260

Pro Val Asn Ser Thr Pro Val Thr His Gly His Ile Thr Thr His
    1265                1270                1275

Leu Leu Ala Glu Glu Ser Glu Asp Glu Trp Thr Arg Arg Glu Phe
    1280                1285                1290

Gln Leu Gln His Gly Ala Glu Gln Lys Gln Arg Arg Val Lys Gln
    1295                1300                1305

Leu Gln Phe Thr Thr Trp Pro Asp His Ser Val Pro Glu Ala Pro
    1310                1315                1320
```

```
Ser Ser Leu Leu Ala Phe Val Glu Leu Val Gln Glu Val Lys
1325                1330                1335

Ala Thr Gln Gly Lys Gly Pro Ile Leu Val His Cys Ser Ala Gly
1340                1345                1350

Val Gly Arg Thr Gly Thr Phe Val Ala Leu Leu Pro Ala Val Arg
1355                1360                1365

Gln Leu Glu Glu Glu Gln Val Val Asp Val Phe Asn Thr Val Tyr
1370                1375                1380

Ile Leu Arg Leu His Arg Pro Leu Met Ile Gln Thr Leu Ser Gln
1385                1390                1395

Tyr Ile Phe Leu His Ser Cys Leu Leu Asn Lys Ile Leu Glu Gly
1400                1405                1410

Pro Ser Asp Ala Ser Asp Ser Gly Pro Ile Pro Val Met Asn Phe
1415                1420                1425

Ala Gln Ala Cys Ala Lys Arg Ala Ala Asn Ala Asn Ala Gly Phe
1430                1435                1440

Leu Lys Glu Tyr Arg Leu Leu Lys Gln Ala Ile Lys Asp Glu Thr
1445                1450                1455

Gly Ser Leu Leu Pro Ser Pro Asp Tyr Asn Gln Asn Ser Ile Ala
1460                1465                1470

Ser Cys His His Ser Gln Glu Gln Leu Ala Leu Val Glu Glu Ser
1475                1480                1485

Pro Ala Asp Asn Met Leu Ala Ala Ser Leu Phe Pro Gly Gly Pro
1490                1495                1500

Ser Gly Arg Asp His Val Val Leu Thr Gly Ser Ala Gly Pro Lys
1505                1510                1515

Glu Leu Trp Glu Met Val Trp Glu His Gly Ala Tyr Val Leu Val
1520                1525                1530

Ser Leu Gly Leu Pro Asp Thr Lys Glu Lys Pro Gln Asp Ile Trp
1535                1540                1545

Pro Met Glu Met Gln Pro Ile Val Thr Asp Met Val Thr Val His
1550                1555                1560

Arg Val Ala Glu Ser Asn Thr Ala Gly Trp Pro Ser Thr Leu Ile
1565                1570                1575

Arg Val Ile His Gly Asp Ser Gly Thr Glu Arg Gln Val Gln Cys
1580                1585                1590

Leu Gln Phe Pro His Cys Glu Thr Gly Ser Glu Leu Pro Ala Asn
1595                1600                1605

Thr Leu Leu Thr Phe Leu Asp Ala Val Gly Gln Cys Cys Ser Arg
1610                1615                1620

Gly Asn Ser Lys Lys Pro Gly Thr Leu Leu Ser His Ser Ser Lys
1625                1630                1635

Val Thr Asn Gln Leu Ser Thr Phe Leu Ala Met Glu Gln Leu Leu
1640                1645                1650

Gln Gln Ala Gly Thr Glu Arg Thr Val Asp Val Phe Ser Val Ala
1655                1660                1665

Leu Lys Gln Thr Gln Ala Cys Gly Leu Lys Thr Pro Thr Leu Glu
1670                1675                1680

Gln Tyr Ile Tyr Leu Tyr Asn Cys Leu Asn Ser Ala Leu Arg Asn
1685                1690                1695

Arg Leu Pro Arg Ala Arg Lys
1700                1705
```

```
<210> SEQ ID NO 12
<211> LENGTH: 49
<212> TYPE: PRT
<213> ORGANISM: Human

<400> SEQUENCE: 12

Tyr Leu Tyr Gln Trp Leu Gly Ala Pro Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val

<210> SEQ ID NO 13
<211> LENGTH: 49
<212> TYPE: PRT
<213> ORGANISM: Human
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 13

Tyr Leu Tyr Gln Trp Leu Gly Ala Pro Val Pro Tyr Pro Asp Pro Leu
1               5                   10                  15

Xaa Pro Arg Arg Xaa Val Cys Xaa Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val

<210> SEQ ID NO 14
<211> LENGTH: 5446
<212> TYPE: DNA
<213> ORGANISM: Rat

<400> SEQUENCE: 14
agaacagcct acaacagctg ccttccggga gggaccaggc tagttcacac ttggaagttg      60
ggatgccagg agcagccttc tgtcttccga ggccttcctg ggtctcctgg tcagctcatt     120
ccacactgag atgattctaa agaaagatcc tcacacagac tctgctggaa gaaacaaagt     180
gaagtgtccc cagactttat caggatgagg ccctgattc tgttagctgc cctcctctgg      240
ctccagggct ttttggccga ggacgacgca tgctcatcct tggaagggag cccagacagg     300
cagggtggag gtccacttct gagtgtgaac gtcagtagcc atggaaagtc taccagcctg     360
tttctgagct gggtagctgc agagctgggc ggatttgact atgccctcag cctcaggagt     420
gtgaactcct caggttctcc agaagggcaa cagctccagg ctcacacaaa tgagtccggc     480
tttgagttcc atggcctggt gccagggagt cgctaccagc taaaactgac tgtcctaaga     540
ccctgttggc agaatgtcac aattaccctc actgccgaa ctgccccgac agtggtccgt      600
ggactgcagc tgcatagcgc tgggagccca gccaggctgg aagcctcgtg gagtgatgcc     660
```

| | |
|---|---|
| cctggagatc aagacagcta ccaacttctc ctctaccacc tggaatccca aactctggca | 720 |
| tgcaatgtct ctgtgtcccc tgacaccctg tcttacagtt ttggcgacct tttgccaggt | 780 |
| actcagtatg tcttggaggt tatcacctgg gctggcagtc tccatgcgaa gactagtatc | 840 |
| ctccagtgga cagagcctgt ccctcctgat cacctagcac tacgtgcctt gggtaccagt | 900 |
| agcctgcaag ccttctggaa cagctctgaa ggggccacct cgtttcacct gatgctcaca | 960 |
| gacctcctcg ggggcaccaa cacgactgcg gtgatcagac aagggcgtctc gacccacacc | 1020 |
| tttcttcacc tatctccggg tacacctcat gagctgaaga tttgtgcttc tgctgggccc | 1080 |
| caccagatct ggggacccag tgccaccgag tggacctatc cctcttaccc atctgacctg | 1140 |
| gtgctgactc ccttacggaa tgagctctgg gccagctgga aggcagggct gggagcccgg | 1200 |
| gacggctatg tactgaagtt aagtgggcca atggagagta cgtctaccct gggcccggaa | 1260 |
| gagtgcaatg cagtcttccc agggcccctg cctccgggac actacacttt gcagctgaag | 1320 |
| gttctagctg gaccttatga tgcctgggtg gagggcagta cctggctggc tgaatctgct | 1380 |
| gcccttccca gggaggtccc tggtgccaga ctgtggctag atggactgga agcttccaag | 1440 |
| cagcctggga cgggcgct actctattct gacgatgccc caggctccct agggaacatc | 1500 |
| tctgtgccct ctggtccac tcacgtcatt ttctgtggcc tggtacctgg agcccactat | 1560 |
| agggtggaca ttgcctcatc cacgggggac atctctcaga gcatctcagg ctatacaagt | 1620 |
| cccctgccac cgcagtcact ggaggtcatc agcaggagca gcccatctga cctgactatt | 1680 |
| gcttggggtc cagcaccagg gcagctggaa ggttataagg ttacctggca tcaggatggc | 1740 |
| agccagaggt ctcctggcga ccttgttgac ttgggccctg acactttgag cctgactctg | 1800 |
| aaatctctgg tacccggctc ctgctacacc gtgtcagcat gggcctgggc cgggaacctc | 1860 |
| gactctgact ctcagaagat tcacagctgc acccgccccg ctcctcccac caacctgagt | 1920 |
| ctgggctttg cccaccagcc tgcggcactg aaggcttcct ggtatcaccc accgggtggc | 1980 |
| agggatgcct ttcacttacg gctttacagg ctgaggcctc tgacactgga aagtgagaag | 2040 |
| gtcctacctc gggaggccca gaacttctcc tgggcccagc tgactgcagg ctgtgagttc | 2100 |
| caggtacagc tgtctaccct gtgggggtct gagagaagca gcagtgccaa cgccacaggc | 2160 |
| tggacacccc cttcagctcc tacactggta aacgtgacca gcgatgctcc tacccagctc | 2220 |
| caagtatcct gggcccacgt tcctgggggc cggagccgct accaagtgac cctataccag | 2280 |
| gagagtaccc ggacagccac cagcatcatg gggcccaagg aagatggcac gagcttttg | 2340 |
| ggtttgactc ctggcactaa gtacaaggtg gaagtcatct cctgggctgg gcccctctac | 2400 |
| actgcagcag ccaacgtttc tgcctggacc tacccactca tacccaatga gctgctcgtg | 2460 |
| tcaatgcagg caggcagtgc tgtggttaac ctggcctggc ccagtggtcc cctggggcaa | 2520 |
| ggggcatgcc acgcccaact ctcagatgct ggacacctct catgggagca acccctgaaa | 2580 |
| ctaggccaag agctcttcat gctaagggat ctcacaccag acataccatc tcgatgtca | 2640 |
| gtgaggtgtc gggcagggcc gctccaggcc tctacgcacc ttgtggtgct gtctgtggag | 2700 |
| cctggcccctg tggaagatgt gctctgtcat ccagaggcca cctacctggc cctgaactgg | 2760 |
| acgatgcctg ctggagacgt ggatgtctgt ctggtggtgg tagagcggct ggtgccggga | 2820 |
| gggggcactc atttttgtctt ccaggtcaac acctcagggg atgctcttct gttgcccaac | 2880 |
| ttgatgccca ccacttctta ccgccttagc ctcaccgttc tgggcaggaa tagtcggtgg | 2940 |
| agccgggcgg tttccctggt gtgcagtact tctgctgagg cttggcaccc cccagagcta | 3000 |
| gctgagcccc cccaggtgga gctggggaca gggatgggtg tgacagtcat gcgtggcatg | 3060 |

-continued

```
tttggtaaag atgacgggca gatccagtgg tatggcataa ttgccaccat caacatgacg    3120
ctggcccagc cttcccggga agccatcaat tacacatggt atgaccacta ctatagagga    3180
tgtgagtcct tcctggctct cctgttccca aacccttct acccagagcc ttgggctggg     3240
ccaagatcct ggacagtacc tgtgggtact gaggactgtg acaacaccca agagatatgc    3300
aatgggcgtc tcaagtcagg cttccagtat aggttcagcg ttgtggcctt tagtaggctc    3360
aacactccag agaccatcct cgccttctcg gccttctcag agccccgggc cagcatctct    3420
ctggcgatca ttcccctgac agttatgctg ggggctgtgg tgggcagcat tgtcattgtg    3480
tgtgcagtgc tatgcttgct ccgctggcgg tgcctgaagg gaccaagatc agagaaggat    3540
ggcttttcca aggagctgat gccttacaac ctgtggcgga cccatcggcc tatccccatc    3600
catagcttcc ggcagagcta tgaggccaag agcgcacatg caccagac cttcttccag      3660 gaatttgagg agttgaagga ggtaggcaag gaccagcccc gactagaggc tgagcatccg    3720
gacaacatca tcaagaaccg gtacccacac gtgctgccct atgaccactc cagggtcagg    3780
ctgacccagc taccaggaga gcctcattct gactacatca atgccaactt catcccaggc    3840
tatagccaca cacaggagat cattgccacc caggggcctc tcaaaaagac gctagaggac    3900
ttctggcggt tggtatggga gcagcaagtc cacgtgatca tcatgctgac tgtgggcatg    3960
gagaacgggc gggtactgtg tgagcactac tggccagcca actccacgcc tgttactcac    4020
ggtcacatca ccatccacct cctggcagag gagcctgagg atgagtggac caggagggaa    4080
ttccagctgc agcacggtac cgagcaaaaa cagaggcgag tgaagcagct gcagttcact    4140
acctggccag accacagtgt cccggaggct cccagctctc tgctcgcttt tgtagaactg    4200
gtacaggagc aggtgcaggc cactcagggc aagggaccca tcctggtgca ttgcagtgct    4260
ggcgtgggga ggacaggcac ctttgtggct ctcttgcggc tactgcgaca actagaggaa    4320
gagaaggtgg ccgatgtgtt caacactgtg tacatactcc ggttgcaccg gcccctcatg    4380
atccagaccc tgagtcaata catcttcctg cacagttgcc tgctgaacaa gattctggaa    4440
gggccccctg acagctccga ctccggcccc atctctgtga tggattttgc acaggcttgt    4500
gccaagaggg cagccaacgc caatgctggt ttcttgaagg agtacaagct cctgaagcag    4560
gccatcaagg atgggactgg ctctctgctg cccccctcctg actacaatca gaacagcatt    4620
gtctcccgtc gtcattctca ggagcagttc gccctggtgg aggagtgccc tgaggatagc    4680
atgctggaag cctcactctt ccctggtggt ccgtctggtt gtgatcatgt ggtgctgact    4740
ggctcagccg gaccaaagga actctgggaa atggtgtggg agcatgatgc ccatgtgctc    4800
gtctccctgg gcctgcctga taccaaggag aagccaccag acatctggcc agtggagatg    4860
cagcctattg tcacagacat ggtgacagtg cacagagtgt ctgagagcaa cacaacaact    4920
ggctggccca gcaccctctt cagagtcata cacggggaga gtggaaagga aaggcaggtt    4980
caatgcctgc aatttccatg ctctgagtct gggtgtgagc tcccagctaa caccctactg    5040
accttccttg atgctgtggg ccagtgctgc ttccggggca agagcaagaa gccagggacc    5100
ctgctcagcc actccagcaa aaacacaaac cagctgggca ccttcttggc tatgaacag    5160 ctgttacagc aagcagggac agagcgcaca gtggacgtct tcaatgtggc cctgaagcag    5220
tcacaggcct gcggccttat gaccccaaca ctggagcagt atatctacct ctacaactgt    5280
ctgaacagcg cactgctgaa cgggctgccc agagctggga gtggcctgc gcctgctag    5340 gcgtcatgtt ccagcaaatc cacccaggcc tgacttccct aggagagtgg atccaccggg    5400
```

```
cctcacactg tccaagggca gagtccagga ataaagagac atggtc                    5446
```

<210> SEQ ID NO 15
<211> LENGTH: 1710
<212> TYPE: PRT
<213> ORGANISM: Rat

<400> SEQUENCE: 15

```
Met Arg Pro Leu Ile Leu Leu Ala Ala Leu Leu Trp Leu Gln Gly Phe
1               5                   10                  15

Leu Ala Glu Asp Asp Ala Cys Ser Ser Leu Glu Gly Ser Pro Asp Arg
            20                  25                  30

Gln Gly Gly Gly Pro Leu Leu Ser Val Asn Val Ser Ser His Gly Lys
        35                  40                  45

Ser Thr Ser Leu Phe Leu Ser Trp Val Ala Ala Glu Leu Gly Gly Phe
    50                  55                  60

Asp Tyr Ala Leu Ser Leu Arg Ser Val Asn Ser Ser Gly Ser Pro Glu
65                  70                  75                  80

Gly Gln Gln Leu Gln Ala His Thr Asn Glu Ser Gly Phe Glu Phe His
                85                  90                  95

Gly Leu Val Pro Gly Ser Arg Tyr Gln Leu Lys Leu Thr Val Leu Arg
            100                 105                 110

Pro Cys Trp Gln Asn Val Thr Ile Thr Leu Thr Ala Arg Thr Ala Pro
        115                 120                 125

Thr Val Val Arg Gly Leu Gln Leu His Ser Ala Gly Ser Pro Ala Arg
    130                 135                 140

Leu Glu Ala Ser Trp Ser Asp Ala Pro Gly Asp Gln Asp Ser Tyr Gln
145                 150                 155                 160

Leu Leu Leu Tyr His Leu Glu Ser Gln Thr Leu Ala Cys Asn Val Ser
                165                 170                 175

Val Ser Pro Asp Thr Leu Ser Tyr Ser Phe Gly Asp Leu Leu Pro Gly
            180                 185                 190

Thr Gln Tyr Val Leu Glu Val Ile Thr Trp Ala Gly Ser Leu His Ala
        195                 200                 205

Lys Thr Ser Ile Leu Gln Trp Thr Glu Pro Val Pro Pro Asp His Leu
    210                 215                 220

Ala Leu Arg Ala Leu Gly Thr Ser Ser Leu Gln Ala Phe Trp Asn Ser
225                 230                 235                 240

Ser Glu Gly Ala Thr Ser Phe His Leu Met Leu Thr Asp Leu Leu Gly
                245                 250                 255

Gly Thr Asn Thr Thr Ala Val Ile Arg Gln Gly Val Ser Thr His Thr
            260                 265                 270

Phe Leu His Leu Ser Pro Gly Thr Pro His Glu Leu Lys Ile Cys Ala
        275                 280                 285

Ser Ala Gly Pro His Gln Ile Trp Gly Pro Ser Ala Thr Glu Trp Thr
    290                 295                 300

Tyr Pro Ser Tyr Pro Ser Asp Leu Val Leu Thr Pro Leu Arg Asn Glu
305                 310                 315                 320

Leu Trp Ala Ser Trp Lys Ala Gly Leu Gly Ala Arg Asp Gly Tyr Val
                325                 330                 335

Leu Lys Leu Ser Gly Pro Met Glu Ser Thr Ser Thr Leu Gly Pro Glu
            340                 345                 350

Glu Cys Asn Ala Val Phe Pro Gly Pro Leu Pro Pro Gly His Tyr Thr
        355                 360                 365
```

```
Leu Gln Leu Lys Val Leu Ala Gly Pro Tyr Asp Ala Trp Val Glu Gly
    370             375                 380
Ser Thr Trp Leu Ala Glu Ser Ala Ala Leu Pro Arg Glu Val Pro Gly
385             390                 395                 400
Ala Arg Leu Trp Leu Asp Gly Leu Glu Ala Ser Lys Gln Pro Gly Arg
                405                 410                 415
Arg Ala Leu Leu Tyr Ser Asp Ala Pro Gly Ser Leu Gly Asn Ile
                420                 425                 430
Ser Val Pro Ser Gly Ala Thr His Val Ile Phe Cys Gly Leu Val Pro
        435                 440                 445
Gly Ala His Tyr Arg Val Asp Ile Ala Ser Ser Thr Gly Asp Ile Ser
450                 455                 460
Gln Ser Ile Ser Gly Tyr Thr Ser Pro Leu Pro Pro Gln Ser Leu Glu
465                 470                 475                 480
Val Ile Ser Arg Ser Ser Pro Ser Asp Leu Thr Ile Ala Trp Gly Pro
                485                 490                 495
Ala Pro Gly Gln Leu Glu Gly Tyr Lys Val Thr Trp His Gln Asp Gly
            500                 505                 510
Ser Gln Arg Ser Pro Gly Asp Leu Val Asp Leu Gly Pro Asp Thr Leu
            515                 520                 525
Ser Leu Thr Leu Lys Ser Leu Val Pro Gly Ser Cys Tyr Thr Val Ser
530                 535                 540
Ala Trp Ala Trp Ala Gly Asn Leu Asp Ser Asp Ser Gln Lys Ile His
545                 550                 555                 560
Ser Cys Thr Arg Pro Ala Pro Pro Thr Asn Leu Ser Leu Gly Phe Ala
                565                 570                 575
His Gln Pro Ala Ala Leu Lys Ala Ser Trp Tyr His Pro Pro Gly Gly
            580                 585                 590
Arg Asp Ala Phe His Leu Arg Leu Tyr Arg Leu Arg Pro Leu Thr Leu
            595                 600                 605
Glu Ser Glu Lys Val Leu Pro Arg Glu Ala Gln Asn Phe Ser Trp Ala
            610                 615                 620
Gln Leu Thr Ala Gly Cys Glu Phe Gln Val Gln Leu Ser Thr Leu Trp
625                 630                 635                 640
Gly Ser Glu Arg Ser Ser Ala Asn Ala Thr Gly Trp Thr Pro Pro
                645                 650                 655
Ser Ala Pro Thr Leu Val Asn Val Thr Ser Asp Ala Pro Thr Gln Leu
                660                 665                 670
Gln Val Ser Trp Ala His Val Pro Gly Gly Arg Ser Arg Tyr Gln Val
            675                 680                 685
Thr Leu Tyr Gln Glu Ser Thr Arg Thr Ala Thr Ser Ile Met Gly Pro
690                 695                 700
Lys Glu Asp Gly Thr Ser Phe Leu Gly Leu Thr Pro Gly Thr Lys Tyr
705                 710                 715                 720
Lys Val Glu Val Ile Ser Trp Ala Gly Pro Leu Tyr Thr Ala Ala Ala
                725                 730                 735
Asn Val Ser Ala Trp Thr Tyr Pro Leu Ile Pro Asn Glu Leu Leu Val
                740                 745                 750
Ser Met Gln Ala Gly Ser Ala Val Val Asn Leu Ala Trp Pro Ser Gly
            755                 760                 765
Pro Leu Gly Gln Gly Ala Cys His Ala Gln Leu Ser Asp Ala Gly His
    770                 775                 780
Leu Ser Trp Glu Gln Pro Leu Lys Leu Gly Gln Glu Leu Phe Met Leu
```

-continued

```
      785                 790                 795                 800
Arg Asp Leu Thr Pro Gly His Thr Ile Ser Met Ser Val Arg Cys Arg
                    805                 810                 815
Ala Gly Pro Leu Gln Ala Ser Thr His Leu Val Val Leu Ser Val Glu
                820                 825                 830
Pro Gly Pro Val Glu Asp Val Leu Cys His Pro Glu Ala Thr Tyr Leu
                835                 840                 845
Ala Leu Asn Trp Thr Met Pro Ala Gly Asp Val Asp Val Cys Leu Val
            850                 855                 860
Val Val Glu Arg Leu Val Pro Gly Gly Thr His Phe Val Phe Gln
865                 870                 875                 880
Val Asn Thr Ser Gly Asp Ala Leu Leu Leu Pro Asn Leu Met Pro Thr
                    885                 890                 895
Thr Ser Tyr Arg Leu Ser Leu Thr Val Leu Gly Arg Asn Ser Arg Trp
                900                 905                 910
Ser Arg Ala Val Ser Leu Val Cys Thr Ser Ala Glu Ala Trp His Pro
            915                 920                 925
Pro Glu Leu Ala Glu Pro Pro Gln Val Glu Leu Gly Thr Gly Met Gly
        930                 935                 940
Val Thr Val Met Arg Gly Met Phe Gly Lys Asp Asp Gly Gln Ile Gln
945                 950                 955                 960
Trp Tyr Gly Ile Ile Ala Thr Ile Asn Met Thr Leu Ala Gln Pro Ser
                    965                 970                 975
Arg Glu Ala Ile Asn Tyr Thr Trp Tyr Asp His Tyr Tyr Arg Gly Cys
                980                 985                 990
Glu Ser Phe Leu Ala Leu Leu Phe Pro Asn Pro Phe Tyr Pro Glu Pro
            995                 1000                1005
Trp Ala Gly Pro Arg Ser Trp Thr Val Pro Val Gly Thr Glu Asp
        1010                1015                1020
Cys Asp Asn Thr Gln Glu Ile Cys Asn Gly Arg Leu Lys Ser Gly
    1025                1030                1035
Phe Gln Tyr Arg Phe Ser Val Ala Phe Ser Arg Leu Asn Thr
    1040                1045                1050
Pro Glu Thr Ile Leu Ala Phe Ser Ala Phe Ser Glu Pro Arg Ala
    1055                1060                1065
Ser Ile Ser Leu Ala Ile Pro Leu Thr Val Met Leu Gly Ala
    1070                1075                1080
Val Val Gly Ser Ile Val Ile Val Cys Ala Val Leu Cys Leu Leu
    1085                1090                1095
Arg Trp Arg Cys Leu Lys Gly Pro Arg Ser Glu Lys Asp Gly Phe
    1100                1105                1110
Ser Lys Glu Leu Met Pro Tyr Asn Leu Trp Arg Thr His Thr Pro
    1115                1120                1125
Ile Pro Ile His Ser Phe Arg Gln Ser Tyr Glu Ala Lys Ser Ala
    1130                1135                1140
His Ala His Gln Thr Phe Phe Gln Glu Phe Glu Glu Leu Lys Glu
    1145                1150                1155
Val Gly Lys Asp Gln Pro Arg Leu Glu Ala Glu His Pro Asp Asn
    1160                1165                1170
Ile Ile Lys Asn Arg Tyr Pro His Val Leu Pro Tyr Asp His Ser
    1175                1180                1185
Arg Val Arg Leu Thr Gln Leu Pro Gly Glu Pro His Ser Asp Tyr
    1190                1195                1200
```

-continued

```
Ile Asn Ala Asn Phe Ile Pro Gly Tyr Ser His Thr Gln Glu Ile
1205                1210                1215

Ile Ala Thr Gln Gly Pro Leu Lys Lys Thr Leu Glu Asp Phe Trp
1220                1225                1230

Arg Leu Val Trp Glu Gln Gln Val His Val Ile Ile Met Leu Thr
1235                1240                1245

Val Gly Met Glu Asn Gly Arg Val Leu Cys Glu His Tyr Trp Pro
1250                1255                1260

Ala Asn Ser Thr Pro Val Thr His Gly His Ile Thr Ile His Leu
1265                1270                1275

Leu Ala Glu Glu Pro Glu Asp Glu Trp Thr Arg Arg Glu Phe Gln
1280                1285                1290

Leu Gln His Gly Thr Glu Gln Lys Gln Arg Arg Val Lys Gln Leu
1295                1300                1305

Gln Phe Thr Thr Trp Pro Asp His Ser Val Pro Glu Ala Pro Ser
1310                1315                1320

Ser Leu Leu Ala Phe Val Glu Leu Val Gln Glu Gln Val Gln Ala
1325                1330                1335

Thr Gln Gly Lys Gly Pro Ile Leu Val His Cys Ser Ala Gly Val
1340                1345                1350

Gly Arg Thr Gly Thr Phe Val Ala Leu Leu Arg Leu Leu Arg Gln
1355                1360                1365

Leu Glu Glu Glu Lys Val Ala Asp Val Phe Asn Thr Val Tyr Ile
1370                1375                1380

Leu Arg Leu His Arg Pro Leu Met Ile Gln Thr Leu Ser Gln Tyr
1385                1390                1395

Ile Phe Leu His Ser Cys Leu Leu Asn Lys Ile Leu Glu Gly Pro
1400                1405                1410

Pro Asp Ser Ser Asp Ser Gly Pro Ile Ser Val Met Asp Phe Ala
1415                1420                1425

Gln Ala Cys Ala Lys Arg Ala Ala Asn Ala Asn Ala Gly Phe Leu
1430                1435                1440

Lys Glu Tyr Lys Leu Leu Lys Gln Ala Ile Lys Asp Gly Thr Gly
1445                1450                1455

Ser Leu Leu Pro Pro Pro Asp Tyr Asn Gln Asn Ser Ile Val Ser
1460                1465                1470

Arg Arg His Ser Gln Glu Gln Phe Ala Leu Val Glu Glu Cys Pro
1475                1480                1485

Glu Asp Ser Met Leu Glu Ala Ser Leu Phe Pro Gly Gly Pro Ser
1490                1495                1500

Gly Cys Asp His Val Val Leu Thr Gly Ser Ala Gly Pro Lys Glu
1505                1510                1515

Leu Trp Glu Met Val Trp Glu His Asp Ala His Val Leu Val Ser
1520                1525                1530

Leu Gly Leu Pro Asp Thr Lys Glu Lys Pro Pro Asp Ile Trp Pro
1535                1540                1545

Val Glu Met Gln Pro Ile Val Thr Asp Met Val Thr Val His Arg
1550                1555                1560

Val Ser Glu Ser Asn Thr Thr Thr Gly Trp Pro Ser Thr Leu Phe
1565                1570                1575

Arg Val Ile His Gly Glu Ser Gly Lys Glu Arg Gln Val Gln Cys
1580                1585                1590
```

| Leu | Gln | Phe | Pro | Cys | Ser | Glu | Ser | Gly | Cys | Glu | Leu | Pro | Ala | Asn |
|---|---|---|---|---|---|---|---|---|---|---|---|---|---|---|
| 1595 | | | | | 1600 | | | | | 1605 | | | | |

| Thr | Leu | Leu | Thr | Phe | Leu | Asp | Ala | Val | Gly | Gln | Cys | Cys | Phe | Arg |
|---|---|---|---|---|---|---|---|---|---|---|---|---|---|---|
| 1610 | | | | | 1615 | | | | | 1620 | | | | |

| Gly | Lys | Ser | Lys | Lys | Pro | Gly | Thr | Leu | Leu | Ser | His | Ser | Ser | Lys |
|---|---|---|---|---|---|---|---|---|---|---|---|---|---|---|
| 1625 | | | | | 1630 | | | | | 1635 | | | | |

| Asn | Thr | Asn | Gln | Leu | Gly | Thr | Phe | Leu | Ala | Met | Glu | Gln | Leu | Leu |
|---|---|---|---|---|---|---|---|---|---|---|---|---|---|---|
| 1640 | | | | | 1645 | | | | | 1650 | | | | |

| Gln | Gln | Ala | Gly | Thr | Glu | Arg | Thr | Val | Asp | Val | Phe | Asn | Val | Ala |
|---|---|---|---|---|---|---|---|---|---|---|---|---|---|---|
| 1655 | | | | | 1660 | | | | | 1665 | | | | |

| Leu | Lys | Gln | Ser | Gln | Ala | Cys | Gly | Leu | Met | Thr | Pro | Thr | Leu | Glu |
|---|---|---|---|---|---|---|---|---|---|---|---|---|---|---|
| 1670 | | | | | 1675 | | | | | 1680 | | | | |

| Gln | Tyr | Ile | Tyr | Leu | Tyr | Asn | Cys | Leu | Asn | Ser | Ala | Leu | Leu | Asn |
|---|---|---|---|---|---|---|---|---|---|---|---|---|---|---|
| 1685 | | | | | 1690 | | | | | 1695 | | | | |

| Gly | Leu | Pro | Arg | Ala | Gly | Lys | Trp | Pro | Ala | Pro | Cys |
|---|---|---|---|---|---|---|---|---|---|---|---|
| 1700 | | | | | 1705 | | | | | 1710 | |

<210> SEQ ID NO 16
<211> LENGTH: 3247
<212> TYPE: DNA
<213> ORGANISM: Human

<400> SEQUENCE: 16

```
gggcgggcct cggggctaag agcgcgacgc ctagagcggc agacggcgca gtgggccgag      60
aaggaggcgc agcagccgcc ctggcccgtc atggagatgg aaaaggagtt cgagcagatc     120
gacaagtccg ggagctgggc ggccatttac caggatatcc acatgaagc cagtgacttc     180
ccatgtagag tggccaagct tcctaagaac aaaaaccgaa ataggtacag agacgtcagt     240
cccttttgacc atagtcggat taaactacat caagaagata tgactatat caacgctagt     300
ttgataaaaa tggaagaagc ccaaaggagt tacattctta cccagggccc tttgcctaac     360
acatgcggtc acttttggga gatggtgtgg gagcagaaaa gcaggggtgt cgtcatgctc     420
aacagagtga tggagaaagg ttcgttaaaa tgcgcacaat actggccaca aaagaagaa     480
aaagagatga tctttgaaga cacaaatttg aaattaacat tgatctctga agatatcaag     540
tcatattata cagtgcgaca gctagaattg aaaaaccta caacccaaga aactcgagag     600
atcttacatt tccactatac cacatggcct gactttggag tccctgaatc accagcctca     660
ttcttgaact ttctttttcaa agtccgagag tcagggtcac tcagcccgga gcacgggccc     720
gttgtggtgc actgcagtgc aggcatcggc aggtctggaa ccttctgtct ggctgatacc     780
tgcctcctgc tgatggacaa gaggaaagac ccttcttccg ttgatatcaa gaaagtgctg     840
ttagaaatga ggaagtttcg gatggggttg atccagacag ccgaccagct gcgcttctcc     900
tacctggctg tgatcgaagg tgccaaattc atcatggggg actcttccgt gcaggatcag     960
tggaaggagc ttccccacga ggacctggag cccccacccg agcatatccc cccacctccc    1020
cggccacca aacgaatcct ggagccacac aatgggaaat gcagggagtt cttcccaaat    1080
caccagtggg tgaaggaaga gacccaggag gataaagact gccccatcaa ggaagaaaa    1140
ggaagcccct taaatgccgc accctacggc atcgaaagca tgagtcaaga cactgaagtt    1200
agaagtcggg tcgtgggggg aagtcttcga ggtgcccagg ctgcctcccc agccaaaggg    1260
gagccgtcac tgcccgagaa ggacgaggac catgcactga gttactggaa gcccttcctg    1320
gtcaacatgt gcgtgctac ggtcctcacg gccggcgctt acctctgcta caggttcctg    1380
ttcaacagca acacatagcc tgaccctcct ccactccacc tccacccact gtccgcctct    1440
```

```
gcccgcagag cccacgcccg actagcaggc atgccgcggt aggtaagggc cgccggaccg    1500
cgtagagagc cgggccccgg acggacgttg gttctgcact aaaacccatc ttccccggat    1560
gtgtgtctca cccctcatcc tttttacttt tgcccctccc actttgagta ccaaatccac    1620
aagccatttt ttgaggagag tgaaagagag taccatgctg cgcggcgcaga gggaaggggc    1680 ctacacccgt cttggggctc gccccaccca gggctccctc ctggagcatc ccaggcggcg    1740
cacgccaaca gccccccct tgaatctgca gggagcaact ctccactcca tatttattta    1800
aacaattttt tccccaaagg catccatagt gcactagcat tttcttgaac caataatgta    1860
ttaaaatttt ttgatgtcag ccttgcatca agggctttat caaaaagtac aataataaat    1920
cctcaggtag tactgggaat ggaaggcttt gccatgggcc tgctgcgtca gaccagtact    1980
gggaaggagg acggttgtaa gcagttgtta tttagtgata ttgtgggtaa cgtgagaaga    2040
tagaacaatg ctataatata taatgaacac gtgggtattt aataagaaac atgatgtgag    2100
attactttgt cccgcttatt ctcctccctg ttatctgcta gatctagttc tcaatcactg    2160
ctcccccgtg tgtattagaa tgcatgtaag gtcttcttgt gtcctgatga aaaatatgtg    2220
cttgaaatga gaaactttga tctctgctta ctaatgtgcc ccatgtccaa gtccaacctg    2280
cctgtgcatg acctgatcat tacatggctg tggttcctaa gcctgttgct gaagtcattg    2340
tcgctcagca atagggtgca gttttccagg aataggcatt tgctaattcc tggcatgaca    2400
ctctagtgac ttcctggtga ggcccagcct gtcctggtac agcagggtct tgctgtaact    2460
cagacattcc aagggtatgg gaagccatat tcacacctca cgctctggac atgatttagg    2520
gaagcaggga caccccccgc ccccaccctt tgggatcagc ctccgccatt ccaagtcaac    2580
actcttcttg agcagaccgt gatttggaag agaggcacct gctggaaacc acacttcttg    2640
aaacagcctg ggtgacggtc ctttaggcag cctgccgccg tctctgtccc ggttcacctt    2700
gccgagagag gcgcgtctgc cccaccctca aaccctgtgg ggcctgatgg tgctcacgac    2760
tcttcctgca aagggaactg aagacctcca cattaagtgg cttttttaaca tgaaaaacac    2820 ggcagctgta gctcccgagc tactctcttg ccagcatttt cacatttgc ctttctcgtg     2880 gtagaagcca gtacagagaa attctgtggt gggaacattc gaggtgtcac cctgcagagc    2940
tatggtgagg tgtggataag gcttaggtgc caggctgtaa gcattctgag ctggcttgtt    3000 gttttttaagt cctgtatatg tatgtagtag tttgggtgtg tatatatagt agcatttcaa    3060
aatggacgta ctggtttaac ctcctatcct tggagagcag ctggctctcc accttgttac    3120
acattatgtt agagaggtag cgagctgctc tgctatatgc cttaagccaa tatttactca    3180
tcaggtcatt attttttaca atggccatgg aataaccat ttttacaaaa ataaaaacaa     3240
aaaaagc                                                              3247
```

<210> SEQ ID NO 17
<211> LENGTH: 435
<212> TYPE: PRT
<213> ORGANISM: Human

<400> SEQUENCE: 17

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

```
Val Ser Pro Phe Asp His Ser Arg Ile Lys Leu His Gln Glu Asp Asn
     50                  55                  60
Asp Tyr Ile Asn Ala Ser Leu Ile Lys Met Glu Ala Gln Arg Ser
 65                  70                  75                  80
Tyr Ile Leu Thr Gln Gly Pro Leu Pro Asn Thr Cys Gly His Phe Trp
                     85                  90                  95
Glu Met Val Trp Glu Gln Lys Ser Arg Gly Val Val Met Leu Asn Arg
                100                 105                 110
Val Met Glu Lys Gly Ser Leu Lys Cys Ala Gln Tyr Trp Pro Gln Lys
             115                 120                 125
Glu Glu Lys Glu Met Ile Phe Glu Asp Thr Asn Leu Lys Leu Thr Leu
         130                 135                 140
Ile Ser Glu Asp Ile Lys Ser Tyr Tyr Thr Val Arg Gln Leu Glu Leu
145                 150                 155                 160
Glu Asn Leu Thr Thr Gln Glu Thr Arg Glu Ile Leu His Phe His Tyr
                    165                 170                 175
Thr Thr Trp Pro Asp Phe Gly Val Pro Glu Ser Pro Ala Ser Phe Leu
                180                 185                 190
Asn Phe Leu Phe Lys Val Arg Glu Ser Gly Ser Leu Ser Pro Glu His
            195                 200                 205
Gly Pro Val Val Val His Cys Ser Ala Gly Ile Gly Arg Ser Gly Thr
        210                 215                 220
Phe Cys Leu Ala Asp Thr Cys Leu Leu Leu Met Asp Lys Arg Lys Asp
225                 230                 235                 240
Pro Ser Ser Val Asp Ile Lys Lys Val Leu Leu Glu Met Arg Lys Phe
                    245                 250                 255
Arg Met Gly Leu Ile Gln Thr Ala Asp Gln Leu Arg Phe Ser Tyr Leu
                260                 265                 270
Ala Val Ile Glu Gly Ala Lys Phe Ile Met Gly Asp Ser Ser Val Gln
            275                 280                 285
Asp Gln Trp Lys Glu Leu Ser His Glu Asp Leu Glu Pro Pro Pro Glu
        290                 295                 300
His Ile Pro Pro Pro Arg Pro Pro Lys Arg Ile Leu Glu Pro His
305                 310                 315                 320
Asn Gly Lys Cys Arg Glu Phe Phe Pro Asn His Gln Trp Val Lys Glu
                    325                 330                 335
Glu Thr Gln Glu Asp Lys Asp Cys Pro Ile Lys Glu Glu Lys Gly Ser
                340                 345                 350
Pro Leu Asn Ala Ala Pro Tyr Gly Ile Glu Ser Met Ser Gln Asp Thr
            355                 360                 365
Glu Val Arg Ser Arg Val Val Gly Gly Ser Leu Arg Gly Ala Gln Ala
        370                 375                 380
Ala Ser Pro Ala Lys Gly Glu Pro Ser Leu Pro Glu Lys Asp Glu Asp
385                 390                 395                 400
His Ala Leu Ser Tyr Trp Lys Pro Phe Leu Val Asn Met Cys Val Ala
                    405                 410                 415
Thr Val Leu Thr Ala Gly Ala Tyr Leu Cys Tyr Arg Phe Leu Phe Asn
                420                 425                 430
Ser Asn Thr
        435
```